United States Patent
Andersen et al.

(10) Patent No.: US 9,499,864 B2
(45) Date of Patent: Nov. 22, 2016

(54) EXPRESSION OF FABP4 AND OTHER GENES ASSOCIATED WITH BLADDER CANCER PROGRESSION

(75) Inventors: Lars Dyrskjøt Andersen, Odder (DK); Torben Falck Orntoft, Silkeborg (DK)

(73) Assignee: AAB Patent Holding ApS, Roskilde (DK)

( * ) Notice: Subject to any disclaimer, the term of this patent is extended or adjusted under 35 U.S.C. 154(b) by 1109 days.

(21) Appl. No.: 13/316,821

(22) Filed: Dec. 12, 2011

(65) Prior Publication Data

US 2012/0077202 A1   Mar. 29, 2012

Related U.S. Application Data

(63) Continuation-in-part of application No. 12/180,321, filed on Jul. 25, 2008, which is a continuation of application No. 10/533,547, filed as application No. PCT/DK03/00750 on Nov. 3, 2003, now abandoned.

(51) Int. Cl.
*C12Q 1/68* (2006.01)

(52) U.S. Cl.
CPC ....... *C12Q 1/6876* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2004/0076955 A1* | 4/2004 | Mack et al. | 435/6 |
| 2006/0019256 A1* | 1/2006 | Clarke et al. | 435/6 |
| 2007/0031905 A1 | 2/2007 | Shariat et al. | |
| 2009/0175827 A1 | 7/2009 | Byrom et al. | |
| 2010/0130527 A1 | 5/2010 | Lehrer et al. | |
| 2011/0236903 A1 | 9/2011 | McClelland et al. | |
| 2011/0262921 A1 | 10/2011 | Sabichi et al. | |

FOREIGN PATENT DOCUMENTS

| | | |
|---|---|---|
| DE | 103 00 861 A1 | 7/2004 |
| EP | 1930445 A1 | 6/2008 |

OTHER PUBLICATIONS

2008 MeSH Heading for the term FABP4 downloaded Mar. 15, 2012.*
Dyrskjot et al, also called Andersen et al, Nature Genetics: vol. 33, pp. 90-96, published online Dec. 9, 2002.*
Bignotti et al in "Gene expression profile of ovarian serous papillary carcinomas: identification of matastasis-associated genes" (American Journal of Obstetrics and Gynecology: Mar. 2007, pp. 245.e1-245.e11.*
Sanchez-Carboyo et al (Clinical Chemistry 49(1):23-31, 2003).*
Wagner (2002) Dis. Markers 18:41-46.*
Frank et al. (2003) Nature Rev. 2:566-580.*
Feng et al. (2004) Pharmacogenomics 5:709-719.*
Cells A., et al., "Short-Term culturing of low-grade superficial bladder transitional cell carcinomas leads to changes in the expression levels of several proteins involved in key cellular activities" Electrophoresis vol. 20, No. 2, 1999, p. 355-61.
Yang, T et al., "aP2 protein expression as a diagnostic marker in soft tissue tumours" Sarcoma, No. 5, 2001 p. 139-42.
Gromova I, et al., "Protein abundancy and mRNA levels of the adipocyte-type fatty acid binding protein correlate in non-invasive and invasive bladder transitional cell carcinomas." Int J Oncol. Aug. 1998;13(2):379-383.
Cells JE, et al., "Loss of adipocyte-type fatty acid binding protein and other protein biomarkers is associated with progression of human bladder transitional cell carcinomas." Cancer Res. Oct. 15, 1996;56(20):4782-90.
Andersen et al., Identifying distinct classes of bladder carcinoma using microarrays; Nature Genetics 33, 90-96 (2002).

* cited by examiner

*Primary Examiner* — Catherine S Hibbert
(74) *Attorney, Agent, or Firm* — Pierce Atwood LLP; Daniel A. Lev

(57) ABSTRACT

Disclosed are methods for predicting the risk of bladder cancer progression, including death from bladder cancer by determining gene expression levels of FABP4 and MBNL2 or other markers where increased levels correlate with lack of progression of the subject's bladder cancer, and decreased levels correlate with progression or death from bladder cancer, and/or determining gene expression levels of COL4A1, UBE2C, BIRC5, COL18A1, KPNA2, MSN, ACTA2, and/or CDC25B or other markers where increased levels correlate with progression of the subject's bladder cancer or death from it, and decreased levels correlate with lack of progression of bladder cancer.

12 Claims, 10 Drawing Sheets

Cross-validation performance

+ indicates moderate recurrence rates; ++ indicates high recurrence rates;
no sign indicates no or moderate recurrence

EXPRESSION OF FABP4 AND OTHER GENES ASSOCIATED WITH BLADDER CANCER PROGRESSION

RELATED APPLICATIONS

This application is a continuation-in-part of U.S. patent application Ser. No. 12/180,321, filed Jul. 5, 2008, and incorporated by reference herein, which is a continuation of U.S. patent application Ser. No. 10/533,547 filed Nov. 16, 2005, which is a US National Phase application of PCT/DK03/00750 filed Nov. 3, 2003.

SEQUENCE LISTING

This application contains a Sequence Listing which has been submitted in ASCII format via EFS-Web and is hereby incorporated by reference in its entirety. Said ASCII copy, created on Nov. 28, 2011, is named SORGE321.txt and is 43,073 bytes in size.

FIELD OF THE INVENTION

The invention relates to predicting the prognosis of bladder cancer from gene expression levels.

BACKGROUND

In industrialized countries, urinary bladder cancer is the fourth most common malignancy in males, and the fifth most common neoplasm overall. The disease basically takes two different courses: one where patients have multiple recurrences of superficial tumors (Ta and T1), and one which progresses to a muscle invasive form (T2+) which can lead to metastasis. About 5-10% of patients with Ta tumors and 20-30% of the patients with T1 tumors will eventually develop a higher stage tumor (Wolf, H. et al. Bladder tumors treated natural history. *Prog Clin Biol Res* 221, 223-55 (1986).). Patients with superficial bladder tumors represent 75% of all bladder cancer patients. No approved clinically useful markers separating such patients by likelihood of progression exist.

It is believed that patients presenting isolated or concomitant carcinoma in situ (CIS) lesions have a higher risk of disease progression to a muscle invasive stage. The CIS lesions may have a widespread manifestation in the bladder (field disease) and are believed to be the most common precursors of invasive carcinomas (Spruck, C. H., et al. Two molecular pathways to transitional cell carcinoma of the bladder. Cancer Res, 54: 784-788, 1994; Rosin, M. P. et al. Partial allelotype of carcinoma in situ of the human bladder. Cancer Res, 55: 5213-5216, 1995). Generally, it is known that class T1 tumors have a higher risk of further progression than class Ta tumors. However, it is often difficult to differentiate Ta from T1 stage tumors, and the two stages are often confused. The ability to predict which tumors are likely to recur or progress would have great impact on the clinical management of patients with superficial disease, as it would be possible to treat high-risk patients more aggressively (e.g. with radical cystectomy or adjuvant therapy).

Although many prognostic markers have been investigated, the most important prognostic factors are still disease stage, dysplasia grade, and especially the presence of areas with CIS (Anderstrom, C., et al., The significance of lamina propria invasion on the prognosis of patients with bladder tumors. J Urol, 124: 23-26, 1980; Cummings, K. B. Carcinoma of the bladder: predictors. Cancer, 45: 1849-1855, 1980; Cheng, L. et al. Survival of patients with carcinoma in situ of the urinary bladder. Cancer, 85: 2469-2474, 1999.). The current standard for detection of CIS is urine cytology and histopathologic analysis of a set of selected site biopsies removed during routine cystoscopy examinations; however these procedures are not sufficiently sensitive. Implementing routine cystoscopy examinations with 5-ALA fluorescence imaging of the tumors and pre-cancerous lesions (CIS lesions and moderate dysplasia lesions) may increase the sensitivity of the procedure (Kriegmair, M. et al., Early clinical experience with 5-aminolevulinic acid for the photodynamic therapy of superficial bladder cancer. Br J Urol, 77: 667-671, 1996). However, this screening is not yet routine.

Monitoring of gene expression levels may be used to find markers whose elevated expression correlates either: with bladder cancer progression or death from bladder cancer; or, with no progression or death. Further, once such markers are found, one may combine the gene expression levels of such markers into sets or signatures, which, in combination, may indicate the likelihood of progression or death more reliably than when monitoring them separately.

Gene expression levels can be monitored by assaying a subject RNA using a method or process that detects a signal coming from the RNA molecules. Examples of methods or processes used to monitor gene expression include nucleic acid hybridization, quantitative polymerase chain reaction (or other nucleic acid replication reactions), nucleic acid sequencing, protein product detection, and visible light or ultra-violet light spectrophotometry or diffraction. Such methods can utilize fluorescent dyes, radioactive tracers, enzymatic reporters, chemical reaction products, or other means of reporting the amounts or concentrations of nucleic acid molecules. Gene expression levels can be monitored by first reverse transcribing the mRNA from a subject's sample to cDNA, then amplifying the cDNA using polymerase chain reaction (PCR).

SUMMARY

The inventions described and claimed herein have many attributes and embodiments including, but not limited to, those set forth or described or referenced in this Summary. It is not intended to be all-inclusive and the inventions described and claimed herein are not limited to or by the features or embodiments identified in this Summary, which is included for purposes of illustration only and not restriction.

The invention relates to determining expression levels of certain markers associated with progression or death from bladder cancer. More particularly, expression levels of markers MBNL2, FABP4, UBE2C, and BIRC5 have been associated with progression or death from bladder cancer. Expression levels of these genes can be combined with expression levels of other genes associated with bladder cancer (including with other genes associated with progression, i.e., certain genes in Table A) in a gene signature. The signature may in some cases provide a more accurate indication of progression or death from bladder cancer, or non-progression, than any gene in isolation. A score can be obtained from a signature, and scores can be compared to known or control values to provide predictive information.

Detection of expression levels of some or all of these markers in early-stage bladder cancer patients can be used to predict patient outcomes and/or tailor treatments. Expression levels can be determined by measuring a gene product of a particular gene in a sample. The products include pre-mRNA, mRNA, cDNA transcribed from the mRNA, and protein translated from mRNA. A preferred measurement technique includes RT-PCR (quantitative "real time" polymerase chain reaction) of cDNA reverse-transcribed from the mRNA present in a subject's sample. Expression arrays, nucleic acid sequencing, fluorescent nucleic acid dyes and/or chelators can also be used to determine cDNA levels, as well as techniques for assaying for particular protein products, including ELISA, Western Blotting, and enzyme assays.

In a preferred embodiment, the relative amount of one or more of the markers is determined relative to one or more other markers in the assay. The relative amount of one or more of the markers can also be determined relative to a standard expression level for each such marker.

Furthermore, the invention relates to a method of determining the likelihood of progression or death from bladder cancer, comprising determining the expression level of at least one of the markers MBNL2, FABP4, UBE2C, and/or BIRC5 in a human tissue sample, and wherein one can also determine the expression level of at least one other gene in the group of genes Nos. 1 to 562 in Table A, and correlating the expression level of the assessed genes to at least one standard level of expression of such genes to determine the likelihood of bladder cancer progression or death therefrom. The human cell sample may be taken from bladder tissue, and the method may be independent of the proportion of submucosal, muscle, or connective tissue cells present.

The invention further relates to a method for reducing tumorigenicity or malignancy comprising contacting a tumor cell with at least one of the genes MBNL2, FABP4, UBE2C, and/or BIRC5 so as to permit introducing said at least one gene into the tumor cell in a manner allowing expression of said gene(s). Alternatively, the method for reducing tumorigenicity or malignancy can include obtaining at least one nucleotide probe capable of hybridizing with at least one of the genes MBNL2, FABP4, UBE2C, and/or BIRC5 and introducing said at least one nucleotide probe into the tumor cell in a manner allowing the probe to hybridize to the at least one gene, thereby inhibiting expression of said at least one gene.

In a further aspect the invention relates to a method for producing antibodies against an expression product of a cell from a biological tissue, said method comprising the steps of obtaining expression product(s) from at least one of the genes MBNL2, FABP4, UBE2C, and/or BIRC5, immunizing a mammal with said expression product(s) obtaining antibodies against the expression product. The antibodies produced may be used for producing a pharmaceutical composition. Further, the invention relates to a vaccine capable of eliciting an immune response against at least one expression product from at least one gene said gene being expressed as defined above. The invention furthermore relates to the use of any of the methods discussed above for producing an assay for diagnosing a biological condition in animal tissue. Also, the invention relates to the use of a peptide as defined above as an expression product and/or the use of a gene as defined above and/or the use of a probe as defined above for preparation of a pharmaceutical composition for the treatment of a biological condition in animal tissue.

As noted above, expression levels for genes including MBNL2, FABP4, UBE2C, and/or BIRC5 as well as the genes COL18A1, COL4A1, ACTA2, MSN and KPNA2 can be determined from monitoring expression products, including those expression products represented by or relating to the Sequence ID Number and listing herein for each of the respective genes. Other sequences which can be monitored to determine expression levels are listed on the NCBI database—and have been publicly available there since the earliest priority date of this application. Again, it is noted that some or all of the expression levels of some or all of these genes can be combined to give a score, which can in turn be used in predicting likelihood of bladder cancer progression or death from bladder cancer.

As is well known in the art, in the sequences identified herein, the first exon includes sequence upstream of the ATG start codon and the final exon includes information downstream of the stop codon including the polyA tail. That is how the mRNA appears after the processing which removes the introns from the transcribed DNA sequence. Within this mRNA sequence is the region known as the CDS, or coding DNA sequence, which goes from start to stop codon. It is only the region from start to stop codon that gets translated into protein, but the mRNA contains both 5' (upstream) and 3' (downstream) untranslated regions and the mRNA sequences are generally what are shown in the NCBI Nucleotide database of sequences.

DRAWINGS

SEQUENCE LISTING GUIDE

Figure 1:
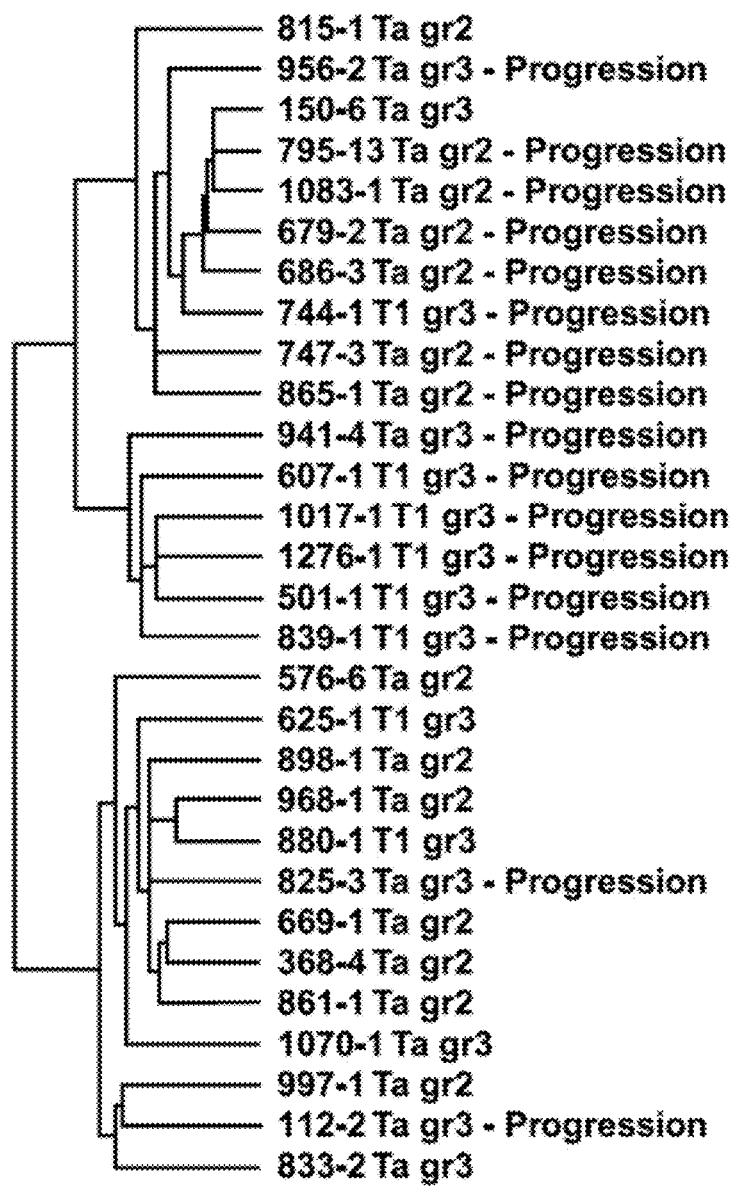
FIG. 1: Hierarchical cluster analysis of tumor samples based on 3,197 genes that show large variation across all tumor samples. Samples with progression are marked "Progression"

The sequences listed below correspond to one complete gene sequence of one isoform of the designated genes, following transcription processing, as posted and available on the NCBI Nucleotide database.

SEQ ID NO. 1: UBE2C also known as UBCH10 (see FIGS. 7c & 8c in Ser. No. 12/180,321)

SEQ ID NO. 2: MBNL2 (see FIG. 4a in Ser. No. 12/180, 321 and Gene No. 295 in Table A)

SEQ ID NO. 3: FABP4 (see FIG. 14a in Ser. No. 12/180,321 and Gene No. 467 in Table A)

SEQ ID NO. 4: BIRC5 (see FIG. 4a in Ser. No. 12/180, 321 and Gene No. 437 in Table A)

SEQ ID NO. 5: COL18A1 (see FIGS. 7g and 8g in Ser. No. 12/180,321)

SEQ ID NO. 6: COL4A1 (see FIG. 8h in Ser. No. 12/180,321)

SEQ ID NO. 7: ACTA2 (see FIG. 8h in Ser. No. 12/180, 321)

SEQ ID NO. 8: MSN (see FIGS. 7g, 8g & 14a in Ser. No. 12/180,321)

SEQ ID NO. 9: KPNA2 (see FIG. 14a in Ser. No. 12/180,321)

SEQ ID NO. 10: CDC25B (see Gene No. 104 in Table A)

DETAILED DESCRIPTION

"Control" refers to a bladder cancer sample or pool of bladder cancer samples that are used for comparison with a bladder cancer sample from a patient. In certain instances, a control can be a normal non-cancerous sample.

"Cut-off score" refers to a score associated with a signature allowing classification of Patients into different prognostic or treatment groups. There may be more than one cut-off score for a diagnostic or prognostic test. For example, a first, lower cut-off score may be useful to separate patients into groups appropriate for treatment options A versus B; and a second, higher cut-off score may be useful to separate patients into groups appropriate for treatment options B versus C. The cut-off score for a signature may be determined from or with reference to the relative expression levels or the standard expression levels for the gene products in the signature, or by other means or from other references.

"Cut-off value" refers to an expression level of a gene product allowing classification of patients into different prognostic or treatment groups. There may be more than one cut-off value for a diagnostic or prognostic test. For example, a first, lower cut-off value may be useful to separate patients into groups appropriate for treatment options A versus B; and a second, higher cut-off value may be useful to separate patients into groups appropriate for treatment options B versus C. The cut-off value for any gene product may be determined from or with reference to the relative expression level or the standard expression level for that gene product, or by other means or from other reference.

"Expression level" when used in connection with gene expression means the total quantities of a gene expressed, or the quantities expressed per unit time or per unit volume.

"Favorable Markers" is used synonymously with protective markers.

"Gene" refers to a genomic DNA sequence, including a marker sequence. Genes may be expressed at different levels, in cells, or not expressed at all. A "gene" may be part of a genomic DNA sequence that is transcribed into RNA molecules. Such RNA molecules may or may not be spliced into mRNA and/or translated into protein. "Gene" as used herein may be any part or several parts of a genomic DNA sequence that may be transcribed into RNA molecules. The genes/markers UBE2C, MBNL2, FABP4, BIRC5, COL18A1, COL4A1, ACTA2, MSN, KPNA2 and CDC25B are designations for these genes as referenced in the US National institutes of Health, National Center for Biotechnology Information (NCBI) database and publicly available since the earliest priority date of this application, and the sequences corresponding to each of the genes in the Sequence Listing Guide above are the complete sequence of one isoform of the designated genes, following transcription processing, and thus; can be used in determination of the quantity of a particular expression product.

"Harmful markers" are indicator genes or indicator gene products for which increased expression levels indicate a less favorable prognosis, i.e., increased expression levels correlate with higher risk of progression; and decreased expression levels correlate with lower risk of progression.

"Marker" refers to a gene or gene product associated with bladder cancer or with bladder cancer progression, including, but not limited to, MBNL2, FABP4, UBE2C, and BIRC5. "Marker" is used synonymously with indicator gene or indicator gene product.

"Non-progression" (or "non-progressors") in reference to bladder cancer or bladder cancer patients refers to lack of progression from earlier stages or lower grades to later stages or higher grades; e.g., it can refer to progression from either bladder cancer stage Ta or T1, including stage Ta or T1 without carcinoma in situ ("CIS"), to: (i) CIS and/or any of stages T2 through T4, or (ii) death from bladder cancer.

"Progression" (or "progressors") in reference to bladder cancer or bladder cancer patients refers to progression from earlier stages or lower grades to later stages or higher grades; e.g., it can refer to progression from either bladder cancer stage Ta or T1, including stage Ta or T1 without carcinoma in situ ("CIS"), to: (i) CIS and/or any of stages T2 through T4, or (ii) death from bladder cancer.

"Protective markers" are indicator genes or indicator gene products for which increased expression levels indicate a more favorable prognosis, i.e., increased expression levels correlate with non-progression; and decreased expression levels correlate with risk of progression.

"Score" refers to the result of a mathematical computation using one or more marker expression levels in a signature, typically treating the unfavorable marker level(s) as a group and the favorable marker level(s) as a group. Expression levels for markers may be combined using various mathematical functions. For example, determining score may involve computing the mean, median, or mode of certain expression levels; or involve computing one or more ratios, products, sums, differences, logarithms, exponents, and/or other mathematical functions. It is contemplated that in some cases only one gene or marker will be present in a group for which a score is determined.

"Signature" refers to sets of markers.

"Standard expression level" refers to the expression level of one or more gene product(s) in a standard situation such as an expression level associated with non-progression of bladder cancer or an expression level associated with progression of bladder cancer.

"Unfavorable markers" is used synonymously with harmful markers.

This invention relates to the predicting the likelihood of progression or non-progression of bladder cancer by determining the relative expression level of one or more of the markers MBNL2, FABP4, UBE2C, and BIRC5 and/or comparing the expression level, or levels, to standard expression level(s) for these markers. The comparison can include determining a cut-off value for an individual marker or a cut-off score such as for a signature including these markers, and determining the relationship of marker expression levels to the cut-off value, or comparing the signature's score to the cut-off score. For some markers, an increased relative expression level may indicate an increased risk of progression, and for other markers, a reduced risk of progression. For some markers, a decreased relative expression level may indicate an increased risk of progression, and for other markers, a reduced risk of progression.

Expression levels of other genes or markers including COL18A1, COL4A1, ACTA2, MSN, and KPNA2 can also be determined and used in predicting an increase or decrease in risk of bladder cancer progression. Similarly, in forming signatures, such additional markers or additional genes can be included in the signature, and used to determine a score, which can be compared to a cut-off score to determine risk of progression.

In one embodiment of the invention, signatures comprising two or more markers significantly correlated with clinically determined progression or non-progression of bladder cancer can be used to determine risk of bladder cancer progression along a continuum. Some patients will be classified as at high risk of progression, others will be identified as at intermediate risk and still others as at low risk of progression. Each of these classifications will have clinical consequences. For example high risk patients may be monitored for bladder cancer recurrence, metastasis or other form of progression more frequently; they may also be good candidates for cystectomy or other more aggressive treatment options. Low risk patients, may for example be monitored at slightly greater intervals, for example every four months rather than every two months. Intermediate risk patients might follow a more standard treatment and monitoring protocol because the signature would not place them into either high or low risk categories distinctly. The methods for assessing the risk of progression from the signature can be using Ct values or ROC (Receiver Operating Characteristic) curves or various other statistical analyses. Non-limiting examples of such analysis methods are Pearson correlation, Wilcoxon signed rank test, and Cox regression analysis.

In certain embodiments it may be useful to assign different significance or weight to particular harmful and protective markers in a signature used to make a determination about an individual's prognosis in a disease. For example, a signature comprising markers significantly correlated with risk of bladder cancer progression, may contain one or more markers that are even more significantly correlated with risk of progression (Note: this can either be a very low risk of progression as with protective markers or a high risk of progression as with harmful markers) than the other markers in the signature. Any marker(s) showing increased correlation with risk of bladder cancer progression compared to other markers in the signature could be weighted more heavily than those other markers in a manner that reflects their increased statistical correlation with the clinical outcome. One example of how this might be achieved is to look at a group of patients whose bladder cancer progressed and a second group of patients whose bladder cancer did not progress. Then for each group of patients weight the preferred protective markers, for example MBNL2 and/or FABP4; and weight the preferred harmful markers, for example UBE2C and/or including any of BIRC5, COL18A1, COL4A1, KPNA2, MSN, ACTA2 and CDC25B. In each instance the objective of the weighting would be to achieve the best correlation with risk of bladder cancer progression in each patient group; high risk and low risk. The weights may be adjusted in many ways depending on the particular clinical needs at the time of assessment. For example, one may adjust the weights to reduce the number of patients who are likely to progress being falsely categorized as at low risk of progression. Alternatively, the weights can be adjusted to reduce the number of patients who are unlikely to progress being falsely categorized as at high risk of progression. It will be apparent to one of skill in the art that other clinical concerns could affect how particular markers are weighted and these methods are all included in this embodiment.

It is contemplated that one might use a Cox regression analysis to determine the independent contribution of the expression level of each marker in a signature to overall likelihood of bladder cancer progression. Each marker in a signature may contribute to the overall risk of progression differently or be weighted differently. One could use the Cox covariate regression analysis to determine the coefficient (i.e. weight) for each marker in the signature and this coefficient may be multiplied by the measure of the expression level for a particular marker such as, but not limited to, a Ct value to determine a score for the signature where individual markers are evaluated based upon the significance of the correlation of the expression levels for each individual marker to the risk of progression. In a signature composed of six markers, where some are protective and some are harmful, the calculation for score might look like:

$$\text{Score} = ((a*Ct(PM1) + b*Ct(PM2) + c*Ct(PM3))/3) - ((d*Ct(HM1) + e*Ct(HM2) + f*Ct(HM3))/3)$$

Or in a preferred alternative, one could calculate score by dividing the sum of the weighted Ct's (or other measure of expression levels) for the protective markers by the sum of the weights for each protective marker in the signature and then dividing the sum of the weighted Ct's (or other measure of expression levels) for the harmful markers by the sum of the weights for each harmful marker in the signature. Finally, you would subtract the score calculated for the harmful markers from the score calculated for the protective markers as shown below. Such a calculation would then allow one to subtract out much of the possible sources of noise in determining the expression levels for the protective and harmful markers of the signature.

$$\text{Score} = ((a*Ct(PM1) + b*Ct(PM2) + c*Ct(PM3))/\Sigma(a,b,c)) - ((d*Ct(HM1) + e*Ct(HM2) + f*Ct(HM3))/\Sigma(d,e,f))$$

Where a-f are the coefficients (i.e. weights) determined by regression analysis;

PM1, PM2 and PM3 are protective markers; and

HM1, HM2 and HM3 are harmful markers.

Other statistical methods or analysis methods could be used to determine coefficients or weights for each marker. Other methods than determining Ct values could be used to determine the expression levels for each marker. The above calculation for score is just one possible method for factoring in the possible differences in significance for each marker in a signature. Other methods will occur to those of skill in the art and are incorporated herein. It will be obvious that each marker in the progression signature may be equally significant in determining likelihood of progression and thus all coefficients a-f will be the same.

The following table A shows the genes whose expression level can reflect likelihood of progression. The genes marked as stage, progression and CIS in the classifier column of Table A are associated with bladder cancer progression. Whenever a gene is referenced herein by a gene number, the number refers to the genes of Table A.

TABLE A

| Gene # | GeneChip | Probeset | Unigene Build | Unigene | description | Classifier |
|---|---|---|---|---|---|---|
| 1 | HUGeneFL | AB000220_at | 168 | Hs.171921 | sema domain, immunoglobulin domain (Ig), short basic domain, secreted, (semaphorin) 3C | stage |
| 2 | HUGeneFL | AF000231_at | 168 | Hs.75618 | RAB11A, member RAS oncogene family | stage |
| 3 | HUGeneFL | D10922_s_at | 168 | Hs.99855 | formyl peptide receptor-like 1 | stage |
| 4 | HUGeneFL | D10925_at | 168 | Hs.301921 | chemokine (C-C motif) receptor 1 | stage |
| 5 | HUGeneFL | D11086_at | 168 | Hs.84 | interleukin 2 receptor, gamma (severe combined immunodeficiency) | stage |
| 6 | HUGeneFL | D11151_at | 168 | Hs.211202 | endothelin receptor type A | stage |
| 7 | HUGeneFL | D13435_at | 168 | Hs.426142 | phosphatidylinositol glycan, class F | stage |
| 8 | HUGeneFL | D13666_s_at | 168 | Hs.136348 | osteoblast specific factor 2 (fasciclin I-like) | stage |
| 9 | HUGeneFL | D14520_at | 168 | Hs.84728 | Kruppel-like factor 5 (intestinal) | stage |
| 10 | HUGeneFL | D21878_at | 168 | Hs.169998 | bone marrow stromal cell antigen 1 | stage |
| 11 | HUGeneFL | D26443_at | 168 | Hs.371369 | solute carrier family 1 (glial high affinity glutamate transporter), member 3 | stage |
| 12 | HUGeneFL | D42046_at | 168 | Hs.194665 | DNA2 DNA replication helicase 2-like (yeast) | stage |
| 13 | HUGeneFL | D45370_at | 168 | Hs.74120 | adipose specific 2 | stage |
| 14 | HUGeneFL | D49372_s_at | 168 | Hs.54460 | chemokine (C-C motif) ligand 11 | stage |
| 15 | HUGeneFL | D50495_at | 168 | Hs.224397 | transcription elongation factor A (SII), 2 | stage |
| 16 | HUGeneFL | D63135_at | 168 | Hs.27935 | tweety homolog 2 (*Drosophila*) | stage |
| 17 | HUGeneFL | D64053_at | 168 | Hs.198288 | protein tyrosine phosphatase, receptor type, R | stage |
| 18 | HUGeneFL | D83920_at | 168 | Hs.440898 | ficolin (collagen/fibrinogen domain containing) 1 | stage |
| 19 | HUGeneFL | D85131_s_at | 168 | Hs.433881 | MYC-associated zinc finger protein (purine-binding transcription factor) | stage |
| 20 | HUGeneFL | D86062_s_at | 168 | Hs.413482 | chromosome 21 open reading frame 33 | stage |
| 21 | HUGeneFL | D86479_at | 168 | Hs.439463 | AE binding protein 1 | stage |
| 22 | HUGeneFL | D86957_at | 168 | Hs.307944 | likely ortholog of mouse septin 8 | stage |
| 23 | HUGeneFL | D86959_at | 168 | Hs.105751 | Ste20-related serine/threonine kinase | stage |
| 24 | HUGeneFL | D86976_at | 168 | Hs.196914 | minor histocompatibility antigen HA-1 | stage |
| 25 | HUGeneFL | D87433_at | 168 | Hs.301989 | stabilin 1 | stage |
| 26 | HUGeneFL | D87443_at | 168 | Hs.409862 | sorting nexin 19 | stage |
| 27 | HUGeneFL | D87682_at | 168 | Hs.134792 | KIAA0241 protein | stage |
| 28 | HUGeneFL | D89077_at | 168 | Hs.75367 | Src-like-adaptor | stage |
| 29 | HUGeneFL | D89377_at | 168 | Hs.89404 | msh homeo box homolog 2 (*Drosophila*) | stage |
| 30 | HUGeneFL | D90279_s_at | 168 | Hs.433695 | collagen, type V, alpha 1 | stage |
| 31 | HUGeneFL | HG1996-HT2044_at | 168 | — | — | stage |
| 32 | HUGeneFL | HG2090-HT2152_s_at | 168 | — | — | stage |
| 33 | HUGeneFL | HG2463-HT2559_at | 168 | — | — | stage |
| 34 | HUGeneFL | HG3044-HT3742_s_at | 168 | — | — | stage |
| 35 | HUGeneFL | HG3187-HT3366_s_at | 168 | — | — | stage |
| 36 | HUGeneFL | HG3342-HT3519_s_at | 168 | — | — | stage |
| 37 | HUGeneFL | HG371-HT26388_s_at | 168 | — | — | stage |
| 38 | HUGeneFL | HG4069-HT4339_s_at | 168 | — | — | stage |
| 39 | HUGeneFL | HG67-HT67_f_at | 168 | — | — | stage |
| 40 | HUGeneFL | HG907-HT907_at | 168 | — | — | stage |
| 41 | HUGeneFL | J02871_s_at | 168 | Hs.436317 | cytochrome P450, family 4, subfamily B, polypeptide 1 | stage |
| 42 | HUGeneFL | J03040_at | 168 | Hs.111779 | secreted protein, acidic, cysteine-rich (osteonectin) | stage |
| 43 | HUGeneFL | J03060_at | 168 | — | — | stage |
| 44 | HUGeneFL | J03068_at | 168 | — | — | stage |
| 45 | HUGeneFL | J03241_s_at | 168 | Hs.2025 | transforming growth factor, beta 3 | stage |
| 46 | HUGeneFL | J03278_at | 168 | Hs.307783 | platelet-derived growth factor receptor, beta polypeptide | stage |
| 47 | HUGeneFL | J03909_at | 168 | — | — | stage |
| 48 | HUGeneFL | J03925_at | 168 | Hs.172631 | integrin, alpha M (complement component receptor 3, alpha; also known as CD11b (p170), macrophage antigen alpha polypeptide) | stage |
| 49 | HUGeneFL | J04056_at | 168 | Hs.88778 | carbonyl reductase 1 | stage |

TABLE A-continued

| Gene # | GeneChip | Probeset | Unigene Build | Unigene | description | Classifier |
|---|---|---|---|---|---|---|
| 50 | HUGeneFL | J04058_at | 168 | Hs.169919 | electron-transfer-flavoprotein, alpha polypeptide (glutaric aciduria II) | stage |
| 51 | HUGeneFL | J04130_s_at | 168 | Hs.75703 | chemokine (C-C motif) ligand 4 | stage |
| 52 | HUGeneFL | J04152_rna1_s_at | 168 | — | — | stage |
| 53 | HUGeneFL | J04162_at | 168 | Hs.372679 | Fc fragment of IgG, low affinity IIIa, receptor for (CD16) | stage |
| 54 | HUGeneFL | J04456_at | 168 | Hs.407909 | lectin, galactoside-binding, soluble, 1 (galectin 1) | stage |
| 55 | HUGeneFL | J05032_at | 168 | Hs.32393 | aspartyl-tRNA synthetase | stage |
| 56 | HUGeneFL | J05070_at | 168 | Hs.151738 | matrix metalloproteinase 9 (gelatinase B, 92 kDa gelatinase, 92 kDa type IV collagenase) | stage |
| 57 | HUGeneFL | J05448_at | 168 | Hs.79402 | polymerase (RNA) II (DNA directed) polypeptide C, 33 kDa | stage |
| 58 | HUGeneFL | K01396_at | 168 | Hs.297681 | serine (or cysteine) proteinase inhibitor, clade A (alpha-1 antiproteinase, antitrypsin), member 1 | stage |
| 59 | HUGeneFL | K03430_at | 168 | — | — | stage |
| 60 | HUGeneFL | L06797_s_at | 168 | Hs.421986 | chemokine (C—X—C motif) receptor 4 | stage |
| 61 | HUGeneFL | L10343_at | 168 | Hs.112341 | protease inhibitor 3, skin-derived (SKALP) | stage |
| 62 | HUGeneFL | L13391_at | 168 | Hs.78944 | regulator of G-protein signalling 2, 24 kDa | stage |
| 63 | HUGeneFL | L13698_at | 168 | Hs.65029 | growth arrest-specific 1 | stage |
| 64 | HUGeneFL | L13720_at | 168 | Hs.437710 | growth arrest-specific 6 | stage |
| 65 | HUGeneFL | L13923_at | 168 | Hs.750 | fibrillin 1 (Marfan syndrome) | stage |
| 66 | HUGeneFL | L15409_at | 168 | Hs.421597 | von Hippel-Lindau syndrome | stage |
| 67 | HUGeneFL | L17325_at | 168 | Hs.195825 | RNA binding protein with multiple splicing | stage |
| 68 | HUGeneFL | L19872_at | 168 | Hs.170087 | aryl hydrocarbon receptor | stage |
| 69 | HUGeneFL | L27476_at | 168 | Hs.75608 | tight junction protein 2 (zona occludens 2) | stage |
| 70 | HUGeneFL | L33799_at | 168 | Hs.202097 | procollagen C-endopeptidase enhancer | stage |
| 71 | HUGeneFL | L40388_at | 168 | Hs.30212 | thyroid receptor interacting protein 15 | stage |
| 72 | HUGeneFL | L40904_at | 168 | Hs.387667 | peroxisome proliferative activated receptor, gamma | stage |
| 73 | HUGeneFL | L41919_rna1_at | 168 | — | — | stage |
| 74 | HUGeneFL | M11433_at | 168 | Hs.101850 | retinol binding protein 1, cellular | stage |
| 75 | HUGeneFL | M11718_at | 168 | Hs.283393 | collagen, type V, alpha 2 | stage |
| 76 | HUGeneFL | M12125_at | 168 | Hs.300772 | tropomyosin 2 (beta) | stage |
| 77 | HUGeneFL | M14218_at | 168 | Hs.442047 | argininosuccinate lyase | stage |
| 78 | HUGeneFL | M15395_at | 168 | Hs.375957 | integrin, beta 2 (antigen CD18 (p95), lymphocyte function-associated antigen 1; macrophage antigen 1 (mac-1) beta subunit) | stage |
| 79 | HUGeneFL | M16591_s_at | 168 | Hs.89555 | hemopoietic cell kinase | stage |
| 80 | HUGeneFL | M17219_at | 168 | Hs.203862 | guanine nucleotide binding protein (G protein), alpha inhibiting activity polypeptide 1 | stage |
| 81 | HUGeneFL | M20530_at | 168 | — | — | stage |
| 82 | HUGeneFL | M23178_s_at | 168 | Hs.73817 | chemokine (C-C motif) ligand 3 | stage |
| 83 | HUGeneFL | M28130_rna1_s_at | 168 | — | — | stage |
| 84 | HUGeneFL | M29550_at | 168 | Hs.187543 | protein phosphatase 3 (formerly 2B), catalytic subunit, beta isoform (calcineurin A beta) | stage |
| 85 | HUGeneFL | M31165_at | 168 | Hs.407546 | tumor necrosis factor, alpha-induced protein 6 | stage |
| 86 | HUGeneFL | M32011_at | 168 | Hs.949 | neutrophil cytosolic factor 2 (65 kDa, chronic granulomatous disease, autosomal 2) | stage |
| 87 | HUGeneFL | M33195_at | 168 | Hs.433300 | Fc fragment of IgE, high affinity I, receptor for; gamma polypeptide | stage |
| 88 | HUGeneFL | M37033_at | 168 | Hs.443057 | CD53 antigen | stage |
| 89 | HUGeneFL | M37766_at | 168 | Hs.901 | CD48 antigen (B-cell membrane protein) | stage |
| 90 | HUGeneFL | M55998_s_at | 168 | Hs.172928 | collagen, type I, alpha 1 | stage |
| 91 | HUGeneFL | M57731_s_at | 168 | Hs.75765 | chemokine (C—X—C motif) ligand 2 | stage |
| 92 | HUGeneFL | M62840_at | 168 | Hs.82542 | acyloxyacyl hydrolase (neutrophil) | stage |
| 93 | HUGeneFL | M63262_at | 168 | — | — | stage |
| 94 | HUGeneFL | M68840_at | 168 | Hs.183109 | monoamine oxidase A | stage |
| 95 | HUGeneFL | M69203_s_at | 168 | Hs.75703 | chemokine (C-C motif) ligand 4 | stage |
| 96 | HUGeneFL | M72885_rna1_s_at | 168 | — | — | stage |
| 97 | HUGeneFL | M77349_at | 168 | Hs.421496 | transforming growth factor, beta-induced, 68 kDa | stage |
| 98 | HUGeneFL | M82882_at | 168 | Hs.124030 | E74-like factor 1 (ets domain transcription factor) | stage |
| 99 | HUGeneFL | M83822_at | 168 | Hs.209846 | LPS-responsive vesicle trafficking, beach and anchor containing | stage |
| 100 | HUGeneFL | M92934_at | 168 | Hs.410037 | connective tissue growth factor | stage |
| 101 | HUGeneFL | M95178_at | 168 | Hs.119000 | actinin, alpha 1 | stage |
| 102 | HUGeneFL | S69115_at | 168 | Hs.10306 | natural killer cell group 7 sequence | stage |
| 103 | HUGeneFL | S77393_at | 168 | Hs.145754 | Kruppel-like factor 3 (basic) | stage |

TABLE A-continued

| Gene # | GeneChip | Probeset | Unigene Build | Unigene | description | Classifier |
|---|---|---|---|---|---|---|
| 104 | HUGeneFL | S78187_at | 168 | Hs.153752 | cell division cycle 25B | stage |
| 105 | HUGeneFL | U01833_at | 168 | Hs.81469 | nucleotide binding protein 1 (MinD homolog, E. coli) | stage |
| 106 | HUGeneFL | U07231_at | 168 | Hs.309763 | G-rich RNA sequence binding factor 1 | stage |
| 107 | HUGeneFL | U09278_at | 168 | Hs.436852 | fibroblast activation protein, alpha | stage |
| 108 | HUGeneFL | U09937_rna1_s_at | 168 | — | — | stage |
| 109 | HUGeneFL | U10550_at | 168 | Hs.79022 | GTP binding protein overexpressed in skeletal muscle | stage |
| 110 | HUGeneFL | U12424_s_at | 168 | Hs.108646 | glycerol-3-phosphate dehydrogenase 2 (mitochondrial) | stage |
| 111 | HUGeneFL | U16306_at | 168 | Hs.434488 | chondroitin sulfate proteoglycan 2 (versican) | stage |
| 112 | HUGeneFL | U20158_at | 168 | Hs.2488 | lymphocyte cytosolic protein 2 (SH2 domain containing leukocyte protein of 76 kDa) | stage |
| 113 | HUGeneFL | U20536_s_at | 168 | Hs.3280 | caspase 6, apoptosis-related cysteine protease | stage |
| 114 | HUGeneFL | U24266_at | 168 | Hs.77448 | aldehyde dehydrogenase 4 family, member A1 | stage |
| 115 | HUGeneFL | U28249_at | 168 | Hs.301350 | FXYD domain containing ion transport regulator 3 | stage |
| 116 | HUGeneFL | U28488_s_at | 168 | Hs.155935 | complement component 3a receptor 1 | stage |
| 117 | HUGeneFL | U29680_at | 168 | Hs.227817 | BCL2-related protein A1 | stage |
| 118 | HUGeneFL | U37143_at | 168 | Hs.152096 | cytochrome P450, family 2, subfamily J, polypeptide 2 | stage |
| 119 | HUGeneFL | U38864_at | 168 | Hs.108139 | zinc finger protein 212 | stage |
| 120 | HUGeneFL | U39840_at | 168 | Hs.163484 | forkhead box A1 | stage |
| 121 | HUGeneFL | U41315_rna1_s_at | 168 | — | — | stage |
| 122 | HUGeneFL | U44111_at | 168 | Hs.42151 | histamine N-methyltransferase | stage |
| 123 | HUGeneFL | U47414_at | 168 | Hs.13291 | cyclin G2 | stage |
| 124 | HUGeneFL | U49352_at | 168 | Hs.414754 | 2,4-dienoyl CoA reductase 1, mitochondrial | stage |
| 125 | HUGeneFL | U50708_at | 168 | Hs.1265 | branched chain keto acid dehydrogenase E1, beta polypeptide (maple syrup urine disease) | stage |
| 126 | HUGeneFL | U52101_at | 168 | Hs.9999 | epithelial membrane protein 3 | stage |
| 127 | HUGeneFL | U59914_at | 168 | Hs.153863 | MAD, mothers against decapentaplegic homolog 6 (Drosophila) | stage |
| 128 | HUGeneFL | U60205_at | 168 | Hs.393239 | sterol-C4-methyl oxidase-like | stage |
| 129 | HUGeneFL | U61981_at | 168 | Hs.42674 | mutS homolog 3 (E. coli) | stage |
| 130 | HUGeneFL | U64520_at | 168 | Hs.66708 | vesicle-associated membrane protein 3 (cellubrevin) | stage |
| 131 | HUGeneFL | U65093_at | 168 | Hs.82071 | Cbo/p300-interacting transactivator, with Glu/Asp-rich carboxy-terminal domain, 2 | stage |
| 132 | HUGeneFL | U66619_at | 168 | Hs.444445 | SWI/SNF related, matrix associated, actin dependent regulator of chromatin, subfamily d, member 3 | stage |
| 133 | HUGeneFL | U68019_at | 168 | Hs.288261 | MAD, mothers against decapentaplegic homolog 3 (Drosophila) | stage |
| 134 | HUGeneFL | U68385_at | 168 | Hs.380923 | likely ortholog of mouse myeloid ecotropic viral integration site-related gene 2 | stage |
| 135 | HUGeneFL | U68485_at | 168 | Hs.193163 | bridging integrator 1 | stage |
| 136 | HUGeneFL | U74324_at | 168 | Hs.90875 | RAB interacting factor | stage |
| 137 | HUGeneFL | U77970_at | 168 | Hs.321164 | neuronal PAS domain protein 2 | stage |
| 138 | HUGeneFL | U83303_cds2_at | 168 | Hs.164021 | chemokine (C—X—C motif) ligand 6 (granulocyte chemotactic protein 2) | stage |
| 139 | HUGeneFL | U88871_at | 168 | Hs.79993 | peroxisomal biogenesis factor 7 | stage |
| 140 | HUGeneFL | U90549_at | 168 | Hs.236774 | high mobility group nucleosomal binding domain 4 | stage |
| 141 | HUGeneFL | U90716_at | 168 | Hs.79187 | coxsackie virus and adenovirus receptor | stage |
| 142 | HUGeneFL | V00594_at | 168 | Hs.118786 | metallothionein 2A | stage |
| 143 | HUGeneFL | V00594_s_at | 168 | Hs.118786 | metallothionein 2A | stage |
| 144 | HUGeneFL | X02761_s_at | 168 | Hs.418138 | fibronectin 1 | stage |
| 145 | HUGeneFL | X04011_at | 168 | Hs.88974 | cytochrome b-245, beta polypeptide (chronic granulomatous disease) | stage |
| 146 | HUGeneFL | X04085_rna1_at | 168 | — | — | stage |
| 147 | HUGeneFL | X07438_s_at | 168 | — | — | stage |
| 148 | HUGeneFL | X07743_at | 168 | Hs.77436 | pleckstrin | stage |
| 149 | HUGeneFL | X13334_at | 168 | Hs.75627 | CD14 antigen | stage |
| 150 | HUGeneFL | X14046_at | 168 | Hs.153053 | CD37 antigen | stage |
| 151 | HUGeneFL | X14813_at | 168 | Hs.166160 | acetyl-Coenzyme A acyltransferase 1 (peroxisomal 3-oxoacyl-Coenzyme A thiolase) | stage |
| 152 | HUGeneFL | X15880_at | 168 | Hs.415997 | collagen, type VI, alpha 1 | stage |
| 153 | HUGeneFL | X15882_at | 168 | Hs.420269 | collagen, type VI, alpha 2 | stage |
| 154 | HUGeneFL | X51408_at | 168 | Hs.380138 | chimerin (chimaerin) 1 | stage |

TABLE A-continued

| Gene # | GeneChip | Probeset | Unigene Build | Unigene | description | Classifier |
|---|---|---|---|---|---|---|
| 155 | HUGeneFL | X53800_s_at | 168 | Hs.89690 | chemokine (C—X—C motif) ligand 3 | stage |
| 156 | HUGeneFL | X54489_rna1_at | 168 | — | — | stage |
| 157 | HUGeneFL | X57351_s_at | 168 | Hs.174195 | interferon induced transmembrane protein 2 (1-8D) | stage |
| 158 | HUGeneFL | X57579_s_at | 168 | — | — | stage |
| 159 | HUGeneFL | X58072_at | 168 | Hs.169946 | GATA binding protein 3 | stage |
| 160 | HUGeneFL | X62048_at | 168 | Hs.249441 | WEE1 homolog (S. pombe) | stage |
| 161 | HUGeneFL | X64072_s_at | 168 | Hs.375957 | integrin, beta 2 (antigen CD18 (p95), lymphocyte function-associated antigen 1; macrophage antigen 1 (mac-1) beta subunit) | stage |
| 162 | HUGeneFL | X65614_at | 168 | Hs.2962 | S100 calcium binding protein P | stage |
| 163 | HUGeneFL | X66945_at | 168 | Hs.748 | fibroblast growth factor receptor 1 (fms-related tyrosine kinase 2, Pfeiffer syndrome) | stage |
| 164 | HUGeneFL | X67491_f_at | 168 | Hs.355697 | glutamate dehydrogenase 1 | stage |
| 165 | HUGeneFL | X68194_at | 168 | Hs.80919 | synaptophysin-like protein | stage |
| 166 | HUGeneFL | X73882_at | 168 | Hs.254605 | microtubule-associated protein 7 | stage |
| 167 | HUGeneFL | X78520_at | 168 | Hs.372528 | chloride channel 3 | stage |
| 168 | HUGeneFL | X78549_at | 168 | Hs.51133 | PTK6 protein tyrosine kinase 6 | stage |
| 169 | HUGeneFL | X78565_at | 168 | Hs.98998 | tenascin C (hexabrachion) | stage |
| 170 | HUGeneFL | X78669_at | 168 | Hs.79088 | reticulocalbin 2, EF-hand calcium binding domain | stage |
| 171 | HUGeneFL | X83618_at | 168 | Hs.59889 | 3-hydroxy-3-methylglutaryl-Coenzyme A synthase 2 (mitochondrial) | stage |
| 172 | HUGeneFL | X84908_at | 168 | Hs.78060 | phosphorylase kinase, beta | stage |
| 173 | HUGeneFL | X90908_at | 168 | Hs.147391 | fatty acid binding protein 6, ileal (gastrotropin) | stage |
| 174 | HUGeneFL | X91504_at | 168 | Hs.389277 | ADP-ribosylation factor related protein 1 | stage |
| 175 | HUGeneFL | X95632_s_at | 168 | Hs.387906 | abl-interactor 2 | stage |
| 176 | HUGeneFL | X97267_rna1_s_at | 168 | — | — | stage |
| 177 | HUGeneFL | Y00705_at | 168 | Hs.407856 | serine protease inhibitor, Kazal type 1 | stage |
| 178 | HUGeneFL | Y00787_s_at | 168 | Hs.624 | interleukin 8 | stage |
| 179 | HUGeneFL | Y00815_at | 168 | Hs.75216 | protein tyrosine phosphatase, receptor type, F | stage |
| 180 | HUGeneFL | Y08374_rna1_at | 168 | — | — | stage |
| 181 | HUGeneFL | Z12173_at | 168 | Hs.334534 | glucosamine (N-acetyl)-6-sulfatase (Sanfilippo disease IIID) | stage |
| 182 | HUGeneFL | Z19554_s_at | 168 | Hs.435800 | vimentin | stage |
| 183 | HUGeneFL | Z26491_s_at | 168 | Hs.240013 | catechol-O-methyltransferase | stage |
| 184 | HUGeneFL | Z29331_at | 168 | Hs.372758 | ubiquitin-conjugating enzyme E2H (UBC8 homolog, yeast) | stage |
| 185 | HUGeneFL | Z35491_at | 168 | Hs.377484 | BCL2-associated athanogene | stage |
| 186 | HUGeneFL | Z48199_at | 168 | Hs.82109 | syndecan 1 | stage |
| 187 | HUGeneFL | Z48605_at | 168 | Hs.421825 | inorganic pyrophosphatase 2 | stage |
| 188 | HUGeneFL | Z74615_at | 168 | Hs.172928 | collagen, type I, alpha 1 | stage |
| 189 | HUGeneFL | D87437_at | 168 | Hs.43660 | chromosome 1 open reading frame 16 | recurrence |
| 190 | HUGeneFL | L49169_at | 168 | Hs.75678 | FBJ murine osteosarcoma viral oncogene homolog B | recurrence |
| 191 | HUGeneFL | AF006041_at | 168 | Hs.336916 | death-associated protein 6 | recurrence |
| 192 | HUGeneFL | D83780_at | 168 | Hs.437991 | KIAA0196 gene product | recurrence |
| 193 | HUGeneFL | D64154_at | 168 | Hs.90107 | adhesion regulating molecule 1 | recurrence |
| 194 | HUGeneFL | D21337_at | 168 | Hs.408 | collagen, type IV, alpha 6 | recurrence |
| 195 | HUGeneFL | M16938_s_at | 168 | Hs.820 | homeo box C6 | recurrence |
| 196 | HUGeneFL | D87258_at | 168 | Hs.75111 | protease, serine, 11 (IGF binding) | recurrence |
| 197 | HUGeneFL | U58516_at | 168 | Hs.3745 | milk fat globule-EGF factor 8 protein | recurrence |
| 198 | HUGeneFL | U45973_at | 168 | Hs.178347 | skeletal muscle and kidney enriched inositol phosphatase | recurrence |
| 199 | HUGeneFL | U62015_at | 168 | Hs.8867 | cysteine-rich, angiogenic inducer, 61 | recurrence |
| 200 | HUGeneFL | U94855_at | 168 | Hs.381255 | eukaryotic translation initiation factor 3, subunit 5 epsilon, 47 kDa | recurrence |
| 201 | HUGeneFL | L34155_at | 168 | Hs.83450 | laminin, alpha 3 | recurrence |
| 202 | HUGeneFL | U70439_s_at | 168 | Hs.84264 | acidic (leucine-rich) nuclear phosphoprotein 32 family, member B | recurrence |
| 203 | HUGeneFL | U66702_at | 168 | Hs.74624 | protein tyrosine phosphatase, receptor type, N polypeptide 2 | recurrence |
| 204 | HUGeneFL | HG511-HT511_at | 168 | — | — | recurrence |
| 205 | HUGeneFL | HG3076-HT3238_s_at | 168 | — | — | recurrence |
| 206 | HUGeneFL | M98528_at | 168 | Hs.79404 | DNA segment on chromosome 4 (unique) 234 expressed sequence | recurrence |
| 207 | HUGeneFL | M63175_at | 168 | Hs.295137 | autocrine motility factor receptor | recurrence |
| 208 | HUGeneFL | D49387_at | 168 | Hs.294584 | leukotriene B4 12-hydroxydehydrogenase | recurrence |
| 209 | HUGeneFL | HG1879-HT1919_at | 168 | — | — | recurrence |
| 210 | HUGeneFL | Z23064_at | 168 | Hs.380118 | RNA binding motif protein, X chromosome | recurrence |

TABLE A-continued

| Gene # | GeneChip | Probeset | Unigene Build | Unigene | description | Classifier |
|---|---|---|---|---|---|---|
| 211 | HUGeneFL | X63469_at | 168 | Hs.77100 | general transcription factor IIE, polypeptide 2, beta 34 kDa | recurrence |
| 212 | HUGeneFL | L38928_at | 168 | Hs.118131 | 5,10-methenyltetrahydrofolate synthetase (5-formyltetrahydrofolate cyclo-ligase) | recurrence |
| 213 | HUGeneFL | U21858_at | 168 | Hs.60679 | TAF9 RNA polymerase II, TATA box binding protein (TBP)-associated factor, 32 kDa | recurrence |
| 214 | HUGeneFL | M64572_at | 168 | Hs.405666 | protein tyrosine phosphatase, non-receptor type 3 | recurrence |
| 215 | HUGeneFL | D83657_at | 168 | Hs.19413 | S100 calcium binding protein A12 (calgranulin C) | SCC |
| 216 | HUGeneFL | HG3945-HT4215_at | 168 | — | — | SCC |
| 217 | HUGeneFL | J00124_at | 168 | — | — | SCC |
| 218 | HUGeneFL | L05187_at | 168 | — | — | SCC |
| 219 | HUGeneFL | L42583_f_at | 168 | Hs.367762 | keratin 6A | SCC |
| 220 | HUGeneFL | L42601_f_at | 168 | Hs.367762 | keratin 6A | SCC |
| 221 | HUGeneFL | L42611_f_at | 168 | Hs.446417 | keratin 6E | SCC |
| 222 | HUGeneFL | M19888_at | 168 | Hs.1076 | small proline-rich protein 1B (cornifin) | SCC |
| 223 | HUGeneFL | M20030_f_at | 168 | Hs.505352 | Human small proline rich protein (sprII) mRNA, clone 930. | SCC |
| 224 | HUGeneFL | M21005_at | 168 | — | — | SCC |
| 225 | HUGeneFL | M21302_at | 168 | Hs.505327 | Human small proline rich protein (sprII) mRNA, clone 174N. | SCC |
| 226 | HUGeneFL | M21539_at | 168 | Hs.2421 | small proline-rich protein 2C | SCC |
| 227 | HUGeneFL | M86757_s_at | 168 | Hs.112408 | S100 calcium binding protein A7 (psoriasin 1) | SCC |
| 228 | HUGeneFL | S72493_s_at | 168 | Hs.432448 | keratin 16 (focal non-epidermolytic palmoplantar keratoderma) | SCC |
| 229 | HUGeneFL | U70981_at | 168 | Hs.336046 | interleukin 13 receptor, alpha 2 | SCC |
| 230 | HUGeneFL | V01516_f_at | 168 | Hs.367762 | keratin 6A | SCC |
| 231 | HUGeneFL | X53065_f_at | 168 | — | — | SCC |
| 232 | HUGeneFL | X57766_at | 168 | Hs.143751 | matrix metalloproteinase 11 (stromelysin 3) | SCC |
| 233 | EOS Hu03 | 400773 | 133 | — | NM_003105*: *Homo sapiens* sortilin-related receptor, L(DLR class) A repeats-containing (SORL1), mRNA. | progression |
| 234 | EOS Hu03 | 400843 | 133 | — | NM_003105*: *Homo sapiens* sortilin-related receptor, L(DLR class) A repeats-containing (SORL1), mRNA. | progression |
| 235 | EOS Hu03 | 400844 | 133 | — | NM_003105*: *Homo sapiens* sortilin-related receptor, L(DLR class) A repeats-containing (SORL1), mRNA. | progression |
| 236 | EOS Hu03 | 400846 | 133 | — | sortilin-related receptor, L(DLR class) A repeats-containing (SORL1) | progression |
| 237 | EOS Hu03 | 402328 | 133 | — | Target Exon | progression |
| 238 | EOS Hu03 | 402384 | 133 | — | NM_007181*: *Homo sapiens* mitogen-activated protein kinase kinase kinase kinase 1 (MAP4K1), mRNA. | progression |
| 239 | EOS Hu03 | 404208 | 133 | — | C6001282: gi|4504223|ref|NP_000172.1| glucuronidase, beta [*Homo sapiens*] gi|114963|sp|P082 | progression |
| 240 | EOS Hu03 | 404606 | 133 | — | Target Exon | progression |
| 241 | EOS Hu03 | 404826 | 133 | — | Target Exon | progression |
| 242 | EOS Hu03 | 404875 | 133 | — | NM_022819*: *Homo sapiens* phospholipase A2, group IIF (PLA2G2F), mRNA. VERSION NM_020245.2 GI | progression |
| 243 | EOS Hu03 | 404913 | 133 | — | NM_024408*: *Homo sapiens* Notch (Drosophila) homolog 2 (NOTCH2), mRNA. VERSION NM_024410.1 GI | progression |
| 244 | EOS Hu03 | 404977 | 133 | — | Insulin-like growth factor 2 (somatomedin A) (IGF2) | progression |
| 245 | EOS Hu03 | 405036 | 133 | — | NM_021628*: *Homo sapiens* arachidonate lipoxygenase 3 (ALOXE3), mRNA. VERSION NM_020229.1 GI | progression |
| 246 | EOS Hu03 | 405371 | 133 | — | NM_005569*: *Homo sapiens* LIM domain kinase 2 (LIMK2), transcript variant 2a, mRNA. | progression |
| 247 | EOS Hu03 | 405667 | 133 | — | Target Exon | progression |
| 248 | EOS Hu03 | 406002 | 133 | — | Target Exon | progression |
| 249 | EOS Hu03 | 407955 | 133 | Hs.9343 | ESTs | progression |
| 250 | EOS Hu03 | 408049 | 133 | Hs.345588 | desmoplakin (DPI, DPII) | progression |
| 251 | EOS Hu03 | 408288 | 133 | Hs.16886 | gb: zI73d06.r1 Stratagene colon (937204) *Homo sapiens* cDNA clone 5', mRNA sequence | progression |
| 252 | EOS Hu03 | 409513 | 133 | Hs.54642 | methionine adenosyltransferase II, beta | progression |
| 253 | EOS Hu03 | 409556 | 133 | Hs.54941 | phosphorylase kinase, alpha 2 (liver) | progression |

TABLE A-continued

| Gene # | GeneChip | Probeset | Unigene Build | Unigene | description | Classifier |
|---|---|---|---|---|---|---|
| 254 | EOS Hu03 | 409586 | 133 | Hs.55044 | DKFZP586H2123 protein | progression |
| 255 | EOS Hu03 | 409632 | 133 | Hs.55279 | serine (or cysteine) proteinase inhibitor, clade B (ovalbumin), member 5 | progression |
| 256 | EOS Hu03 | 410047 | 133 | Hs.379753 | zinc finger protein 36 (KOX 18) | progression |
| 257 | EOS Hu03 | 411817 | 133 | Hs.72241 | mitogen-activated protein kinase kinase 2 | progression |
| 258 | EOS Hu03 | 412649 | 133 | Hs.74369 | integrin, alpha 7 | progression |
| 259 | EOS Hu03 | 412841 | 133 | Hs.101395 | hypothetical protein MGC11352 | progression |
| 260 | EOS Hu03 | 413564 | 133 | — | gb: 601146990F1 NIH_MGC_19 Homo sapiens cDNA clone 5', mRNA sequence | progression |
| 261 | EOS Hu03 | 413786 | 133 | Hs.13500 | ESTs | progression |
| 262 | EOS Hu03 | 413840 | 133 | Hs.356228 | RNA binding motif protein, X chromosome | progression |
| 263 | EOS Hu03 | 413929 | 133 | Hs.75617 | collagen, type IV, alpha 2 | progression |
| 264 | EOS Hu03 | 414223 | 133 | Hs.238246 | hypothetical protein FLJ22479 | progression |
| 265 | EOS Hu03 | 414732 | 133 | Hs.77152 | minichromosome maintenance deficient (S. cerevisiae) 7 | progression |
| 266 | EOS Hu03 | 414762 | 133 | Hs.77257 | KIAA0068 protein | progression |
| 267 | EOS Hu03 | 414840 | 133 | Hs.23823 | hairy/enhancer-of-split related with YRPW motif-like | progression |
| 268 | EOS Hu03 | 414843 | 133 | Hs.77492 | heterogeneous nuclear ribonucleoprotein A0 | progression |
| 269 | EOS Hu03 | 414895 | 133 | Hs.116278 | Homo sapiens cDNA FLJ13571 fis, clone PLACE1008405 | progression |
| 270 | EOS Hu03 | 414907 | 133 | Hs.77597 | polo (Drosophia)-like kinase | progression |
| 271 | EOS Hu03 | 414918 | 133 | Hs.72222 | hypothetical protein FLJ13459 | progression |
| 272 | EOS Hu03 | 415200 | 133 | Hs.78202 | SWI/SNF related, matrix associated, actin dependent regulator of chromatin, subfamily a, member 4 | Progression |
| 273 | EOS Hu03 | 416640 | 133 | Hs.79404 | neuron-specific protein | Progression |
| 274 | EOS Hu03 | 416815 | 133 | Hs.80120 | UDP-N-acetyl-alpha-D-galactosamine:polypeptide N-acetylgalactosaminyltransferase 1 (GalNAc-T1) | Progression |
| 275 | EOS Hu03 | 416977 | 133 | Hs.406103 | hypothetical protein FKSG44 | Progression |
| 276 | EOS Hu03 | 417615 | 133 | Hs.82314 | hypoxanthine phosphoribosyltransferase 1 (Lesch-Nyhan syndrome) | Progression |
| 277 | EOS Hu03 | 417839 | 133 | Hs.82712 | fragile X mental retardation, autosomal homolog 1 | Progression |
| 278 | EOS Hu03 | 417900 | 133 | Hs.82906 | CDC20 (cell division cycle 20, S. cerevisiae, homolog) | Progression |
| 279 | EOS Hu03 | 417924 | 133 | Hs.82932 | cyclin D1 (PRAD1: parathyroid adenomatosis 1) | Progression |
| 280 | EOS Hu03 | 418127 | 133 | Hs.83532 | membrane cofactor protein (CD46, trophoblast-lymphocyte cross-reactive antigen) | Progression |
| 281 | EOS Hu03 | 418321 | 133 | Hs.84087 | KIAA0143 protein | Progression |
| 282 | EOS Hu03 | 418504 | 133 | Hs.85335 | Homo sapiens mRNA; cDNA DKFZp564D1462 (from clone DKFZp564D1462) | Progression |
| 283 | EOS Hu03 | 418629 | 133 | Hs.86859 | growth factor receptor-bound protein 7 | Progression |
| 284 | EOS Hu03 | 419602 | 133 | Hs.91521 | hypothetical protein | Progression |
| 285 | EOS Hu03 | 419847 | 133 | Hs.184544 | Homo sapiens, clone IMAGE: 3355383, mRNA, partial cds | Progression |
| 286 | EOS Hu03 | 420079 | 133 | Hs.94896 | PTD011 protein | Progression |
| 287 | EOS Hu03 | 420116 | 133 | Hs.95231 | FH1/FH2 domain-containing protein | Progression |
| 288 | EOS Hu03 | 420307 | 133 | Hs.66219 | ESTs | Progression |
| 289 | EOS Hu03 | 420613 | 133 | Hs.406637 | ESTs, Weakly similar to A47582 B-cell growth factor precursor [H. sapiens] | Progression |
| 290 | EOS Hu03 | 420732 | 133 | Hs.367762 | ESTs | Progression |
| 291 | EOS Hu03 | 421026 | 133 | Hs.101067 | GCN5 (general control of amino-acid synthesis, yeast, homolog)-like 2 | Progression |
| 292 | EOS Hu03 | 421075 | 133 | Hs.101474 | KIAA0807 protein | Progression |
| 293 | EOS Hu03 | 421101 | 133 | Hs.101840 | major histocompatibility complex, class I-like sequence | Progression |
| 294 | EOS Hu03 | 421186 | 133 | Hs.270563 | ESTs, Moderately similar to T12512 hypothetical protein DKFZp434G232.1 [H. sapiens] | Progression |
| 295 | EOS Hu03 | 421311 | 133 | Hs.283609 | hypothetical protein PRO2032 | progression |
| 296 | EOS Hu03 | 421475 | 133 | Hs.104640 | HIV-1 inducer of short transcripts binding protein; lymphoma related factor | progression |
| 297 | EOS Hu03 | 421505 | 133 | Hs.285641 | KIAA1111 protein | progression |
| 298 | EOS Hu03 | 421595 | 133 | Hs.301685 | KIAA0620 protein | progression |
| 299 | EOS Hu03 | 421628 | 133 | Hs.106210 | hypothetical protein FLJ10813 | progression |
| 300 | EOS Hu03 | 421649 | 133 | Hs.106415 | peroxisome proliferative activated receptor, delta | progression |
| 301 | EOS Hu03 | 421733 | 133 | Hs.1420 | fibroblast growth factor receptor 3 (achondroplasia, thanatophoric dwarfism) | progression |

TABLE A-continued

| Gene # | GeneChip | Probeset | Unigene Build | Unigene | description | Classifier |
|---|---|---|---|---|---|---|
| 302 | EOS Hu03 | 421782 | 133 | Hs.108258 | actin binding protein; macrophin (microfilament and actin filament cross-linker protein) | progression |
| 303 | EOS Hu03 | 421989 | 133 | Hs.110457 | Wolf-Hirschhorn syndrome candidate 1 | progression |
| 304 | EOS Hu03 | 422043 | 133 | Hs.110953 | retinoic acid induced 1 | progression |
| 305 | EOS Hu03 | 422068 | 133 | Hs.104520 | Homo sapiens cDNA FLJ13694 fis, clone PLACE2000115 | progression |
| 306 | EOS Hu03 | 422506 | 133 | Hs.300741 | sorcin | progression |
| 307 | EOS Hu03 | 422913 | 133 | Hs.121599 | CGI-18 protein | progression |
| 308 | EOS Hu03 | 422929 | 133 | Hs.94011 | ESTs, Weakly similar to MGB4_HUMAN MELANOMA-ASSOCIATED ANTIGEN B4 [H. sapiens] | progression |
| 309 | EOS Hu03 | 422959 | 133 | Hs.349256 | paired immunoglobulin-like receptor beta | progression |
| 310 | EOS Hu03 | 423138 | 133 | — | gb: EST385571 MAGE resequences, MAGM Homo sapiens cDNA, mRNA sequence | progression |
| 311 | EOS Hu03 | 423185 | 133 | Hs.380062 | ornithine decarboxylase antizyme 1 | progression |
| 312 | EOS Hu03 | 423599 | 133 | Hs.31731 | peroxiredoxin 5 | progression |
| 313 | EOS Hu03 | 423810 | 133 | Hs.132955 | BCL2/adenovirus E1B 19 kD-interacting protein 3-like | progression |
| 314 | EOS Hu03 | 423960 | 133 | Hs.136309 | SH3-containing protein SH3GLB1 | progression |
| 315 | EOS Hu03 | 424244 | 133 | Hs.143601 | hypothetical protein hCLA-iso | progression |
| 316 | EOS Hu03 | 424415 | 133 | Hs.146580 | enolase 2, (gamma, neuronal) | progression |
| 317 | EOS Hu03 | 424909 | 133 | Hs.153752 | cell division cycle 25B | progression |
| 318 | EOS Hu03 | 424959 | 133 | Hs.153937 | activated p21cdc42Hs kinase | progression |
| 319 | EOS Hu03 | 425093 | 133 | Hs.154525 | KIAA1076 protein | progression |
| 320 | EOS Hu03 | 425097 | 133 | Hs.154545 | PDZ domain containing guanine nucleotide exchange factor(GEF)1 | progression |
| 321 | EOS Hu03 | 425205 | 133 | Hs.155106 | receptor (calcitonin) activity modifying protein 2 | progression |
| 322 | EOS Hu03 | 425221 | 133 | Hs.155188 | TATA box binding protein (TBP)-associated factor, RNA polymerase II, F, 55 kD | progression |
| 323 | EOS Hu03 | 425243 | 133 | Hs.155291 | KIAA0005 gene product | progression |
| 324 | EOS Hu03 | 425380 | 133 | Hs.32148 | AD-015 protein | progression |
| 325 | EOS Hu03 | 426028 | 133 | Hs.172028 | a disintegrin and metalloproteinase domain 10 (ADAM10) | progression |
| 326 | EOS Hu03 | 426125 | 133 | Hs.166994 | FAT tumor suppressor (Drosophila) homolog | progression |
| 327 | EOS Hu03 | 426177 | 133 | Hs.167700 | Homo sapiens cDNA FLJ10174 fis, clone HEMBA1003959 | progression |
| 328 | EOS Hu03 | 426252 | 133 | Hs.28917 | ESTs | progression |
| 329 | EOS Hu03 | 426468 | 133 | Hs.117558 | ESTs | progression |
| 330 | EOS Hu03 | 426469 | 133 | Hs.363039 | methylmalonate-semialdehyde dehydrogenase | progression |
| 331 | EOS Hu03 | 426508 | 133 | Hs.170171 | glutamate-ammonia ligase (glutamine synthase) | progression |
| 332 | EOS Hu03 | 426682 | 133 | Hs.2056 | UDP glycosyltransferase 1 family, polypeptide A9 | progression |
| 333 | EOS Hu03 | 426799 | 133 | Hs.303154 | popeye protein 3 | progression |
| 334 | EOS Hu03 | 426982 | 133 | Hs.173091 | ubiquitin-like 3 | progression |
| 335 | EOS Hu03 | 427239 | 133 | Hs.356512 | ubiquitin carrier protein | progression |
| 336 | EOS Hu03 | 427351 | 133 | Hs.123253 | hypothetical protein FLJ22009 | progression |
| 337 | EOS Hu03 | 427681 | 133 | Hs.284232 | tumor necrosis factor receptor superfamily, member 12 (translocating chain-association membrane protein) | progression |
| 338 | EOS Hu03 | 427722 | 133 | Hs.180479 | hypothetical protein FLJ20116 | progression |
| 339 | EOS Hu03 | 427747 | 133 | Hs.180655 | serine/threonine kinase 12 | progression |
| 340 | EOS Hu03 | 427999 | 133 | Hs.181369 | ubiquitin fusion degradation 1-like | progression |
| 341 | EOS Hu03 | 428115 | 133 | Hs.300855 | KIAA0977 protein | progression |
| 342 | EOS Hu03 | 428284 | 133 | Hs.183435 | NM_004545: Homo sapiens NADH dehydrogenase (ubiquinone) 1 beta subcomplex, 1 (7 kD, MNLL) (NDUFB1), mRNA. | progression |
| 343 | EOS Hu03 | 428318 | 133 | Hs.356190 | ubiquitin B | progression |
| 344 | EOS Hu03 | 428712 | 133 | Hs.190452 | KIAA0365 gene product | progression |
| 345 | EOS Hu03 | 428901 | 133 | Hs.146668 | KIAA1253 protein | progression |
| 346 | EOS Hu03 | 429124 | 133 | Hs.196914 | minor histocompatibility antigen HA-1 | progression |
| 347 | EOS Hu03 | 429187 | 133 | Hs.163872 | ESTs, Weakly similar to S65657 alpha-1C-adrenergic receptor splice form 2 [H. sapiens] | progression |
| 348 | EOS Hu03 | 429311 | 133 | Hs.198998 | conserved helix-loop-helix ubiquitous kinase | progression |
| 349 | EOS Hu03 | 429561 | 133 | Hs.250646 | baculoviral IAP repeat-containing 6 | progression |
| 350 | EOS Hu03 | 429802 | 133 | Hs.5367 | ESTs, Weakly similar to I38022 hypothetical protein [H. sapiens] | progression |
| 351 | EOS Hu03 | 429953 | 133 | Hs.226581 | COX15 (yeast) homolog, cytochrome c oxidase assembly protein | progression |

TABLE A-continued

| Gene # | GeneChip | Probeset | Unigene Build | Unigene | description | Classifier |
|---|---|---|---|---|---|---|
| 352 | EOS Hu03 | 430604 | 133 | Hs.247309 | succinate-CoA ligase, GDP-forming, beta subunit | progression |
| 353 | EOS Hu03 | 430677 | 133 | Hs.359784 | desmoglein 2 | progression |
| 354 | EOS Hu03 | 430746 | 133 | Hs.406256 | ESTs | progression |
| 355 | EOS Hu03 | 431604 | 133 | Hs.264190 | vacuolar protein sorting 35 (yeast homolog) | progression |
| 356 | EOS Hu03 | 431842 | 133 | Hs.271473 | epithelial protein up-regulated in carcinoma, membrane associated protein 17 | progression |
| 357 | EOS Hu03 | 431857 | 133 | Hs.271742 | ADP-ribosyltransferase (NAD; poly (ADP-ribose) polymerase)-like 3 | progression |
| 358 | EOS Hu03 | 432258 | 133 | Hs.293039 | ESTs | progression |
| 359 | EOS Hu03 | 432327 | 133 | Hs.274363 | neuroglobin | progression |
| 360 | EOS Hu03 | 432554 | 133 | Hs.278411 | NCK-associated protein 1 | progression |
| 361 | EOS Hu03 | 432864 | 133 | Hs.359682 | calpastatin | progression |
| 362 | EOS Hu03 | 433052 | 133 | Hs.293003 | ESTs, Weakly similar to PC4259 ferritin associated protein [*H. sapiens*] | progression |
| 363 | EOS Hu03 | 433282 | 133 | Hs.49007 | hypothetical protein | progression |
| 364 | EOS Hu03 | 433844 | 133 | Hs.179647 | *Homo sapiens* cDNA FLJ12195 fis, clone MAMMA1000865 | progression |
| 365 | EOS Hu03 | 433914 | 133 | Hs.112160 | *Homo sapiens* DNA helicase homolog (PIF1) mRNA, partial cds | progression |
| 366 | EOS Hu03 | 434055 | 133 | Hs.3726 | x 003 protein | progression |
| 367 | EOS Hu03 | 434263 | 133 | Hs.79187 | ESTs | progression |
| 368 | EOS Hu03 | 434547 | 133 | Hs.106124 | ESTs | progression |
| 369 | EOS Hu03 | 434831 | 133 | Hs.273397 | KIAA0710 gene product | progression |
| 370 | EOS Hu03 | 434978 | 133 | Hs.4310 | eukaryotic translation initiation factor 1A | progression |
| 371 | EOS Hu03 | 435158 | 133 | Hs.65588 | DAZ associated protein 1 | progression |
| 372 | EOS Hu03 | 435320 | 133 | Hs.117864 | ESTs | progression |
| 373 | EOS Hu03 | 435521 | 133 | Hs.6361 | mitogen-activated protein kinase kinase 1 interacting protein 1 | progression |
| 374 | EOS Hu03 | 436472 | 133 | Hs.46366 | KIAA0948 protein | progression |
| 375 | EOS Hu03 | 436576 | 133 | Hs.77542 | ESTs | progression |
| 376 | EOS Hu03 | 437223 | 133 | Hs.330716 | *Homo sapiens* cDNA FLJ14368 fis, clone HEMBA1001122 | progression |
| 377 | EOS Hu03 | 437256 | 133 | Hs.97871 | *Homo sapiens*, clone IMAGE: 3845253, mRNA, partial cds | progression |
| 378 | EOS Hu03 | 437524 | 133 | Hs.385719 | ESTs | progression |
| 379 | EOS Hu03 | 438013 | 133 | Hs.15670 | ESTs | progression |
| 380 | EOS Hu03 | 438644 | 133 | Hs.129037 | ESTs | progression |
| 381 | EOS Hu03 | 438818 | 133 | Hs.30738 | ESTs | progression |
| 382 | EOS Hu03 | 438942 | 133 | Hs.6451 | PRO0659 protein | progression |
| 383 | EOS Hu03 | 439010 | 133 | Hs.75216 | *Homo sapiens* cDNA FLJ13713 fis, clone PLACE2000398, moderately similar to LAR PROTEIN PRECURSOR (LEUKOCYTE ANTIGEN RELATED) (EC 3.1.3.48) | progression |
| 384 | EOS Hu03 | 439130 | 133 | Hs.375195 | ESTs | progression |
| 385 | EOS Hu03 | 439578 | 133 | Hs.350547 | nuclear receptor co-repressor/HDAC3 complex subunit | progression |
| 386 | EOS Hu03 | 439632 | 133 | Hs.334437 | hypothetical protein MGC4248 | progression |
| 387 | EOS Hu03 | 440014 | 133 | Hs.6856 | ash2 (absent, small, or homeotic, *Drosophila*, homolog)-like | progression |
| 388 | EOS Hu03 | 440100 | 133 | Hs.158549 | ESTs, Weakly similar to T2D3_HUMAN TRANSCRIPTION INITIATION FACTOR TFIID 135 KDA SUBUNIT [*H. sapiens*] | progression |
| 389 | EOS Hu03 | 440197 | 133 | Hs.317714 | pallid (mouse) homolog, pallidin | progression |
| 390 | EOS Hu03 | 440357 | 133 | Hs.20950 | phospholysine phosphohistidine inorganic pyrophosphate phosphatase | progression |
| 391 | EOS Hu03 | 441650 | 133 | Hs.132545 | ESTs | progression |
| 392 | EOS Hu03 | 442220 | 133 | Hs.8148 | selenoprotein T | progression |
| 393 | EOS Hu03 | 442549 | 133 | Hs.8375 | TNF receptor-associated factor 4 | progression |
| 394 | EOS Hu03 | 443407 | 133 | Hs.348514 | ESTs, Moderately similar to 2109260A B cell growth factor [*H. sapiens*] | progression |
| 395 | EOS Hu03 | 443471 | 133 | Hs.398102 | *Homo sapiens* clone FLB3442 PRO0872 mRNA, complete cds | progression |
| 396 | EOS Hu03 | 443679 | 133 | Hs.9670 | hypothetical protein FLJ10948 | progression |
| 397 | EOS Hu03 | 443893 | 133 | Hs.115472 | ESTs, Weakly similar to 2004399A chromosomal protein [*H. sapiens*] | progression |
| 398 | EOS Hu03 | 444037 | 133 | Hs.380932 | CHMP1.5 protein | progression |
| 399 | EOS Hu03 | 444312 | 133 | Hs.351142 | ESTs | progression |
| 400 | EOS Hu03 | 444336 | 133 | Hs.10882 | HMG-box containing protein 1 | progression |
| 401 | EOS Hu03 | 444604 | 133 | Hs.11441 | chromosome 1 open reading frame 8 | progression |
| 402 | EOS Hu03 | 445084 | 133 | Hs.250848 | hypothetical protein FLJ14761 | progression |
| 403 | EOS Hu03 | 445462 | 133 | Hs.288649 | hypothetical protein MGC3077 | progression |
| 404 | EOS Hu03 | 445692 | 133 | Hs.182099 | ESTs | progression |
| 405 | EOS Hu03 | 445831 | 133 | Hs.13351 | LanC (bacterial lantibiotic synthetase component C)-like 1 | progression |

TABLE A-continued

| Gene # | GeneChip | Probeset | Unigene Build | Unigene | description | Classifier |
|---|---|---|---|---|---|---|
| 406 | EOS Hu03 | 446556 | 133 | Hs.15303 | KIAA0349 protein | progression |
| 407 | EOS Hu03 | 446847 | 133 | Hs.82845 | *Homo sapiens* cDNA: FLJ21930 fis, clone HEP04301, highly similar to HSU90916 Human clone 23815 mRNA sequence | progression |
| 408 | EOS Hu03 | 447343 | 133 | Hs.236894 | ESTs, Highly similar to S02392 alpha-2-macroglobulin receptor precursor [*H. sapiens*] | progression |
| 409 | EOS Hu03 | 447400 | 133 | Hs.18457 | hypothetical protein FLJ20315 | progression |
| 410 | EOS Hu03 | 448357 | 133 | Hs.108923 | RAB38, member RAS oncogene family | progression |
| 411 | EOS Hu03 | 448524 | 133 | Hs.21356 | hypothetical protein DKFZp762K2015 | progression |
| 412 | EOS Hu03 | 448625 | 133 | Hs.178470 | hypothetical protein FLJ22662 | progression |
| 413 | EOS Hu03 | 448780 | 133 | Hs.267749 | Human DNA sequence from clone 366N23 on chromosome 6q27. Contains two genes similar to consecutive parts of the *C. elegans* UNC-93 (protein 1, C46F11.1) gene, a KIAA0173 and Tubulin-Tyrosine Ligase LIKE gene, a Mitotic Feedback Control Protein MADP2 H | progression |
| 414 | EOS Hu03 | 448813 | 133 | Hs.22142 | cytochrome b5 reductase b5R.2 | progression |
| 415 | EOS Hu03 | 449268 | 133 | Hs.23412 | hypothetical protein FLJ20160 | progression |
| 416 | EOS Hu03 | 449626 | 133 | Hs.112860 | zinc finger protein 258 | progression |
| 417 | EOS Hu03 | 450893 | 133 | Hs.25625 | hypothetical protein FLJ11323 | progression |
| 418 | EOS Hu03 | 450997 | 133 | Hs.35254 | hypothetical protein FLB6421 | progression |
| 419 | EOS Hu03 | 451164 | 133 | Hs.60659 | ESTs, Weakly similar to T46471 hypothetical protein DKFZp434L0130.1 [*H. sapiens*] | progression |
| 420 | EOS Hu03 | 451225 | 133 | Hs.57655 | ESTs | progression |
| 421 | EOS Hu03 | 451867 | 133 | Hs.27192 | hypothetical protein dJ1057B20.2 | progression |
| 422 | EOS Hu03 | 451970 | 133 | Hs.211046 | ESTs | progression |
| 423 | EOS Hu03 | 452012 | 133 | Hs.279766 | kinesin family member 4A | progression |
| 424 | EOS Hu03 | 452170 | 133 | Hs.28285 | patched related protein translocated in renal cancer | progression |
| 425 | EOS Hu03 | 452517 | 133 | — | gb: RC-BT068-130399-068 BT068 *Homo sapiens* cDNA, mRNA sequence | progression |
| 426 | EOS Hu03 | 452829 | 133 | Hs.63368 | ESTs, Weakly similar to TRHY_HUMAN TRICHOHYALI [*H. sapiens*] | progression |
| 427 | EOS Hu03 | 452929 | 133 | Hs.172816 | neuregulin 1 | progression |
| 428 | EOS Hu03 | 453395 | 133 | Hs.377915 | mannosidase, alpha, class 2A, member 1 | progression |
| 429 | EOS Hu03 | 454639 | 133 | — | gb: RC2-ST0158-091099-011-d05 ST0158 *Homo sapiens* cDNA, mRNA sequence | progression |
| 430 | EOS Hu03 | 456332 | 133 | Hs.399939 | gb: nc39d05.r1 NCL_CGAP_Pr2 *Homo sapiens* cDNA clone, mRNA sequence | progression |
| 431 | EOS Hu03 | 457228 | 133 | Hs.195471 | Human cosmid CRI-JC2015 at D10S289 in 10sp13 | progression |
| 432 | EOS Hu03 | 458132 | 133 | Hs.103267 | hypothetical protein FLJ22548 similar to gene trap PAT 12 | progression |
| 433 | EOS Hu03 | 408688 | 133 | Hs.152925 | KIAA1268 protein | progression |
| 434 | EOS Hu03 | 410691 | 133 | Hs.65450 | reticulon 4 | progression |
| 435 | EOS Hu03 | 420269 | 133 | Hs.96264 | alpha thalassemia/mental retardation syndrome X-linked (RAD54 (*S. cerevisiae*) homolog) | progression |
| 436 | EOS Hu03 | 422119 | 133 | Hs.111862 | KIAA0590 gene product | progression |
| 437 | EOS Hu03 | 422765 | 133 | Hs.1578 | baculoviral IAP repeat-containing 5 (survivin) | progression |
| 438 | EOS Hu03 | 422984 | 133 | Hs.351597 | ESTs | progression |
| 439 | EOS Hu03 | 428016 | 133 | Hs.181461 | ariadne homolog, ubiquitin-conjugating enzyme E2 binding protein, 1 (*Drosophila*) | progression |
| 440 | EOS Hu03 | 437325 | 133 | Hs.5548 | F-box and leucine-rich repeat protein 5 | progression |
| 441 | EOS Hu03 | 444773 | 133 | Hs.11923 | hypothetical protein DJ167A19.1 | progression |
| 442 | EOS Hu03 | 445926 | 133 | Hs.334826 | splicing factor 3b, subunit 1, 155 kDa | progression |
| 443 | EOS Hu03 | 452714 | 133 | Hs.30340 | KIAA1165: likely ortholog of mouse Nedd4 WW domain-binding protein 5A | progression |
| 444 | EOS Hu03 | 452866 | 133 | Hs.268016 | ESTs | progression |
| 445 | EOS Hu03 | 453963 | 133 | Hs.28959 | cDNA FLJ36513 fis, clone TRACH2001523 | progression |
| 446 | EOS Hu03 | 457329 | 133 | Hs.359682 | calpastatin | progression |
| 447 | U133A | 200600_at | 168 | Hs.170328 | NM_001910; cathepsin E isoform a preproprotein NM_148964; cathepsin E isoform b preproprotein | CIS |
| 448 | U133A | 200762_at | 168 | Hs.173381 | NM_019894; transmembrane protease, serine 4 isoform 1 NM_183247; transmembrane protease, serine 4 isoform 2 | CIS |
| 449 | U133A | 201088_at | 168 | Hs.159557 | NM_000228; laminin subunit beta 3 precursor | CIS |
| 450 | U133A | 201291_s_at | 168 | Hs.156346 | NM_030570; uroplakin 3B isoform a NM_182683; uroplakin 3B isoform c NM_182684; uroplakin 3B isoform b | CIS |

TABLE A-continued

| Gene # | GeneChip | Probeset | Unigene Build | Unigene | description | Classifier |
|---|---|---|---|---|---|---|
| 451 | U133A | 201560_at | 168 | Hs.25035 | NM_005547; involucrin | CIS |
| 452 | U133A | 201616_s_at | 168 | Hs.443811 | NM_004692; NM_032727; internexin neuronal intermediate filament protein, alpha | CIS |
| 453 | U133A | 201641_at | 168 | Hs.118110 | NM_016233; peptidylarginine deiminase type III | CIS |
| 454 | U133A | 201744_s_at | 168 | Hs.406475 | NM_014417; BCL2 binding component 3 | CIS |
| 455 | U133A | 201842_s_at | 168 | Hs.76224 | NM_020142; NADH:ubiquinone oxidoreductase MLRQ subunit homolog | CIS |
| 456 | U133A | 201858_s_at | 168 | Hs.1908 | NM_018058; cartilage acidic protein 1 | CIS |
| 457 | U133A | 201859_at | 168 | Hs.1908 | NM_000497; cytochrome P450, subfamily XIB (steroid 11-beta-hydroxylase), polypeptide 1 precursor | CIS |
| 458 | U133A | 202746_at | 168 | Hs.17109 | NM_007193; annexin A10 | CIS |
| 459 | U133A | 202917_s_at | 168 | Hs.416073 | NM_001958; eukaryotic translation elongation factor 1 alpha 2 | CIS |
| 460 | U133A | 203009_at | 168 | Hs.155048 | NM_005581; Lutheran blood group (Auberger b antigen included) | CIS |
| 461 | U133A | 203287_at | 168 | Hs.18141 | NM_005581; Lutheran blood group (Auberger b antigen included) | CIS |
| 462 | U133A | 203477_at | 168 | Hs.409034 | NM_030570; uroplakin 3B isoform a NM_182683; uroplakin 3B isoform c NM_182684; uroplakin 3B isoform b | CIS |
| 463 | U133A | 203649_s_at | 168 | Hs.76422 | NM_000300; phospholipase A2, group IIA (platelets, synovial fluid) | CIS |
| 464 | U133A | 203759_at | 168 | Hs.75268 | NM_007193; annexin A10 | CIS |
| 465 | U133A | 203792_x_at | 168 | Hs.371617 | NM_007144; ring finger protein 110 | CIS |
| 466 | U133A | 203842_s_at | 168 | Hs.172740 | NM_014417; BCL2 binding component 3 | CIS |
| 467 | U133A | 203980_at | 168 | Hs.391561 | NM_001442; fatty acid binding protein 4, adipocyte | CIS |
| 468 | U133A | 204141_at | 168 | Hs.300701 | NM_017689; hypothetical protein FLJ20151 | CIS |
| 469 | U133A | 204380_s_at | 168 | Hs.1420 | NM_007144; ring finger protein 110 | CIS |
| 470 | U133A | 204465_s_at | 168 | Hs.76888 | NM_004692; NM_032727; internexin neuronal intermediate filament protein, alpha | CIS |
| 471 | U133A | 204487_s_at | 168 | Hs.367809 | NM_001248; ectonucleoside triphosphate diphosphohydrolase 3 | CIS |
| 472 | U133A | 204508_s_at | 168 | Hs.279916 | NM_017689; hypothetical protein FLJ20151 | CIS |
| 473 | U133A | 204540_at | 168 | Hs.433839 | NM_001958; eukaryotic translation elongation factor 1 alpha 2 | CIS |
| 474 | U133A | 204688_at | 168 | Hs.409798 | NM_016233; peptidylarginine deiminase type III | CIS |
| 475 | U133A | 204952_at | 168 | Hs.377028 | NM_000445; plectin 1, intermediate filament binding protein 500 kDa | CIS |
| 476 | U133A | 204990_s_at | 168 | Hs.85266 | NM_000213; integrin, beta 4 | CIS |
| 477 | U133A | 205073_at | 168 | Hs.152096 | NM_019894; transmembrane protease, serine 4 isoform 1 NM_183247; transmembrane protease, serine 4 isoform 2 | CIS |
| 478 | U133A | 205382_s_at | 168 | Hs.155597 | NM_000213; integrin, beta 4 | CIS |
| 479 | U133A | 205453_at | 168 | Hs.290432 | NM_002145; homeo box B2 | CIS |
| 480 | U133A | 205455_at | 168 | Hs.2942 | NM_006760; uroplakin 2 | CIS |
| 481 | U133A | 205927_s_at | 168 | Hs.1355 | NM_001910; cathepsin E isoform a preproprotein NM_148964; cathepsin E isoform b preproprotein | CIS |
| 482 | U133A | 206122_at | 168 | Hs.95582 | NM_006942; SRY-box 15 | CIS |
| 483 | U133A | 206191_at | 168 | Hs.47042 | NM_001248; ectonucleoside triphosphate diphosphohydrolase 3 | CIS |
| 484 | U133A | 206392_s_at | 168 | Hs.82547 | NM_005522; homeobox A1 protein isoform a NM_153620; homeobox A1 protein isoform b | CIS |
| 485 | U133A | 206393_at | 168 | Hs.83760 | NM_003282; troponin I, skeletal, fast | CIS |
| 486 | U133A | 206465_at | 168 | Hs.277543 | NM_015162; lipidosin | CIS |
| 487 | U133A | 206561_s_at | 168 | Hs.116724 | NM_015162; lipidosin | CIS |
| 488 | U133A | 206658_at | 168 | Hs.284211 | NM_030570; uroplakin 3B isoform a NM_182683; uroplakin 3B isoform c NM_182684; uroplakin 3B isoform b | CIS |
| 489 | U133A | 207173_x_at | 168 | Hs.443435 | NM_000213; integrin, beta 4 | CIS |
| 490 | U133A | 207862_at | 168 | Hs.379613 | NM_006760; uroplakin 2 | CIS |
| 491 | U133A | 209138_x_at | 168 | Hs.505407 | NM_015162; lipidosin | CIS |
| 492 | U133A | 209270_at | 168 | Hs.436983 | NM_000228; laminin subunit beta 3 precursor | CIS |
| 493 | U133A | 209340_at | 168 | Hs.21293 | NM_007144; ring finger protein 110 | CIS |
| 494 | U133A | 209591_s_at | 168 | Hs.170195 | NM_000228; laminin subunit beta 3 precursor | CIS |

TABLE A-continued

| Gene # | GeneChip | Probeset | Unigene Build | Unigene | description | Classifier |
|---|---|---|---|---|---|---|
| 495 | U133A | 209732_at | 168 | Hs.85201 | NM_001248; ectonucleoside triphosphate diphosphohydrolase 3 | CIS |
| 496 | U133A | 210143_at | 168 | Hs.188401 | NM_007193; annexin A10 | CIS |
| 497 | U133A | 210735_s_at | 168 | Hs.5338 | NM_017689; hypothetical protein FLJ20151 | CIS |
| 498 | U133A | 210761_s_at | 168 | Hs.86859 | NM_020142; NADH:ubiquinone oxidoreductase MLRQ subunit homolog | CIS |
| 499 | U133A | 211002_s_at | 168 | Hs.82237 | NM_001958; eukaryotic translation elongation factor 1 alpha 2 | CIS |
| 500 | U133A | 211161_s_at | 168 | | NM_000300; phospholipase A2, group IIA (platelets, synovial fluid) | CIS |
| 501 | U133A | 211430_s_at | 168 | Hs.413826 | NM_001910; cathepsin E isoform a preproprotein NM_148964; cathepsin E isoform b preproprotein | CIS |
| 502 | U133A | 211671_s_at | 168 | Hs.126608 | NM_007144; ring finger protein 110 | CIS |
| 503 | U133A | 211692_s_at | 168 | Hs.87246 | NM_014417; BCL2 binding component 3 | CIS |
| 504 | U133A | 211896_s_at | 168 | Hs.156316 | NM_005581; Lutheran blood group (Auberger b antigen included) | CIS |
| 505 | U133A | 212077_at | 168 | Hs.443811 | NM_003282; troponin I, skeletal, fast | CIS |
| 506 | U133A | 212192_at | 168 | Hs.109438 | NM_020142; NADH:ubiquinone oxidoreductase MLRQ subunit homolog | CIS |
| 507 | U133A | 212195_at | 168 | Hs.71968 | NM_000445; plectin 1, intermediate filament binding protein 500 kDa | CIS |
| 508 | U133A | 212386_at | 168 | Hs.359289 | NM_005547; involucrin | CIS |
| 509 | U133A | 212667_at | 168 | Hs.111779 | NM_000299; plakophilin 1 | CIS |
| 510 | U133A | 212671_s_at | 168 | Hs.387679 | NM_002145; homeo box B2 | CIS |
| 511 | U133A | 212998_x_at | 168 | Hs.375115 | NM_000497; cytochrome P450, subfamily XIB (steroid 11-beta-hydroxylase), polypeptide 1 precursor | CIS |
| 512 | U133A | 213891_s_at | 168 | Hs.359289 | NM_007193; annexin A10 | CIS |
| 513 | U133A | 213975_s_at | 168 | Hs.234734 | NM_005522; homeobox A1 protein isoform a NM_153620; homeobox A1 protein isoform b | CIS |
| 514 | U133A | 214352_s_at | 168 | Hs.412107 | NM_006760; uroplakin 2 | CIS |
| 515 | U133A | 214599_at | 168 | Hs.157091 | NM_005547; involucrin | CIS |
| 516 | U133A | 214630_at | 168 | Hs.184927 | NM_000497; cytochrome P450, subfamily XIB (steroid 11-beta-hydroxylase), polypeptide 1 precursor | CIS |
| 517 | U133A | 214639_s_at | 168 | Hs.67397 | NM_005522; homeobox A1 protein isoform a NM_153620; homeobox A1 protein isoform b | CIS |
| 518 | U133A | 214651_s_at | 168 | Hs.127428 | NM_002145; homeo box B2 | CIS |
| 519 | U133A | 214669_x_at | 168 | Hs.377975 | NM_001442; fatty acid binding protein 4, adipocyte | CIS |
| 520 | U133A | 214677_x_at | 168 | Hs.449601 | NM_006942; SRY-box 15 | CIS |
| 521 | U133A | 214752_x_at | 168 | Hs.195464 | NM_006942; SRY-box 15 | CIS |
| 522 | U133A | 215076_s_at | 168 | Hs.443625 | NM_016233; peptidylarginine deiminase type III | CIS |
| 523 | U133A | 215121_x_at | 168 | Hs.356861 | NM_018058; cartilage acidic protein 1 | CIS |
| 524 | U133A | 215176_x_at | 168 | Hs.503443 | NM_001248; ectonucleoside triphosphate diphosphohydrolase 3 | CIS |
| 525 | U133A | 215379_x_at | 168 | Hs.449601 | NM_006760; uroplakin 2 | CIS |
| 526 | U133A | 215812_s_at | 168 | Hs.499113 | NM_018058; cartilage acidic protein 1 | CIS |
| 527 | U133A | 216641_s_at | 168 | Hs.18141 | NM_005547; involucrin | CIS |
| 528 | U133A | 216971_s_at | 168 | Hs.79706 | NM_000445; plectin 1, intermediate filament binding protein 500 kDa | CIS |
| 529 | U133A | 217028_at | 168 | Hs.421986 | NM_003282; troponin I, skeletal, fast | CIS |
| 530 | U133A | 217040_x_at | 168 | Hs.95582 | NM_001910; cathepsin E isoform a preproprotein NM_148964; cathepsin E isoform b preproprotein | CIS |
| 531 | U133A | 217388_s_at | 168 | Hs.444471 | NM_000228; laminin subunit beta 3 precursor | CIS |
| 532 | U133A | 217626_at | 168 | Hs.201967 | NM_000299; plakophilin 1 | CIS |
| 533 | U133A | 218484_at | 168 | Hs.221447 | NM_020142; NADH:ubiquinone oxidoreductase MLRQ subunit homolog | CIS |
| 534 | U133A | 218656_s_at | 168 | Hs.93765 | NM_001442; fatty acid binding protein 4, adipocyte | CIS |
| 535 | U133A | 218718_at | 168 | Hs.43080 | NM_000445; plectin 1, intermediate filament binding protein 500 kDa | CIS |
| 536 | U133A | 218918_at | 168 | Hs.8910 | NM_000300; phospholipase A2, group IIA (platelets, synovial fluid) | CIS |
| 537 | U133A | 218960_at | 168 | Hs.414005 | NM_019894; transmembrane protease, serine 4 isoform 1 NM_183247; transmembrane protease, serine 4 isoform 2 | CIS |

TABLE A-continued

| Gene # | GeneChip | Probeset | Unigene Build | Unigene | description | Classifier |
|---|---|---|---|---|---|---|
| 538 | U133A | 219410_at | 168 | Hs.104800 | NM_004692; NM_032727; internexin neuronal intermediate filament protein, alpha | CIS |
| 539 | U133A | 219922_s_at | 168 | Hs.289019 | NM_030570; uroplakin 3B isoform a NM_182683; uroplakin 3B isoform c NM_182684; uroplakin 3B isoform b | CIS |
| 540 | U133A | 220026_at | 168 | Hs.227059 | NM_001442; fatty acid binding protein 4, adipocyte | CIS |
| 541 | U133A | 220779_at | 168 | Hs.149195 | NM_016233; peptidylarginine deiminase type III | CIS |
| 542 | U133A | 221204_s_at | 168 | Hs.326444 | NM_018058; cartilage acidic protein 1 | CIS |
| 543 | U133A | 221660_at | 168 | Hs.247831 | NM_000300; phospholipase A2, group IIA (platelets, synovial fluid) | CIS |
| 544 | U133A | 221671_x_at | 168 | Hs.377975 | NM_000299; plakophilin 1 | CIS |
| 545 | U133A | 221854_at | 168 | Hs.313068 | NM_000299; plakophilin 1 | CIS |
| 546 | U133A | 221872_at | 168 | Hs.82547 | NM_001958; eukaryotic translation elongation factor 1 alpha 2 | CIS |
| 547 | U133A | 200958_s_at | 168 | Hs.164067 | NM_005625; syndecan binding protein (syntenin) | CIS |
| 548 | U133A | 201877_s_at | 168 | Hs.249955 | NM_002719; gamma isoform of regulatory subunit B56, protein phosphatase 2A isoform a NM_178586; gamma isoform of regulatory subunit B56, protein phosphatase 2A isoform b NM_178587; gamma isoform of regulatory subunit B56, protein phosphatase 2A isoform c NM_178588; gamma isoform of regulatory subunit B56, protein phosphatase 2A isoform d | CIS |
| 549 | U133A | 201887_at | 168 | Hs.285115 | NM_001560; interleukin 13 receptor, alpha 1 precursor | CIS |
| 550 | U133A | 202076_at | 168 | Hs.289107 | NM_001166; baculoviral IAP repeat-containing protein 2 | CIS |
| 551 | U133A | 202777_at | 168 | Hs.104315 | NM_007373; soc-2 suppressor of clear homolog | CIS |
| 552 | U133A | 204640_s_at | 168 | Hs.129951 | NM_003563; speckle-type POZ protein | CIS |
| 553 | U133A | 209004_s_at | 168 | Hs.5548 | NM_012161; F-box and leucine-rich repeat protein 5 isoform 1 NM_033535; F-box and leucine-rich repeat protein 5 isoform 2 | CIS |
| 554 | U133A | 209241_x_at | 168 | Hs.112028 | NM_015716; misshapen/NIK-related kinase isoform 1 NM_153827; misshapen/NIK-related kinase isoform 3 NM_170663; misshapen/NIK-related kinase isoform 2 | CIS |
| 555 | U133A | 209579_s_at | 168 | Hs.35947 | NM_003925; methyl-CpG binding domain protein 4 | CIS |
| 556 | U133A | 209630_s_at | 168 | Hs.444354 | NM_012164; F-box and WD-40 domain protein 2 | CIS |
| 557 | U133A | 212784_at | 168 | Hs.388236 | NM_015125; capicua homolog | CIS |
| 558 | U133A | 212802_s_at | 168 | Hs.287266 | | CIS |
| 559 | U133A | 212899_at | 168 | Hs.129836 | NM_015076; cyclin-dependent kinase (CDC2-like) 11 | CIS |
| 560 | U133A | 213633_at | 168 | Hs.97858 | NM_018957; SH3-domain binding protein 1 | CIS |
| 561 | U133A | 217941_s_at | 168 | Hs.8117 | NM_018695; erbb2 interacting protein | CIS |
| 562 | U133A | 218150_at | 168 | Hs.342849 | NM_012097; ADP-ribosylation factor-like 5 isoform 1 NM_177985; ADP-ribosylation factor-like 5 isoform 2 | CIS |

The relative expression level of at least one gene in a sample is determined, wherein at least one of said genes is selected from the genes of Table A, or preferably, the gene is one of the markers MBNL2, FABP4, UBE2C, or BIRC5. The sample according to the present invention may be any tissue sample or body fluid sample, but may preferably be epithelial tissue, such as epithelial tissue from the bladder. In particular the epithelial tissue may be mucosa. In another embodiment the sample is a urine sample comprising the tissue cells. The gene can also be one or more of the markers COL18A1, COL4A1, ACTA2, MSN and KPNA2, preferably when combined in a signature with one or more of the markers MBNL2, FABP4, UBE2C, or BIRC5. One can also have signatures with different combinations of the markers, which is preferred where combinations of markers lend additional weight or statistical significance to the likelihood of progression or non-progression. For example, scores reflecting the expression levels of two or more progression markers may correlate with a determination of a specified likelihood of progression, with greater statistical significance than such correlation when using fewer markers or only one marker.

The sample may be obtained by any suitable manner known to those skilled in the art, such as a biopsy of the tumor tissue, or a superficial sample scraped from tumor tissue. The sample may be prepared by forming a cell suspension made from the tissue, or by obtaining an extract from the tissue.

In one embodiment it is preferred that the sample comprises substantially only cells from said tissue, such as substantially only cells from mucosa of the bladder. The methods according to the invention may be used for determining any bladder cancer condition, wherein said condition leads to a change in relative expression level of at least one marker, and preferably a change in a variety of markers.

Thus, the cancer may be any malignant or premalignant condition, in particular in the bladder, such as a tumor or an adenocarcinoma, a carcinoma, a teratoma, a sarcoma, and/or a lymphoma, and/or carcinoma-in-situ, and/or dysplasia-in-situ.

The expression level of single markers or one or two or a few markers can be determined. Or, expression levels of several markers, forming an expression pattern for a signature, are obtained.

In a preferred embodiment expression from at least one marker from a first group is determined, said first gene group representing markers being expressed at a higher level in one type of tissue, i.e. tissue in one stage or one risk group, in combination with determination of expression of at least one marker from a second group, said second group representing markers being expressed at a higher level in tissue from another stage or from another risk group.

Thereby, the validity of the prediction can increase, since expression levels from markers from more than one group are determined. However, determining the expression level of a single marker, whether belonging to the first group or second group is also within the scope of the invention. It is preferred that at least one marker monitored is MBNL2, FABP4, UBE2C, or BIRC5, or the marker monitored is selected among markers having a large change in expression level from normal cells to tumor cells, and may include COL18A1, COL4A1, ACTA2, MSN, KPNA2 and CDC25B.

Another approach is determination of an expression pattern from a variety of markers, in a signature, wherein the determination of the biological condition in the tissue relies on information from a signature rather than from expression of single genes or single markers. As noted above, the signature can include any of the markers MBNL2, FABP4, UBE2C, BIRC5, COL18A1, COL4A1, ACTA2, MSN, KPNA2 and CDC25B.

The following data relates to bladder tumors, and therefore the description has focused on the gene expression level as one way of identifying markers that lose or gain function in cancer tissue. Markers showing a remarkable down-regulation (or complete loss) or up-regulation (gene expression gained de novo) of the expression level, measured as the mRNA transcript, during the malignant progression in bladder from normal mucosa through Ta superficial tumors, and Carcinoa in situ (CIS) to T1, slightly invasive tumors, to T2, T3 and T4 which have spread to muscle or even further into lymph nodes or other organs, are monitored in the methods described herein, as are markers gaining importance during the differentiation from normal towards malignancy.

The invention relates to a variety of markers identified either by an EST identification number and/or by a gene identification number. Both types of identification numbers relate to identification numbers of UniGene database, NCBI, build 18.

The various markers have been identified using Affymetrix arrays (Affymetrix, CA) having the following product numbers:

HUGeneFL (sold in 2000-2002)
EOS Hu03 (customized Affymetrix array)
U133A (product #900367 sold in 2003)

The stage of a bladder tumor indicates how deeply the tumor has penetrated. Superficial tumors are termed Ta, and Carcinoma in situ (CIS), and T1, T2, T3 and T4 are used to describe increasing degrees of penetration into the muscle. The grade of a bladder tumor is expressed on a scale of I-IV (1-4) according to Bergkvist, A. et al. "Classification of bladder tumours based on the cellular pattern. Preliminary report of a clinical-pathological study of 300 cases with a minimum follow-up of eight years" Acta Chir. Scand., 1965, 130(4):371-8). The grade reflects the cytological appearance of the cells. Grade I cells are almost normal. Grade II cells are slightly deviant. Grade III cells are clearly abnormal. And Grade IV cells are highly abnormal. A special form of bladder malignancy is carcinoma-in-situ or dysplasia-in-situ in which the altered cells are located in-situ.

It is important to predict the prognosis of a cancer disease, as superficial tumors may require a less intensive treatment than invasive tumors. According to the invention the expression level of markers may be used to identify genes whose expression can be used to identify a certain stage and/or the prognosis of the disease. These markers are divided into those which can be used to identify Ta, Carcinoma in situ (CIS), T1, and T2 stages, as well as those identifying risk of recurrence or progression. In one aspect of the invention, measuring the transcript level of one or more of these markers may lead to a classifier that can add supplementary information to the information obtained from the pathological classification. For example gene expression levels that signify a T2 stage will be unfavorable to detect in a Ta tumor, as they may signal that the Ta tumor has the potential to become a T2 tumor. The opposite is probably also true, i.e., that an expression level that signifies Ta will be favorable to have in a T2 tumor. In that way independent information may be obtained from pathological classification, and a classification based on gene expression levels is made.

In the present context, a standard expression level is as defined, and includes the level of expression of a marker in a standard situation, such as a standard Ta tumor or a standard T2 tumor. For use in the present invention, standard expression levels are determined for each stage as well as for each group of progression, recurrence, and other prognostic indices. It is then possible to compare the results of a determination of the expression level from a gene of a given biological condition with a standard for each stage, progression, recurrence, and other indices, to obtain a classification of the biological condition.

From the standard expression levels of a number of genes, one can generate a reference pattern, which can be used in determining likelihood of progression. It is known from the histopathological classification of bladder tumors that some information is obtained from merely classifying into stage and grade of tumor. Accordingly, in one aspect, the invention relates to a method of predicting the prognosis of the biological condition by determining the stage of the biological condition, by determining an expression level of at least one marker, wherein said marker is one or more of gene Nos. 1 to 562. In this aspect information about the stage directly reveals information about the prognosis as well. An example hereof is when a bladder tumor is classified, for example, as stage T2—then the prognosis for the bladder tumor is obtained directly from the prognosis related generally to stage T2 tumors. In one embodiment the markers for predicting the prognosis by establishing the stage of the tumor may be selected from markers No. 1 to gene No. 188. Markers for predicting the prognosis by establishing the stage of the tumor can also include any of MBNL2, FABP4, UBE2C BIRC5, COL18A1, COL4A1, ACTA2, MSN, KPNA2 and CDC25B.

It is often preferred that the expression level of more than one marker is determined, such as the expression level of at least two markers, to as many markers as deemed relevant. As discussed above, in relation to bladder cancer the stages of a bladder tumor are selected from bladder cancer stages Ta, Carcinoma in situ, T1, T2, T3 and T4. In one embodiment the determination of a stage comprises assaying at least the expression of Ta stage marker from a Ta stage marker group, at least one expression of a CIS marker, at least the expression of T1 stage marker from a T1 stage marker group, at least the expression of T2 stage marker from a T2 stage marker group, and more preferably assaying at least the expression of Ta stage marker from a Ta stage marker group, at least one expression of a marker gene; at least one expression of T1 stage marker from a T1 stage marker group, at least the expression of T2 stage marker from a T2 stage marker group, at least the expression of T3 stage marker from a T3 stage marker group, at least the expression of T4 stage marker from a T4 stage marker group wherein at least one marker from each gene marker group is expressed in a significantly different amount in that stage than in one of the other stages.

Preferably, the markers selected may be a marker from a group being expressed in a significantly higher amount in that stage than in one of the other stages as compared to normal controls. The marker(s) selected may be a marker from a group being expressed in a significantly lower amount in that stage than in one of the other stages.

In another embodiment the invention relates to a method of predicting the prognosis of a biological condition by obtaining information in addition to the stage classification as such. As described above, by determining gene expression levels that signify a T2 stage in a tumor otherwise classified as a Ta tumor, the expression levels signal that the Ta tumor has the potential to become a T2 tumor ("harmful" markers). The opposite can also be true, that an expression level that signifies Ta will be favorable to have in a T2 tumor ("protective" markers). Some markers are particularly relevant as they relate to this additional information. Also, in one embodiment the invention relates to a further method of predicting the prognosis of a biological condition by obtaining information in addition to the stage classification as such. For example, determination of squamous metaplasia in a tumor, in particular in a T2 stage tumor, is indicative of risk of progression. In particular the markers may be selected from gene Nos. 215 to No. 232. In another embodiment the invention relates to markers bearing information of recurrence of the biological condition as such. In particular the markers may be selected from gene Nos. 189 to No. 214. An alternative is to determine a first expression level of at least one marker from a first group, wherein the first group is representative of markers wherein expression is increased in case of recurrence, genes No. 189 to gene No. 199 (recurrence genes), and to also determine a second expression level of at least one marker from a gene group, wherein the second group is selected from the group of markers wherein expression is increased in case of non-recurrence, genes No. 200 to No. 214 (non-recurrence genes), and correlate the first expression level to a standard expression level for progressors, and/or the second expression level to a standard expression level for non-progressors to predict the prognosis of the biological condition in the animal tissue.

Furthermore, in another embodiment the invention relates to markers bearing information of progression or non-progression including gene Nos. 233 to No. 446. More preferably the markers may be selected from gene Nos. 255, 273, 279, 280, 281, 282, 287, 295 (MBNL2), 300, 311, 317, 320, 333, 346, 347, 349, 352, 364, 365, 373, 383, 386, 390, 394, 401, 407, 414, 417, 426; 427, 428, 433, 434, 435, 436, 437 (BIRC5), 438, 439, 440, 441, 442, 443, 444, 445, 446, and 467 (FABP4).

Furthermore, it is within the scope of the invention to predict the prognosis of a biological condition in animal tissue by determining the expression level of at least two markers, by determining a first expression level of at least one marker from a first group, wherein the first group is selected from the group of gene Nos. 237, 238, 239, 240, 241, 242, 243, 245, 246, 247, 248, 250, 253, 254, 257, 258, 260, 263, 264, 265, 267, 270, 271, 272, 278, 283, 284, 287, 288, 290, 291, 292, 294, 297, 298, 300, 302, 303, 305, 309, 310, 315, 316, 317, 318, 319, 321, 324, 329, 335, 336, 337, 339, 340, 344, 346, 347, 354, 356, 358, 359, 362, 364, 365, 368, 369, 371, 372, 277, 378, 379, 380, 381, 382, 383, 384, 388, 391, 393, 395, 396, 397, 399, 402, 403, 404, 409, 413, 417, 419, 420, 421, 422, 423, 425, 427, 429, 430, 431, 432, 437 (BIRC5), 444 (progressor genes), and determining a second expression level of at least one marker from a second group, wherein the second group is selected from the group of genes Nos. 233, 234, 235, 236, 244, 249, 251, 252, 255, 256, 259, 261, 262, 266, 268, 269, 273, 274, 275, 276, 277, 279, 280, 281, 282, 285, 286, 289, 293, 295 (MBNL2), 296, 299, 301, 304, 306, 307, 308, 311, 312, 313, 314, 320, 322, 323, 325, 326, 327, 328, 330, 331, 332, 333, 334, 338, 341, 342, 343, 345, 348, 349, 350, 351, 352, 353, 355, 357, 360, 361, 363, 366, 367, 370, 373, 374, 375, 376, 385, 386, 387, 389, 390, 392, 394, 398, 400, 401, 405, 406, 407, 408, 410, 411, 412, 414, 415, 416, 418, 424, 426, 428, 433, 434, 435, 436, 438, 439, 440, 441, 442, 443, 445, 446, 467 (FABP4) (non-progressor genes), and correlating the first expression level to a standard expression level for progressors, and/or the second expression level to a standard expression level for non-progressors to predict the prognosis of the biological condition in the animal tissue.

In particular the markers of the first group and the second group for predicting the prognosis of a Ta stage tumor may be selected from markers selected from the group of progression/non-progression genes described above.

In yet another embodiment the present invention offers the possibility to predict the presence or absence of carcinoma in situ in the same organ as the primary tumor. An example hereof is where a Ta bladder tumor is present, predicting whether in addition to the Ta tumor carcinoma in situ (CIS) is present. The presence of carcinoma in situ in a bladder containing a superficial Ta tumor is a signal that the Ta tumor has the potential of recurrence and invasiveness. Accordingly, by predicting the presence of carcinoma in situ important information about the prognosis is obtained. In this context, markers for predicting the presence of carcinoma in situ for a Ta stage tumor may be selected from gene Nos. 447 to No. 562. Alternatively or preferably the markers are selected from gene Nos. 447, 448, 449, 450, 451, 452, 453, 454, 455, 456, 457, 458, 459, 460, 461, 462, 463, 464, 465, 466, 467 (FABP4), 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, or from gene Nos. 547, 548, 549, 550, 551, 552, 553, 554, 555, 556, 557, 558, 559, 560, 561, 562.

It is also an alternative to determine a first expression level of at least one marker from a first group, wherein expression level of this marker is increased in case of CIS, i.e., genes Nos. 447, 448, 449, 450, 451, 452, 454, 455, 456, 457, 458, 459, 462, 468, 474, 478, 484, 489, 491, 493, 495, 500, 501, 502, 504, 505, 506, 507, 508, 509, 510, 511, 512, 513, 514, 518, 519, 520, 522, 523, 524, 525, 529, 531, 534, 535, 536, 538, 544, 546, 547, 548, 549, 550, 551, 552, 553, 555, 556, 558, 559, 561, 562 (CIS genes), and to determine an expression level of at least one marker from a second group, wherein expression level of this marker is increased in case of no CIS, genes Nos. 453, 460, 461, 463, 464, 465, 466, 467 (FABP4), 469, 470, 471, 472, 473, 475, 476, 477, 479, 480, 481, 482, 483, 485, 486, 487, 488, 490, 492, 494, 496, 497, 498, 499, 503, 515, 516, 517, 521, 526, 527, 528, 530, 532, 533, 537, 539, 540, 541, 542, 543, 545, 554, 557, 560 (non-CIS genes), and correlate the first expression level to a standard expression level for CIS, and/or the second expression level to a standard expression level for non-CIS to predict the prognosis of the cancer.

Another alternative when determining the expression level of at least one marker from a first group and at least one marker from a second group is that the expression level of more than one marker from each group is determined. In one embodiment, the stage of the biological condition is determined before the prediction of prognosis. The stage may be determined by any suitable means such as by histological examination of the tissue or by genotyping of the tissue, preferably by genotyping of the tissue such as described herein or as described in international application WO 02/02804 incorporated herein by reference.

In another aspect the invention relates to determining the stage of a biological condition in animal tissue, comprising collecting a sample of cells from the tissue, determining an expression level of at least one marker selected from gene Nos. 1 to No. 562, correlating the markers' gene expression level to at least one standard level of expression relating to the stage of the condition. In particular the expression level of at least one marker from gene Nos. 1-457 and gene Nos. 459-535 and gene Nos. 537-562 is determined.

In one embodiment the expression level of at least two markers is determined by determining the expression of at least a first stage marker from a first group and at least a second stage marker from a second group, wherein at least one of said markers has a higher gene expression level in said first stage than in said second stage, and the other marker has a lower gene expression level in said first stage than in said second stage, and correlating the expression level of the assessed genes to a standard level of expression indicating the stage of the condition.

In general, markers being downregulated for higher stage tumors as well as for progression and recurrence may be of importance as predictive markers for the disease, as they may signal a poor outcome or an aggressive disease course. Furthermore, they may be important targets for therapy because restoring their expression level, e.g. by gene therapy, or substitution with those peptide products or small molecules with a similar biological effect, may suppress the malignant growth.

Markers that are up-regulated (or gained de novo) during the malignant progression of bladder cancer from normal tissue through Ta, T1, T2, T3 and T4 are also within the scope of the invention. These markers are potential oncogenes and may create or enhance the malignant growth of the cells. The expression level of these markers may serve as predictive markers for the disease course and treatment response, i.e., a high level may signal an aggressive disease course, and they may serve as targets for therapy, as blocking these markers by, e.g., anti-sense therapy, or by biochemical means could inhibit, or slow the tumor growth.

The markers used according to the invention show a sufficient difference in expression from one group to another and/or from one stage to another to use them as a classifier for the group and/or stage. Thus, comparison of an expression pattern from a signature to another expression pattern from another signature may indicate a change in stage, or identify a grouping. Alternatively, changes in intensity of expression may be scored, either as increases or decreases. Any significant change can be used. Typical changes which are more than 2-fold are suitable. Changes which are greater than 5-fold are highly suitable. The invention in particular relates to methods using markers wherein a significant change in gene expression level is seen between two groups.

As described above the invention relates to the use of information about expression levels. In one embodiment the expression patterns from signatures are obtained. Thus, the invention relates to a method of determining such an expression pattern, comprising: collecting a sample of bladder cells and/or gene products from bladder cells, determining the expression level of more than one marker in the sample, said marker being selected from gene Nos. 1 to 562, and obtaining an expression pattern for the signature.

The expression pattern preferably relates to one or more of the markers discussed above with respect to prognosis relating to stage, progression, recurrence and/or CIS.

In order to predict prognosis and/or stages it is preferred to determine an expression pattern of a signature from a cell sample preferably independent of the proportion of submucosal, muscle and connective tissue cells present. Expression is determined from one or more genes in a sample comprising cells, said genes being selected from the same genes as discussed above and shown in the tables.

It is an object of the invention that characteristic patterns of expression of signatures can be used to characterize different types of tissue. Thus, for example gene expression patterns can be used to characterize stages and grades of bladder tumors. Similarly, gene expression patterns can be used to distinguish cells having a bladder origin from other cells. Moreover, expression products which routinely contaminate bladder tumor biopsies have been identified, and such expression products can be removed or subtracted from patterns obtained from bladder biopsies. Further, the gene expression patterns of single-cell solutions of bladder tumor cells have been found to be substantially without interfering expression of contaminating muscle, submucosal, and connective tissue cells.

The markers in a signature monitored generally are not genes which are expressed in the submucosal, muscle, and connective tissue. A pattern of expression is formed for the sample which is independent of the proportion of submucosal, muscle, and connective tissue cells in the sample.

In another aspect of the invention, a method of determining an expression pattern of signatures from a cell sample is provided. Expression is determined from one or more markers in a sample comprising cells. A first pattern of expression is thereby formed for the sample. Genes which are expressed in submucosal, muscle, and connective tissue cells are removed from the first pattern of expression, forming a second pattern of expression which is independent of the proportion of submucosal, muscle, and connective tissue cells in the sample.

Another embodiment of the invention provides a method for determining an expression pattern of a signature from a bladder mucosa or bladder cancer cell independent of the proportion of submucosal, muscle, and connective tissue cells present in the sample. Expression is determined from one or more markers in a sample comprising bladder mucosa or bladder cancer cells; the expression determined forms a first pattern of expression. A second pattern of expression which was formed using the one or more genes and a sample comprising predominantly submucosal, muscle, and connective tissue cells, is subtracted from the first pattern of expression, forming a third pattern of expression. The third pattern of expression reflects expression of the bladder mucosa or bladder cancer cells independent of the proportion of submucosal, muscle, and connective tissue cells present in the sample.

In one embodiment the invention provides a method to predict the prognosis of a bladder tumor as described above. A first pattern of expression is determined from more than one marker in a bladder tumor sample. The first pattern is compared to one or more reference patterns of expression determined for bladder tumors at different stages and/or in different groups. The reference patterns which share the most similarity with the first pattern are identified. The stage of the reference pattern with the maximum similarity indicates the stage of the tumor in the bladder tumor sample.

Since a biopsy of the tissue often contains more extraneous tissue material such as connective tissue than the tissue to be examined, when the tissue to be examined is epithelial or mucosa, the invention also relates to methods wherein the expression pattern of the tissue is independent of the amount of connective tissue in the sample.

Biopsies contain epithelial cells that most often are the targets for the studies, but in addition contain many other cells that contaminate the epithelial cell fraction to a varying extent. The contaminants include histiocytes, endothelial cells, leukocytes, nerve cells, muscle cells, etc.

Micro dissection is the method of choice for DNA examination, but in the case of expression studies this procedure is difficult due to RNA degradation during the procedure. The epithelium may be removed and the expression in the remaining submucosa and underlying connective tissue (the bladder wall) monitored. Genes expressed at high or low levels in the bladder wall should be interrogated when performing expression monitoring of the mucosa and tumors. A similar approach could be used for studies of epithelia in other organs. In one embodiment of the invention, normal mucosa lining the bladder lumen of bladders from cancer subjects is scraped off. Then biopsies are taken from the denuded submucosa and connective tissue, reaching approximately 5 mm into the bladder wall, and immediately disintegrated in guanidinium isothiocyanate. Total RNA may be extracted, pooled, and polyA mRNA may be prepared from the pool followed by conversion to double-stranded cDNA and in vitro transcription into cRNA containing biotin-labeled CTP and UTP.

Genes that are expressed and genes that are not expressed in the bladder wall can both interfere with the interpretation of the expression in a biopsy, and should be considered when interpreting expression intensities in tumor biopsies, as the bladder wall component of a biopsy varies in amount from biopsy to biopsy.

When having determined the pattern of genes expressed in bladder wall components, said pattern may be subtracted from a pattern of a signature obtained from the sample, resulting in a third pattern related to the mucosa (epithelial) cells.

In another embodiment of the invention a method is provided for determining an expression pattern of a signature from a bladder tissue sample independent of the proportion of submucosal, muscle and connective tissue cells present. A single-cell suspension of disaggregated bladder tumor cells is isolated from a bladder tissue sample comprising bladder tumor cells, submucosal cells, muscle cells, and connective tissue cells. A pattern of expression is thus formed for the signature in the sample which is independent of the proportion of submucosal, muscle, and connective tissue cells in the bladder tissue sample.

Yet another method relates to the elimination of mRNA from bladder wall components before determining the expression pattern, e.g. by filtration and/or affinity chromatography to remove mRNA related to the bladder wall. Working with tumor material requires biopsies or body fluids suspected of containing relevant cells. Working with RNA requires freshly frozen or immediately processed biopsies, or chemical pretreatment of the biopsy. Apart from the cancer tissue, biopsies do inevitably contain many different cell types, such as cells present in the blood, connective and muscle tissue, endothelium, etc. In the case of DNA studies, microdissection or laser capture are methods of choice, however the time-dependent degradation of RNA makes it difficult to perform manipulation of the tissue for more than a few minutes. Furthermore, studies of expressed sequences may be difficult on the few cells obtained via microdissection or laser capture, as these cells may have an expression pattern that deviates from the predominant pattern in a tumor due to large intratumoral heterogeneity.

In the present context, high density expression arrays may be used to evaluate the impact of bladder wall components in bladder tumor biopsies, and single cell solutions may be a means of eliminating the contaminants. The results of these evaluations permit for the design of methods of evaluating bladder samples without the interfering background noise caused by ubiquitous contaminating submucosal, muscle, and connective tissue cells. The evaluating assays of the invention may be of any type.

While high density expression arrays can be used, other techniques are also contemplated.

These include other techniques for assaying for specific mRNA species, including RT-PCR and Northern Blotting, as well as techniques for assaying for particular protein products, such as ELISA, Western blotting, and enzyme assays. Gene expression patterns or scores according to the present invention are determined by measuring any gene product. A pattern or score may be for one or more genes or markers. RNA or protein can be isolated and assayed from a test sample using any techniques known in the art. They can for example be isolated from a fresh or frozen biopsy, from formalin-fixed tissue, or from body fluids, such as blood, plasma, serum, urine, or sputum.

Expression of genes may in general be detected by either detecting mRNA from the cells and/or detecting expression products, such as peptides and proteins. The detection of mRNA expression may be a tool for determining the developmental stage of a cell type which may be definable by its pattern of expression of messenger RNA. Where a pattern is shown to be characteristic of a stage, said stage may be defined by that particular pattern of messenger RNA expression. The mRNA population is a good determinant of a developmental stage, and may be correlated with other structural features of the cell. In this manner, cells at specific developmental stages will be characterized by the intracellular environment, as well as the extracellular environment.

The present invention also allows the combination of classifiers of tumors based in part upon antigens and in part upon mRNA expression. In one embodiment, the two may be combined in a single incubation step. A particular incubation condition may be found which is compatible with both hybridization recognition and non-hybridization recognition molecules. Thus, e.g. an incubation condition may be selected which allows both specificity of antibody binding and specificity of nucleic acid hybridization. This allows simultaneous performance of both types of interactions on a single matrix in one assay. Again, where developmental mRNA patterns are correlated with structural features, or with probes which are able to hybridize to intracellular mRNA populations, a cell sorter may be used to sort specifically those cells having desired mRNA population patterns.

It is within the general scope of the invention to provide methods for the detection of mRNA. Such methods often involve sample extraction, PCR amplification, nucleic acid fragmentation and labeling, extension reactions, and transcription reactions. The nucleic acid (either genomic DNA or mRNA) may be isolated from the sample according to any of a number of methods well known to those of skill in the art. One of skill will appreciate that where alterations in the copy number of a gene are to be detected; genomic DNA is preferably isolated and analyzed. Conversely, where gene expression levels are to be detected, preferably RNA (mRNA) is isolated and analyzed.

Methods of isolating total RNA are well known to those of skill in the art. In one embodiment, the total nucleic acid is isolated from a given sample using, for example, an acid guanidinium-phenol-chloroform extraction method and polyA selection for mRNA using oligo dT column chromatography or by using beads or magnetic beads with (dT)n groups attached (see, e.g., Sambrook et al., Molecular Cloning: A Laboratory Manual (2nd ed.), Vols. 1-3, Cold Spring Harbor Laboratory, (1989), or Current Protocols in Molecular Biology, F. Ausubel et al., ed. Greene Publishing and Wiley-Interscience, New York (1987)).

The sample may be from tissue and/or body fluids, as defined elsewhere herein. Before analyzing the sample, e.g., on an oligonucleotide array, it will often be desirable to perform one or more sample preparation operations upon the sample. Typically, these sample preparation operations will include manipulations such as extraction of intracellular material, e.g., nucleic acids from whole cell samples, viruses, amplification of nucleic acids, fragmentation, transcription, labeling and/or extension reactions. One or more of these various operations may be readily incorporated into the methods of the invention.

DNA extraction may be relevant under circumstances where possible mutations in the genes are to be determined in addition to the determination of expression of the genes. For those embodiments where whole cells, or other tissue samples are being analyzed, it will typically be necessary to extract the nucleic acids from the cells or viruses, prior to continuing with the various sample preparation operations. Accordingly, following sample collection, nucleic acids may be liberated from the collected cells, viral coat etc. into a crude extract followed by additional treatments to prepare the sample for subsequent operations, such as denaturation of contaminating (DNA binding) proteins, purification, filtration and desalting.

Liberation of nucleic acids from the sample cells, and denaturation of DNA binding proteins may generally be performed by physical or chemical methods. For example, chemical methods generally employ lysing agents to disrupt the cells and extract the nucleic acids from the cells, followed by treatment of the extract with chaotropic salts such as guanidinium isothiocyanate or urea to denature any contaminating and potentially interfering proteins.

Alternatively, physical methods may be used to extract the nucleic acids and denature DNA binding proteins, such as employing physical protrusions within microchannels or sharp edged particles to pierce cell membranes and extract their contents. Combinations of such structures with piezoelectric elements for agitation can provide suitable shear forces for lysis.

More traditional methods of cell extraction may also be used, e.g., employing a channel with restricted cross-sectional dimension which causes cell lysis when the sample is passed through the channel with sufficient flow pressure. Alternatively, cell extraction and denaturing of contaminating proteins may be carried out by applying an alternating electrical current to the sample. More specifically, the sample of cells is flowed through a microtubular array while an alternating electric current is applied across the fluid flow. Subjecting cells to ultrasonic agitation, or forcing cells through microgeometry apertures, thereby subjecting the cells to high shear stress resulting in rupture, are also possible extraction methods.

Following extraction, it will often be desirable to separate the nucleic acids from other elements of the crude extract, e.g. denatured proteins, cell membrane particles and salts. Removal of particulate matter is generally accomplished by filtration or flocculation. Further, where chemical denaturing methods are used, it may be desirable to desalt the sample prior to proceeding to the next step. Desalting of the sample and isolation of the nucleic acid may generally be carried out in a single step, e.g. by binding the nucleic acids to a solid phase and washing away the contaminating salts, or performing gel filtration chromatography on the sample. Suitable solid supports for nucleic acid binding include e.g. diatomaceous earth or silica (i.e., glass wool). Suitable gel exclusion media, also well known in the art, may be readily incorporated into the devices of the present invention and is commercially available from, e.g., Pharmacia and Sigma Chemical.

Alternatively, desalting methods may generally take advantage of the high electrophoretic mobility and negativity of DNA compared to other elements. Electrophoretic methods may also be utilized in the purification of nucleic acids from other cell contaminants and debris. Upon application of an appropriate electric field, the nucleic acids present in the sample will migrate toward the positive electrode and become trapped on the capture membrane. Sample impurities remaining free of the membrane are then washed away by applying an appropriate fluid flow. Upon reversal of the voltage, the nucleic acids are released from the membrane in a substantially purer form. Further, coarse filters may also be overlaid on the barriers to avoid any fouling of the barriers by particulate matter, proteins or nucleic acids, thereby permitting repeated use.

In a similar aspect, the high electrophoretic mobility of nucleic acids with their negative charges may be utilized to separate nucleic acids from contaminants by utilizing a short column of a gel or other appropriate matrices or gels which will slow or retard the flow of other contaminants, while allowing the faster nucleic acids to pass.

This invention provides nucleic acid affinity matrices that bear a large number of different nucleic acid affinity ligands, allowing the simultaneous selection and removal of a large number of preselected nucleic acids from the sample. Methods of producing such affinity matrices are also provided. In general the methods involve the steps of a) providing a nucleic acid amplification template array comprising a surface to which are attached at least 50 oligonucleotides having different nucleic acid sequences, and wherein each different oligonucleotide is localized in a predetermined region of said surface, the density of said oligonucleotides is greater than about 60 different oligonucleotides per $cm^2$, and all of said different oligonucleotides have an identical terminal 3' nucleic acid sequence and an identical terminal 5' nucleic acid sequence; b) amplifying said multiplicity of oligonucleotides to provide a pool of amplified nucleic acids; and c) attaching the pool of nucleic acids to a solid support.

For example, nucleic acid affinity chromatography is based on the tendency of complementary, single-stranded nucleic acids to form a double-stranded or duplex structure through complementary base pairing. A nucleic acid (either DNA or RNA) can easily be attached to a solid substrate (matrix) where it acts as an immobilized ligand that interacts with and forms duplexes with complementary nucleic acids present in a solution contacted to the immobilized ligand. Unbound components can be washed away from the bound complex to either provide a solution lacking the target molecules bound to the affinity column, or to provide the isolated target molecules themselves. The nucleic acids captured in a hybrid duplex can be separated and released from the affinity matrix by denaturation either through heat, adjustment of salt concentration, or the use of a destabilizing agent such as formamide, TWEEN™-20 denaturing agent, or sodium dodecyl sulfate (SOS).

Affinity columns (matrices) are typically used either to isolate a single nucleic acid typically by providing a single species of affinity ligand. Alternatively, affinity columns bearing a single affinity ligand (e.g. oligo dT columns) have been used to isolate a multiplicity of nucleic acids where the nucleic acids all share a common sequence (e.g. a polyA).

The type of affinity matrix used depends on the purpose of the analysis. For example, where it is desired to analyze mRNA expression levels of particular genes in a complex nucleic acid sample (e.g., total mRNA) it is often desirable to eliminate nucleic acids produced by genes that are constitutively over-expressed and thereby tend to mask gene products expressed at characteristically lower levels. Thus, in one embodiment, the affinity matrix can be used to remove a number of preselected gene products (e.g., actin, GAPDH, etc.). This is accomplished by providing an affinity matrix bearing nucleic acid affinity ligands complementary to the gene products (e.g., mRNAs or nucleic acids derived therefrom) or to subsequences thereof. Hybridization of the nucleic acid sample to the affinity matrix will result in duplex formation between the affinity ligands and their target nucleic acids. Upon elution of the sample from the affinity matrix, the matrix will retain the duplexed nucleic acids, leaving a sample depleted of the over-expressed target nucleic acids.

The affinity matrix can also be used to identify unknown mRNAs or cDNAs in a sample. Where the affinity matrix contains nucleic acids complementary to every known gene (e.g., in a cDNA library, DNA reverse transcribed from an mRNA, mRNA used directly or amplified or polymerized from a DNA template) in a sample, capture of the known nucleic acids by the affinity matrix leaves a sample enriched for those nucleic acid sequences that are unknown.

In effect, the affinity matrix is used to perform a subtractive hybridization to isolate unknown nucleic acid sequences. The unknown sequences can then be purified and sequenced according to standard methods.

Another type of affinity matrix can also be used to capture (isolate) and thereby purify unknown nucleic acid sequences. For example, an affinity matrix can be prepared that contains nucleic acid (affinity ligands) that are complementary to sequences not previously identified, or not previously known to be expressed in a particular nucleic acid sample. The sample is then hybridized to the affinity matrix and those sequences that are retained on the affinity matrix are "unknown" nucleic acids. The retained nucleic acids can be eluted from the matrix (e.g. at increased temperature, increased destabilizing agent concentration, or decreased salt) and the nucleic acids can then be sequenced according to standard methods. Similarly, the affinity matrix can be used to efficiently capture (isolate) a number of known nucleic acid sequences. Again, the matrix is prepared bearing nucleic acids complementary to those nucleic acids it is desired to isolate. The sample is contacted with the matrix under hybridization conditions. The non-hybridized material is washed off the matrix leaving the desired sequences bound. The hybrid duplexes are then denatured providing a pool of the isolated nucleic acids. The different nucleic acids in the pool can be subsequently separated according to standard methods (e.g. gel electrophoresis).

As indicated above, the affinity matrices can be used to selectively remove nucleic acids from virtually any sample containing nucleic acids (e.g. in a cDNA library, DNA reverse transcribed from an mRNA, mRNA used directly or amplified, or polymerized from a DNA template, and so forth). The nucleic acids adhering to the column can be removed by washing with a low salt concentration buffer, a buffer containing a destabilizing agent such as formamide, or by elevating the column temperature.

In one particularly preferred embodiment, the affinity matrix can be used in a method to enrich a sample for unknown RNA sequences (e.g. expressed sequence tags (ESTs)). The method involves first providing an affinity matrix bearing a library of oligonucleotide probes specific to known RNA (e.g., EST) sequences. Then, RNA from undifferentiated and/or unactivated cells and RNA from differentiated or activated or pathological (e.g., transformed) cells, or cells otherwise having a different metabolic state, are separately hybridized against the affinity matrices to provide two pools of RNAs lacking the known RNA sequences.

In one embodiment, the affinity matrix is packed into a columnar casing. The sample is then applied to the affinity matrix (e.g. injected onto a column or applied to a column by a pump such as a sampling pump driven by an autosampler). The affinity matrix (e.g. an affinity column) bearing the sample is subjected to conditions under which the nucleic acid probes comprising the affinity matrix hybridize specifically with complementary target nucleic acids. Such conditions are accomplished by maintaining appropriate pH, salt and temperature conditions to facilitate hybridization, as discussed above.

For a number of applications, it may be desirable to extract and separate messenger RNA from cells, cellular debris, and other contaminants. As such, the device of the present invention may, in some cases, include an mRNA purification chamber or channel. In general, such purification takes advantage of the poly-A tails on mRNA. In particular and as noted above, poly-T oligonucleotides may be immobilized within a chamber or channel of the device, or upon a solid support incorporated within the chamber or channel, to serve as affinity ligands for mRNA. Immobilization of oligonucleotides on the surface of the chambers or channels may be carried out by methods described herein including, e.g., oxidation and silanation of the surface followed by standard DMT synthesis of the oligonucleotides. In operation, the lysed sample is introduced to a high salt solution to increase the ionic strength for hybridization, whereupon the mRNA will hybridize to the immobilized poly-T. The mRNA bound to the immobilized poly-T oligonucleotides is then washed free in a low ionic strength buffer. The poly-T oligonucleotides may be immobilized upon porous surfaces, e.g., porous silicon, zeolites silica xerogels, scintered particles, or other solid supports. Following sample preparation, the sample can be subjected to one or more different analysis operations. A variety of analysis operations may generally be performed, including size based analysis using, e.g., microcapillary electrophoresis, and/or sequence based analysis using, e.g., hybridization to an oligonucleotide array. In the latter case, the nucleic acid sample may be probed using an array of oligonucleotide probes. Oligonucleotide arrays generally include a substrate having a large number of positionally distinct oligonucleotide probes attached to the substrate. These arrays may be produced using mechanical or light directed synthesis methods which incorporate a combination of photolithographic methods and solid phase oligonucleotide synthesis methods.

The basic strategy for light directed synthesis of oligonucleotide arrays is as follows. The surface of a solid support, modified with photosensitive protecting groups is illuminated through a photolithographic mask, yielding reactive hydroxyl groups in the illuminated regions. A selected nucleotide, typically in the form of a 3'-O-phosphoramidite-activated deoxynucleoside (protected at the 5' hydroxyl with a photosensitive protecting group), is then presented to the surface and coupling occurs at the sites that were exposed to light. Following capping and oxidation, the substrate is rinsed and the surface is illuminated through a second mask to expose additional hydroxyl groups for coupling. A second selected nucleotide (e.g., 5'-protected, 3'-O-phosphoramidite-activated deoxynucleoside) is presented to the surface. The selective deprotection and coupling cycles are repeated until the desired set of products is obtained. Since photolithography is used, the process can be readily miniaturized to generate high density arrays of oligonucleotide probes. Furthermore, the sequence of the oligonucleotides at each site is known. See Pease et al. Mechanical synthesis methods are similar to the light directed methods except they involve mechanical direction of fluids for deprotection and addition in the synthesis steps.

For some embodiments, oligonucleotide arrays may be prepared having all possible probes of a given length. The hybridization pattern of the target sequence on the array may be used to reconstruct the target DNA sequence. Hybridization analysis of large numbers of probes can be used to sequence long stretches of DNA or provide an oligonucleotide array which is specific and complementary to a particular nucleic acid sequence. For example, in particularly preferred aspects, the oligonucleotide array will contain oligonucleotide probes which are complementary to specific target sequences and individual or multiple mutations of these. Such arrays are particularly useful in the diagnosis of specific disorders which are characterized by the presence of a particular nucleic acid sequence.

Following sample collection and nucleic acid extraction, the nucleic acid portion of the sample is typically subjected to one or more preparative reactions. These preparative reactions include in vitro transcription, labeling, fragmentation, amplification and other reactions. Nucleic acid amplification increases the number of copies of the target nucleic acid sequence of interest. A variety of amplification methods are suitable for use in the methods and devices of the present invention, including for example, the polymerase chain reaction method or (PCR), the ligase chain reaction (LCR), self sustained sequence replication, and nucleic acid based sequence amplification (NASBA). The latter two amplification methods involve isothermal reactions based on isothermal transcription, which produces both single stranded RNA (ssRNA) and double stranded DNA (dsDNA) as the amplification products in a ratio of approximately 30 or 100 to 1, respectively. As a result, where these latter methods are employed, sequence analysis may be carried out using a substrate with oligonucleotides attached which are complementary to either DNA or RNA.

Frequently, it is desirable to amplify the nucleic acid sample prior to hybridization. One of skill in the art will appreciate that whatever amplification method is used, if a quantitative result is desired, especially where that is how expression levels are determined, care must be taken to use a method that maintains or controls for the relative frequencies of the amplified nucleic acids.

PCR

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid. Thus, in one embodiment, this invention provides for a method of optimizing a probe set for detection of a particular gene. Generally, this method involves providing a high density array containing a multiplicity of probes of one or more particular length(s) that are complementary to subsequences of the mRNA transcribed by the target gene. In one embodiment, the high density array may contain every probe of a particular length that is complementary to a particular mRNA. The probes of the high density array are then hybridized with their target nucleic acid alone, and then hybridized with a high complexity, high concentration nucleic acid sample that does not contain the targets complementary to the probes. Thus, for example, where the target nucleic acid is an RNA, the probes are first hybridized with their target nucleic acid alone and then hybridized with RNA made from a cDNA library (e.g., reverse transcribed polyA$^+$ mRNA) where the sense of the hybridized RNA is opposite that of the target nucleic acid (to insure that the high complexity sample does not contain targets for the probes). Those probes that show a strong hybridization signal with their target and little or no cross-hybridization with the high complexity sample are preferred probes for use in such high density arrays.

PCR amplification generally involves the use of one strand of the target nucleic acid sequence as a template for producing a large number of complements to that sequence. Generally, two primer sequences complementary to different ends of a segment of the complementary strands of the target sequence hybridize with their respective strands of the target sequence, and in the presence of polymerase enzymes and nucleoside triphosphates, the primers are extended along the target sequence. The extensions are melted from the target sequence and the process is repeated, this time with the additional copies of the target sequence synthesized in the preceding steps. PCR amplification typically involves repeated cycles of denaturation, hybridization and extension reactions to produce sufficient amounts of the target nucleic acid. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In PCR methods, strand separation is normally achieved by heating the reaction to a sufficiently high temperature for a sufficient time to cause the denaturation of the duplex, but not to cause an irreversible denaturation of the polymerase. Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. In addition to PCR and IVT reactions, the methods and devices of the present invention are also applicable to a number of other reaction types, e.g., reverse transcription, nick translation, and the like.

The nucleic acids in a sample will generally be labeled to facilitate detection in subsequent steps. Labeling may be carried out during the amplification, in vitro transcription or nick translation processes. In particular, amplification, in vitro transcription or nick translation may incorporate a label into the amplified or transcribed sequence, either through the use of labeled primers or the incorporation of labeled dNTPs into the amplified sequence.

Hybridization between the sample nucleic acid and the oligonucleotide probes on the array is then detected, using, e.g., epifluorescence confocal microscopy. Typically, the sample is mixed during hybridization to enhance hybridization of nucleic acids in the sample to nucleic acid probes on the array.

In some cases, hybridized oligonucleotides may be labeled following hybridization. For example, where biotin labeled dNTPs are used in, e.g. amplification or transcription, streptavidin linked reporter groups may be used to label hybridized complexes. Such operations are readily integrated into the systems of the present invention. Alternatively, the nucleic acids in the sample may be labeled following amplification. Post amplification labeling typically involves the covalent attachment of a particular detectable group to the amplified sequences. Suitable labels or detectable groups include a variety of fluorescent or radioactive labeling groups well known in the art, coupled to the sequences using methods that are well known in the art.

Methods for detection depend upon the label selected. A fluorescent label is preferred because of its extreme sensitivity and simplicity. Standard labeling procedures are used to determine the positions where interactions between a sequence and a reagent take place. For example, if a target sequence is labeled and exposed to a matrix of different probes, only those locations where probes interact with the target will exhibit any signal. Alternatively, other methods may be used to scan the matrix to determine where interaction takes place. Of course, the spectrum of interactions may be determined in a temporal manner by repeated scans of interactions which occur at each of a multiplicity of conditions. However, instead of testing each individual interaction separately, a multiplicity of sequence interactions may be simultaneously determined on a matrix.

Means of detecting labeled target (sample) nucleic acids hybridized to the probes of the high density array are known to those of skill in the art. Thus, for example, where a colorimetric label is used, the label is visualized. Where a radioactive labeled probe is used, detection of the radiation (e.g with photographic film or a solid state detector) is sufficient. In a preferred embodiment, the target nucleic acids are labeled with a fluorescent label and the localization of the label on the probe array is accomplished with fluorescent microscopy. The hybridized array is excited with a light source at the excitation wavelength of the particular fluorescent label and the resulting fluorescence at the emission wavelength is detected. In one preferred embodiment, the excitation light source is a laser appropriate for the excitation of the fluorescent label.

The target polynucleotide may be labeled by any of a number of convenient detectable markers. A fluorescent label is preferred because it provides a very strong signal with low background. It is also optically detectable at high resolution and sensitivity through a quick scanning procedure.

Other potential labeling moieties include, radioisotopes, chemiluminescent compounds, labeled binding proteins, heavy metal atoms, spectroscopic markers, magnetic labels, and linked enzymes.

Another method for labeling may bypass any label of the target sequence. The target may be exposed to the probes, and a double-stranded hybrid is formed at those positions only. Addition of a double-stranded specific reagent will detect where hybridization takes place. An intercalating dye such as ethidium bromide may be used as long as the probes do not fold back on themselves to a significant extent forming hairpin loops. However, the length of the hairpin loops in short oligonucleotide probes would typically be insufficient to form a stable duplex.

Suitable labels and chromogens will include molecules and compounds which absorb light in a distinctive range of wavelengths so that a color may be observed, or emit light when irradiated with radiation of a particular wave length or wave length range, e.g., fluorescers, biliproteins, e.g., phycoerythrin, may also serve as labels.

A wide variety of suitable dyes are available, including those chosen to provide an intense color with minimal absorption by their surroundings. Illustrative dye types include quinolone dyes, triarylmethane dyes, acridine dyes, alizarine dyes, phthaleins, insect dyes, azo dyes, anthraquinoid dyes, cyanine dyes, phenazathionium dyes, and phenazoxonium dyes. A wide variety of fluorescers may be employed either by themselves or in conjunction with quencher molecules. Fluorescers of interest fall into a variety of categories having certain primary functionalities, including 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidzaolylphenylamine, 2-oxo-3-chromen, indole, xanthen, 7-ydroxycoumarin, phenoxazine, salicylate, strophanthidin, porphyrins, triarylmethanes and flavin. Individual fluorescent compounds which have functionalities for linking or which can be modified to incorporate such functionalities include, e.g., dansyl chloride; fluoresceins such as 3,6-dihydroxy-9-phenylxanthhydrol; rhodamineisothiocyanate; N-phenyl 1-amino-8-sulfonatonaphthalene; N-phenyl 2-amino-6-sulfonatonaphthalene; 4-acetamido-4-10 isothiocyanato-stilbene-2,2'-disulfonic acid; pyrene-3-sulfonic acid; 2-toluidinonaphthalene-6-sulfonate; N-phenyl, N-methyl 2-aminoaphthalene-6-sulfonate; ethidium bromide; stebrine; Auromine 0,2-(9'-anthroyl) palmitate; dansyl phosphatidylethanolamine; N,N'-dioctadecyl oxacarbocyanine; N,N'-dihexyl oxacarbocyanine; merocyanine, 4-(3' pyrenyl)butyrate; d-3-aminodesoxy-equilenin; 1,2-(9'-anthroyl) stearate; 2-methylanthracene; 9-vinylanthracene; 2,2'-(vinylene-p-phenylene)bisbenzoxazole; p-bis 2-(4-methyl-5-phenyl-oxazolyl) benzene; 6-dimethylamino-1,2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3-chromenyl) maleimide; N-p-(2-benzimidazolyl)-phenyl-maieimide; N-(4-fluoranthyl) maleimide; bis(homovanillic acid); resazarin; 4-chloro-7-nitro-2,1,3-benzooxadiazole; merocyanine 540; resorufin; rose bengal; and 2,4-diphenyl-3(2H)furanone.

Desirably, fluorescers should absorb light above about 300 nm, preferably about 350 nm, and more preferably above about 400 nm, usually emitting at wavelengths greater than about 10 nm higher than the wavelength of the light absorbed. It should be noted that the absorption and emission characteristics of the bound dye may differ from the unbound dye. Therefore, when referring to the various wavelength ranges and characteristics of the dyes, it is intended to indicate this refers to the dyes as employed and not the dye which is unconjugated and characterized in an arbitrary solvent.

Fluorescers are generally preferred because by irradiating a fluorescer with light, one can obtain a plurality of emissions. Thus, a single label can provide for a plurality of measurable events. Detectable signal may also be provided by chemiluminescent and bioluminescent sources. Chemiluminescent sources include a compound which becomes electronically excited by a chemical reaction and may then emit light which serves as the detectable signal or donates energy to a fluorescent acceptor. A diverse number of families of compounds have been found to provide chemiluminescence under a variety of conditions. One family of compounds is 2,3-dihydro-1,-4-phthalazinedione. The most popular compound is luminol, which is the 5-amino compound. Other members of the family include the 5-amino-6,7,8-trimethoxy- and the dimethylamino)calbenz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents. Chemiluminescence may also be obtained with oxalates, usually oxalyl active esters, e.g., p-nitrophenyl and a peroxide, e.g., hydrogen peroxide, under basic conditions. Alternatively, luciferins may be used in conjunction with luciferase or lucigenins to provide bioluminescence. Spin labels are provided by reporter molecules with an unpaired electron spin which can be detected by electron spin resonance (ESR) spectroscopy. Exemplary spin labels include organic free radicals, transitional metal complexes, particularly vanadium, copper, iron, and manganese, and the like. Exemplary spin labels include nitroxide free radicals. In addition, amplified sequences may be subjected to other post amplification treatments. For example, in some cases, it may be desirable to fragment the sequence prior to hybridization with an oligonucleotide array, in order to provide segments which are more readily accessible to the probes, and to avoid looping and/or hybridization to multiple probes. Fragmentation of the nucleic acids may generally be carried out by physical, chemical or enzymatic methods that are known in the art.

Following the various sample preparation operations, the sample will generally be subjected to one or more analysis operations. Particularly preferred analysis operations include, e.g. sequence based analyses using an oligonucleotide array and/or size based analyses using, e.g. microcapillary array electrophoresis. In some embodiments it may be desirable to provide an additional or alternative means for analyzing the nucleic acids from the sample. Microcapillary array electrophoresis generally involves the use of a thin capillary or channel which may or may not be filled with a particular separation medium. Electrophoresis of a sample through the capillary provides a size based separation profile for the sample.

Microcapillary array electrophoresis generally provides a rapid method for size based sequencing, PCR product analysis and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods these methods provide sensitivity in the range of attomoles, which is comparable to the sensitivity of radioactive sequencing methods.

In many capillary electrophoresis methods, the capillaries which are formed, e.g. by fused silica capillaries or channels etched, machined or molded into planar substrates, are filled with an appropriate separation/sieving matrix. Typically, a variety of sieving matrices known in the art may be used in the microcapillary arrays. Examples of such matrices include, e.g. hydroxyethyl cellulose, polyacrylamide and agarose. Gel matrices may be introduced and polymerized within the capillary channel. However, in some cases this may result in entrapment of bubbles within the channels, which can interfere with sample separations. Accordingly, it is often desirable to place a preformed separation matrix within the capillary channel(s), prior to mating the planar elements of the capillary portion. Fixing the two parts, e.g. through sonic welding, permanently fixes the matrix within the channel. Polymerization outside of the channels helps to ensure that no bubbles are formed. Further, the pressure of the welding process helps to ensure a void-free system.

In addition to its use in nucleic acid "fingerprinting" and other sized-based analyses the capillary arrays may also be used in sequencing applications. In particular, gel based sequencing techniques may be readily adapted for capillary array electrophoresis. In addition to detection of mRNA or as the sole detection method, gene products from the markers discussed above may be detected as indicators of the biological condition of the tissue. Gene products may be detected in either the tissue sample as such, or in a body fluid sample, such as blood, serum, plasma, feces, mucus, sputum, cerebrospinal fluid, and/or urine of the individual. The expression products, peptides and proteins, may be detected by any suitable technique known to the person skilled in the art.

In a preferred embodiment the expression products are detected by means of specific antibodies directed to the various expression products, such as immunofluorescent and/or immunohistochemical staining of the tissue. Immunohistochemical localization of expressed proteins may be carried out by immunostaining of tissue sections from the single tumors to determine which cells expressed the protein encoded by the transcript in question. The transcript levels may be used to select a group of proteins supposed to show variation from sample to sample, making a rough correlation between the level of protein detected and the intensity of the transcript on the microarray possible. For example sections may be cut from paraffin-embedded tissue blocks, mounted, and deparaffinized by incubation at 80° C. for 10 minutes, followed by immersion in heated oil at 60° C. for 10 min. (Estisol 312, Estichem A/S, Denmark) and rehydration.

Antigen retrieval is achieved in TEG (TrisEDTA-Glycerol) buffer using microwaves at 900 W. The tissue sections may be cooled in the buffer for 15 min before a brief rinse in tap water. Endogenous peroxidase activity is blocked by incubating the sections with 1% $H_2O_2$ for 20 min.; followed by three rinses in tap water, 1 min each. The sections may then be soaked in PBS buffer for 2 min. The next steps can be modified from the descriptions given by Oncogene Science Inc., in the Mouse Immunohistochemistry Detection System, XHC01 (UniTect, Uniondale, N.Y., USA). Briefly, the tissue sections are incubated overnight at 4° C. with primary antibody (against beta-2 microglobulin (Dako), cytokeratin 8, cystatin-C (both from Europa, US), junB, CD59, E-cadherin, apo-E, cathepsin E, vimentin, IGFII (all from Santa Cruz), followed by three rinses in PBS buffer for 5 min each. Afterwards, the sections are incubated with biotinylated secondary antibody for 30 min, rinsed three times with PBS buffer and subsequently incubated with ABC (avidin-biotinlylated horseradish peroxidase complex) for 30 min. followed by three rinses in PBS buffer.

Staining may be performed by incubation with AEC (3-amino-ethylcarbazole) for 10 min. The tissue sections are counter-stained with Mayers hematoxylin, washed in tap water for 5 min. and mounted with glycerol-gelatin. Positive and negative controls may be included in each staining round with all antibodies.

In yet another embodiment the expression products may be detected by means of conventional enzyme assays, such as ELISA methods. Furthermore, the expression products may be detected by means of peptide/protein chips capable of specifically binding the peptides and/or protein's assessed. Thereby an expression pattern may be obtained.

Assay

In a further aspect the invention relates to an assay for predicting the prognosis of a biological condition in animal tissue, comprising detecting an expression level of at least one gene selected from the group of genes consisting of gene Nos. 1 to 562, and more preferably, expression levels of one or more of the genes MBNL2, FABP4, UBE2C, and BIRC5, Preferably the assay further comprises means for correlating the expression level to at least one standard expression level and/or at least one reference pattern for a signature including two or more of the genes MBNL2, FABP4, UBE2C, and BIRC5. In another preferred embodiment, said signature further includes a second group, consisting of one or more of the genes COL18A1, COL4A1, ACTA2, MSN, KPNA2 and CDC25B.

The means for correlating preferably includes one or more expression levels and/or reference patterns or scores for use in comparing or correlating the expression levels or patterns obtained from a tumor under examination to a standard expression level. Preferably the invention relates to an assay for determining an expression pattern of a bladder cell, comprising at least a first marker and optionally another marker, wherein the first marker is a gene from a first gene group as defined above, and the other marker is a gene from the second gene group as defined above (COL18A1, COL4A1, ACTA2, MSN, KPNA2 and CDC25B), correlating the first expression level and/or the second expression level to a standard level of the assessed genes to predict the prognosis of a biological condition in the animal tissue.

As discussed above the marker may be detected with any nucleotide probe, such as a DNA, RNA, PNA, or LNA probe capable of hybridizing to mRNA or gene products indicative of the expression level. The hybridization conditions are preferably as described below for probes. In another embodiment the marker is detected with an antibody capable of specifically binding the expression product in question.

Patterns or scores can be compared manually by a person or by a computer. An algorithm can be used to detect similarities and differences. The algorithm may score and compare, for example, the genes which are expressed and the genes which are not expressed. Alternatively, the algorithm may look for changes in intensity of expression of a particular gene or marker and score changes in intensity between two samples. Similarities may be determined on the basis of genes which are expressed in both samples and genes which are not expressed in both samples or on the basis of genes whose intensities of expression are numerically similar.

Generally, the detection operation will be performed using a reader device external to the diagnostic device. However, it may be desirable in some cases to incorporate the data gathering operation into the diagnostic device itself. The detection apparatus may be a fluorescence detector, or a spectroscopic detector, or another detector.

Although hybridization is one type of specific interaction which is clearly useful for this mapping embodiment, antibody reagents may also be very useful. Gathering data from the various analysis operations, e.g. oligonucleotide and/or microcapillary arrays will typically be carried out using methods known in the art. For example, the arrays may be scanned using lasers to excite fluorescently labeled targets that have hybridized to regions of probe arrays mentioned above, which can then be imaged using charged coupled devices ("CCDs") for a wide field scanning of the array. Alternatively, another particularly useful method for gathering data from the arrays is through the use of laser confocal microscopy which combines the ease and speed of a readily automated process with high resolution detection.

Following the data gathering operation, the data will typically be reported to a data analysis operation. To facilitate the sample analysis operation, the data obtained by the reader from the device will typically be analyzed using a digital computer. Typically, the computer will be appropriately programmed for receipt and storage of the data from the device, as well as for analysis and reporting of the data gathered, i.e., interpreting fluorescence data to determine the sequence of hybridizing probes, normalization of background and single base mismatch hybridizations, ordering of sequence data in SBH applications, and the like.

The invention also relates to a pharmaceutical composition for treating a biological condition, such as bladder tumors. In one embodiment the pharmaceutical composition comprises one or more of the peptides being expression products as defined above. In a preferred embodiment, the peptides are bound to carriers. The peptides may suitably be coupled to a polymer carrier, for example a protein carrier, such as BSA. Such formulations are well-known to the person skilled in the art.

The peptides may be suppressor peptides normally lost or decreased in tumor tissue administered in order to stabilize tumors towards a less malignant stage. In another embodiment the peptides are onco-peptides capable of eliciting an immune response towards the tumor cells.

In another embodiment the pharmaceutical composition comprises genetic material, either genetic material for substitution therapy, or for suppressing therapy as discussed below. In a third embodiment the pharmaceutical composition comprises at least one antibody produced as described above.

In the present context the term pharmaceutical composition is used synonymously with the term medicament. The medicament of the invention comprises an effective amount of one or more of the compounds as defined above, or a composition as defined above in combination with pharmaceutically acceptable additives. Such medicament may suitably be formulated for oral, percutaneous, intramuscular, intravenous, intracranial, intrathecal, tracerebroventricular, intranasal or pulmonary administration. For most indications a localized or substantially localized application is preferred.

Strategies in formulation development of medicaments and compositions based on the compounds of the present invention generally correspond to formulation strategies for any other protein-based drug product. Potential problems and the guidance required to overcome these problems are addressed in several textbooks, e.g. "Therapeutic Peptides and Protein Formulation. Processing and Delivery Systems", Ed. A. K. Banga, Technomic Publishing AG, Basel, 1995. Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH buffering agents, or substances which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules and nanoparticles. The preparation may suitably be administered by injection, optionally at the site, where the active ingredient is to exert its effect. Additional formulations which are suitable for other modes of administration include suppositories, and in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are of the order of several hundred µg of active ingredient per administration with a preferred range of from about 0.1 µg to 1,000 µg, such as in the range of from about 1 µg to 300 µg, and especially in the range of from about 10 µg to 50 µg. Administration may be performed once or may be followed by subsequent administrations. The dosage will also depend on the route of administration and will vary with the age and weight of the subject to be treated. A preferred dosage would be at about 30 mg to 70 mg per 70 kg body weight.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promotes delivery of the active substance to its target.

In many instances, it will be necessary to administrate the formulation multiple times. Administration may be a continuous infusion, such as intraventricular infusion or administration in more doses such as more times a day, daily, more times a week, weekly, etc.

Vaccines

In a further embodiment the present invention relates to a vaccine for the prophylaxis or treatment of a biological condition comprising at least one expression product from at least one gene, said gene being expressed as defined above.

The term vaccines is used with its normal meaning, i.e preparations of immunogenic material for administration to induce in the recipient an immunity to infection or intoxication by a given infecting agent. Vaccines may be administered by intravenous injection or through oral, nasal and/or mucosal administration. Vaccines may be either simple vaccines prepared from one species of expression products, such as proteins or peptides, or a variety of expression products, or they may be mixed vaccines containing two or more simple vaccines. They are prepared in such a manner as not to destroy the immunogenic material, although the methods of preparation vary, depending on the vaccine.

The enhanced immune response achieved according to the invention can be attributable to e.g. an enhanced increase in the level of immunoglobulins or in the level of T-cells including cytotoxic T-cells, which will result in immunization of a significant portion of individuals exposed to said immunogenic composition or vaccine.

Compositions according to the invention may also comprise any carrier and/or adjuvant known in the art including functional equivalents thereof. Functionally equivalent carriers are capable of presenting the same immunogenic determinant in essentially the same steric conformation when used under similar conditions. Functionally equivalent adjuvants are capable of providing similar increases in the efficacy of the composition when used under similar conditions.

Therapy

The invention further relates to a method of treating individuals suffering from the biological condition in question, in particular for treating a bladder tumor. Accordingly, the invention relates to a method for reducing cell tumorigenicity or malignancy of a cell, said method comprising contacting a tumor cell with at least one peptide expressed by at least one gene selected from the group of genes consisting of gene No. 200-214, 233, 234, 235, 236, 244, 249, 251, 252, 255, 256, 259, 261, 262, 266, 268, 269, 273, 274, 275, 276, 277, 279, 280, 281, 282, 285, 286, 289, 293, 295 (MBNL2), 296, 299, 301, 304, 306, 307, 308, 311, 312, 313, 314, 320, 322, 323, 325, 326, 327, 328, 330, 331, 332, 333, 334, 338, 341, 342, 343, 345, 348, 349, 350, 351, 352, 353, 355, 357, 360, 361, 363, 366, 367, 370, 373, 374, 375, 376, 385, 386, 387, 389, 390, 392, 394, 398, 400, 401, 405, 406, 407, 408, 410, 411, 412, 414, 415, 416, 418, 424, 426, 428, 433, 434, 435, 436, 438, 439, 440, 441, 442, 443, 445, 446, 453, 460, 461, 463, 464, 465, 466, 467 (FABP4), 469, 470, 471, 472, 473, 475, 476, 477, 479, 480, 481, 482, 483, 485, 486, 487, 488, 490, 492, 494, 496, 497, 498, 499, 503, 515, 516, 517, 521, 526, 527, 528, 530, 532, 533, 537, 539, 540, 541, 542, 543, 545, 554, 557, 560. In order to increase the effect, several different peptides may be used simultaneously, such as wherein the tumor cell is contacted with at least two different peptides.

In one embodiment the invention relates to a method of substitution therapy, i.e., administration of genetic material generally expressed in normal cells, but lost decreased in biological condition cells (tumor suppressors). Thus, the invention relates to a method for reducing cell tumorigenicity or malignancy of a cell, said method comprising obtaining at least one gene selected from the group of genes consisting of gene No. 200-214, 233, 234, 235, 236, 244, 249, 251, 252, 255, 256, 259, 261, 262, 266, 268, 269, 273, 274, 275, 276, 277, 279, 280, 281, 282, 285, 286, 289, 293, 295 (MBNL2), 296, 299, 301, 304, 306, 307, 308, 311, 312, 313, 314, 320, 322, 323, 325, 326, 327, 328, 330, 331, 332, 333, 334, 338, 341, 342, 343, 345, 348, 349, 350, 351, 352, 353, 355, 357, 360, 361, 363, 366, 367, 370, 373, 374, 375, 376, 385, 386, 387, 389, 390, 392, 394, 398, 400, 401, 405, 406, 407, 408, 410, 411, 412, 414, 415, 416, 418, 424, 426, 428, 433, 434, 435, 436, 438, 439, 440, 441, 442, 443, 445, 446, 453, 460, 461, 463, 464, 465, 466, 467, 469, 470, 471, 472, 473, 475, 476 (FABP4), 477, 479, 480, 481, 482, 483, 485, 486, 487, 488, 490, 492, 494, 496, 497, 498, 499, 503, 515, 516, 517, 521, 526, 527, 528, 530, 532, 533, 537, 539, 540, 541, 542, 543, 545, 554, 557, 560, introducing said at least one gene into the tumor cell in a manner allowing expression of said gene(s).

In one embodiment at least one gene is introduced into the tumor cell. In another embodiment at least two genes are introduced into the tumor cell. In one aspect of the invention, small molecules that either inhibit increased gene expression or their effects or substitute decreased gene expression or their effects, are introduced to the cellular environment or the cells. Application of small molecules to tumor cells may be performed by e.g. local application or intravenous injection or by oral ingestion. Small molecules have the ability to restore function of reduced gene expression in tumor or cancer tissue.

In another aspect the invention relates to a therapy whereby genes (increase and/or decrease) which generally are correlated to disease are inhibited by one or more of the following methods: A method for reducing cell tumorigenicity or malignancy of a cell, said method comprising obtaining at least one nucleotide probe capable of hybridizing with at least one gene of a tumor cell, said at least one gene being selected from the group of genes consisting of gene Nos. 1-199, 215-232, 237, 238, 239, 240, 241, 242, 243, 245, 246, 247, 248, 250, 253, 254, 257, 258, 260, 263, 264, 265, 267, 270, 271, 272, 278, 283, 284, 287, 288, 290, 291, 292, 294, 297, 298, 300, 302, 303, 305, 309, 310, 315, 316, 317, 318, 319, 321, 324, 329, 335, 336, 337, 339, 340, 344, 346, 347, 354, 356, 358, 359, 362, 364, 365, 368, 369, 371, 372, 377, 378, 379, 380, 381, 382, 383, 384, 388, 391, 393, 395, 396, 397, 399, 402, 403, 404, 409, 413, 417, 419, 420, 421, 422, 423, 425, 427, 429, 430, 431, 432, 437 (BIRC5), 444, 447, 448, 449, 450, 451, 452, 454, 455, 456, 457, 458, 459, 462, 468, 474, 478, 484, 489, 491, 493, 495, 500, 501, 502, 504, 505, 506, 507, 508, 509, 510, 511, 512, 513, 514, 518, 519, 520, 522, 523, 524, 525, 529, 531, 534, 535, 536, 538, 544, 546, 547, 548, 549, 550, 551, 552, 553, 555, 556, 558, 559, 561, 562, introducing said at least one nucleotide probe into the tumor cell in a manner allowing the probe to hybridize to the at least one gene, thereby inhibiting expression of said at least one gene. This method is preferably based on anti-sense technology, whereby the hybridization of said probe to the gene leads to a down-regulation of said gene.

In another preferred embodiment, the method for reducing cell tumorigenicity or malignancy of a cell is based on RNA interference, comprising small interfering RNAs (siRNAs) specifically directed against at least one gene being selected from the group of genes consisting of gene Nos. 1-199, 215-232, 237, 238, 239, 240, 241, 242, 243, 245, 246, 247, 248, 250, 253, 254, 257, 258, 260, 263, 264, 265, 267, 270, 271, 272, 278, 283, 284, 287, 288, 290, 291, 292, 294, 297, 298, 300, 302, 303, 305, 309, 310, 315, 316, 317, 318, 319, 321, 324, 329, 335, 336, 337, 339, 340, 344, 346, 347, 354, 356, 358, 359, 362, 364, 365, 368, 369, 371, 372, 377, 378, 379, 380, 381, 382, 383, 384, 388, 391, 393, 395, 396, 397, 399, 402, 403, 404, 409, 413, 417, 419, 420, 421, 422, 423, 425, 427, 429, 430, 431, 432, 437 (BIRC5), 444, 447, 448, 449, 450, 451, 452, 454, 455, 456, 457, 458, 459, 462, 468, 474, 478, 484, 489, 491, 493, 495, 500, 501, 502, 504, 505, 506, 507, 508, 509, 510, 511, 512, 513, 514, 518, 519, 520, 522, 523, 524, 525, 529, 531, 534, 535, 536, 538, 544, 546, 547, 548, 549, 550, 551, 552, 553, 555, 556, 558, 559, 561, 562.

The down-regulation may of course also be based on a probe capable of hybridizing to regulatory components of the genes in question, such as promoters. The hybridization may be tested in vitro under conditions corresponding to in vivo conditions. Typically, hybridization conditions are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary. There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example on a filter).

An example of a progression from lower to higher stringency conditions is the following: where the salt content is given as the relative abundance of SSG (a salt solution containing sodium chloride and sodium citrate; 2×SSG is 10-fold more concentrated than 0.2×SSG). Nucleic acids are hybridized at 42"C in 2×SSG/0.1% SOS (sodium dodecylsulfate; a detergent) and then washed in 0.2×SSG/0.1% SOS at room temperature (for conditions of low stringency); 0.2×SSG/0.1% SOS at 42° C. (for conditions of moderate stringency); and 0.1×SSG at 68° C. (for conditions of high stringency). Washing can be carried out using only one of the conditions given, or each of the conditions can be used (for example, washing for 10-15 minutes each in the order listed above). Any or all of the washes can be repeated. As mentioned above, optimal conditions will vary and can be determined empirically.

In another aspect a method of reducing tumoregeneicity relates to the use of antibodies against an expression product of a cell from the biological tissue. The antibodies may be produced by any suitable method, such as a method comprising the steps of obtaining expression product(s) from at least one gene said gene being expressed as defined above, immunizing a mammal with said expression product(s) and obtaining antibodies against the expression product.

The methods described above may be used for producing an assay for diagnosing a biological condition in animal tissue, or for identification of the origin of a piece of tissue. Further, the methods of the invention may be used for prediction of a disease course and treatment response. Furthermore, the invention relates to the use of a peptide as defined above for preparation of a pharmaceutical composition for the treatment of a biological condition in animal tissue. Furthermore, the invention relates to the use of a gene as defined above for preparation of a pharmaceutical composition for the treatment of a biological condition in animal tissue.

Also, the invention relates to the use of a probe as defined above for preparation of a pharmaceutical composition for the treatment of a biological condition in animal tissue.

The genetic material discussed above may be any of the described genes or functional parts thereof. The constructs may be introduced as a single DNA molecule encoding all of the genes, or different DNA molecules having one or more genes. The constructs may be introduced simultaneously or consecutively, each with the same or different markers. The gene may be linked to the complex as such or protected by any suitable system normally used for transfection, such as viral vectors or artificial viral envelope, liposomes or micelles, wherein the system is linked to the complex.

Numerous techniques for introducing DNA into eukaryotic cells are known to the skilled artisan. Often this is done by means of vectors, and often in the form of nucleic acid encapsulated by a (frequently virus-like) proteinaceous coat. Gene delivery systems may be applied to a wide range of clinical as well as experimental applications.

Vectors containing useful elements such as selectable and/or amplifiable markers, promoter/enhancer elements for expression in mammalian, particularly human, cells, and which may be used to prepare stocks of construct DNAs and for carrying out transfections are well known in the art. Many are commercially available.

Various techniques have been developed for modification of target tissue and cells in vivo. A number of virus vectors, discussed below, are known which allow transfection and random integration of the virus into the host. See, for example, Dubensky et al. (1984) Proc. Natl. Acad. Sci. USA 81:7529-7533; Kaneda et al., (1989) Science 243:375-378; Hiebert et al. (1989) Proc. Natl. Acad. Sci. USA 86:3594-3598; Hatzoglu et al., (1990) J. Biol. Chem. 265:17285-17293; Ferry et al. (1991) Proc. Natl. Acad. Sci. USA 88:8377-8381. Routes and modes of administering the vector include injection, e.g intravascularly or intramuscularly, inhalation, or other parenteral administration.

Advantages of adenovirus vectors for human gene therapy include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organism. Another vector which can express the DNA molecule of the present invention, and is useful in gene therapy, particularly in humans, is vaccinia virus, which can be rendered non-replicating (U.S. Pat. Nos. 5,225,336; 5,204,243; 5,155,020; 4,769,330).

Based on the concept of viral mimicry, artificial viral envelopes (AVE) are designed based on the structure and composition of a viral membrane, such as HIV-1 or RSV and used to deliver genes into cells in vitro and in vivo. See, for example, U.S. Pat. No. 5,252,348, Schreier H. et al., J. Mol. Recognit., 1995, 8:59-62; Schreier H et al., J. Biol. Chem., 1994, 269:9090-9098; Schreier, H., Pharm. Acta Helv. 1994, 68:145-159; Chander, R et al. Life Sci., 1992, 30 50:481-489, which references are hereby incorporated by reference in their entirety. The envelope is preferably produced in a two-step dialysis procedure where the "naked" envelope is formed initially, followed by unidirectional insertion of the viral surface glycoprotein of interest. This process and the physical characteristics of the resulting AVE are described in detail by Chander et al., (supra). Examples of AVE systems are (a) an AVE containing the HIV-1 surface glycoprotein gp160 (Chander et al., supra; Schreier et al., 1995, supra) or glycosyl phosphatidylinositol (GPI)-linked gp120 (Schreier et al., 1994, supra), respectively, and (b) an AVE containing the respiratory syncytial virus (RSV) attachment (G) and fusion (F) glycoproteins (Stecenko, A. A. et al., Pharm. Pharmacol. Lett. 1:127-129 (1992)). Thus, vesicles are constructed which mimic the natural membranes of enveloped viruses in their ability to bind to and deliver materials to cells bearing corresponding surface receptors. AVEs are used to deliver genes both by intravenous injection and by instillation in the lungs.

For example, AVEs are manufactured to mimic RSV, exhibiting the RSV F surface glycoprotein which provides selective entry into epithelial cells. F-AVE are loaded with a plasmid coding for the gene of interest (or a reporter gene such as CAT not present in mammalian tissue). The AVE system described herein in physically and chemically essentially identical to the natural virus yet is entirely "artificial", as it is constructed from phospholipids, cholesterol, and recombinant viral surface glycoproteins. Hence, there is no carry-over of viral genetic information and no danger of inadvertant viral infection. Construction of the AVEs in two independent steps allows for bulk production of the plain lipid envelopes which, in a separate second step, can then be marked with the desired viral glycoprotein, also allowing for the preparation of protein cocktail formulations if desired.

Another delivery vehicle for use in the present invention is based on the recent description of attenuated Shigella as a DNA delivery system (Sizemore, D. R. et al., Science 270:299-20 302 (1995), which reference is incorporated by reference in its entirety). This approach exploits the ability of Shigellae to enter epithelial cells and escape the phagocytic vacuole as a method for delivering the gene construct into the cytoplasm of the target cell. Invasion with as few as one to five bacteria can result in expression of the foreign plasmid DNA delivered by these bacteria.

A preferred type of mediator of nonviral transfection in vitro and in vivo is cationic (ammonium derivatized) lipids. These positively charged lipids form complexes with negatively charged DNA, resulting in DNA charged neutralization and compaction. The complexes are endocytosed upon association with the cell membrane, and the DNA somehow escapes the endosome, gaining access to the cytoplasm. Cationic lipid:DNA complexes appear highly stable under normal conditions. Studies of the cationic lipid DOTAP suggest the complex dissociates when the inner layer of the cell membrane is destabilized and anionic lipids from the inner layer displace DNA from the cationic lipid. Several cationic lipids are available commercially. Two of these, DMR1 and DC-cholesterol, have been used in human clinical trials. First generation cationic lipids are less efficient than viral vectors. For delivery to lung, any inflammatory responses accompanying the liposome administration are reduced by changing the delivery mode to aerosol administration, which distributes the dose more evenly.

Drug Screening

Genes identified as changing in various stages of bladder cancer can be used as markers for drug screening. Thus, by treating bladder cancer cells with test compounds or extracts, and monitoring the expression of genes identified as changing in the progression of bladder cancers, one can identify compounds or extracts which change expression of genes to a pattern which is of an earlier stage or even of normal bladder mucosa. It is also within the scope of the invention to use small molecules in drug screening.

The following are non-limiting examples illustrating the present invention.

EXAMPLES

Example 1

Identification of a Molecular Signature Defining Disease Progression in Patients with Superficial Bladder Carcinoma Patient Samples Bladder tumor biopsies were obtained directly from surgery after removal of the necessary amount of tissue for routine pathology examination. The tumors were frozen at −80° C. in a guanidinium thiocyanate solution for preservation of the RNA. Informed consent was obtained in all cases, and the protocols were approved by the scientific ethical committee of Aarhus County. The samples for the no progression group were selected by the following criteria: a) Ta or T1 tumors with no prior higher stage tumors; b) a minimum follow up period of 12 months to the most recent routine cystoscopy examination of the bladder with no occurrence of tumors of higher stage. The samples for the progression group were selected by two criteria: a) Ta or T1 tumors with no prior higher stage tumors; b) subsequent progression to a higher stage tumor, see Table 1.

TABLE 1

Clinical data on all patients involved in the study

| Group | Sample | Hist. | Progressed to: | Time to progression | Follow-up time months |
|---|---|---|---|---|---|
| Training set | | | | | |
| No prog. | 150-6 | Ta gr3 | — | — | 44 |
| No prog. | 997-1 | Ta gr2 | — | — | 24 |
| No prog. | 833-2 | Ta gr3 | — | — | 35 |
| No prog. | 1070-1 | Ta gr3 | — | — | 33 |
| No prog. | 968-1 | Ta gr2 | — | — | 26 |
| No prog. | 625-1 | T1 gr3 | — | — | 12 |

TABLE 1-continued

Clinical data on all patients involved in the study

| Group | Sample | Hist. | Progressed to: | Time to progression | Follow-up time months |
|---|---|---|---|---|---|
| No prog. | 880-1 | T1 gr3 | — | — | 47 |
| No prog. | 815-1 | Ta gr2 | — | — | 49 |
| No prog. | 861-1 | Ta gr2 | — | — | 45 |
| No prog. | 669-1 | Ta gr2 | — | — | 55 |
| No prog. | 368-4 | Ta gr2 | — | — | 16 |
| No prog. | 898-1 | Ta gr2 | — | — | 17 |
| No prog. | 576-6 | Ta gr2 | — | — | 36 |
| Prog. | 747-3 | Ta gr2 | T1 gr3 | 6 | — |
| Prog. | 956-2 | Ta gr3 | T1 gr3 | 27 | — |
| Prog. | 1083-1 | Ta gr2 | T1 gr3 | 1 | — |
| Prog. | 686-3 | Ta gr2 | T1 gr2 | 6 | — |
| Prog. | 795-13 | Ta gr2 | T1 gr3 | 4 | — |
| Prog. | 865-1 | Ta gr2 | T1 gr2 | 5 | — |
| Prog. | 112-2 | Ta gr3 | T1 gr3 | 7 | — |
| Prog. | 825-3 | Ta gr3 | T1 gr3 | 6 | — |
| Prog. | 679-2 | Ta gr2 | T2+ gr3 | 31 | — |
| Prog. | 941-4 | Ta gr3 | T2+ gr3 | 10 | — |
| Prog. | 607-1 | T1 gr2 | T2+ gr3 | 3 | — |
| Prog. | 1017-1 | T1 gr3 | T2+ gr3 | 8 | — |
| Prog. | 1276-1 | T1 gr3 | T2+ gr3 | 7 | — |
| Prog. | 501-1 | T1 gr3 | T2+ gr3 | 26 | — |
| Prog. | 744-1 | T1 gr3 | T2+ gr3 | 14 | — |
| Prog. | 839-1 | T1 gr3 | T2+ gr3 | 12 | — |
| Test set | | | | | |
| No prog. | 1008-1 | Ta gr2 | — | — | 55 |
| No prog. | 1060-1 | Ta gr2 | — | — | 48 |
| No prog. | 1086-1 | Ta gr2 | — | — | 34 |
| No prog. | 1105-1 | Ta gr2 | — | — | 31 |
| No prog. | 1145-1 | Ta gr2 | — | — | 39 |
| No prog. | 1352-1 | Ta gr2 | — | — | 26 |
| No prog. | 829-1 | Ta gr2 | — | — | 37 |
| No prog. | 942-1 | Ta gr2 | — | — | 37 |
| No prog. | 780-1 | Ta gr2 | — | — | 50 |
| Prog | 1327-1 | Ta gr2 | T1 gr3 | 8 | — |
| Prog. | 1062-2 | Ta gr3 | T1 gr3 | 4 | — |
| Prog. | 1354-1 | Ta gr3 | T1 gr3 | 8 | — |
| Prog. | 1093-1 | Ta gr3 | T1 gr3 | 5 | — |
| Prog. | 925-7 | Ta gr2 | T1 gr3 | 4 | — |
| Prog. | 962-10 | Ta gr0 | T2+ gr3 | 1 | — |
| Prog. | 970-1 | Ta gr3 | T2+ gr3 | 1 | — |
| Prog. | 1027-1 | Ta gr3 | T2+ gr3 | 2 | — |
| Prog. | 1252-1 | T1 gr3 | T2+ gr3 | 5 | — |
| Prog. | 1191-1 | T1 gr4 | T2+ gr4 | 1 | — |

Delineation of Non-Progressing Tumors from Progressing Tumors

To delineate non-progressing tumors from progressing tumors we now profiled a total of 29 bladder tumor samples; 13 early stage bladder tumor samples without progression (median follow-up time 35 months) and 16 early stage bladder tumor samples with progression (median time to progression 7 months). See Table 1 for description of patient disease courses. We analyzed gene expression changes between the two groups of tumors by hybridizing the labeled RNA samples to customized Affymetrix GeneChips with 59,000 probe-sets to cover virtually the entire transcriptome (~95% coverage). Low expressed and non-varying probe-sets were eliminated from the data set and the resulting 6,647 probe-sets that showed variation across the tumor samples were subjected to further analysis. These probe-sets represent 5,356 unique genes (Unigene clusters).

Gene Expression Similarities Between Tumor Biopsies

We analyzed gene expression similarities between the tumor biopsies using unsupervised hierarchical cluster analysis (FIG. 1). This showed a notable distinction between the non-progressing and the progressing tumors when using the 3,197 most varying probe-sets (s.d.≥75) for clustering (4 errors; $\chi^2$ test, P=0.0001). Using other gene-sets based on different gene variation criteria demonstrated the same distinction between the tumor groups. Two of the samples that show later progression (825-3 and 112-2) were found in the non-progression branch of the cluster dendrogram and two of the non-progressing samples (815-1 and 150-6) were found in the progression branch. This distinct separation of the samples indicated a considerable biological difference between the two groups of tumors. Notably, the T1 tumors did not cluster separately from Ta tumors; however, they did form a sub-cluster in the progressing branch of the dendrogram. Based on this we decided to look for a general signature of progression disregarding pathologic staging of the tumors.

Selection of the 100 Most Significantly Up-Regulated Genes in Each Group Using T-Test Statistics We delineated the non-progressing tumors from the progressing tumors by selecting the 100 most significantly up-regulated genes in each group using t-test statistics (Table 2). Among the genes up regulated in the non-progressing group we found the SERPINIB5 and FAT tumor suppressor genes and the FGFR3 gene, which has been shown to be frequently mutated in superficial bladder tumors with low recurrence rates (van Rhijn et al. 2001). Among the genes up regulated in the progressing group we found the PLK (Yuan et al. 1997), CDC25B (Galaktionov et al. 1991), CDC20 (Weinstein et al. 1994) and MCM7 (Hiraiwa et al. 1997) genes, which are involved in regulating cell cycle and cell proliferation. Furthermore, in this group we identified the WHISC1, DD96 and GRB7 genes, which have been predicted/computed (Gene Ontology) to be involved in oncogenic transformation. Another interesting candidate in this group is the NRG1 gene, which through interaction with the HER2/HER3 receptors has been found to induce differentiation of lung epithelial cells (Liu & Kern 2002). The PPARD gene was also identified as up regulated in the tumors that show later progression. Disruption of this gene was found to decrease tumorigenicity in colon cancer cells (Park et al. 2001). Furthermore, PPARD regulates VEGF expression in bladder cancer cell lines (Fauconnet et al. 2002).

TABLE 2

The 200 best markers of progression

| Eos Hu03 ID | Unigene Build 133 | Description | T-test | 5% perm | Exemplar accession# |
|---|---|---|---|---|---|
| 416640 | Hs.79404 | neuron-specific protein | 6.03 | 5.62 | BE262478 |
| 442220 | Hs.8148 | selenoprotein T | 5.98 | 5.06 | AL037800 |
| 426982 | Hs.173091 | ubiquitin-like 3 | 5.9 | 4.88 | AA149707 |
| 416815 | Hs.80120 | UDP-N-acetyl-alpha-D-galactosamine:polypeptide N-acetylgalactosaminyltransferase 1 (GalNAc-T1) | 5.52 | 4.67 | U41514 |
| 435521 | Hs.6361 | mitogen-activated protein kinase kinase 1 interacting protein 1 | 5.24 | 4.51 | W23814 |
| 447343 | Hs.236894 | ESTs, Highly similar to S02392 alpha-2-macroglobulin receptor precursor [*H. sapiens*] | 5.23 | 4.44 | AA256641 |
| 452829 | Hs.63368 | ESTs, Weakly similar to TRHY_HUMAN TRICHOHYALI [*H. sapiens*] | 4.95 | 4.39 | AI955579 |
| 414895 | Hs.116278 | *Homo sapiens* cDNA FLJ13571 fis, clone PLACE1008405 | 4.94 | 4.31 | AW894856 |
| 426252 | Hs.28917 | ESTs | 4.9 | 4.26 | BE176980 |
| 444604 | Hs.11441 | chromosome 1 open reading frame 8 | 4.89 | 4.17 | AW327695 |
| 409632 | Hs.55279 | serine (or cysteine) proteinase inhibitor, clade B (ovalbumin), member 5 | 4.89 | 4.13 | W74001 |
| 446556 | Hs.15303 | KIAA0349 protein | 4.87 | 4.08 | AB002347 |
| 426799 | Hs.303154 | popeye protein 3 | 4.86 | 4.03 | H14843 |
| 428115 | Hs.300855 | KIAA0977 protein | 4.86 | 4.00 | AB023194 |
| 419847 | Hs.184544 | *Homo sapiens*, clone IMAGE: 3355383, mRNA, partial cds | 4.82 | 3.97 | AW390601 |
| 417839 | Hs.82712 | fragile X mental retardation, autosomal homolog 1 | 4.8 | 3.93 | AI815732 |
| 428284 | Hs.183435 | NM_004545: *Homo sapiens* NADH dehydrogenase (ubiquinone) 1 beta subcomplex, 1 (7 kD, MNLL) (NDUFB1), mRNA. | 4.78 | 3.92 | AA535762 |
| 422929 | Hs.94011 | ESTs, Weakly similar to MGB4_HUMAN MELANOMA-ASSOCIATED ANTIGEN B4 [*H. sapiens*] | 4.77 | 3.90 | AA356694 |
| 414762 | Hs.77257 | KIAA0068 protein | 4.72 | 3.86 | AW068349 |
| 453395 | Hs.377915 | mannosidase, alpha, class 2A, member 1 | 4.71 | 3.84 | D63998 |
| 421311 | Hs.283609 | hypothetical protein PRO2032 | 4.65 | 3.82 | N71848 |
| 446847 | Hs.82845 | *Homo sapiens* cDNA: FLJ21930 fis. clone HEP04301, highly similar to HSU90916 Human clone 23815 mRNA sequence | 4.65 | 3.82 | T51454 |
| 413840 | Hs.356228 | RNA binding motif protein, X chromosome | 4.62 | 3.79 | AI301558 |
| 418321 | Hs.84087 | KIAA0143 protein | 4.62 | 3.78 | D63477 |
| 430604 | Hs.247309 | succinate-CoA ligase, GDP-forming, beta subunit | 4.61 | 3.74 | AV650537 |
| 423185 | Hs.380062 | ornithine decarboxylase antizyme 1 | 4.61 | 3.74 | BE299590 |
| 417615 | Hs.82314 | hypoxanthine phosphoribosyltransferase 1 (Lesch-Nyhan syndrome) | 4.6 | 3.70 | BE548641 |
| 418504 | Hs.85335 | *Homo sapiens* mRNA; cDNA DKFZp564D1462 (from clone DKFZp564D1462) | 4.59 | 3.68 | BE159718 |
| 400846 | — | sortilin-related receptor, L(DLR class) A repeats-containing (SORL1) | 4.57 | 3.66 | — |
| 426028 | Hs.172028 | a disintegrin and metalloproteinase domain 10 (ADAM10) | 4.53 | 3.65 | NM_001110 |

TABLE 2-continued

The 200 best markers of progression

| Eos Hu03 ID | Unigene Build 133 | Description | T-test | 5% perm | Exemplar accession# |
|---|---|---|---|---|---|
| 425243 | Hs.155291 | KIAA0005 gene product | 4.47 | 3.63 | N89487 |
| 434978 | Hs.4310 | eukaryotic translation initiation factor 1A | 4.45 | 3.62 | AA321238 |
| 409513 | Hs.54642 | methionine adenosyltransferase II, beta | 4.43 | 3.59 | AW966728 |
| 433282 | Hs.49007 | hypothetical protein | 4.43 | 3.56 | BE539101 |
| 421628 | Hs.106210 | hypothetical protein FLJ10813 | 4.37 | 3.56 | AL121317 |
| 452170 | Hs.28285 | patched related protein translocated in renal cancer | 4.37 | 3.54 | AF064801 |
| 440014 | Hs.6856 | ash2 (absent, small, or homeotic, *Drosophila*, homolog)-like | 4.37 | 3.52 | AW960782 |
| 431857 | Hs.271742 | ADP-ribosyltransferase (NAD; poly (ADP-ribose) polymerase)-like 3 | 4.36 | 3.52 | W19144 |
| 417924 | Hs.82932 | cyclin D1 (PRAD1: parathyroid adenomatosis 1) | 4.35 | 3.51 | AU077231 |
| 421733 | Hs.1420 | fibroblast growth factor receptor 3 (achondroplasia, thanatophoric dwarfism) | 4.34 | 3.50 | AL119671 |
| 440197 | Hs.317714 | pallid (mouse) homolog, pallidin | 4.32 | 3.49 | AW340708 |
| 434055 | Hs.3726 | x 003 protein | 4.32 | 3.48 | AF168712 |
| 445831 | Hs.13351 | LanC (bacterial lantibiotic synthetase component C)-like 1 | 4.31 | 3.46 | NM_006055 |
| 439632 | Hs.334437 | hypothetical protein MGC4248 | 4.29 | 3.45 | AW410714 |
| 448813 | Hs.22142 | cytochrome b5 reductase b5R.2 | 4.28 | 3.44 | AF169802 |
| 449268 | Hs.23412 | hypothetical protein FLJ20160 | 4.28 | 3.43 | AW369278 |
| 429311 | Hs.198998 | conserved helix-loop-helix ubiquitous kinase | 4.28 | 3.42 | AF080157 |
| 423599 | Hs.31731 | peroxiredoxin 5 | 4.27 | 3.41 | AI805664 |
| 422913 | Hs.121599 | CGI-18 protein | 4.26 | 3.40 | NM_015947 |
| 418127 | Hs.83532 | membrane cofactor protein (CD46, trophoblast-lymphocyte cross-reactive antigen) | 4.26 | 3.39 | BE243982 |
| 425221 | Hs.155188 | TATA box binding protein (TBP)-associated factor, RNA polymerase II, F, 55 kD | 4.25 | 3.38 | AV649864 |
| 426682 | Hs.2056 | UDP glycosyltransferase 1 family, polypeptide A9 | 4.23 | 3.37 | AV660038 |
| 421101 | Hs.101840 | major histocompatibility complex, class I-like sequence | 4.23 | 3.37 | AF010446 |
| 444037 | Hs.380932 | CHMP1.5 protein | 4.22 | 3.35 | AV647686 |
| 443407 | Hs.348514 | ESTs, Moderately similar to 2109260A B cell growth factor [*H. sapiens*] | 4.21 | 3.35 | AA037683 |
| 448625 | Hs.178470 | hypothetical protein FLJ22662 | 4.21 | 3.34 | AW970786 |
| 450997 | Hs.35254 | hypothetical protein FLB6421 | 4.16 | 3.34 | AW580830 |
| 444336 | Hs.10882 | HMG-box containing protein 1 | 4.15 | 3.33 | AF019214 |
| 416977 | Hs.406103 | hypothetical protein FKSG44 | 4.14 | 3.32 | AW130242 |
| 420613 | Hs.406637 | ESTs, Weakly similar to A47582 B-cell growth factor precursor [*H. sapiens*] | 4.13 | 3.31 | AI873871 |
| 414843 | Hs.77492 | heterogeneous nuclear ribonucleoprotein A0 | 4.1 | 3.30 | BE386038 |
| 408288 | Hs.16886 | gb: zI73d06.r1 Stratagene colon (937204) *Homo sapiens* cDNA clone 5', mRNA sequence | 4.09 | 3.29 | AA053601 |
| 422043 | Hs.110953 | retinoic acid induced 1 | 4.09 | 3.29 | AL133649 |
| 432864 | Hs.359682 | calpastatin | 4.08 | 3.28 | D16217 |
| 410047 | Hs.379753 | zinc finger protein 36 (KOX 18) | 4.06 | 3.28 | AI167810 |
| 400773 | — | NM_003105*: *Homo sapiens* sortilin-related receptor, L(DLR class) A repeats-containing (SORL1), mRNA. | 4.06 | 3.27 | — |
| 423960 | Hs.136309 | SH3-containing protein SH3GLB1 | 4.05 | 3.27 | AA164516 |
| 449626 | Hs.112860 | zinc finger protein 258 | 4.04 | 3.27 | AA774247 |
| 429953 | Hs.226581 | COX15 (yeast) homolog, cytochrome c oxidase assembly protein | 4.04 | 3.24 | NM_004376 |
| 428901 | Hs.146668 | KIAA1253 protein | 4.02 | 3.24 | AI929568 |
| 420079 | Hs.94896 | PTD011 protein | 3.99 | 3.22 | NM_014051 |
| 436576 | Hs.77542 | ESTs, *Homo sapiens* platelet-activating factor receptor (PTAFR) | 3.98 | 3.21 | AI458213 |
| 412841 | Hs.101395 | hypothetical protein MGC11352 | 3.97 | 3.21 | AI751157 |
| 431604 | Hs.264190 | vacuolar protein sorting 35 (yeast homolog) | 3.96 | 3.21 | AF175265 |
| 428318 | Hs.356190 | ubiquitin B | 3.96 | 3.19 | BE300110 |
| 430677 | Hs.359784 | desmoglein 2 | 3.95 | 3.19 | Z26317 |
| 407955 | Hs.9343 | ESTs, RPTOR independent companion of MTOR, complex 2, RICTOR | 3.94 | 3.18 | BE536739 |
| 426177 | Hs.167700 | *Homo sapiens* cDNA FLJ10174 fis, clone HEMBA1003959 | 3.92 | 3.17 | AA373452 |
| 429802 | Hs.5367 | ESTs, Weakly similar to I38022 hypothetical protein [*H. sapiens*] | 3.92 | 3.17 | H09548 |
| 423810 | Hs.132955 | BCL2/adenovirus E1B 19 kD-interacting protein 3-like | 3.92 | 3.16 | AL132665 |
| 421475 | Hs.104640 | HIV-1 inducer of short transcripts binding protein; lymphoma related factor | 3.91 | 3.15 | AF000561 |
| 436472 | Hs.46366 | KIAA0948 protein | 3.91 | 3.14 | AL045404 |
| 434263 | Hs.79187 | ESTs, coxsackie virus and adenovirus receptor, CXADR | 3.9 | 3.13 | N34895 |
| 400843 | — | NM_003105*: *Homo sapiens* sortilin-related receptor, L(DLR class) A repeats-containing (SORL1), mRNA. | 3.9 | 3.13 | — |

TABLE 2-continued

The 200 best markers of progression

| Eos Hu03 ID | Unigene Build 133 | Description | T-test | 5% perm | Exemplar accession# |
|---|---|---|---|---|---|
| 440357 | Hs.20950 | phospholysine phosphohistidine inorganic pyrophosphate phosphatase | 3.89 | 3.12 | AA379353 |
| 437223 | Hs.330716 | Homo sapiens cDNA FLJ14368 fis, clone HEMBA1001122 | 3.88 | 3.12 | C15105 |
| 426125 | Hs.166994 | FAT tumor suppressor (Drosophila) homolog | 3.86 | 3.11 | X87241 |
| 432554 | Hs.278411 | NCK-associated protein 1 | 3.86 | 3.10 | AI479813 |
| 422506 | Hs.300741 | sorcin | 3.85 | 3.10 | R20909 |
| 413786 | Hs.13500 | ESTs, Homo sapiens major histocompatibility complex, class I-related, MR1 | 3.83 | 3.09 | AW613780 |
| 429561 | Hs.250646 | baculoviral IAP repeat-containing 6 | 3.83 | 3.08 | AF265555 |
| 404977 | — | Insulin-like growth factor 2 (somatomedin A) (IGF2) | 3.83 | 3.08 | — |
| 427722 | Hs.180479 | hypothetical protein FLJ20116 | 3.82 | 3.08 | AK000123 |
| 400844 | — | NM_003105*: Homo sapiens sortilin-related receptor, L(DLR class) A repeats-containing (SORL1), mRNA. | 3.82 | 3.08 | — |
| 426469 | Hs.363039 | methylmalonate-semialdehyde dehydrogenase | 3.81 | 3.07 | BE297886 |
| 439578 | Hs.350547 | nuclear receptor co-repressor/HDAC3 complex subunit | 3.81 | 3.06 | AW263124 |
| 426508 | Hs.170171 | glutamate-ammonia ligase (glutamine synthase) | 3.8 | 3.06 | W23184 |
| 448524 | Hs.21356 | hypothetical protein DKFZp762K2015 | 3.79 | 3.06 | AB032948 |
| 448357 | Hs.108923 | RAB38, member RAS oncogene family | 3.79 | 3.06 | N20169 |
| 425097 | Hs.154545 | PDZ domain containing guanine nucleotide exchange factor(GEF)1 | 3.77 | 3.05 | NM_014247 |
| 421649 | Hs.106415 | peroxisome proliferative activated receptor, delta | 5.76 | 5.50 | AA721217 |
| 427747 | Hs.180655 | serine/threonine kinase 12 | 5.41 | 5.03 | AW411425 |
| 439010 | Hs.75216 | Homo sapiens cDNA FLJ13713 fis, clone PLACE2000398, moderately similar to LAR PROTEIN PRECURSOR (LEUKOCYTE ANTIGEN RELATED) (EC 3.1.3.48) | 4.57 | 4.80 | AW170332 |
| 438818 | Hs.30738 | ESTs | 4.49 | 4.59 | AW979008 |
| 438013 | Hs.15670 | ESTs, transcribed locus from chromosome 16 | 4.42 | 4.50 | AI002106 |
| 452929 | Hs.172816 | neuregulin 1 | 4.37 | 4.40 | AW954938 |
| 404826 | — | Target Exon | 4.22 | 4.32 | — |
| 429124 | Hs.196914 | minor histocompatibility antigen HA-1 | 4.2 | 4.26 | AW505086 |
| 421505 | Hs.285641 | KIAA1111 protein | 4.16 | 4.24 | AW249934 |
| 428712 | Hs.190452 | KIAA0365 gene product | 4.14 | 4.19 | AW085131 |
| 427239 | Hs.356512 | ubiquitin carrier protein | 4.11 | 4.10 | BE270447 |
| 421595 | Hs.301685 | KIAA0620 protein | 4.1 | 4.07 | AB014520 |
| 433844 | Hs.179647 | Homo sapiens cDNA FLJ12195 fis, clone MAMMA1000865 | 4.04 | 4.02 | AA610175 |
| 443679 | Hs.9670 | hypothetical protein FLJ10948 | 4.01 | 4.00 | AK001810 |
| 422959 | Hs.349256 | paired immunoglobulin-like receptor beta | 4.01 | 3.98 | AV647015 |
| 452012 | Hs.279766 | kinesin family member 4A | 3.98 | 3.96 | AA307703 |
| 435320 | Hs.117864 | ESTs | 3.97 | 3.91 | AA677934 |
| 456332 | Hs.399939 | gb: nc39d05.r1 NCI_CGAP_Pr2 Homo sapiens cDNA clone, mRNA sequence | 3.95 | 3.88 | AA228357 |
| 427999 | Hs.181369 | ubiquitin fusion degradation 1-like | 3.94 | 3.86 | AI435128 |
| 427681 | Hs.284232 | tumor necrosis factor receptor superfamily, member 12 (translocating chain-association membrane protein) | 3.93 | 3.81 | AB018263 |
| 413929 | Hs.75617 | collagen, type IV, alpha 2 | 3.93 | 3.79 | BE501689 |
| 420116 | Hs.95231 | FH1/FH2 domain-containing protein | 3.9 | 3.77 | NM_013241 |
| 433914 | Hs.112160 | Homo sapiens DNA helicase homolog (PIF1) mRNA, partial cds | 3.88 | 3.75 | AF108138 |
| 420732 | Hs.367762 | ESTs | 3.87 | 3.74 | AA789133 |
| 452517 | — | gb: RC-BT068-130399-068 BT068 Homo sapiens cDNA, mRNA sequence | 3.84 | 3.70 | AI904891 |
| 437524 | Hs.385719 | ESTs, meiosis inhibitor 1, MEI1 | 3.82 | 3.68 | AI627565 |
| 435158 | Hs.65588 | DAZ associated protein 1 | 3.8 | 3.66 | AW663317 |
| 448780 | Hs.267749 | Human DNA sequence from clone 366N23 on chromosome 6q27. Contains two genes similar to consecutive parts of the C. elegans UNC-93 (protein 1, C46F11.1) gene, a KIAA0173 and Tubulin-Tyrosine Ligase LIKE gene, a Mitotic Feedback Control Protein MADP2 H | 3.8 | 3.65 | W92071 |
| 445084 | Hs.250848 | hypothetical protein FLJ14761 | 3.79 | 3.64 | H38914 |
| 423138 | — | gb: EST385571 MAGE resequences, MAGM Homo sapiens cDNA, mRNA sequence | 3.75 | 3.60 | AW973426 |
| 419602 | Hs.91521 | hypothetical protein | 3.74 | 3.59 | AW248434 |
| 442549 | Hs.8375 | TNF receptor-associated factor 4 | 3.74 | 3.58 | AI751601 |
| 450893 | Hs.25625 | hypothetical protein FLJ11323 | 3.73 | 3.55 | AK002185 |
| 414223 | Hs.238246 | hypothetical protein FLJ22479 | 3.73 | 3.55 | AA954566 |
| 444312 | Hs.351142 | ESTs | 3.72 | 3.53 | R44007 |
| 425205 | Hs.155106 | receptor (calcitonin) activity modifying protein 2 | 3.71 | 3.51 | NM_005854 |
| 432327 | Hs.274363 | neuroglobin | 3.71 | 3.49 | R36571 |

TABLE 2-continued

The 200 best markers of progression

| Eos Hu03 ID | Unigene Build 133 | Description | T-test | 5% perm | Exemplar accession# |
|---|---|---|---|---|---|
| 451970 | Hs.211046 | ESTs, WD repeat domain 88, WDR88 | 3.67 | 3.48 | AI825732 |
| 408049 | Hs.345588 | desmoplakin (DPI, DPII) | 3.67 | 3.45 | AW076098 |
| 440100 | Hs.158549 | ESTs, Weakly similar to T2D3_HUMAN TRANSCRIPTION INITIATION FACTOR TFIID 135 KDA SUBUNIT [H. sapiens] | 3.66 | 3.45 | BE382685 |
| 426468 | Hs.117558 | ESTs, transcribed locus from chromosome 17 | 3.65 | 3.43 | AA379306 |
| 402384 | — | NM_007181*: Homo sapiens mitogen-activated protein kinase kinase kinase kinase 1 (MAP4K1), mRNA. | 3.64 | 3.43 | — |
| 458132 | Hs.103267 | hypothetical protein FLJ22548 similar to gene trap PAT 12 | 3.64 | 3.42 | AW247012 |
| 447400 | Hs.18457 | hypothetical protein FLJ20315 | 3.64 | 3.42 | AK000322 |
| 443893 | Hs.115472 | ESTs, Weakly similar to 2004399A chromosomal protein [H. sapiens] | 3.63 | 3.41 | BE079602 |
| 424959 | Hs.153937 | activated p21cdc42Hs kinase | 3.62 | 3.40 | NM_005781 |
| 409586 | Hs.55044 | DKFZP586H2123 protein | 3.6 | 3.39 | AL050214 |
| 445692 | Hs.182099 | ESTs, Transcription factor B1, mitochondrial (TFB1M) | 3.6 | 3.37 | AI248322 |
| 433052 | Hs.293003 | ESTs, Weakly similar to PC4259 ferritin associated protein [H. sapiens] | 3.6 | 3.36 | AW971983 |
| 421782 | Hs.108258 | actin binding protein; macrophin (microfilament and actin filament cross-linker protein) | 3.59 | 3.35 | AB029290 |
| 414907 | Hs.77597 | polo (Drosophia)-like kinase | 3.58 | 3.34 | X90725 |
| 454639 | — | gb: RC2-ST0158-091099-011-d05 ST0158 Homo sapiens cDNA, mRNA sequence | 3.57 | 3.33 | AW811633 |
| 434547 | Hs.106124 | ESTs | 3.56 | 3.32 | R26240 |
| 439130 | Hs.375195 | ESTs, family with sequence similarity 101, member B, FAM101B | 3.55 | 3.32 | AA306090 |
| 413564 | — | gb: 601146990F1 NIH_MGC_19 Homo sapiens cDNA clone 5', mRNA sequence | 3.54 | 3.31 | BE260120 |
| 443471 | Hs.398102 | Homo sapiens clone FLB3442 PRO0872 mRNA, complete cds | 3.53 | 3.31 | AW236939 |
| 424415 | Hs.146580 | enolase 2, (gamma, neuronal) | 3.52 | 3.30 | NM_001975 |
| 405036 | — | NM_021628*: Homo sapiens arachidonate lipoxygenase 3 (ALOXE3), mRNA. VERSION NM_020229.1 GI | 3.52 | 3.29 | — |
| 422068 | Hs.104520 | Homo sapiens cDNA FLJ13694 fis, clone PLACE2000115 | 3.52 | 3.29 | AI807519 |
| 424244 | Hs.143601 | hypothetical protein hCLA-iso | 3.52 | 3.28 | AV647184 |
| 451867 | Hs.27192 | hypothetical protein dJ1057B20.2 | 3.51 | 3.26 | W74157 |
| 429187 | Hs.163872 | ESTs, Weakly similar to S65657 alpha-1C-adrenergic receptor splice form 2 [H. sapiens] | 3.49 | 3.26 | AA447648 |
| 415200 | Hs.78202 | SWI/SNF related, matrix associated, actin dependent regulator of chromatin, subfamily a, member 4 | 3.48 | 3.25 | AL040328 |
| 405667 | — | Target Exon | 3.48 | 3.25 | — |
| 421075 | Hs.101474 | KIAA0807 protein | 3.47 | 3.23 | AB018350 |
| 424909 | Hs.153752 | cell division cycle 25B | 3.46 | 3.22 | S78187 |
| 451164 | Hs.60659 | ESTs, Weakly similar to T46471 hypothetical protein DKFZp434L0130.1 [H. sapiens] | 3.46 | 3.21 | AA015912 |
| 438644 | Hs.129037 | ESTs | 3.46 | 3.20 | AI126162 |
| 432258 | Hs.293039 | ESTs, transcribed locus from chromosome 7 | 3.45 | 3.19 | AW973078 |
| 411817 | Hs.72241 | mitogen-activated protein kinase kinase 2 | 3.45 | 3.19 | BE302900 |
| 414918 | Hs.72222 | hypothetical protein FLJ13459 | 3.45 | 3.18 | AI219207 |
| 437256 | Hs.97871 | Homo sapiens, clone IMAGE: 3845253, mRNA, partial cds | 3.43 | 3.17 | AL137404 |
| 404208 | — | C6001282: gi|4504223|ref|NP_000172.1| glucuronidase, beta [Homo sapiens] gi|114963|sp|P082 | 3.42 | 3.16 | — |
| 421989 | Hs.110457 | Wolf-Hirschhorn syndrome candidate 1 | 3.4 | 3.15 | AJ007042 |
| 438942 | Hs.6451 | PRO0659 protein | 3.39 | 3.14 | AW875398 |
| 412649 | Hs.74369 | integrin, alpha 7 | 3.38 | 3.14 | NM_002206 |
| 414840 | Hs.23823 | hairy/enhancer-of-split related with YRPW motif-like | 3.37 | 3.13 | R27319 |
| 434831 | Hs.273397 | KIAA0710 gene product | 3.35 | 3.12 | AA248060 |
| 431842 | Hs.271473 | epithelial protein up-regulated in carcinoma, membrane associated protein 17 | 3.34 | 3.11 | NM_005764 |
| 402328 | — | Target Exon | 3.34 | 3.10 | — |
| 405371 | — | NM_005569*: Homo sapiens LIM domain kinase 2 (LIMK2), transcript variant 2a, mRNA. | 3.33 | 3.10 | — |
| 441650 | Hs.132545 | ESTs, transcribed locus from chromosome 17 | 3.32 | 3.09 | AI261960 |
| 418629 | Hs.86859 | growth factor receptor-bound protein 7 | 3.3 | 3.09 | BE247550 |
| 406002 | — | Target Exon | 3.3 | 3.08 | — |
| 420307 | Hs.66219 | ESTs, chromosome 17 open reading frame 56 (C17orf56) | 3.29 | 3.08 | AW502869 |
| 425093 | Hs.154525 | KIAA1076 protein | 3.28 | 3.07 | AB028999 |

TABLE 2-continued

The 200 best markers of progression

| Eos Hu03 ID | Unigene Build 133 | Description | T-test | 5% perm | Exemplar accession# |
|---|---|---|---|---|---|
| 427351 | Hs.123253 | hypothetical protein FLJ22009 | 3.28 | 3.07 | AW402593 |
| 417900 | Hs.82906 | CDC20 (cell division cycle 20, *S. cerevisiae*, homolog) | 3.28 | 3.06 | BE250127 |
| 457228 | Hs.195471 | Human cosmid CRI-JC2015 at D10S289 in 10sp13 | 3.27 | 3.05 | U15177 |
| 421026 | Hs.101067 | GCN5 (general control of amino-acid synthesis, yeast, homolog)-like 2 | 3.27 | 3.04 | AL047332 |
| 430746 | Hs.406256 | ESTs, transcribed locus from chromosome 21 | 3.27 | 3.03 | AW977370 |
| 409556 | Hs.54941 | phosphorylase kinase, alpha 2 (liver) | 3.27 | 3.03 | D38616 |
| 451225 | Hs.57655 | ESTs | 3.26 | 3.03 | AI433694 |
| 404913 | — | NM_024408*: *Homo sapiens* Notch () homolog 2 (NOTCH2), mRNA. VERSION NM_024410.1 GI | 3.25 | 3.02 | — |
| 404875 | — | NM_022819*: *Homo sapiens* phospholipase A2, group IIF (PLA2G2F), mRNA. VERSION NM_020245.2 GI | 3.23 | 3.02 | — |
| 404606 | — | Target Exon | 3.23 | 3.01 | — |
| 414732 | Hs.77152 | minichromosome maintenance deficient (*S. cerevisiae*) 7 | 3.22 | 3.01 | AW410976 |
| 425380 | Hs.32148 | AD-015 protein | 3.22 | 3.00 | AA356389 |
| 421186 | Hs.270563 | ESTs, Moderately similar to T12512 hypothetical protein DKFZp434G232.1 [*H. sapiens*] | 3.21 | 2.98 | AI798039 |
| 445462 | Hs.288649 | hypothetical protein MGC3077 | 3.2 | 2.97 | AA378776 |

Permutation Analysis of 100 Most Significantly Up-Regulated Genes in Each Group

By permuting the sample labels 500 times, the significance of the differentially expressed genes was estimated. The permutation analysis revealed that it was highly unlikely to find markers that were as good by chance, as similarly good markers were only found in 5% of the permutated data sets, see Table 2.

Molecular Predictor of Progression

A molecular predictor of progression using a combination of genes may have higher prediction accuracy than when using single marker genes. Therefore, to identify the gene-set that gives the best prediction results using the lowest number of genes, a predictor using the "leave one out" cross-validation approach was built, as previously described (Golub et al. 1999).

Figure 2:
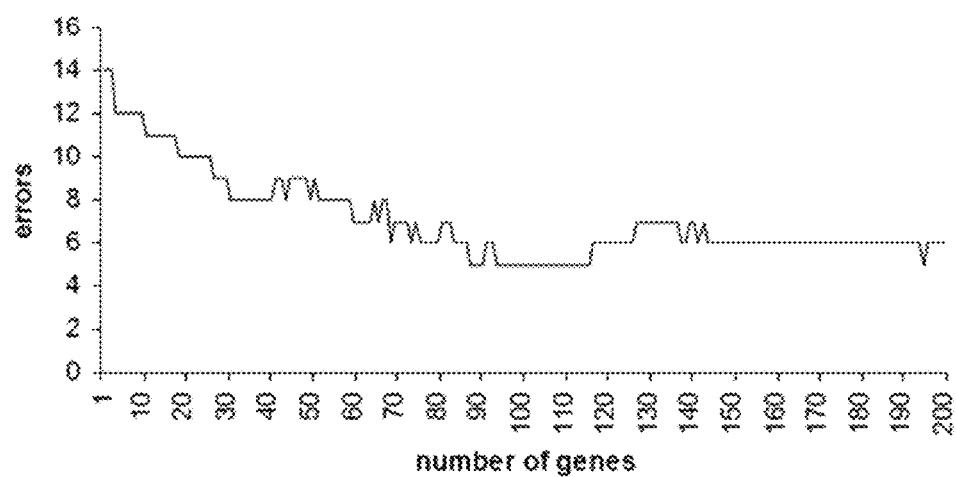
FIG. 2. Cross-validation performance using from 1 to 200 genes.

Selecting the 100 best genes in each cross-validation loop gave the lowest number of prediction errors (5 errors, 83% correct classification) in the training set consisting of the 29 tumors (see FIG. 2). As in a previous study, a maximum likelihood classification approach was used. A gene-expression signature consisting of those 45 genes that were present in 75% of the cross-validation loops was selected, and these represent the optimal gene-set for progression prediction (Table 3).

Many of these 45 genes were also found among the 200 best markers of progression, however, the cross-validation approach also identified other interesting markers of progression like BIRC5 (Survivin), an apoptosis inhibitor that is up regulated in the tumors that show later progression. BIRC5 has been reported to be expressed in most common cancers (Ambrosini et al. 1997). To validate the significance of the 45-gene expression signature, a test set consisting of 19 early stage bladder tumors (9 tumors with no progression and 10 tumors with later progression) was used. Total RNA from these samples were amplified, labeled and hybridized to customized 60-meroligonucleotide microarray glass slides and the relative expressions of the 45 classifier genes were measured following appropriate normalization and background adjustments of the microarray data. The independent tumor samples were classified as non-progressing or progressing according to the degree of correlation to the average no progression profile from the training samples. When applying no cutoff limits to the predictions, the predictor identified 74% of the samples correctly. However, as done recently in a breast cancer study (van't Veer et al. 2002), correlation cutoff limits of 0.1 and −0.1 were applied in order to disregard samples with really low correlation values, and in this way 92% correct prediction of samples with correlation values above 0.1 or below −0.1 were obtained. Although the test-set is limited in size, the performance is notable and could be of clinical use.

TABLE 3

The 45 optimal genes for disease progression prediction.

| Eos Hu03 ID | Unigene Build 133 | Description | T-Test | 5% perm | Gene Name | Exemplar Accession | CV |
|---|---|---|---|---|---|---|---|
| 439010 | Hs.75216 | protein tyrosine phosphatase, receptor type, F | 4.57 | 4.39 | PTPRF | AW170332 | 29 |
| 429124 | Hs.196914 | minor histocompatibility antigen HA-1 | 4.20 | 4.09 | HA-1 | AW505086 | 29 |
| 421649 | Hs.106415 | peroxisome proliferative activated receptor, delta | 5.76 | 5.64 | PPARD | AA721217 | 29 |
| 433914 | Hs.112160 | DNA helicase homolog (PIF1) | 3.88 | 3.61 | PIF1 | AF108138 | 29 |
| 429187 | Hs.163872 | ESTs, Weakly similar to hypothetical protein FLJ20489 | 3.49 | 3.17 | — | AA447648 | 28 |
| 422765 | Hs.1578 | baculoviral IAP repeat-containing 5 (survivin) | 2.68 | 2.56 | BIRC5 | AW409701 | 28 |

TABLE 3-continued

The 45 optimal genes for disease progression prediction.

| Eos Hu03 ID | Unigene Build 133 | Description | T-Test | 5% perm | Gene Name | Exemplar Accession | CV |
|---|---|---|---|---|---|---|---|
| 433844 | Hs.179647 | ESTs | 4.04 | 3.80 | SLC25A29 | AA610175 | 26 |
| 450893 | Hs.25625 | Hypothetical protein FLJ11323 | 3.73 | 3.46 | FLJ11323 | AK002185 | 25 |
| 452866 | Hs.268016 | ESTs | 3.10 | 3.02 | SLC5A3 | R26969 | 24 |
| 424909 | Hs.153752 | cell division cycle 25B | 3.46 | 3.16 | CDC25B | S78187 | 24 |
| 452929 | Hs.172816 | neuregulin 1 | 4.37 | 4.23 | NRG1 | AW954938 | 23 |
| 420116 | Hs.95231 | formin homology 2 domain containing 1 | 3.90 | 3.63 | FHOD1 | NM_013241 | 22 |
| 453963 | Hs.28959 | cDNA FLJ36513 fis, clone TRACH2001523 | 3.44 | 2.88 | BMPR2 | AA040311 | 29 |
| 429561 | Hs.250646 | baculoviral IAP repeat-containing 6 (apollon) | 3.83 | 3.03 | BIRC6 | AF265555 | 29 |
| 418127 | Hs.83532 | membrane cofactor protein (CD46, trophoblast-lymphocyte cross-reactive antigen) | 4.26 | 3.37 | MCP | BE243982 | 29 |
| 422119 | Hs.111862 | KIAA0590 gene product | 2.33 | 1.95 | KIAA0590 | AI277829 | 29 |
| 435521 | Hs.6361 | mitogen-activated protein kinase kinase 1 interacting protein 1 | 5.24 | 4.53 | MAP2K1/P1 | W23814 | 29 |
| 409632 | Hs.55279 | serine (or cysteine) proteinase inhibitor, clade B (ovalbumin), member 5 | 4.89 | 4.11 | SERPINB5 | W74001 | 29 |
| 452829 | Hs.63368 | ESTs | 4.95 | 4.31 | MAN2A1 | AI955579 | 29 |
| 416640 | Hs.79404 | DNA segment on chromosome 4 (unique) 234 expressed sequence | 6.03 | 5.51 | D4S234E | BE262478 | 29 |
| 425097 | Hs.154545 | PDZ domain containing guanine nucleotide exchange factor(GEF)1 | 3.77 | 3.18 | PDZ-GEF1 | NM_014247 | 28 |
| 445926 | Hs.334826 | splicing factor 3b, subunit 1, 155 kDa | 2.40 | 2.03 | SF3B1 | AF054284 | 28 |
| 437325 | Hs.5548 | F-box and leucine-rich repeat protein 5 | 2.48 | 2.09 | FBXL5 | AF142481 | 28 |
| 448813 | Hs.22142 | cytochrome b5 reductase b5R.2 | 4.28 | 3.41 | LOC51700 | AF169802 | 28 |
| 426799 | Hs.303154 | ESTs | 4.86 | 4.04 | IDS | H14843 | 28 |
| 446847 | Hs.82845 | ESTs | 4.65 | 3.79 | SOLR1 | T51454 | 28 |
| 428016 | Hs.181461 | ariadne homolog, ubiquitin-conjugating enzyme E2 binding protein, 1 (Drosophila) | 3.77 | 3.15 | ARIH1 | AJ243190 | 27 |
| 418321 | Hs.84087 | KIAA0143 protein | 4.62 | 3.76 | KIAA0143 | D63477 | 27 |
| 422984 | Hs.351597 | ESTs | 3.50 | 2.93 | PLEKHB2 | W28614 | 26 |
| 408688 | Hs.152925 | KIAA1268 protein | 3.52 | 2.95 | KIAA1268 | AI634522 | 26 |
| 440357 | Hs.20950 | phospholysine phosphohistidine inorganic pyrophosphate phosphatase | 3.89 | 3.07 | LHPP | AA379353 | 26 |
| 420269 | Hs.96264 | alpha thalassemia/mental retardation syndrome X-linked (RAD54 (S. cerevisiae) homolog) | 3.39 | 2.85 | ATRX | U72937 | 26 |
| 423185 | Hs.38006 | ornithine decarboxylase antizyme 1 | 4.61 | 3.71 | OAZ1 | BE299590 | 26 |
| 443407 | Hs.348514 | clone IMAGE: 4052238, mRNA, partial cds | 4.21 | 3.32 | TMEM33 | AA037683 | 25 |
| 457329 | Hs.359682 | calpastatin | 3.59 | 2.99 | CAST | AI634860 | 25 |
| 452714 | Hs.30340 | KIAA1165: likely ortholog of mouse Nedd4 WW domain-binding protein 5A | 3.62 | 3.01 | KIAA1165 | AW770994 | 25 |
| 444773 | Hs.11923 | hypothetical protein DJ167A19.1 | 3.71 | 3.11 | DJ167A19.1 | BE156256 | 24 |
| 418504 | Hs.85335 | ESTs | 4.59 | 3.67 | TMEM30B | BE159718 | 24 |
| 444604 | Hs.11441 | Chromosome 1 open reading frame 8 | 4.89 | 4.17 | C1orf8 | AW327695 | 23 |
| 410691 | Hs.65450 | reticulon 4 | | | RTN4 | AW239226 | 23 |
| 430604 | Hs.247309 | succinate-CoA ligase, GDP-forming, beta subunit | 4.61 | 3.72 | SUCLG2 | AV650537 | 23 |
| 421311 | Hs.283609 | muscleblind-like protein MBLL39 | 4.65 | 3.82 | MBLL39 | N71848 | 23 |
| 439632 | Hs.334437 | hypothetical protein MGC4248 | 4.29 | 3.42 | MGC4248 | AW410714 | 22 |
| 417924 | Hs.82932 | cyclin D1 (PRAD1: parathyroid adenomatosis 1) | 4.35 | 3.49 | CCND1 | AU077231 | 22 |
| 453395 | Hs.377915 | mannosidase, alpha, class 2A, member 1 | 4.71 | 3.84 | MAN2A1 | D63998 | 22 |

Permutation Analysis of 45 Genes

Again permutation analysis revealed that for all of the 45 genes similarly good markers were only found in 5% of the 500 permuted datasets (see Table 3).

Expression Profiling of Metachrone Higher Stage Tumors

Expression profiling of the metachrone higher stage tumors could provide important information on the degree of expression similarities between the primary and the secondary tumors. Tissues from secondary tumors were available from 14 of the patients with disease progression and these were also hybridized to the customized Affymetrix GeneChips.

Figure 3:
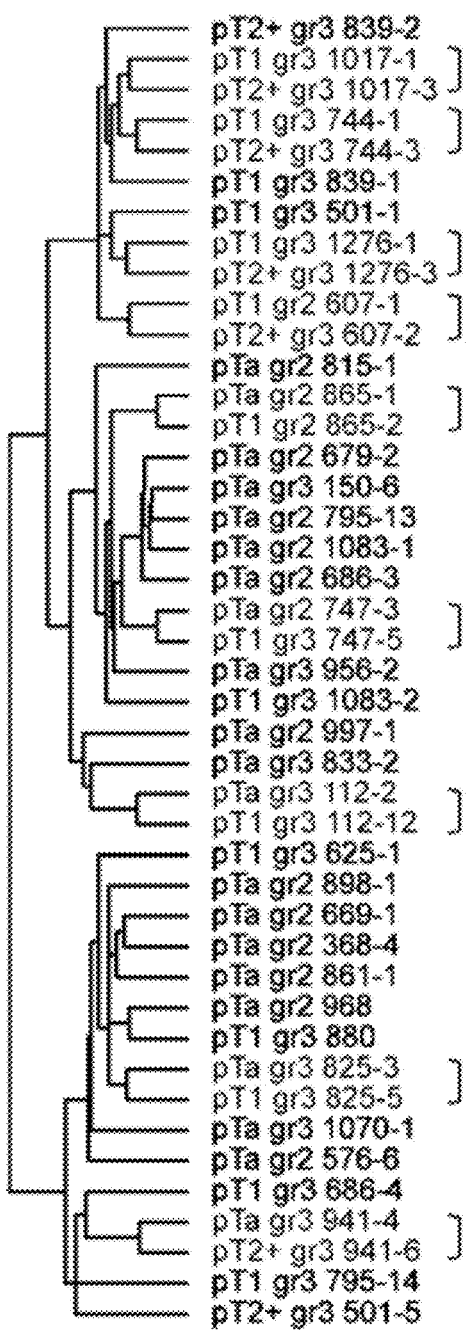
FIG. 3. Hierarchical cluster analysis of the metachronous tumor samples. Tightly clustering tumors of different stages from the same patients are indicated with a square bracket to their right.

Hierarchical cluster analysis of all tumor samples based on the 3,213 most varying probe sets showed that tumors originating from the same patient in 9 of the cases clustered tightly together, indicating a high degree of intra individual similarity in expression profiles (FIG. 3). Notably, one tightly clustering pair of tumors was a Ta and a T2+ tumor (patient 941). It was remarkable that Ta and T1 tumors and T1 or T2+ tumors from a single individual were more similar than e.g. Ta tumors from two individuals. There was no correlation between presence and absence of the tight clustering of samples from the same patient and time interval to tumor progression. The tight clustering of the 9 tumor pairs probably reflects the monoclonal nature of many bladder tumors (Sidransky et al. 1997). A set of genomic abnormalities like chromosomal gains and losses characterize bladder tumors of different stages from single individuals (Primdahl et al. 2002), and such physical abnormalities could be one of the causes of the strong similarity of metachronous tumors.

The fact that 5 of the tumor pairs clustered apart may be explained by an oligoclonal origin of these tumors.

Customized GeneChip Design, Normalization and Expression Measures

We used a customized Affymetrix GeneChip (Eos Hu03) designed by Eos Biotech Inc., as described (Eaves et al. 2002). Approximately 45,000 mRNA/EST clusters and 6,200 predicted exons are represented by the 59,000 probe sets on Eos Hu03 array. Data were normalized using protocols and software developed at Eos Biotechnology, Inc. (WO0079465). An "average intensity" (AI) for each probe set was calculated by taking the trimean of probe intensities following background subtraction and normalization to a gamma distribution (Turkey 1977).

cRNA Preparation, Array Hybridization and Scanning

Preparation of cRNA from total RNA and subsequent hybridization and scanning of the customized GeneChip microarrays (Eos Hu03) were performed as described previously (Dyrskjot et al. 2003).

Custom Oligonucleotide Microarray Procedures

Three 60-mer oligonucleotides were designed for each of the 45 genes using Array Designer 2.0. All steps in the customized oligonucleotide microarray analysis were performed essentially as described (Kruhoffer et al.) Each of the probes was spotted in duplicates and all hybridizations were carried out twice. The samples were labeled with Cy3 and a common reference pool was labelled with Cy5. The reference pool was made by pooling of cRNA generated from investigated samples and from universal human RNA. Following scanning of the glass slides the fluorescent intensities were quantified and background adjusted using SPOT 2.0 (Jain et al. 2002). Data were subsequently normalized using a LOWESS normalization procedure implemented in the SMA package to R. To select the best oligonucleotide probe for each of the 45 genes, 13 of the samples from the training set were re-analyzed on the custom oligonucleotide microarray platform and the obtained expression ratios were compared to the expression levels from the Affymetrix GeneChips. The oligonucleotide probes with the highest correlation to the Affymetrix GeneChip probes were selected.

Expression Data Analysis

Before analysing the expression data from the Eos Hu03 GeneChips control probes were removed and only probes with AI levels above 100 in at least 8 experiments and with max/min equal to or above 1.6 were selected. This filtering generated a gene-set consisting of 6,647 probes for further analysis. Average linkage hierarchical cluster analysis of the tumour samples was carried out using a modified Pearson correlation as a similarity metric (Eisen et al. 1998). Genes and arrays were median centered and normalized to the magnitude of 1 before clustering. We used the GeneCluster 2.0 software for the supervised selection of markers and for performing permutation tests. The 45 genes for predicting progression were selected by t-test statistics and cross-validation performance as previously described (Dyrskjot et al. 2003) and independent samples were classified according to the correlation to the average no progression signature profile of the 45 genes.

Example 2

Identifying Distinct Classes of Bladder Carcinoma Using Microarrays

Patient Disease Course Information—Class Discovery

We selected tumors from the entire spectrum of bladder carcinoma for expression profiling in order to discover the molecular classes of the disease. The tumors analyzed are listed in Table 4 below together with the available patient disease course information.

TABLE 4

Disease course information of all patients involved-class discovery.

| Group | Patient | Previous tumors | Tumor examined on array | Pattern | Reviewed histology | Subsequent tumors | Carcinoma in situ* |
|---|---|---|---|---|---|---|---|
| A | 709-1 | | Ta gr 2 (200297) | Papillary | Ta gr3 | | no |
| | 968-1 | | Ta gr 2 (011098) | Papillary | + | Ta gr 2 (150101) | no |
| | 934-1 | | Ta gr 2 (220798) | Papillary | + | | no |
| | 928-1 | | Ta gr 2 (240698) | Papillary | + | | no |
| | 930-1 | | Ta gr 2 (300698) | Papillary | + | | no |
| B | 989-1 | | Ta gr 3 (281098) | Papillary | + | | no |
| | 1264-1 | | Ta gr 3 (130600) | Papillary | + | Ta gr 2 (231000) | no |
| | | | | | | Ta gr 2 (220101) | |
| | | | | | | Ta gr 2 (300401) | |
| | 876-5 | Ta gr 2 (230398) | Ta gr 3 (170400) | Papillary | + | | no |
| | | Ta gr 2 (271098) | | | | | |
| | | Ta gr 2 (090699) | | | | | |
| | | Ta gr 2 (011199) | | | | | |
| | 669-7 | Ta gr 2 (101296) | Ta gr 3 (230899) | Papillary | Ta gr2 | Ta gr 2 (120100) | no |
| | | Ta gr 2 (150897) | | | | Ta gr 2 (250500) | |
| | | Ta gr 1 (161297) | | | | Ta gr 2 (250900) | |
| | | Ta gr 3 (270498) | | | | Ta gr 2 (050201) | |
| | | Ta gr 2 (220299) | | | | | |
| | 716-2 | Ta gr 2 (070397) | Ta gr 3 (230497) | Papillary | + | Ta gr 2 (040697) | no |
| | | | | | | Ta gr 1 (170698) | |
| C | 1070-1 | | Ta gr 3 (150399) | Papillary | + | Ta gr 3 (291099) | Subsequent visit |
| | 956-2 | | Ta gr 3 (061299) | Papillary | + | Ta gr 3 (061200) | Sampling visit |
| | 1062-2 | | Ta gr 3 (120799) | Papillary | + | T1 gr 3 (161199) | Sampling visit |
| | 1166-1 | | Ta gr 3 (271099) | Papillary | + | | Sampling visit |
| | 1330-1 | | Ta gr 3 (311000) | Papillary | + | | Sampling visit |

TABLE 4-continued

Disease course information of all patients involved-class discovery.

| Group | Patient | Previous tumors | Tumor examined on array | Pattern | Reviewed histology | Subsequent tumors | Carcinoma in situ* |
|---|---|---|---|---|---|---|---|
| D | 112-10 | Ta gr 2 (070794)<br>Ta gr 3 (011294)<br>T1 gr 3(150695)<br>Ta gr 3 (121095)<br>T1 gr 3(040396)<br>Ta gr 2 (200896)<br>Ta gr 2 (111296)<br>Ta gr 2 (230497)<br>Ta gr 2 (030997) | Ta gr 3 (060198) | Papillary | + | Ta gr 3 (110698)<br>T1 gr 3 (191098)<br>Ta gr 3 (240299)<br>T1 gr 3 (050799)<br>T1 gr 3 (081199)<br>T1 gr 3 (180400) | Previous visit |
|  | 320-7 | T1 gr 3 (011194)<br>T1 gr 3 (150896)<br>Ta gr 3 (100897) | Ta gr 3 (290997) | Papillary | + | Ta gr 3 (290198)<br>Ta gr 3 (290698) | Sampling visit |
|  | 747-7 | Ta gr 2 (010597)<br>Ta gr 2 (220597)<br>Ta gr 2 (230997)<br>Ta gr 2 (260198)<br>T1 gr 3 (270498)<br>Ta gr 2 (170898) | Ta gr 3 (161298) | Papillary | + | Ta gr 2 (050599)<br>Ta gr 2 (280999)<br>Ta gr 2 (141299) | Sampling visit |
|  | 967-3 | T1 gr 3 (280998)<br>T1 gr 3 (250199) | Ta gr 3 (140699) | Papillary | + | T1 gr 3 (080999) | Sampling visit |
| E | 625-1 |  | T1 gr 3 (200996) | Papillary | + |  | No |
|  | 847-1 |  | T1 gr 3 (210198) | Papillary | + |  | No |
|  | 1257-1 |  | T1 gr 3 (240500) | Solid | + |  | Sampling visit |
|  | 919-1 |  | T1 gr 3 (220698) | Papillary | + |  | No |
|  | 880-1 |  | T1 gr 3 (300398) | Papillary | + | Ta gr 2 (091198)<br>Ta gr 1 (090399)<br>Ta gr 2 (050900)<br>Ta gr 2 (190301) | No |
|  | 812-1 |  | T1 gr 3 (061098) | Papillary | + |  | No |
|  | 1269-1 |  | T1 gr 3 (230600) | Papillary | − |  | No |
|  | 1083-2 | Ta gr 2 (280499) | T1 gr 3 (120599) | Papillary | − |  | No |
|  | 1238-1 |  | T1 gr 3 (020500) | Papillary | + | T2 gr 3 (211100)<br>Ta gr 2 (211100) | No |
|  | 1065-1 |  | T1 gr 3 (160399) | Papillary | − |  | Subsequent visit |
|  | 1134-1 |  | T1 gr 3 (181099) | Papillary | T2 gr3 | T1 gr 3 (280200)<br>T1 gr 3 (020500)<br>T1 gr 3 (131100) | Sampling visit |
| F | 1164-1 |  | T2+ gr 4 (101299) | Solid | gr 3 |  | No |
|  | 1032-1 |  | T2+ gr ? (050199) | Mixed | − |  | Not measured |
|  | 1117-1 |  | T2+ gr 3 (010999) | Solid | + |  | Sampling visit |
|  | 1178-1 |  | T2+ gr 3 (200100) | Solid | + |  | Not measured |
|  | 1078-1 |  | T2+ gr 3 (120499) | Solid | + |  | Not measured |
|  | 875-1 |  | T2+ gr 3 (180398) | Solid | + |  | No |
|  | 1044-1 |  | T2+ gr 3 (010299) | Solid | + | T2+ gr 3 (060999) | Not measured |
|  | 1133-1 |  | T2+ gr 3 (081099) | Solid | + |  | Not measured |
|  | 1068-1 |  | T2+ gr 3 (220399) | Solid | + |  | No |
|  | 937-1 |  | T2+ gr 3 (280798) | Solid | − |  | Not measured |

Group A: Ta gr2 tumours - no recurrence within 2 years.
Group B: Ta gr3 tumours - no prior T1 tumour and no carcinoma in situ in random biopsies.
Group C: Ta gr3 tumours - no prior T1 tumour but carcinoma in situ in random biopsies.
Group D: Ta gr3 tumours - a prior T1 tumour and carcinoma in situ in random biopsies.
Group E: T1 gr3 tumours - no prior T2+ tumour.
Group F: T2+ tumours gr3/4 - only primary tumours.
*Carcinoma in situ detected in selected site biopsies at previous, sampling or subsequent visits.

Two-Way Hierarchical Cluster Analysis of Tumor Samples

Figures 4A, 4B:
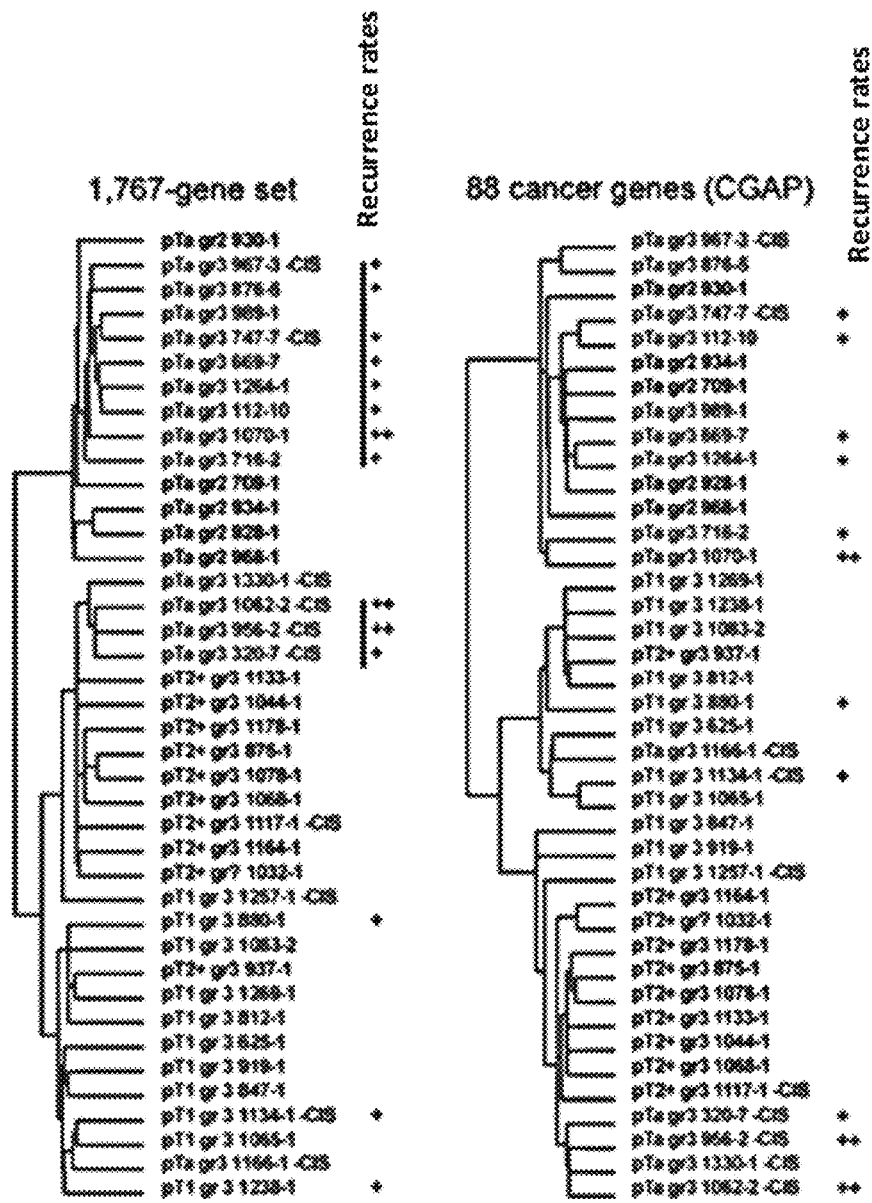
FIG. 4A. Two-way hierarchical clustering and multidimensional scaling analysis of gene expression data from 40 bladder tumor biopsies. Tumor cluster dendrogram based on the 1767 gene-set. CIS annotations following the sample names indicate concomitant carcinoma in situ. Tumor recurrence rates are shown to the right of the dendrogram as + and ++ indicating moderate and high recurrence rates, respectively, while no sign indicates no or moderate recurrence.
FIG. 4B. Two-way hierarchical clustering and multidimensional scaling analysis of gene expression data from 40 bladder tumor biopsies. Tumor cluster dendrogram based on 88 cancer related genes. Tumor recurrence rates are shown to the right of the dendrogram as + and ++ indicating moderate and high recurrence rates, respectively, while no sign indicates no or moderate recurrence.
Figure 4C:
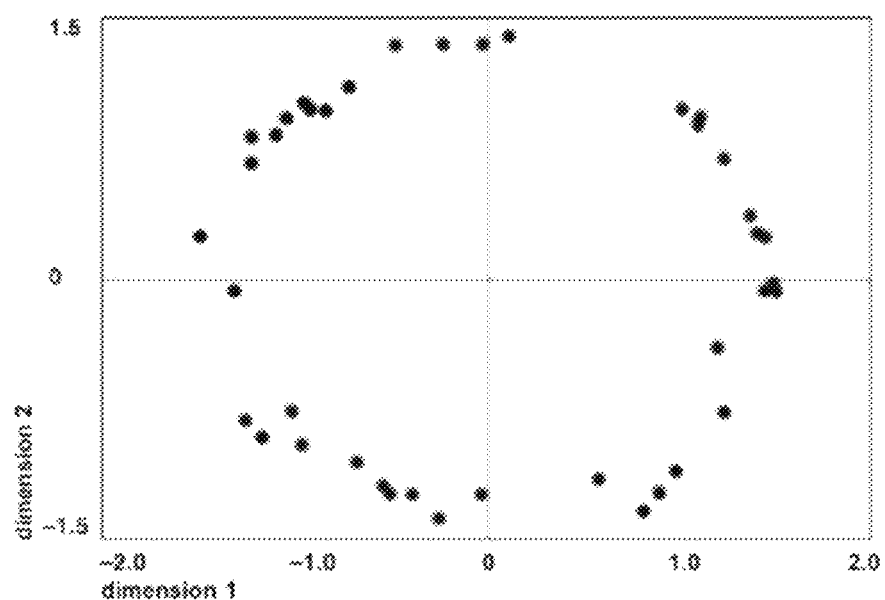
FIG. 4C. Plot of multidimensional scaling analysis of the 40 tumors based on the 1767 gene set.
Figure 5:
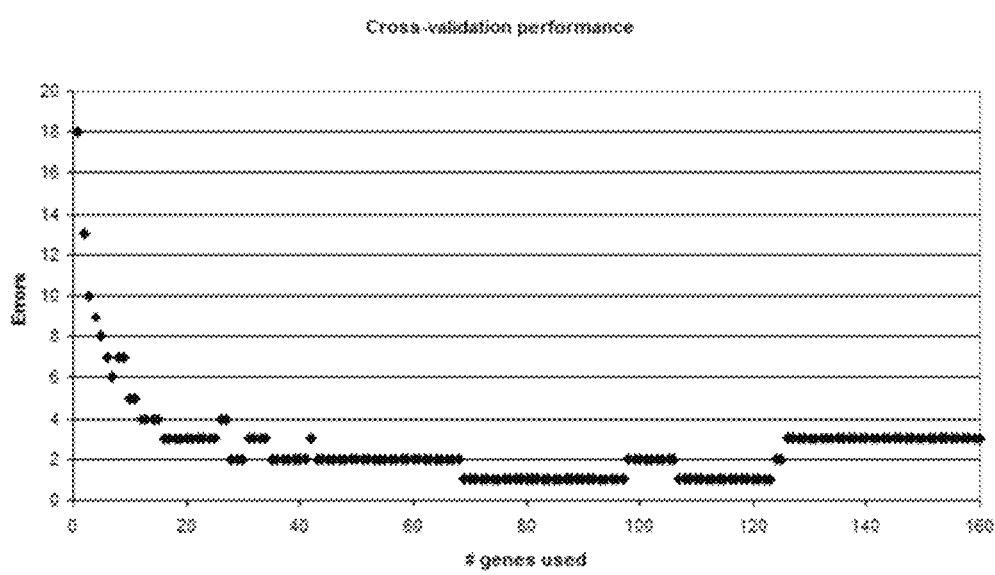
FIG. 5. Number of classification errors vs. number of genes used in cross-validation loops.

A two-way hierarchical cluster analysis of the tumor samples based on the 1767 gene-set (see class discovery using hierarchical clustering) remarkably separated all 40 tumors according to conventional pathological stages and grades with only few exceptions (FIG. 4A). Two main branches were identified containing the superficial Ta tumors, and the invasive T1 and T2+ tumors. In the superficial branch, two sub-clusters of tumors could be identified, one holding 8 tumors that had frequent recurrences and one holding 3 out of the five Ta grade 2 tumors with no recurrences. In the invasive branch, it was notable that four Ta grade 3 tumors clustered tightly with the muscle invasive T2+ tumors. These four Ta tumors, from patients with no previous tumor history, showed concomitant CIS in the surrounding mucosa, indicating that this sub-fraction of Ta tumors has some of the more aggressive features found in muscle invasive tumors. The stage T1 cluster could be separated into three sub-clusters with no clear clinical difference. The one stage T1 grade 3 tumor that clustered with the stage T2+ muscle invasive tumors was the only T1 tumor that showed a solid growth pattern, all others showing papillary growth. Nine out of ten T2+ tumors were found in one single cluster. The remarkable distinct separation of the tumor groups according to stage, with practically no overlap between groups, was also demonstrated by multidimensional scaling analysis (FIG. 4C).

In an attempt to reduce the number of genes needed for class prediction, those genes were identified that were scored by the Cancer Genome Anatomy Project (at NCI) as belonging to cancer-related groups such as tumor suppressors, oncogenes, cell cycle, etc. These genes were then selected from the initial 1767 gene-set, and those 88 which showed largest variation (SD of the gene vector≥4), were used for hierarchical clustering of the tumor samples. The obtained cluster was almost identical to the 1767 gene-set cluster dendrogram (FIG. 4B), indicating that the tumor clustering does not simply reflect larger amounts of stromal components in the invasive tumour biopsies.

The clustering of the 1767 genes revealed several characteristic profiles in which there was a distinct difference between the tumor groups.

Figure 7A:
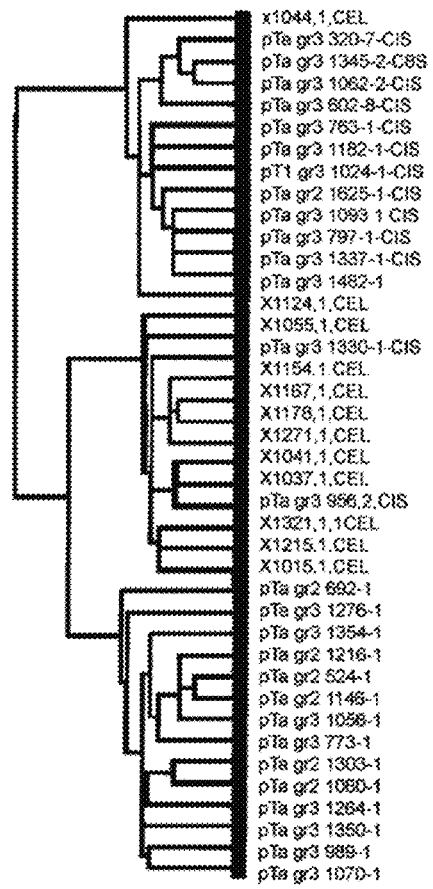
FIG. 7. Hierarchical cluster analysis of the gene expression in 41 TCC, 9 normal samples and 10 samples from cystectomy specimens with CIS lesions. 7A. Cluster dendrogram of all 41 TCC biopsies based on the expression of 5,491 genes. 7B. Cluster dendrogram of all superficial TCC biopsies based on the expression of 5,252 genes.

Cluster a of the 1767 genes, showed a high expression level in all the Ta grade 3 tumors (FIG. 7a in application Ser. No. 12/180,321) and, as a novel finding, contains genes encoding 8 transcription factors as well as other nuclear genes related to transcriptional activity. Cluster c (FIG. 7c in application Ser. No. 12/180,321) contains genes that are up-regulated in Ta grade 3 with a high recurrence rate and CIS, in T2+ and some T1 tumors. This cluster c shows a remarkably tight co-regulation of genes related to cell cycle control and mitosis. Genes encoding cyclins, PCNA as well as a number of centromere related proteins are present in this cluster. They indicate increased cellular proliferation and may form new targets for small molecule therapy (Seymour 1999). Cluster f shows a tight cluster of genes related to keratinization (FIG. 7f in application Ser. No. 12/180,321). Two tumors (875-1 and 1178-1) had a very high expression of these genes and a re-evaluation of the pathology slides revealed that these were the only two samples to show squamous metaplasia. Thus, activation of this cluster of genes promotes the squamous metaplasia not infrequently seen by light microscopy in invasive bladder tumors. The genes in this cluster are listed in Table 5.

TABLE 5

Genes for classifying samples with squamous metaplasia

| Chip acc. # | UniGene Build 162 | description |
|---|---|---|
| D83657_at | Hs.19413 | NM_005621; S100 calcium-binding protein A12 |
| HG3945-HT4215_at | | |
| J00124_at | | Keratin 14; KRT14 |
| L05187_at | | Small proline-rich protein 1A SPRK; SPRR1A |
| L05188_f_at | Hs.505327 | Small proline-rich protein 2B; SPRR2B |
| L10343_at | Hs.112341 | NM_002638; skin-derived protease inhibitor 3 preproprotein |

TABLE 5-continued

Genes for classifying samples with squamous metaplasia

| Chip acc. # | UniGene Build 162 | description |
|---|---|---|
| L42583_f_at | Hs.367762 | NM_005554; keratin 6A |
| L42601_f_at | Hs.367762 | NM_005554; keratin 6A |
| L42611_f_at | Hs.446417 | NM_173086; keratin 6 isoform K6e |
| M19888_at | Hs.1076 | NM_003125; small proline-rich protein 1B (cornifin) |
| M20030_f_at | Hs.505352 | Small proline-rich protein 2E; SPRR2E |
| M21005_at | | S100 calcium binding protein A8; S100A8 |
| M21302_at | Hs.505327 | Small proline-rich protein 2D; SPRR2D |
| M21539_at | Hs.2421 | NM_006518; small proline-rich protein 2C |
| M86757_s_at | Hs.112408 | NM_002963; S100 calcium-binding protein A7 |
| S72493_s_at | Hs.432448 | NM_005557; keratin 16 |
| U70981_at | Hs.336046 | NM_000640; interleukin 13 receptor, alpha 2 precursor |
| V01516_f_at | Hs.367762 | NM_005554; keratin 6A |
| X53065_f_at | | Small proline-rich protein 2A; SPRR2A |
| X57766_at | Hs.143751 | NM_005940; matrix metalloproteinase 11 preproprotein |
| Z19574_rna1_at | | Keratin 17; KRT17 |

Cluster g contains genes that are up-regulated in T2+ tumors and in the Ta grade 3 tumors with CIS that cluster in the invasive branch (FIG. 7g in application Ser. No. 12/180,321). This cluster contains genes related to angiogenesis and connective tissue such as laminin, myosin, caldesmon, collagen, dystrophin, fibronectin, and endoglin. The increased transcription of these genes may indicate a profound remodeling of the stroma that could reflect signaling from the tumor cells, from infiltrating lymphocytes, or both. Some of these may also form new drug targets (Fox et al. 2001). It is remarkable that these genes are those that most clearly separate the Ta grade 3 tumors surrounded by OS from all other Ta grade 3 tumors. The presence of adjacent CIS is usually diagnosed by taking a set of eight biopsies from different places in the bladder mucosa. However, the present data clearly indicate that analysis of stroma remodeling genes in the Ta tumors could eliminate this invasive procedure.

Figure 8:
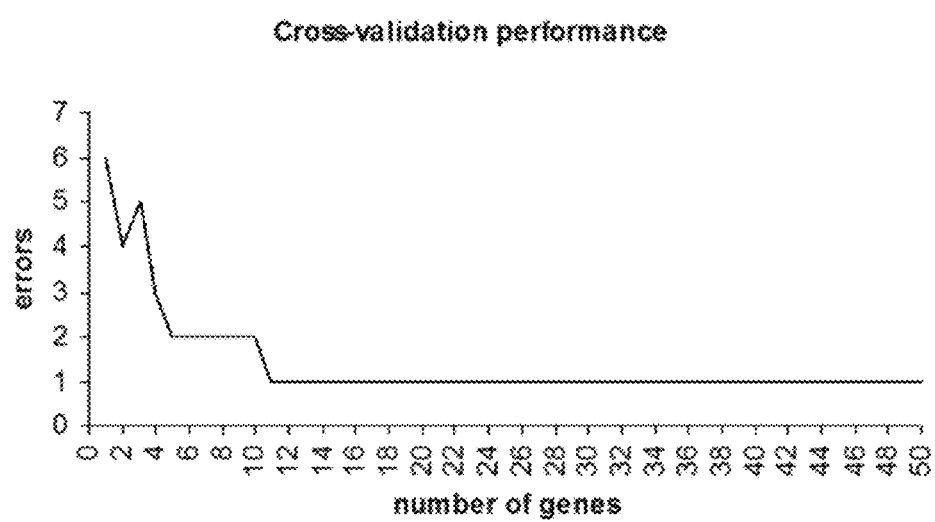
FIG. 8. Cross validation performance using all samples.

The clusters b, d, e, h, i, and j contain genes related to nuclear proteins, cell adhesion, growth factors, stromal proteins, immune system, and proteases, respectively (see FIG. 8 in application Ser. No. 12/180,321). A summary of the stage related gene expression is shown in Table 6.

TABLE 6

Table 6• Summary of stage related gene expression
Functional gene clusters[a]

| Tumor stage | Transcription | Nuclear processes | Proliferation | Matrix remodelling | Extracellular matrix | Immune system |
|---|---|---|---|---|---|---|
| Ta gr2 | ↑ | — | — | — | ↓↓ | ↓ |
| Ta gr3 | ↑↑↑ | ↑↑ | ↑↑ | — | ↓↓ | ↓ |
| T1 gr3 | ↑[b] | — | ↑↑[b] | — | ↓ | ↑[b] |
| T2 gr3 | ↑ | — | ↑↑↑ | ↑↑↑ | ↑ | ↑ |
| Ta gr3 + CIS | ↑↑↑ | ↑↑ | ↑↑↑ | ↑↑↑ | ↑ | ↑ |

Figure 7B:
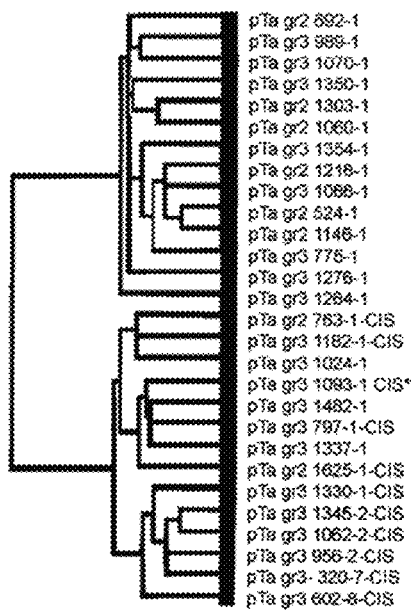

[a]For a detailed description of gene clusters see FIG. 7.
[b]An increase in gene expression was only found in about half of the samples analysed.

Class Prediction of Bladder Tumors

An objective class prediction of bladder tumors based on a limited gene-set is clinically useful. A classifier was built using tumors correctly separated in the three main groups as identified in the cluster dendrogram (FIG. 4A). A maximum likelihood classification method was used with a "leave one out" cross-validation scheme (Shipp et al. 2002; van't Veer et al. 2002) in which one test tumor was removed from the set, and a set of predictive genes was selected from the remaining tumor samples for classifying the test tumor. This process was repeated for all tumors. Predictive genes that showed the largest possible separation of the three groups were selected for classification, and each tumor was classified according to how close it was to the mean of the three groups (FIG. 8a in application Ser. No. 12/180,321).

Classification of Samples

From the hierarchical cluster analysis of the samples (class discovery) three major "molecular classes" of bladder carcinoma highly associated with the pathologic staging of the samples were identified. Based on this finding it was decided to build a molecular classifier that assigns tumors to these three "molecular classes." To build the classifier, only the tumours in which there was a correlation between the "molecular class" and the associated pathologic stage were used. Consequently, a T1 tumour clustering in the "molecular class" of 72 tumours was not used to build the classifier.

The genes used in the classifier were those genes with the highest values of the ratio (B/W) of the variation between the groups (B) to the variation within the groups (W). High values of the ratio (B/W) signify genes with good group separation performance. The sum over the genes of the squared distance from the sample value to the group mean was calculated, and the sample classified as belonging to the group where the distance to the group mean was smallest. If the relative difference between the distance to the closest and the second closest group compared to the distance to the closest group was below 5%, the classification failed and the sample was classified as belonging to both groups. The relative difference is referred to as the classifier strength.

Classifier Performance

Figure 6:
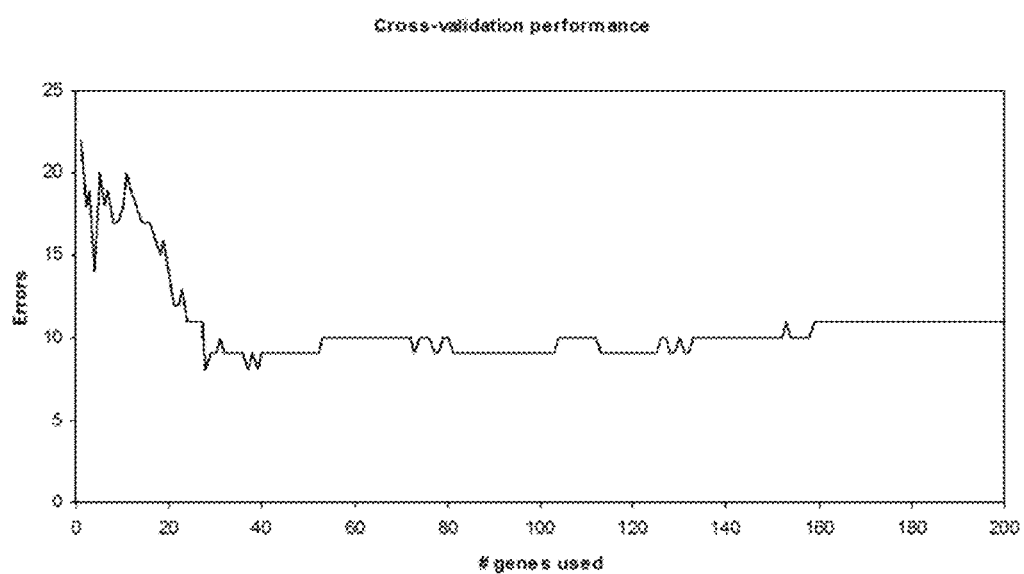
FIG. 6. Number of prediction errors vs. number of genes used in cross-validation loops.

The classifier performance was tested using from 1-160 genes in cross-validation loops. FIG. 6 shows that the closest correlation to histopathology is obtained in the cross-validation model using from 69-97 genes. Based on this model, using 80 genes for cross-validation was chosen as the final classifier model.

Classifier Model Using 71 Genes

The genes selected for the final classifier model were those that were used in at least 75% (25 times) of the cross-validation loops. These 71 genes are listed in table 7.

TABLE 7

Feature: Accession number on HuGene fl array. Number: Number of times used in the 80 genes cross validation loops. Test (B/W): see below.

| Feature | Unigene Build 162 | Description | Number | Test (B/W) |
|---|---|---|---|---|
| AF000231_at | Hs.75618 | NM_004663; Ras-related protein Rab-11A | 33 | 26.77 |
| D13666_s_at | Hs.136348 | NM_006475; osteoblast specific factor 2 (fasciclin I-like) | 33 | 27.71 |
| D49372_s_at | Hs.54460 | NM_002986; small inducible cytokine A11 precursor | 31 | 25.78 |
| D83920_at | Hs.440898 | NM_002003; ficolin 1 precursor | 33 | 31.18 |
| D86479_at | Hs.439463 | NM_001129; adipocyte enhancer binding protein 1 precursor | 33 | 28.29 |
| D89077_at | Hs.75367 | NM_006748; Src-like-adaptor | 33 | 30.03 |
| D89377_at | Hs.89404 | NM_002449; msh homeo box homolog 2 | 33 | 51.50 |
| HG4069-HT4339_s_at | | | 27 | 25.06 |
| HG67-HT67_f_at | | | 33 | 27.81 |
| HG907-HT907_at | | | 33 | 25.76 |
| J02871_s_at | Hs.436317 | NM_000779; cytochrome P450, family 4, subfamily B, polypeptide 1 | 33 | 32.61 |
| J03278_at | Hs.307783 | NM_002609; platelet-derived growth factor receptor beta precursor | 33 | 28.02 |
| J04058_at | Hs.169919 | NM_000126; electron transfer flavoprotein, alpha polypeptide | 33 | 29.46 |
| J05032_at | Hs.32393 | NM_001349; aspartyl-tRNA synthetase | 33 | 38.21 |
| J05070_at | Hs.151738 | NM_004994; matrix metalloproteinase 9 preproprotein | 33 | 35.34 |
| J05448_at | Hs.79402 | NM_002694; DNA directed RNA polymerase II polypeptide C NM_032940; DNA directed RNA polymerase II polypeptide C | 32 | 26.51 |
| K01396_at | Hs.297681 | NM_000295; serine (or cysteine) proteinase inhibitor, clade A (alpha-1 antiproteinase, antitrypsin), member 1 | 33 | 28.66 |
| L13720_at | Hs.437710 | NM_000820; growth arrest-specific 6 | 33 | 29.69 |
| M12125_at | Hs.300772 | NM_003289; tropomyosin 2 (beta) | 28 | 24.89 |
| M15395_at | Hs.375957 | NM_000211; integrin beta chain, beta 2 precursor | 33 | 29.40 |
| M16591_s_at | Hs.89555 | NM_002110; hemopoietic cell kinase isoform p61HCK | 33 | 32.34 |
| M20530_at | | Serine peptidase inhibitor; SPINK1 | 33 | 30.28 |
| M23178_s_at | Hs.73817 | NM_002983; chemokine (C-C motif) ligand 3 | 33 | 35.36 |
| M32011_at | Hs.949 | NM_000433; neutrophil cytosolic factor 2 | 33 | 41.88 |
| M33195_at | Hs.433300 | NM_004106; Fc fragment of IgE, high affinity I, receptor for, gamma polypeptide precursor | 33 | 30.40 |
| M55998_s_at | Hs.172928 | NM_000088; alpha 1 type I collagen preproprotein | 33 | 26.83 |
| M57731_s_at | Hs.75765 | NM_002089; chemokine (C—X—C motif) ligand 2 | 33 | 31.84 |
| M68840_at | Hs.183109 | NM_000240; monoamine oxidase A | 33 | 32.39 |
| M69203_s_at | Hs.75703 | NM_002984; chemokine (C-C motif) ligand 4 precursor | 33 | 36.21 |
| M72885_rna1_s_at | | G0/G1 switch 2 RP1-28O10.2; G0S2 | 33 | 27.94 |
| M83822_at | Hs.209846 | NM_006726; LPS-responsive vesicle trafficking, beach and anchor containing | 33 | 26.44 |
| S77393_at | Hs.145754 | NM_016531; Kruppel-like factor 3 (basic) | 33 | 49.85 |
| U01833_at | Hs.81469 | NM_002484; nucleotide binding protein 1 (MinD homolog, E. coli) | 33 | 30.62 |
| U07231_at | Hs.309763 | NM_002092; G-rich RNA sequence binding factor 1 | 33 | 39.10 |
| U09937_rna1_s_at | | Plasminogen activator, urokinase receptor CD87; PLAUR | 33 | 30.88 |

TABLE 7-continued

Feature: Accession number on HuGene fl array. Number: Number of times used in the 80 genes cross validation loops. Test (B/W): see below.

| Feature | Unigene Build 162 | Description | Number | Test (B/W) |
|---|---|---|---|---|
| U10550_at | Hs.79022 | NM_005261; GTP-binding mitogen-induced T-cell protein NM_181702; GTP-binding mitogen-induced T-cell protein | 28 | 25.26 |
| U20158_at | Hs.2488 | NM_005565; lymphocyte cytosolic protein 2 | 33 | 32.41 |
| U41315_rna1_s_at | | Makorin ring finger protein 1; MKRN1 | 33 | 43.56 |
| U47414_at | Hs.13291 | NM_004354; cyclin G2 | 33 | 44.42 |
| U49352_at | Hs.414754 | NM_001359; 2,4-dienoyl CoA reductase 1 precursor | 33 | 37.04 |
| U50708_at | Hs.1265 | NM_000056; branched chain keto acid dehydrogenase E1, beta polypeptide precursor NM_183050; branched chain keto acid dehydrogenase E1, beta polypeptide precursor | 33 | 42.89 |
| U52101_at | Hs.9999 | NM_001425; epithelial membrane protein 3 | 33 | 29.86 |
| U64520_at | Hs.66708 | NM_004781; vesicle-associated membrane protein 3 (cellubrevin) | 33 | 30.17 |
| U65093_at | Hs.82071 | NM_006079; Cbp/p300-interacting transactivator, with Glu/Asp-rich carboxy-terminal domain, 2 | 33 | 32.07 |
| U68019_at | Hs.288261 | NM_005902; MAD, mothers against decapentaplegic homolog 3 | 31 | 26.70 |
| U68385_at | Hs.380923 | Meis homeobox 3 pseudogene 1; MEIS3P1 | 33 | 31.56 |
| U74324_at | Hs.90875 | NM_002871; RAB-interacting factor | 33 | 30.26 |
| U77970_at | Hs.321164 | NM_002518; neuronal PAS domain protein 2 NM_032235; | 33 | 50.37 |
| U90549_at | Hs.236774 | NM_006353; high mobility group nucleosomal binding domain 4 | 33 | 32.16 |
| X04085_rna1_at | | Catalase; CAT | 28 | 25.13 |
| X07743_at | Hs.77436 | NM_002664; pleckstrin | 33 | 28.13 |
| X13334_at | Hs.75627 | NM_000591; CD14 antigen precursor | 33 | 35.79 |
| X14046_at | Hs.153053 | NM_001774; CD37 antigen | 30 | 24.70 |
| X15880_at | Hs.415997 | NM_001848; collagen, type VI, alpha 1 precursor | 33 | 31.51 |
| X15882_at | Hs.420269 | NM_001849; alpha 2 type VI collagen isoform 2C2 precursor NM_058174; alpha 2 type VI collagen isoform 2C2a precursor NM_058175; alpha 2 type VI collagen isoform 2C2a precursor | 33 | 32.32 |
| X51408_at | Hs.380138 | NM_001822; chimerin (chimaerin) 1 | 33 | 30.51 |
| X53800_s_at | Hs.89690 | NM_002090; chemokine (C—X—C motif) ligand 3 | 33 | 33.63 |
| X54489_rna1_at | | Chemokine (C—X—C motif) ligand 1 (melanoma growth stimulating activity, alpha); CXCL1 | 33 | 33.57 |
| X57579_s_at | | Inhibin, beta A; INHBA | 33 | 41.43 |
| X64072_s_at | Hs.375957 | NM_000211; integrin beta chain, beta 2 precursor | 33 | 43.21 |
| X67491_f_at | Hs.355697 | NM_005271; glutamate dehydrogenase 1 | 33 | 30.97 |
| X68194_at | Hs.80919 | NM_006754; synaptophysin-like protein isoform a NM_182715; synaptophysin-like protein isoform b | 33 | 46.53 |
| X73882_at | Hs.254605 | NM_003980; microtubule-associated protein 7 | 33 | 53.16 |
| X78520_at | Hs.372528 | NM_001829; chloride channel 3 | 33 | 47.38 |
| Y00787_s_at | Hs.624 | NM_000584; interleukin 8 precursor | 32 | 27.54 |
| Z12173_at | Hs.334582 | NM_002076; glucosamine (N-acetyl)-6-sulfatase precursor | 30 | 25.44 |
| Z19554_s_at | Hs.435800 | NM_003380; vimentin | 27 | 24.59 |
| Z26491_s_at | Hs.240013 | NM_000754; catechol-O-methyltransferase isoform MB-COMT NM_007310; catechol-O-methyltransferase isoform S-COMT | 32 | 26.92 |
| Z29331_at | Hs.372758 | NM_003344; ubiquitin-conjugating enzyme E2H isoform 1 NM_182697; ubiquitin-conjugating enzyme E2H isoform 2 | 33 | 33.49 |
| Z48605_at | Hs.421825 | NM_006903; inorganic pyrophosphatase 2 isoform 2 NM_176865; NM_176866; inorganic pyrophosphatase 2 isoform 3 NM_176867; inorganic pyrophosphatase 2 isoform 4 NM_176869; inorganic pyrophosphatase 2 isoform 1 | 33 | 44.45 |
| Z74615_at | Hs.172928 | NM_000088; alpha 1 type I collagen preproprotein | 33 | 55.18 |

Test for Significance of Classifier

To test the class separation performance of the 71 selected genes we compared the B/W ratios with the similar ratios of all the genes calculated from permutations of the arrays. For each permutation we constructed three pseudogroups, pseudo-Ta, pseudo-T1, and pseudo-T2, so that the proportion of samples from the three original groups was approximately the same in the three pseudogroups. We then calculated the ratio of the variation between the pseudogroups to the variation within the pseudogroups for all the genes. In 500 permutations only twice did we see one gene for which the B/W value was higher than the lowest value for the original B/W values of the 71 selected genes (the two values being 25.28 and 25.93).

The classifier performance was tested using from 1-160 genes in cross-validation loops, and a model using an 80 gene cross-validation scheme showed the best correlation to pathologic staging ($p<10^{-9}$). The 71 genes that were used in at least 75% of the cross validation loops were selected to constitute our final classifier model. See the expression profiles of the 71 genes in FIG. 10. The genes are clustered to obtain a better overview of similar expression patterns. From this it is obvious that the T1 stage is characterized by having expression patterns in common with either Ta or T2 tumours. There are no single genes that can be used as a T1 marker.

Permutation Analysis

To test the class separation performance of the 71 selected genes we compared their performance to those of a permutated set of pseudo-Ta, T1 and T2 tumours. In 500 permutations we only detected two genes with a performance equal to the poorest performing classifying genes.

Classification Using 80 Predictive Genes and Other Gene-Sets

The classification using 80 predictive genes in cross-validation loops identified the Ta group with no surrounding CIS and no previous tumor or no previous tumor of a higher stage (Table 8). Interestingly, the Ta tumours surrounded by CIS that were classified as T2 or T1 clearly demonstrate the potential of the classification method for identifying surrounding CIS in a non-invasive way, thereby supplementing clinical and pathologic information.

TABLE 8

Clinical data on disease courses and results of molecular classification

| Tumors | Patient | Previous tumors | Tumor analysed | Subsequent tumors | Carcinoma in situ[a] | Reviewed histology[b] | Molecular classifier[c] 320 | 80 | 20 |
|---|---|---|---|---|---|---|---|---|---|
| Ta grade II tumors - no progression |||||||||||
| | 709-1 | | Ta gr2 | | No | Ta gr3 | Ta | Ta | Ta |
| | 908-1 | | Ta gr2 | 1 Ta | No | | Ta/T1 | Ta | Ta |
| | 934-1 | | Ta gr2 | | No | | T1 | Ta | Ta |
| | 928-1 | | Ta gr2 | | No | | Ta | Ta | T1 |
| | 930-1 | | Ta gr2 | | No | | Ta | Ta | Ta |
| Ta grade III tumors - no prior T1 tumor or CIS |||||||||||
| | 989-1 | | Ta gr3 | | No | | Ta | Ta | Ta |
| | 1264-1 | | Ta gr3 | 3 Ta | No | | Ta | Ta | Ta |
| | 876-5 | 4 Ta | Ta gr3 | | No | | Ta | Ta | Ta |
| | 669-7 | 5 Ta | Ta gr3 | 4 Ta | No | Ta gr2 | Ta | Ta | Ta |
| | 716-2 | 1 Ta | Ta gr3 | 2 Ta | No | | Ta | Ta | Ta |
| Ta grade III tumors - no prior T1 tumor but CIS in selected site biopsies |||||||||||
| | 1070-1 | | Ta gr3 | 1 Ta | Subsequent visit | | Ta | Ta | Ta |
| | 956-2 | | Ta gr3 | 1 Ta | Sampling visit | | T2 | T2 | T2/T1 |
| | 1062-2 | | Ta gr3 | 1 T1 | Sampling visit | | T2/Ta | T1/Ta | Ta |
| | 1166-1 | | Ta gr3 | | Sampling visit | | Ta/T1 | Ta | Ta |
| | 1330-1 | | Ta gr3 | | Sampling visit | | T2 | T2 | Ta |
| Ta grade III tumors - a prior T1 tumor and CIS in selected site biopsies |||||||||||
| | 747-7 | 5 Ta, 1 T1 | Ta gr3 | 3 Ta | Sampling visit | | Ta | Ta | Ta |
| | 112-10 | 7 Ta, 2 T1 | Ta gr3 | 2 Ta, 4 T1 | Previous visit | | Ta | Ta | Ta |
| | 320-7 | 1 Ta, 2 T1 | Ta gr3 | 2 Ta | Sampling visit | | T2 | T2 | Ta |
| | 967-3 | 2 T1 | Ta gr3 | 1 T1 | Sampling visit | | Ta | Ta | Ta |
| T1 grade III tumors - no prior muscle invasive tumor |||||||||||
| | 625-1 | | T1 gr3 | | No | | T1 | T1 | T1 |
| | 847-1 | | T1 gr3 | | No | | T1 | T1 | T1 |
| | 1257-1 | | T1 gr3 | | Sampling visit | | T1 | T1 | T1 |
| | 919-1 | | T1 gr3 | | No | | T1 | T1 | T1 |
| | 880-1 | | T1 gr3 | 4 Ta | No | | T1 | T1 | T1 |
| | 812-1 | | T1 gr3 | | No | | T1 | T1 | T1 |
| | 1269-1 | | T1 gr3 | | No | No review | T1 | T1 | T1 |
| | 1083-2 | 1 Ta | T1 gr3 | | No | No review | T1 | T1 | T1 |
| | 1238-1 | | T1 gr3 | 1 Ta, 1 T2+ | No | | T1 | T1 | T1 |
| | 1065-1 | | T1 gr3 | | Subsequent visit | No review | T1 | T1 | T1 |
| | 1134-1 | | T1 gr3 | 3 T1 | Sampling visit | T2 gr3 | T1 | T1 | T1 |
| T2+ grade III/IV tumors - only primary tumors |||||||||||
| | 1164-1 | | T2+ gr4 | | No | T2+ gr3 | T2/T1 | T1 | T1 |
| | 1032-1 | | T2+ gr? | | ND | No review | T2 | T2 | T2 |
| | 1117-1 | | T2+ gr3 | | ND | | T2 | T2 | T1 |
| | 1178-1 | | T2+ gr3 | | ND | | T2 | T2 | T2 |
| | 1078-1 | | T2+ gr3 | | ND | | T2 | T2 | T2 |
| | 875-1 | | T2+ gr3 | | No | | T2 | T2 | T2 |
| | 1044-1 | | T2+ gr3 | 1 T2+ | ND | | T2 | T2 | T2 |
| | 1133-1 | | T2+ gr3 | | ND | | T2 | T2 | T2 |
| | 1068-1 | | T2+ gr3 | | No | | T2 | T2 | T2 |
| | 937-1 | | T2+ gr3 | | ND | No review | T1 | T1 | T1 |

[a]Carcinoma in situ detected in selected site biopsies at the time of sampling tumor tissue for the arrays or at previous or subsequent visits.
[b]All tumors were reviewed by a single uro-pathologist and any change compared to the routine classification is listed.
[c]Molecular classification based on 320, 80, and 20 genes cross-validation loops.

Classification Using Other Gene-Sets

Classification was also carried out using other gene-sets (10, 20, 32, 40, 80, 160, and 320 genes). These gene-sets demonstrated the same classification tendency as the 71 genes. See Tables 9-15 for gene-sets.

TABLE 9

| 320 genes for classifier | | |
|---|---|---|
| Chip acc. # | UniGene Build 162 | description |
| AB000220_at | Hs.171921 | NM_006379; semaphorin 3C |
| AB000220_at | Hs.171921 | NM_006379; semaphorin 3C |
| AC002073_cds1_at | | Phosphoinositide-3-kinase interacting protein 1; PIK3IP1 |
| AF000231_at | Hs.75618 | NM_004663; Ras-related protein Rab-11A |
| D10922_s_at | Hs.99855 | NM_001462; formyl peptide receptor-like 1 |
| D10925_at | Hs.301921 | NM_001295; chemokine (C-C motif) receptor 1 |
| D11086_at | Hs.84 | NM_000206; interleukin 2 receptor, gamma chain, precursor |
| D11151_at | Hs.211202 | NM_001957; endothelin receptor type A |
| D13435_at | Hs.426142 | NM_002643; phosphatidylinositol glycan, class F isoform 1 NM_173074; phosphatidylinositol glycan, class F isoform 2 |
| D13666_s_at | Hs.136348 | NM_006475; osteoblast specific factor 2 (fasciclin I-like) |
| D14520_at | Hs.84728 | NM_001730; Kruppel-like factor 5 |
| D21878_at | Hs.169998 | NM_004334; bone marrow stromal cell antigen 1 precursor |
| D26443_at | Hs.371369 | NM_004172; solute carrier family 1 (glial high affinity glutamate transporter), member 3 |
| D28589_at | Hs.17719 | KIAA0114 |
| D42046_at | Hs.194665 | DNA replication helicase 2 homolog (yeast); DNA2 |
| D45370_at | Hs.74120 | NM_006829; adipose specific 2 |
| D49372_s_at | Hs.54460 | NM_002986; small inducible cytokine A11 precursor |
| D50495_at | Hs.224397 | NM_003195; transcription elongation factor A (SII), 2 |
| D63135_at | Hs.27935 | NM_032646; tweety homolog 2 |
| D64053_at | Hs.198288 | NM_002849; protein tyrosine phosphatase, receptor type, R isoform 1 precursor NM_130846; protein tyrosine phosphatase, receptor type, R isoform 2 |
| D83920_at | Hs.440898 | NM_002003; ficolin 1 precursor |
| D85131_s_at | Hs.433881 | NM_002383; MYC-associated zinc finger protein |
| D86062_s_at | Hs.413482 | NM_004649; chromosome 21 open reading frame 33 |
| D86479_at | Hs.439463 | NM_001129; adipocyte enhancer binding protein 1 precursor |
| D86957_at | Hs.307944 | Septin 8; SEPT8 |

TABLE 9-continued

| 320 genes for classifier | | |
|---|---|---|
| Chip acc. # | UniGene Build 162 | description |
| D86959_at | Hs.105751 | NM_014720; Ste20-related serine/threonine kinase |
| D86976_at | Hs.196914 | Histocompatibility (minor) HA-1; HMHA1 |
| D87433_at | Hs.301989 | NM_015136; stabilin 1 |
| D87443_at | Hs.409862 | NM_014758; sorting nexin 19 |
| D87682_at | Hs.134792 | AVL9 homolog (S. cerevisiase); AVL9 |
| D89077_at | Hs.75367 | NM_006748; Src-like-adaptor |
| D89377_at | Hs.89404 | NM_002449; msh homeo box homolog 2 |
| D90279_s_at | Hs.433695 | NM_000093; alpha 1 type V collagen preproprotein |
| HG1996-HT2044_at | | |
| HG2090-HT2152_s_at | | |
| HG2463-HT2559_at | | |
| HG2994-HT4850_s_at | | |
| HG3044-HT3742_s_at | | |
| HG3187-HT3366_s_at | | |
| HG3342-HT3519_s_at | | |
| HG371-HT26388_s_at | | |
| HG4069-HT4339_s_at | | |
| HG67-HT67_f_at | | |
| HG907-HT907_at | | |
| J02871_s_at | Hs.436317 | NM_000779; cytochrome P450, family 4, subfamily B, polypeptide 1 |
| J03040_at | Hs.111779 | NM_003118; secreted protein, acidic, cysteine-rich (osteonectin) |
| J03060_at | | Glucosidase, beta, acid pseudogene 1; GBAP1 |
| J03068_at | | Trafficking protein, kinesin binding 1; TRAK1 |
| J03241_s_at | Hs.2025 | NM_003239; transforming growth factor, beta 3 |
| J03278_at | Hs.307783 | NM_002609; platelet-derived growth factor receptor beta precursor |
| J03909_at | | Interferon, gamma-inducible protein 30; IFI30 |
| J03925_at | Hs.172631 | NM_000632; integrin alpha M precursor |
| J04056_at | Hs.88778 | NM_001757; carbonyl reductase 1 |
| J04058_at | Hs.169919 | NM_000126; electron transfer flavoprotein, alpha polypeptide |
| J04093_s_at | Hs.278896 | NM_019075; UDP glycosyltransferase 1 family, polypeptide A10 |
| J04130_s_at | Hs.75703 | NM_002984; chemokine (C-C motif) ligand 4 precursor |
| J04152_rna1_s_at | | Tumor-associated calcium signal transducer 2; TACSTD2 |
| J04162_at | Hs.372679 | NM_000569; Fc fragment of IgG, low affinity IIIa, receptor for (CD16) |
| J04456_at | Hs.407909 | NM_002305; beta-galactosidase binding lectin precursor |
| J05032_at | Hs.32393 | NM_001349; aspartyl-tRNA synthetase |
| J05036_s_at | Hs.1355 | NM_001910; cathepsin E isoform a preproprotein NM_148964; cathepsin E isoform b preproprotein |

TABLE 9-continued 320 genes for classifier

| Chip acc. # | UniGene Build 162 | description |
|---|---|---|
| J05070_at | Hs.151738 | NM_004994; matrix metalloproteinase 9 preproprotein |
| J05448_at | Hs.79402 | NM_002694; DNA directed RNA polymerase II polypeptide C NM_032940; DNA directed RNA polymerase II polypeptide C |
| K01396_at | Hs.297681 | NM_000295; serine (or cysteine) proteinase inhibitor, clade A (alpha-1 antiproteinase, antitrypsin), member 1 |
| K03430_at | | Complement component 1, q subcomponent, B chain; C1QB |
| L06797_s_at | Hs.421986 | NM_003467; chemokine (C—X—C motif) receptor 4 |
| L10343_at | Hs.112341 | NM_002638; skin-derived protease inhibitor 3 preproprotein |
| L11708_at | Hs.155109 | NM_002153; hydroxysteroid (17-beta) dehydrogenase 2 |
| L13391_at | Hs.78944 | NM_002923; regulator of G-protein signalling 2, 24 kDa |
| L13698_at | Hs.65029 | NM_002048; growth arrest-specific 1 |
| L13720_at | Hs.437710 | NM_000820; growth arrest-specific 6 |
| L13923_at | Hs.750 | NM_000138; fibrillin 1 |
| AB000220_at | Hs.171921 | NM_006379; semaphorin 3C |
| AC002073_cds1_at | | Phosphoinositide-3-kinase interacting protein 1; PIK3IP1 |
| AF000231_at | Hs.75618 | NM_004663; Ras-related protein Rab-11A |
| D10922_s_at | Hs.99855 | NM_001462; formyl peptide receptor-like 1 |
| D10925_at | Hs.301921 | NM_001295; chemokine (C-C motif) receptor 1 |
| D11086_at | Hs.84 | NM_000206; interleukin 2 receptor, gamma chain, precursor |
| D11151_at | Hs.211202 | NM_001957; endothelin receptor type A |
| D13435_at | Hs.426142 | NM_002643; phosphatidylinositol glycan, class F isoform 1 NM_173074; phosphatidylinositol glycan, class F isoform 2 |
| D13666_s_at | Hs.136348 | NM_006475; osteoblast specific factor 2 (fasciclin I-like) |
| D14520_at | Hs.84728 | NM_001730; Kruppel-like factor 5 |
| D21878_at | Hs.169998 | NM_004334; bone marrow stromal cell antigen 1 precursor |
| D26443_at | Hs.371369 | NM_004172; solute carrier family 1 (glial high affinity glutamate transporter), member 3 |
| D28589_at | Hs.17719 | KIAA0114 |
| D42046_at | Hs.194665 | |
| D45370_at | Hs.74120 | NM_006829; adipose specific 2 |
| D49372_s_at | Hs.54460 | NM_002986; small inducible cytokine A11 precursor |
| D50495_at | Hs.224397 | NM_003195; transcription elongation factor A (SII), 2 |
| D63135_at | Hs.27935 | NM_032646; tweety homolog 2 |
| D64053_at | Hs.198288 | NM_002849; protein tyrosine phosphatase, receptor type, R isoform 1 precursor NM_130846; protein tyrosine phosphatase, receptor type, R isoform 2 |
| D83920_at | Hs.440898 | NM_002003; ficolin 1 precursor |
| D85131_s_at | Hs.433881 | NM_002383; MYC-associated zinc finger protein |
| D86062_s_at | Hs.413482 | NM_004649; chromosome 21 open reading frame 33 |
| D86479_at | Hs.439463 | NM_001129; adipocyte enhancer binding protein 1 precursor |
| D86957_at | Hs.307944 | |
| D86959_at | Hs.105751 | NM_014720; Ste20-related serine/threonine kinase |
| D86976_at | Hs.196914 | |
| D87433_at | Hs.301989 | NM_015136; stabilin 1 |
| D87443_at | Hs.409862 | NM_014758; sorting nexin 19 |
| D87682_at | Hs.134792 | |
| D89077_at | Hs.75367 | NM_006748; Src-like-adaptor |
| D89377_at | Hs.89404 | NM_002449; msh homeo box homolog 2 |
| D90279_s_at | Hs.433695 | NM_000093; alpha 1 type V collagen preproprotein |
| HG1996-HT2044_at | | |
| HG2090-HT2152_s_at | | |
| HG2463-HT2559_at | | |
| HG2994-HT4850_s_at | | |
| HG3044-HT3742_s_at | | |
| HG3187-HT3366_s_at | | |
| HG3342-HT3519_s_at | | |
| HG371-HT26388_s_at | | |
| HG4069-HT4339_s_at | | |
| HG67-HT67_f_at | | |
| HG907-HT907_at | | |
| J02871_s_at | Hs.436317 | NM_000779; cytochrome P450, family 4, subfamily B, polypeptide 1 |
| J03040_at | Hs.111779 | NM_003118; secreted protein, acidic, cysteine-rich (osteonectin) |
| J03060_at | | |
| J03068_at | | |
| J03241_s_at | Hs.2025 | NM_003239; transforming growth factor, beta 3 |
| J03278_at | Hs.307783 | NM_002609; platelet-derived growth factor receptor beta precursor |
| J03909_at | | |
| J03925_at | Hs.172631 | NM_000632; integrin alpha M precursor |
| J04056_at | Hs.88778 | NM_001757; carbonyl reductase 1 |
| J04058_at | Hs.169919 | NM_000126; electron transfer flavoprotein, alpha polypeptide |
| J04093_s_at | Hs.278896 | NM_019075; UDP glycosyltransferase 1 family, polypeptide A10 |

TABLE 9-continued

320 genes for classifier

| Chip acc. # | UniGene Build 162 | description |
|---|---|---|
| J04130_s_at | Hs.75703 | NM_002984; chemokine (C-C motif) ligand 4 precursor |
| J04152_rna1_s_at | | |
| J04162_at | Hs.372679 | NM_000569; Fc fragment of IgG, low affinity IIIa, receptor for (CD16) |
| J04456_at | Hs.407909 | NM_002305; beta-galactosidase binding lectin precursor |
| J05032_at | Hs.32393 | NM_001349; aspartyl-tRNA synthetase |
| J05036_s_at | Hs.1355 | NM_001910; cathepsin E isoform a preproprotein NM_148964; cathepsin E isoform b preproprotein |
| J05070_at | Hs.151738 | NM_004994; matrix metalloproteinase 9 preproprotein |
| J05448_at | Hs.79402 | NM_002694; DNA directed RNA polymerase II polypeptide C NM_032940; DNA directed RNA polymerase II polypeptide C |
| K01396_at | Hs.297681 | NM_000295; serine (or cysteine) proteinase inhibitor, clade A (alpha-1 antiproteinase, antitrypsin), member 1 |
| K03430_at | | |
| L06797_s_at | Hs.421986 | NM_003467; chemokine (C—X—C motif) receptor 4 |
| L10343_at | Hs.112341 | NM_002638; skin-derived protease inhibitor 3 preproprotein |
| L11708_at | Hs.155109 | NM_002153; hydroxysteroid (17-beta) dehydrogenase 2 |
| L13391_at | Hs.78944 | NM_002923; regulator of G-protein signalling 2, 24 kDa |
| L13698_at | Hs.65029 | NM_002048; growth arrest-specific 1 |
| L13720_at | Hs.437710 | NM_000820; growth arrest-specific 6 |
| L13923_at | Hs.750 | NM_000138; fibrillin 1 |
| AB000220_at | Hs.171921 | NM_006379; semaphorin 3C |
| AC002073_cds1_at | | |
| AF000231_at | Hs.75618 | NM_004663; Ras-related protein Rab-11A |
| D10922_s_at | Hs.99855 | NM_001462; formyl peptide receptor-like 1 |
| D10925_at | Hs.301921 | NM_001295; chemokine (C-C motif) receptor 1 |
| D11086_at | Hs.84 | NM_000206; interleukin 2 receptor, gamma chain, precursor |
| D11151_at | Hs.211202 | NM_001957; endothelin receptor type A |
| D13435_at | Hs.426142 | NM_002643; phosphatidylinositol glycan, class F isoform 1 NM_173074; phosphatidylinositol glycan, class F isoform 2 |
| D13666_s_at | Hs.136348 | NM_006475; osteoblast specific factor 2 (fasciclin I-like) |
| D14520_at | Hs.84728 | NM_001730; Kruppel-like factor 5 |
| D21878_at | Hs.169998 | NM_004334; bone marrow stromal cell antigen 1 precursor |
| D26443_at | Hs.371369 | NM_004172; solute carrier family 1 (glial high affinity glutamate transporter), member 3 |
| D28589_at | Hs.17719 | |
| D42046_at | Hs.194665 | |
| D45370_at | Hs.74120 | NM_006829; adipose specific 2 |
| D49372_s_at | Hs.54460 | NM_002986; small inducible cytokine A11 precursor |
| D50495_at | Hs.224397 | NM_003195; transcription elongation factor A (SII), 2 |
| D63135_at | Hs.27935 | NM_032646; tweety homolog 2 |
| D64053_at | Hs.198288 | NM_002849; protein tyrosine phosphatase, receptor type, R isoform 1 precursor NM_130846; protein tyrosine phosphatase, receptor type, R isoform 2 |
| D83920_at | Hs.440898 | NM_002003; ficolin 1 precursor |
| D85131_s_at | Hs.433881 | NM_002383; MYC-associated zinc finger protein |
| D86062_s_at | Hs.413482 | NM_004649; chromosome 21 open reading frame 33 |
| D86479_at | Hs.439463 | NM_001129; adipocyte enhancer binding protein 1 precursor |
| D86957_at | Hs.307944 | |
| D86959_at | Hs.105751 | NM_014720; Ste20-related serine/threonine kinase |
| D86976_at | Hs.196914 | |
| D87433_at | Hs.301989 | NM_015136; stabilin 1 |
| D87443_at | Hs.409862 | NM_014758; sorting nexin 19 |
| D87682_at | Hs.134792 | |
| D89077_at | Hs.75367 | NM_006748; Src-like-adaptor |
| D89377_at | Hs.89404 | NM_002449; msh homeo box homolog 2 |
| D90279_s_at | Hs.433695 | NM_000093; alpha 1 type V collagen preproprotein |
| HG1996-HT2044_at | | |
| HG2090-HT2152_s_at | | |
| HG2463-HT2559_at | | |
| HG2994-HT4850_s_at | | |
| HG3044-HT3742_s_at | | |
| HG3187-HT3366_s_at | | |
| HG3342-HT3519_s_at | | |
| HG371-HT26388_s_at | | |
| HG4069-HT4339_s_at | | |
| HG67-HT67_f_at | | |
| HG907-HT907_at | | |
| J02871_s_at | Hs.436317 | NM_000779; cytochrome P450, family 4, subfamily B, polypeptide 1 |
| J03040_at | Hs.111779 | NM_003118; secreted protein, acidic, cysteine-rich (osteonectin) |
| J03060_at | | |
| J03068_at | | |
| J03241_s_at | Hs.2025 | NM_003239; transforming growth factor, beta 3 |
| J03278_at | Hs.307783 | NM_002609; platelet-derived growth factor receptor beta precursor |
| J03909_at | | |

TABLE 9-continued

320 genes for classifier

| Chip acc. # | UniGene Build 162 | description |
|---|---|---|
| J03925_at | Hs.172631 | NM_000632; integrin alpha M precursor |
| J04056_at | Hs.88778 | NM_001757; carbonyl reductase 1 |
| J04058_at | Hs.169919 | NM_000126; electron transfer flavoprotein, alpha polypeptide |
| J04093_s_at | Hs.278896 | NM_019075; UDP glycosyltransferase 1 family, polypeptide A10 |
| J04130_s_at | Hs.75703 | NM_002984; chemokine (C-C motif) ligand 4 precursor |
| J04152_rna1_s_at | | |
| J04162_at | Hs.372679 | NM_000569; Fc fragment of IgG, low affinity IIIa, receptor for (CD16) |
| J04456_at | Hs.407909 | NM_002305; beta-galactosidase binding lectin precursor |
| J05032_at | Hs.32393 | NM_001349; aspartyl-tRNA synthetase |
| J05036_s_at | Hs.1355 | NM_001910; cathepsin E isoform a preproprotein NM_148964; cathepsin E isoform b preproprotein |
| J05070_at | Hs.151738 | NM_004994; matrix metalloproteinase 9 preproprotein |
| J05448_at | Hs.79402 | NM_002694; DNA directed RNA polymerase II polypeptide C NM_032940; DNA directed RNA polymerase II polypeptide C |
| K01396_at | Hs.297681 | NM_000295; serine (or cysteine) proteinase inhibitor, clade A (alpha-1 antiproteinase, antitrypsin), member 1 |
| K03430_at | | |
| L06797_s_at | Hs.421986 | NM_003467; chemokine (C—X—C motif) receptor 4 |
| L10343_at | Hs.112341 | NM_002638; skin-derived protease inhibitor 3 preproprotein |
| L11708_at | Hs.155109 | NM_002153; hydroxysteroid (17-beta) dehydrogenase 2 |
| L13391_at | Hs.78944 | NM_002923; regulator of G-protein signalling 2, 24 kDa |
| L13698_at | Hs.65029 | NM_002048; growth arrest-specific 1 |
| L13720_at | Hs.437710 | NM_000820; growth arrest-specific 6 |
| L13923_at | Hs.750 | NM_000138; fibrillin 1 |
| AB000220_at | Hs.171921 | NM_006379; semaphorin 3C |
| AC002073_cds1_at | | |
| AF000231_at | Hs.75618 | NM_004663; Ras-related protein Rab-11A |
| D10922_s_at | Hs.99855 | NM_001462; formyl peptide receptor-like 1 |
| D10925_at | Hs.301921 | NM_001295; chemokine (C-C motif) receptor 1 |
| D11086_at | Hs.84 | NM_000206; interleukin 2 receptor, gamma chain, precursor |
| D11151_at | Hs.211202 | NM_001957; endothelin receptor type A |
| D13435_at | Hs.426142 | NM_002643; phosphatidylinositol glycan, class F isoform 1 NM_173074; phosphatidylinositol glycan, class F isoform 2 |
| D13666_s_at | Hs.136348 | NM_006475; osteoblast specific factor 2 (fasciclin I-like) |
| D14520_at | Hs.84728 | NM_001730; Kruppel-like factor 5 |
| D21878_at | Hs.169998 | NM_004334; bone marrow stromal cell antigen 1 precursor |
| D26443_at | Hs.371369 | NM_004172; solute carrier family 1 (glial high affinity glutamate transporter), member 3 |
| D28589_at | Hs.17719 | |
| D42046_at | Hs.194665 | |
| D45370_at | Hs.74120 | NM_006829; adipose specific 2 |
| D49372_s_at | Hs.54460 | NM_002986; small inducible cytokine A11 precursor |
| D50495_at | Hs.224397 | NM_003195; transcription elongation factor A (SII), 2 |
| D63135_at | Hs.27935 | NM_032646; tweety homolog 2 |
| D64053_at | Hs.198288 | NM_002849; protein tyrosine phosphatase, receptor type, R isoform 1 precursor NM_130846; protein tyrosine phosphatase, receptor type, R isoform 2 |
| D83920_at | Hs.440898 | NM_002003; ficolin 1 precursor |
| D85131_s_at | Hs.433881 | NM_002383; MYC-associated zinc finger protein |
| D86062_s_at | Hs.413482 | NM_004649; chromosome 21 open reading frame 33 |
| D86479_at | Hs.439463 | NM_001129; adipocyte enhancer binding protein 1 precursor |
| D86957_at | Hs.307944 | |
| D86959_at | Hs.105751 | NM_014720; Ste20-related serine/threonine kinase |
| D86976_at | Hs.196914 | |
| D87433_at | Hs.301989 | NM_015136; stabilin 1 |
| D87443_at | Hs.409862 | NM_014758; sorting nexin 19 |
| D87682_at | Hs.134792 | |
| D89077_at | Hs.75367 | NM_006748; Src-like-adaptor |
| D89377_at | Hs.89404 | NM_002449; msh homeo box homolog 2 |
| D90279_s_at | Hs.433695 | NM_000093; alpha 1 type V collagen preproprotein |
| HG1996-HT2044_at | | |
| HG2090-HT2152_s_at | | |
| HG2463-HT2559_at | | |
| HG2994-HT4850_s_at | | |
| HG3044-HT3742_s_at | | |
| HG3187-HT3366_s_at | | |
| HG3342-HT3519_s_at | | |
| HG371-HT26388_s_at | | |
| HG4069-HT4339_s_at | | |
| HG67-HT67_f_at | | |
| HG907-HT907_at | | |

TABLE 9-continued

320 genes for classifier

| Chip acc. # | UniGene Build 162 | description |
|---|---|---|
| J02871_s_at | Hs.436317 | NM_000779; cytochrome P450, family 4, subfamily B, polypeptide 1 |
| J03040_at | Hs.111779 | NM_003118; secreted protein, acidic, cysteine-rich (osteonectin) |
| J03060_at | | |
| J03068_at | | |
| J03241_s_at | Hs.2025 | NM_003239; transforming growth factor, beta 3 |
| J03278_at | Hs.307783 | NM_002609; platelet-derived growth factor receptor beta precursor |
| J03909_at | | |
| J03925_at | Hs.172631 | NM_000632; integrin alpha M precursor |
| J04056_at | Hs.88778 | NM_001757; carbonyl reductase 1 |
| J04058_at | Hs.169919 | NM_000126; electron transfer flavoprotein, alpha polypeptide |
| J04093_s_at | Hs.278896 | NM_019075; UDP glycosyltransferase 1 family, polypeptide A10 |
| J04130_s_at | Hs.75703 | NM_002984; chemokine (C-C motif) ligand 4 precursor |
| J04152_rna1_s_at | | |
| J04162_at | Hs.372679 | NM_000569; Fc fragment of IgG, low affinity IIIa, receptor for (CD16) |
| J04456_at | Hs.407909 | NM_002305; beta-galactosidase binding lectin precursor |
| J05032_at | Hs.32393 | NM_001349; aspartyl-tRNA synthetase |
| J05036_s_at | Hs.1355 | NM_001910; cathepsin E isoform a preproprotein NM_148964; cathepsin E isoform b preproprotein |
| J05070_at | Hs.151738 | NM_004994; matrix metalloproteinase 9 preproprotein |
| J05448_at | Hs.79402 | NM_002694; DNA directed RNA polymerase II polypeptide C NM_032940; DNA directed RNA polymerase II polypeptide C |
| K01396_at | Hs.297681 | NM_000295; serine (or cysteine) proteinase inhibitor, clade A (alpha-1 antiproteinase, antitrypsin), member 1 |
| K03430_at | | |
| L06797_s_at | Hs.421986 | NM_003467; chemokine (C—X—C motif) receptor 4 |
| L10343_at | Hs.112341 | NM_002638; skin-derived protease inhibitor 3 preproprotein |
| L11708_at | Hs.155109 | NM_002153; hydroxysteroid (17-beta) dehydrogenase 2 |
| L13391_at | Hs.78944 | NM_002923; regulator of G-protein signalling 2, 24 kDa |
| L13698_at | Hs.65029 | NM_002048; growth arrest-specific 1 |
| L13720_at | Hs.437710 | NM_000820; growth arrest-specific 6 |
| L13923_at | Hs.750 | NM_000138; fibrillin 1 |
| AB000220_at | Hs.171921 | NM_006379; semaphorin 3C |
| AC002073_cds1_at | | |
| AF000231_at | Hs.75618 | NM_004663; Ras-related protein Rab-11A |
| D10922_s_at | Hs.99855 | NM_001462; formyl peptide receptor-like 1 |
| D10925_at | Hs.301921 | NM_001295; chemokine (C-C motif) receptor 1 |
| D11086_at | Hs.84 | NM_000206; interleukin 2 receptor, gamma chain, precursor |
| D11151_at | Hs.211202 | NM_001957; endothelin receptor type A |
| D13435_at | Hs.426142 | NM_002643; phosphatidylinositol glycan, class F isoform 1 NM_173074; phosphatidylinositol glycan, class F isoform 2 |
| D13666_s_at | Hs.136348 | NM_006475; osteoblast specific factor 2 (fasciclin I-like) |
| D14520_at | Hs.84728 | NM_001730; Kruppel-like factor 5 |
| D21878_at | Hs.169998 | NM_004334; bone marrow stromal cell antigen 1 precursor |
| D26443_at | Hs.371369 | NM_004172; solute carrier family 1 (glial high affinity glutamate transporter), member 3 |
| D28589_at | Hs.17719 | |
| D42046_at | Hs.194665 | |
| D45370_at | Hs.74120 | NM_006829; adipose specific 2 |
| D49372_s_at | Hs.54460 | NM_002986; small inducible cytokine A11 precursor |
| D50495_at | Hs.224397 | NM_003195; transcription elongation factor A (SII), 2 |
| D63135_at | Hs.27935 | NM_032646; tweety homolog 2 |
| D64053_at | Hs.198288 | NM_002849; protein tyrosine phosphatase, receptor type, R isoform 1 precursor NM_130846; protein tyrosine phosphatase, receptor type, R isoform 2 |
| D83920_at | Hs.440898 | NM_002003; ficolin 1 precursor |
| D85131_s_at | Hs.433881 | NM_002383; MYC-associated zinc finger protein |
| D86062_s_at | Hs.413482 | NM_004649; chromosome 21 open reading frame 33 |
| D86479_at | Hs.439463 | NM_001129; adipocyte enhancer binding protein 1 precursor |
| D86957_at | Hs.307944 | |
| D86959_at | Hs.105751 | NM_014720; Ste20-related serine/threonine kinase |
| D86976_at | Hs.196914 | |
| D87433_at | Hs.301989 | NM_015136; stabilin 1 |
| D87443_at | Hs.409862 | NM_014758; sorting nexin 19 |
| D87682_at | Hs.134792 | |
| D89077_at | Hs.75367 | NM_006748; Src-like-adaptor |
| D89377_at | Hs.89404 | NM_002449; msh homeo box homolog 2 |
| D90279_s_at | Hs.433695 | NM_000093; alpha 1 type V collagen preproprotein |

TABLE 9-continued

320 genes for classifier

| Chip acc. # | UniGene Build 162 | description |
|---|---|---|
| HG1996-HT2044_at | | |
| HG2090-HT2152_s_at | | |
| HG2463-HT2559_at | | |
| HG2994-HT4850_s_at | | |

TABLE 10

160 Genes for classifier

| Chip acc. # | UniGene Build 162 | Description |
|---|---|---|
| AF000231_at | Hs.75618 | NM_004663; Ras-related protein Rab-11A |
| D13666_s_at | Hs.136348 | NM_006475; osteoblast specific factor 2 (fasciclin I-like) |
| D21878_at | Hs.169998 | NM_004334; bone marrow stromal cell antigen 1 precursor |
| D45370_at | Hs.74120 | NM_006829; adipose specific 2 |
| D49372_s_at | Hs.54460 | NM_002986; small inducible cytokine A11 precursor |
| D83920_at | Hs.440898 | NM_002003; ficolin 1 precursor |
| D85131_s_at | Hs.433881 | NM_002383; MYC-associated zinc finger protein |
| D86062_s_at | Hs.413482 | NM_004649; chromosome 21 open reading frame 33 |
| D86479_at | Hs.439463 | NM_001129; adipocyte enhancer binding protein 1 precursor |
| D86957_at | Hs.307944 | Septin 8; SEPT 8 |
| D86976_at | Hs.196914 | Histocompatibility (minor) HA-1; HMHA1 |
| D87433_at | Hs.301989 | NM_015136; stabilin 1 |
| D89077_at | Hs.75367 | NM_006748; Src-like-adaptor |
| D89377_at | Hs.89404 | NM_002449; msh homeo box homolog 2 |
| HG3044-HT3742_s_at | | |
| HG371-HT26388_s_at | | |
| HG4069-HT4339_s_at | | |
| HG67-HT67_f_at | | |
| HG907-HT907_at | | |
| J02871_s_at | Hs.436317 | NM_000779; cytochrome P450, family 4, subfamily B, polypeptide 1 |
| J03040_at | Hs.111779 | NM_003118; secreted protein, acidic, cysteine-rich (osteonectin) |
| J03068_at | | Trafficking protein, kinesin binding 1; TRAK1 |
| J03241_s_at | Hs.2025 | NM_003239; transforming growth factor, beta 3 |
| J03278_at | Hs.307783 | NM_002609; platelet-derived growth factor receptor beta precursor |
| J03909_at | | Interferon, gamma-inducible protein 30; IFI30 |
| J04058_at | Hs.169919 | NM_000126; electron transfer flavoprotein, alpha polypeptide |
| J04130_s_at | Hs.75703 | NM_002984; chemokine (C-C motif) ligand 4 precursor |
| J04162_at | Hs.372679 | NM_000569; Fc fragment of IgG, low affinity IIIa, receptor for (CD16) |
| J04456_at | Hs.407909 | NM_002305; beta-galactosidase binding lectin precursor |
| J05032_at | Hs.32393 | NM_001349; aspartyl-tRNA synthetase |
| J05070_at | Hs.151738 | NM_004994; matrix metalloproteinase 9 preproprotein |
| J05448_at | Hs.79402 | NM_002694; DNA directed RNA polymerase II polypeptide C NM_032940; DNA directed RNA polymerase II polypeptide C |
| K01396_at | Hs.297681 | NM_000295; serine (or cysteine) proteinase inhibitor, clade A (alpha-1 antiproteinase, antitrypsin), member 1 |
| K03430_at | | Complement component1, q subcomponent, B chain; C1QB |
| L13698_at | Hs.65029 | NM_002048; growth arrest-specific 1 |
| L13720_at | Hs.437710 | NM_000820; growth arrest-specific 6 |
| L13923_at | Hs.750 | NM_000138; fibrillin 1 |
| L15409_at | Hs.421597 | NM_000551; elogin binding protein |
| L17325_at | Hs.195825 | NM_006867; RNA-binding protein with multiple splicing |
| L19872_at | Hs.170087 | NM_001621; aryl hydrocarbon receptor |
| L27476_at | Hs.75608 | NM_004817; tight junction protein 2 (zona occludens 2) |
| L33799_at | Hs.202097 | NM_002593; procollagen C-endopeptidase enhancer |
| L40388_at | Hs.30212 | NM_004236; thyroid receptor interacting protein 15 |
| L40904_at | Hs.387667 | NM_005037; peroxisome proliferative activated receptor gamma isoform 1 NM_015869; peroxisome proliferative activated receptor gamma isoform 2 NM_138711; peroxisome proliferative activated receptor gamma isoform 1 NM_138712; peroxisome proliferative activated receptor gamma isoform 1 |
| L41919_rna1_at | | Hypermethylated in cancer 1; HIC1 |
| M11433_at | Hs.101850 | NM_002899; retinol binding protein 1, cellular |
| M11718_at | Hs.283393 | NM_000393; alpha 2 type V collagen preproprotein |
| M12125_at | Hs.300772 | NM_003289; tropomyosin 2 (beta) |
| M14218_at | Hs.442047 | NM_000048; argininosuccinate lyase |
| M15395_at | Hs.375957 | NM_000211; integrin beta chain, beta 2 precursor |
| M16591_s_at | Hs.89555 | NM_002110; hemopoietic cell kinase isoform p61HCK |
| M17219_at | Hs.203862 | NM_002069; guanine nucleotide binding protein (G protein), alpha inhibiting activity polypeptide 1 |
| M20530_at | | Serine peptidase inhibitor, Kazal type 1; SPINK1 |
| M23178_s_at | Hs.73817 | NM_002983; chemokine (C-C motif) ligand 3 |

TABLE 10-continued

160 Genes for classifier

| Chip acc. # | UniGene Build 162 | Description |
|---|---|---|
| M28130_rna1_s_at | | Interleukin 8; IL8 |
| M29550_at | Hs.187543 | NM_021132; protein phosphatase 3 (formerly 2B), catalytic subunit, beta isoform (calcineurin A beta) |
| M31165_at | Hs.407546 | NM_007115; tumor necrosis factor, alpha-induced protein 6 precursor |
| M32011_at | Hs.949 | NM_000433; neutrophil cytosolic factor 2 |
| M33195_at | Hs.433300 | NM_004106; Fc fragment of IgE, high affinity I, receptor for, gamma polypeptide precursor |
| M37033_at | Hs.443057 | NM_000560; CD53 antigen |
| M37766_at | Hs.901 | NM_001778; CD48 antigen (B-cell membrane protein) |
| M55998_s_at | Hs.172928 | NM_000088; alpha 1 type I collagen preproprotein |
| M57731_s_at | Hs.75765 | NM_002089; chemokine (C—X—C motif) ligand 2 |
| M62840_at | Hs.82542 | NM_001637; acyloxyacyl hydrolase precursor |
| M63262_at | | Arachidonate 5-lipoxygenase-activating protein; ALOX5AP |
| M68840_at | Hs.183109 | NM_000240; monoamine oxidase A |
| M69203_s_at | Hs.75703 | NM_002984; chemokine (C-C motif) ligand 4 precursor |
| M72885_rna1_s_at | | G0/G1 switch 2; G0S2 |
| M77349_at | Hs.421496 | NM_000358; transforming growth factor, beta-induced, 68 kDa |
| M82882_at | Hs.124030 | NM_172373; E74-like factor 1 (ets domain transcription factor) |
| M83822_at | Hs.209846 | NM_006726; LPS-responsive vesicle trafficking, beach and anchor containing |
| M92934_at | Hs.410037 | NM_001901; connective tissue growth factor |
| M95178_at | Hs.119000 | NM_001102; actinin, alpha 1 |
| S69115_at | Hs.10306 | NM_005601; natural killer cell group 7 sequence |
| S77393_at | Hs.145754 | NM_016531; Kruppel-like factor 3 (basic) |
| S78187_at | Hs.153752 | NM_004358; cell division cycle 25B isoform 1 NM_021872; cell division cycle 25B isoform 2 NM_021873; cell division cycle 25B isoform 3 NM_021874; cell division cycle 25B isoform 4 |
| U01833_at | Hs.81469 | NM_002484; nucleotide binding protein 1 (MinD homolog, E. coli) |
| U07231_at | Hs.309763 | NM_002092; G-rich RNA sequence binding factor 1 |
| U09278_at | Hs.436852 | NM_004460; fibroblast activation protein, alpha subunit |
| U09937_rna1_s_at | | Plasminogen activator, urokinase receptor CD87; PLAUR |
| U10550_at | Hs.79022 | NM_005261; GTP-binding mitogen-induced T-cell protein NM_181702; GTP-binding mitogen-induced T-cell protein |
| U12424_s_at | Hs.108646 | NM_000408; glycerol-3-phosphate dehydrogenase 2 (mitochondrial) |
| U16306_at | Hs.434488 | NM_004385; chondroitin sulfate proteoglycan 2 (versican) |
| U20158_at | Hs.2488 | NM_005565; lymphocyte cytosolic protein 2 |
| U20536_s_at | Hs.3280 | NM_001226; caspase 6 isoform alpha preproprotein NM_032992; caspase 6 isoform beta |
| U24266_at | Hs.77448 | NM_003748; aldehyde dehydrogenase 4A1 precursor NM_170726; aldehyde dehydrogenase 4A1 precursor |
| U28249_at | Hs.301350 | NM_005971; FXYD domain containing ion transport regulator 3 isoform 1 precursor NM_021910; FXYD domain containing ion transport regulator 3 isoform 2 precursor |
| U28488_s_at | Hs.155935 | NM_004054; complement component 3a receptor 1 |
| U29680_at | Hs.227817 | NM_004049; BCL2-related protein A1 |
| U37143_at | Hs.152096 | NM_000775; cytochrome P450, family 2, subfamily 1, polypeptide 2 |
| U38864_at | Hs.108139 | NM_012256; zinc finger protein 212 |
| U39840_at | Hs.163484 | NM_004496; forkhead box A1 |
| U41315_rna1_s_at | | Makorin ring finger protein 1; MKRN1 |
| U44111_at | Hs.42151 | NM_006895; histamine N-methyltransferase |
| U47414_at | Hs.13291 | NM_004354; cyclin G2 |
| U49352_at | Hs.414754 | NM_001359; 2,4-dienoyl CoA reductase 1 precursor |
| U50708_at | Hs.1265 | NM_000056; branched chain keto acid dehydrogenase E1, beta polypeptide precursor NM_183050; branched chain keto acid dehydrogenase E1, beta polypeptide precursor |
| U52101_at | Hs.9999 | NM_001425; epithelial membrane protein 3 |
| U59914_at | Hs.153863 | NM_005585; MAD, mothers against decapentaplegic homolog 6 |
| U60205_at | Hs.393239 | NM_006745; sterol-C4-methyl oxidase-like |
| U61981_at | Hs.42674 | NM_002439; mutS homolog 3 |
| U64520_at | Hs.66708 | NM_004781; vesicle-associated membrane protein 3 (cellubrevin) |
| U65093_at | Hs.82071 | NM_006079; Cbp/p300-interacting transactivator, with Glu/Asp-rich carboxy-terminal domain, 2 |
| U66619_at | Hs.444445 | NM_003078; SWI/SNF-related matrix-associated actin-dependent regulator of chromatin d3 |
| U68019_at | Hs.288261 | NM_005902; MAD, mothers against decapentaplegic homolog 3 |
| U68385_at | Hs.380923 | Meis homeobox 3 pseudogene 1; MEIS3P1 |
| U68485_at | Hs.193163 | NM_004305; bridging integrator 1 isoform 8 NM_139343; bridging integrator 1 isoform 1 NM_139344; bridging integrator 1 isoform 2 NM_139345; bridging integrator 1 isoform 3 NM_139346; bridging integrator 1 isoform 4 NM_139347; bridging integrator 1 isoform 5 NM_139348; bridging integrator 1 isoform 6 NM_139349; bridging integrator 1 isoform 7 NM_139350; bridging integrator 1 isoform 9 NM_139351; bridging integrator 1 isoform 10 |

TABLE 10-continued

160 Genes for classifier

| Chip acc. # | UniGene Build 162 | Description |
|---|---|---|
| U74324_at | Hs.90875 | NM_002871; RAB-interacting factor |
| U77970_at | Hs.321164 | NM_002518; neuronal PAS domain protein 2 NM_032235; |
| U83303_cds2_at | Hs.164021 | NM_002993; chemokine (C—X—C motif) ligand 6 (granulocyte chemotactic protein 2) |
| U88871_at | Hs.79993 | NM_000288; peroxisomal biogenesis factor 7 |
| U90549_at | Hs.236774 | NM_006353; high mobility group nucleosomal binding domain 4 |
| U90716_at | Hs.79187 | NM_001338; coxsackie virus and adenovirus receptor |
| V00594_at | Hs.118786 | NM_005953; metallothionein 2A |
| V00594_s_at | Hs.118786 | NM_005953; metallothionein 2A |
| X02761_s_at | Hs.418138 | NM_002026; fibronectin 1 isoform 1 preproprotein NM_054034; fibronectin 1 isoform 2 preproprotein |
| X04011_at | Hs.88974 | NM_000397; cytochrome b-245, beta polypeptide (chronic granulomatous disease) |
| X04085_rna1_at | | Catalase; CAT |
| X07438_s_at | | Retinol binding protein 1, cellular; RBP1 |
| X07743_at | Hs.77436 | NM_002664; pleckstrin |
| X13334_at | Hs.75627 | NM_000591; CD14 antigen precursor |
| X14046_at | Hs.153053 | NM_001774; CD37 antigen |
| X14813_at | Hs.166160 | NM_001607; acetyl-Coenzyme A acyltransferase 1 |
| X15880_at | Hs.415997 | NM_001848; collagen, type VI, alpha 1 precursor |
| X15882_at | Hs.420269 | NM_001849; alpha 2 type VI collagen isoform 2C2 precursor NM_058174; alpha 2 type VI collagen isoform 2C2a precursor NM_058175; alpha 2 type VI collagen isoform 2C2a precursor |
| X51408_at | Hs.380138 | NM_001822; chimerin (chimaerin) 1 |
| X53800_s_at | Hs.89690 | NM_002090; chemokine (C—X—C motif) ligand 3 |
| X54489_rna1_at | | Chemokine (C—X—C motif) ligand 1 (melanoma growth stimulating activity, alpha); CXCL1 |
| X57351_s_at | Hs.174195 | NM_006435; interferon induced transmembrane protein 2 (1-8D) |
| X57579_s_at | | Inhibin, beta A; INHBA |
| X58072_at | Hs.169946 | NM_002051; GATA binding protein 3 NM_032742; |
| X62048_at | Hs.249441 | NM_003390; wee1 tyrosine kinase |
| X64072_s_at | Hs.375957 | NM_000211; integrin beta chain, beta 2 precursor |
| X65614_at | Hs.2962 | NM_005980; S100 calcium binding protein P |
| X66945_at | Hs.748 | NM_000604; fibroblast growth factor receptor 1 isoform 1 precursor NM_015850; fibroblast growth factor receptor 1 isoform 2 precursor NM_023105; fibroblast growth factor receptor 1 isoform 3 precursor NM_023106; fibroblast growth factor receptor 1 isoform 4 precursor NM_023107; fibroblast growth factor receptor 1 isoform 5 precursor NM_023108; fibroblast growth factor receptor 1 isoform 6 precursor NM_023109; fibroblast growth factor receptor 1 isoform 7 precursor NM_023110; fibroblast growth factor receptor 1 isoform 8 precursor NM_023111; fibroblast growth factor receptor 1 isoform 9 precursor |
| X67491_f_at | Hs.355697 | NM_005271; glutamate dehydrogenase 1 |
| X68194_at | Hs.80919 | NM_006754; synaptophysin-like protein isoform a NM_182715; synaptophysin-like protein isoform b |
| X73882_at | Hs.254605 | NM_003980; microtubule-associated protein 7 |
| X78520_at | Hs.372528 | NM_001829; chloride channel 3 |
| X78549_at | Hs.51133 | NM_005975; PTK6 protein tyrosine kinase 6 |
| X78565_at | Hs.98998 | NM_002160; tenascin C (hexabrachion) |
| AF000231_at | Hs.75618 | NM_004663; Ras-related protein Rab-11A |
| D13666_s_at | Hs.136348 | NM_006475; osteoblast specific factor 2 (fasciclin I-like) |
| D49372_s_at | Hs.54460 | NM_002986; small inducible cytokine A11 precursor |
| D83920_at | Hs.440898 | NM_002003; ficolin 1 precursor |
| D86479_at | Hs.439463 | NM_001129; adipocyte enhancer binding protein 1 precursor |
| D87433_at | Hs.301989 | NM_015136; stabilin 1 |
| D89077_at | Hs.75367 | NM_006748; Src-like-adaptor |
| D89377_at | Hs.89404 | NM_002449; msh homeo box homolog 2 |
| HG4069-HT4339_s_at | | |
| HG67-HT67_f_at | | |
| HG907-HT907_at | | |
| J02871_s_at | Hs.436317 | NM_000779; cytochrome P450, family 4, subfamily B, polypeptide 1 |
| J03278_at | Hs.307783 | NM_002609; platelet-derived growth factor receptor beta precursor |
| J04058_at | Hs.169919 | NM_000126; electron transfer flavoprotein, alpha polypeptide |
| J05032_at | Hs.32393 | NM_001349; aspartyl-tRNA synthetase |
| J05070_at | Hs.151738 | NM_004994; matrix metalloproteinase 9 preproprotein |
| J05448_at | Hs.79402 | NM_002694; DNA directed RNA polymerase II polypeptide C NM_032940; DNA directed RNA polymerase II polypeptide C |
| K01396_at | Hs.297681 | NM_000295; serine (or cysteine) proteinase inhibitor, clade A (alpha-1 antiproteinase, antitrypsin), member 1 |
| L13720_at | Hs.437710 | NM_000820; growth arrest-specific 6 |

TABLE 10-continued

160 Genes for classifier

| Chip acc. # | UniGene Build 162 | Description |
|---|---|---|
| L40904_at | Hs.387667 | NM_005037; peroxisome proliferative activated receptor gamma isoform 1 NM_015869; peroxisome proliferative activated receptor gamma isoform 2 NM_138711; peroxisome proliferative activated receptor gamma isoform 1 NM_138712; peroxisome proliferative activated receptor gamma isoform 1 |
| M12125_at | Hs.300772 | NM_003289; tropomyosin 2 (beta) |
| M15395_at | Hs.375957 | NM_000211; integrin beta chain, beta 2 precursor |
| M16591_s_at | Hs.89555 | NM_002110; hemopoietic cell kinase isoform p61HCK |
| M20530_at | | |
| M23178_s_at | Hs.73817 | NM_002983; chemokine (C-C motif) ligand 3 |
| M32011_at | Hs.949 | NM_000433; neutrophil cytosolic factor 2 |
| M33195_at | Hs.433300 | NM_004106; Fc fragment of IgE, high affinity I, receptor for, gamma polypeptide precursor |
| M55998_s_at | Hs.172928 | NM_000088; alpha 1 type I collagen preproprotein |
| M57731_s_at | Hs.75765 | NM_002089; chemokine (C—X—C motif) ligand 2 |
| M63262_at | | |
| M68840_at | Hs.183109 | NM_000240; monoamine oxidase A |
| M69203_s_at | Hs.75703 | NM_002984; chemokine (C-C motif) ligand 4 precursor |
| M72885_rna1_s_at | | G0/G1 switch 2; G0S2 |
| M83822_at | Hs.209846 | NM_006726; LPS-responsive vesicle trafficking, beach and anchor containing |
| S77393_at | Hs.145754 | NM_016531; Kruppel-like factor 3 (basic) |
| U01833_at | Hs.81469 | NM_002484; nucleotide binding protein 1 (MinD homolog, E. coli) |
| U07231_at | Hs.309763 | NM_002092; G-rich RNA sequence binding factor 1 |
| U09937_rna1_s_at | | Plasminogen activator, urokinase receptor CD87; PLAUR |
| U10550_at | Hs.79022 | NM_005261; GTP-binding mitogen-induced T-cell protein NM_181702; GTP-binding mitogen-Induced T-cell protein |
| U20158_at | Hs.2488 | NM_005565; lymphocyte cytosolic protein 2 |
| U28488_s_at | Hs.155935 | NM_004054; complement component 3a receptor 1 |
| U29680_at | Hs.227817 | NM_004049; BCL2-related protein A1 |
| U41315_rna1_s_at | | Makorin ring finger protein 1; MKRN1 |
| U47414_at | Hs.13291 | NM_004354; cyclin G2 |
| U49352_at | Hs.414754 | NM_001359; 2,4-dienoyl CoA reductase 1 precursor |
| U50708_at | Hs.1265 | NM_000056; branched chain keto acid dehydrogenase E1, beta polypeptide precursor NM_183050; branched chain keto acid dehydrogenase E1, beta polypeptide precursor |
| U52101_at | Hs.9999 | NM_001425; epithelial membrane protein 3 |
| U59914_at | Hs.153863 | NM_005585; MAD, mothers against decapentaplegic homolog 6 |
| U64520_at | Hs.66708 | NM_004781; vesicle-associated membrane protein 3 (cellubrevin) |
| U65093_at | Hs.82071 | NM_006079; Cbp/p300-interacting transactivator, with Glu/Asp-rich carboxy-terminal domain, 2 |
| U68019_at | Hs.288261 | NM_005902; MAD, mothers against decapentaplegic homolog 3 |
| U68385_at | Hs.380923 | Meis homeobox 3 pseudogene 1; MEIS3P1 |
| U74324_at | Hs.90875 | NM_002871; RAB-interacting factor |
| U77970_at | Hs.321164 | NM_002518; neuronal PAS domain protein 2 NM_032235; |
| U90549_at | Hs.236774 | NM_006353; high mobility group nucleosomal binding domain 4 |
| X04085_rna1_at | | Catalase; CAT |
| X07438_s_at | | Retinol binding protein 1, cellular; RBP1 |
| X07743_at | Hs.77436 | NM_002664; pleckstrin |
| X13334_at | Hs.75627 | NM_000591; CD14 antigen precursor |
| X14046_at | Hs.153053 | NM_001774; CD37 antigen |
| X15880_at | Hs.415997 | NM_001848; collagen, type VI, alpha 1 precursor |
| X15882_at | Hs.420269 | NM_001849; alpha 2 type VI collagen isoform 2C2 precursor NM_058174; alpha 2 type VI collagen isoform 2C2a precursor NM_058175; alpha 2 type VI collagen isoform 2C2a precursor |
| X51408_at | Hs.380138 | NM_001822; chimerin (chimaerin) 1 |
| X53800_s_at | Hs.89690 | NM_002090; chemokine (C—X—C motif) ligand 3 |
| X54489_rna1_at | | chemokine (C—X—C motif) ligand 1 (melanoma growth stimulating activity, alpha); CXCL1 |
| X57579_s_at | | Inhibin, beta A; INHBA |
| X62048_at | Hs.249441 | NM_003390; wee1 tyrosine kinase |
| X64072_s_at | Hs.375957 | NM_000211; integrin beta chain, beta 2 precursor |
| X67491_f_at | Hs.355697 | NM_005271; glutamate dehydrogenase 1 |
| X68194_at | Hs.80919 | NM_006754; synaptophysin-like protein isoform a NM_182715; synaptophysin-like protein isoform b |
| X73882_at | Hs.254605 | NM_003980; microtubule-associated protein 7 |
| X78520_at | Hs.372528 | NM_001829; chloride channel 3 |
| X97267_rna1_s_at | | Protein tyrosine phosphatase, receptor type, C-associated protein; PTPRCAP |
| Y00787_s_at | Hs.624 | NM_000584; interleukin 8 precursor |
| Z12173_at | Hs.334534 | NM_002076; glucosamine (N-acetyl)-6-sulfatase precursor |
| Z19554_s_at | Hs.435800 | NM_003380; vimentin |

TABLE 10-continued

160 Genes for classifier

| Chip acc. # | UniGene Build 162 | Description |
|---|---|---|
| Z26491_s_at | Hs.240013 | NM_000754; catechol-O-methyltransferase isoform MB-COMT NM_007310; catechol-O-methyltransferase isoform S-COMT |
| Z29331_at | Hs.372758 | NM_003344; ubiquitin-conjugating enzyme E2H isoform 1 NM_182697; ubiquitin-conjugating enzyme E2H isoform 2 |
| Z48605_at | Hs.421825 | NM_006903; inorganic pyrophosphatase 2 isoform 2 NM_176865; NM_176866; inorganic pyrophosphatase 2 isoform 3 NM_176867; inorganic pyrophosphatase 2 isoform 4 NM_176869; inorganic pyrophosphatase 2 isoform 1 |
| Z74615_at | Hs.172928 | NM_000088; alpha 1 type I collagen preproprotein |

TABLE 12

40 genes for classifier

| Chip acc. # | UniGene Build 162 | description |
|---|---|---|
| D83920_at | Hs.440898 | NM_002003; ficolin 1 precursor |
| D89377_at | Hs.89404 | NM_002449; msh homeo box homolog 2 |
| J02871_s_at | Hs.436317 | NM_000779; cytochrome P450, family 4, subfamily B, polypeptide 1 |
| J05032_at | Hs.32393 | NM_001349; aspartyl-tRNA synthetase |
| J05070_at | Hs.151738 | NM_004994; matrix metalloproteinase 9 preproprotein |
| M16591_s_at | Hs.89555 | NM_002110; hemopoietic cell kinase isoform p61HCK |
| M23178_s_at | Hs.73817 | NM_002983; chemokine (C-C motif) ligand 3 |
| M32011_at | Hs.949 | NM_000433; neutrophil cytosolic factor 2 |
| M33195_at | Hs.433300 | NM_004106; Fc fragment of IgE, high affinity I, receptor for, gamma polypeptide precursor |
| M57731_s_at | Hs.75765 | NM_002089; chemokine (C—X—C motif) ligand 2 |
| M68840_at | Hs.183109 | NM_000240; monoamine oxidase A |
| M69203_s_at | Hs.75703 | NM_002984; chemokine (C-C motif) ligand 4 precursor |
| S77393_at | Hs.145754 | NM_016531; Kruppel-like factor 3 (basic) |
| U01833_at | Hs.81469 | NM_002484; nucleotide binding protein 1 (MinD homolog, E. coli) |
| U07231_at | Hs.309763 | NM_002092; G-rich RNA sequence binding factor 1 |
| U09937_rna1_s_at | | Plasminogen activator, urokinase receptor CD87; PLAUR |
| U20158_at | Hs.2488 | NM_005565; lymphocyte cytosolic protein 2 |
| U41315_rna1_s_at | | Makorin ring finger protein 1; MKRN1 |
| U47414_at | Hs.13291 | NM_004354; cyclin G2 |
| U49352_at | Hs.414754 | NM_001359; 2,4-dienoyl CoA reductase 1 precursor |
| U50708_at | Hs.1265 | NM_000056; branched chain keto acid dehydrogenase E1, beta polypeptide precursor NM_183050; branched chain keto acid dehydrogenase E1, beta polypeptide precursor |
| U65093_at | Hs.82071 | NM_006079; Cbp/p300-interacting transactivator, with Glu/Asp-rich carboxy-terminal domain, 2 |
| U68385_at | Hs.380923 | Meis homeobox 3 pseudogene 1; MEISP1 |
| U77970_at | Hs.321164 | NM_002518; neuronal PAS domain protein 2 NM_032235; |
| U90549_at | Hs.236774 | NM_006353; high mobility group nucleosomal binding domain 4 |
| X13334_at | Hs.75627 | NM_000591; CD14 antigen precursor |
| X15880_at | Hs.415997 | NM_001848; collagen, type VI, alpha 1 precursor |
| X15882_at | Hs.420269 | NM_001849; alpha 2 type VI collagen isoform 2C2 precursor NM_058174; alpha 2 type VI collagen isoform 2C2a precursor NM_058175; alpha 2 type VI collagen isoform 2C2a precursor |
| X51408_at | Hs.380138 | NM_001822; chimerin (chimaerin) 1 |
| X53800_s_at | Hs.89690 | NM_002090; chemokine (C—X—C motif) ligand 3 |
| X54489_rna1_at | | Chemokine (C—X—C motif) ligand 1 (melanoma growth stimulating activity, alpha): CXCL1 |
| X57579_s_at | | Inhibin, beta A; INHBA |
| X64072_s_at | Hs.375957 | NM_000211; integrin beta chain, beta 2 precursor |
| X67491_f_at | Hs.355697 | NM_005271; glutamate dehydrogenase 1 |
| X68194_at | Hs.80919 | NM_006754; synaptophysin-like protein isoform a NM_182715; synaptophysin-like protein isoform b |
| X73882_at | Hs.254605 | NM_003980; microtubule-associated protein 7 |
| X78520_at | Hs.372528 | NM_001829; chloride channel 3 |
| Z29331_at | Hs.372758 | NM_003344; ubiquitin-conjugating enzyme E2H isoform 1 NM_182697; ubiquitin-conjugating enzyme E2H isoform 2 |
| Z48605_at | Hs.421825 | NM_006903; inorganic pyrophosphatase 2 isoform 2 NM_176865; NM_176866; inorganic pyrophosphatase 2 isoform 3 NM_176867; inorganic pyrophosphatase 2 isoform 4 NM_176869; inorganic pyrophosphatase 2 isoform 1 |
| Z74615_at | Hs.172928 | NM_000088; alpha 1 type I collagen preproprotein |

TABLE 13

20 genes for classifier

| Chip acc. # | UniGene Build 162 | description |
|---|---|---|
| D89377_at | Hs.89404 | NM_002449; msh homeo box homolog 2 |
| J05032_at | Hs.32393 | NM_001349; aspartyl-tRNA synthetase |
| M23178_s_at | Hs.73817 | NM_002983; chemokine (C-C motif) ligand 3 |
| M32011_at | Hs.949 | NM_000433; neutrophil cytosolic factor 2 |
| M69203_s_at | Hs.75703 | NM_002984; chemokine (C-C motif) ligand 4 precursor |
| S77393_at | Hs.145754 | NM_016531; Kruppel-like factor 3 (basic) |
| U07231_at | Hs.309763 | NM_002092; G-rich RNA sequence binding factor 1 |
| U41315_rna1_s_at | | Makorin ring finger protein 1; MKRN1 |
| U47414_at | Hs.13291 | NM_004354; cyclin G2 |
| U49352_at | Hs.414754 | NM_001359; 2,4-dienoyl CoA reductase 1 precursor |
| U50708_at | Hs.1265 | NM_000056; branched chain keto acid dehydrogenase E1, beta polypeptide precursor NM_183050; branched chain keto acid dehydrogenase E1, beta polypeptide precursor |
| U77970_at | Hs.321164 | NM_002518; neuronal PAS domain protein 2 NM_032235; |
| X13334_at | Hs.75627 | NM_000591; CD14 antigen precursor |
| X57579_s_at | | Inhibin, beta A; INHBA |
| X64072_s_at | Hs.375957 | NM_000211; integrin beta chain, beta 2 precursor |
| X68194_at | Hs.80919 | NM_006754; synaptophysin-like protein isoform a NM_182715; synaptophysin-like protein isoform b |
| X73882_at | Hs.254605 | NM_003980; microtubule-associated protein 7 |
| X78520_at | Hs.372528 | NM_001829; chloride channel 3 |
| Z48605_at | Hs.421825 | NM_006903; inorganic pyrophosphatase 2 isoform 2 NM_176865; NM_176866; inorganic pyrophosphatase 2 isoform 3 NM_176867; inorganic pyrophosphatase 2 isoform 4 NM_176869; inorganic pyrophosphatase 2 isoform 1 |
| Z74615_at | Hs.172928 | NM_000088; alpha 1 type I collagen preproprotein |

TABLE 14

10 genes for classifier

| Chip acc. # | UniGene Build 162 | description |
|---|---|---|
| D89377_at | Hs.89404 | NM_002449; msh homeo box homolog 2 |
| S77393_at | Hs.145754 | NM_016531; Kruppel-like factor 3 (basic) |
| U41315_rna1_s_at | | Makorin ring finger protein 1; MKRN1 |
| U47414_at | Hs.13291 | NM_004354; cyclin G2 |
| U77970_at | Hs.321164 | NM_002518; neuronal PAS domain protein 2 NM_032235; |
| X68194_at | Hs.80919 | NM_006754; synaptophysin-like protein isoform a NM_182715; synaptophysin-like protein isoform b |
| X73882_at | Hs.254605 | NM_003980; microtubule-associated protein 7 |
| X78520_at | Hs.372528 | NM_001829; chloride channel 3 |
| Z48605_at | Hs.421825 | NM_006903; inorganic pyrophosphatase 2 isoform 2 NM_176865; NM_176866; inorganic pyrophosphatase 2 isoform 3 NM_176867; inorganic pyrophosphatase 2 isoform 4 NM_176869; inorganic pyrophosphatase 2 isoform 1 |
| Z74615_at | Hs.172928 | NM_000088; alpha 1 type I collagen preproprotein |

TABLE 15

32 genes for classifier

| Chip acc. # | UniGene Build 162 | description |
|---|---|---|
| D83920_at | Hs.440898 | NM_002003; ficolin 1 precursor |
| HG67-HT67_f_at | | |
| HG907-HT907_at | | |
| J05032_at | Hs.32393 | NM_001349; aspartyl-tRNA synthetase |
| K01396_at | Hs.297681 | NM_000295; serine (or cysteine) proteinase inhibitor, clade A (alpha-1 antiproteinase, antitrypsin), member 1 |
| M16591_s_at | Hs.89555 | NM_002110; hemopoietic cell kinase isoform p61HCK |
| M32011_at | Hs.949 | NM_000433; neutrophil cytosolic factor 2 |
| M33195_at | Hs.433300 | NM_004106; Fc fragment of IgE, high affinity I, receptor for, gamma polypeptide precursor |
| M37033_at | Hs.443057 | NM_000560; CD53 antigen |
| M57731_s_at | Hs.75765 | NM_002089; chemokine (C—X—C motif) ligand 2 |
| M63262_at | | Arachidonate 5-lipoxygenase-activating protein; ALOX5AP |
| S77393_at | Hs.145754 | NM_016531; Kruppel-like factor 3 (basic) |
| U01833_at | Hs.81469 | NM_002484; nucleotide binding protein 1 (MinD homolog, E. coli) |
| U07231_at | Hs.309763 | NM_002092; G-rich RNA sequence binding factor 1 |
| U41315_rna1_s_at | | Makorin ring finger protein 1; MKRN1 |

TABLE 15-continued

32 genes for classifier

| Chip acc. # | UniGene Build 162 | description |
|---|---|---|
| U47414_at | Hs.13291 | NM_004354; cyclin G2 |
| U50708_at | Hs.1265 | NM_000056; branched chain keto acid dehydrogenase E1, beta polypeptide precursor NM_183050; branched chain keto acid dehydrogenase E1, beta polypeptide precursor |
| U52101_at | Hs.9999 | NM_001425; epithelial membrane protein 3 |
| U74324_at | Hs.90875 | NM_002871; RAB-interacting factor |
| U77970_at | Hs.321164 | NM_002518; neuronal PAS domain protein 2 NM_032235; |
| U90549_at | Hs.236774 | NM_006353; high mobility group nucleosomal binding domain 4 |
| X13334_at | Hs.75627 | NM_000591; CD14 antigen precursor |
| X54489_rna1_at | | chemokine (C—X—C motif) ligand 1 (melanoma growth stimulating activity, alpha) FSP; CXCL1 |
| X57579_s_at | | Inhibin, beta A; INHBA |
| X64072_s_at | Hs.375957 | NM_000211; integrin beta chain, beta 2 precursor |
| X68194_at | Hs.80919 | NM_006754; synaptophysin-like protein isoform a NM_182715; synaptophysin-like protein isoform b |
| X73882_at | Hs.254605 | NM_003980; microtubule-associated protein 7 |
| X78520_at | Hs.372528 | NM_001829; chloride channel 3 |
| X95632_s_at | Hs.387906 | NM_005759; abl-interactor 2 |
| Z29331_at | Hs.372758 | NM_003344; ubiquitin-conjugating enzyme E2H isoform 1 NM_182697; ubiquitin-conjugating enzyme E2H isoform 2 |
| Z48605_at | Hs.421825 | NM_006903; inorganic pyrophosphatase 2 isoform 2 NM_176865; NM_176866; inorganic pyrophosphatase 2 isoform 3 NM_176867; inorganic pyrophosphatase 2 isoform 4 NM_176869; inorganic pyrophosphatase 2 isoform 1 |
| Z74615_at | Hs.172928 | NM_000088; alpha 1 type I collagen preproprotein |

Recurrence Predictor

An outcome predictor able to identify the likely presence or absence of recurrence in patients with superficial Ta tumors was also tested (see Table 16).

Table 16. Patient Disease Course Information—Recurrence vs. No Recurrence

From the hierarchical cluster analysis of the tumor samples it was found that the tumors with a high recurrence frequency were separated from the tumors with low recurrence frequency. To study this further two groups of Ta tumors were profiled—15 tumors with low recurrence frequency and 16 tumors with high recurrence frequency. To avoid influence from other tumor characteristics only tumors that showed the same growth pattern and tumors that showed no sign of concomitant carcinoma in situ were used. Furthermore, the tumors were all primary tumors. The tumors used for identifying genes differentially expressed in recurrent and non-recurrent tumors are listed in Table 16 below.

TABLE 16

Disease course information of all patients involved.

| Group | Patient | Tumor (date) | Pattern | Carcinoma in situ | Time to recurrence |
|---|---|---|---|---|---|
| A | 968-1 | Ta gr2 | Papillary | no | 27 month. |
| A | 928-1 | Ta gr2 | Papillary | no | 38 month. |
| A | 934-1 | Ta gr2 (220798) | Papillary | no | — |
| A | 709-1 | Ta gr2 (210798) | Papillary | no | — |
| A | 930-1 | Ta gr2 (300698) | Papillary | no | — |
| A | 524-1 | Ta gr2 (201095) | Papillary | no | — |
| A | 455-1 | Ta gr2 (060695) | Papillary | no | — |
| A | 370-1 | Ta gr2 (100195) | Papillary | no | — |
| A | 810-1 | Ta gr2 (031097) | Papillary | no | — |
| A | 1146-1 | Ta gr2 (231199) | Papillary | no | — |
| A | 1161-1 | Ta gr2 (101299) | Mixed | no | — |
| A | 1006-1 | Ta gr2 (231198) | Papillary | no | — |
| A | 942-1 | Ta gr2 | Papillary | no | 24 month. |
| A | 1060-1 | Ta gr2 | Papillary | no | 36 month. |
| A | 1255-1 | Ta gr2 | Papillary | no | 24 month. |
| B | 441-1 | Ta gr2 | Papillary | no | 6 month. |
| B | 780-1 | Ta gr2 | Papillary | no | 2 month. |
| B | 815-2 | Ta gr2 | Papillary | no | 6 month. |
| B | 829-1 | Ta gr2 | Papillary | no | 4 month. |
| B | 861-1 | Ta gr2 | Papillary | no | 4 month. |
| B | 925-1 | Ta gr2 | Papillary | no | 5 month. |
| B | 1008-1 | Ta gr2 | Papillary | no | 5 month. |
| B | 1086-1 | Ta gr2 | Papillary | no | 6 month. |
| B | 1105-1 | Ta gr2 | Papillary | no | 8 month. |
| B | 1145-1 | Ta gr2 | Papillary | no | 4 month. |
| B | 1327-1 | Ta gr2 | Papillary | no | 5 month. |
| B | 1352-1 | Ta gr2 | Papillary | no | 6 month. |
| B | 1379-1 | Ta gr2 | Papillary | no | 5 month. |
| B | 533-1 | Ta gr2 | Papillary | no | 4 month. |
| B | 679-1 | Ta gr2 | Papillary | no | 4 month. |
| B | 692-1 | Ta gr2 | Papillary | no | 5 month. |

Group A: Primary tumors from patients with no recurrence of the disease for 2 years.
Group B: Primary tumors from patients with recurrence of the disease within 8 months.

Supervised Learning Prediction of Recurrence

Herein, genes differentially expressed between non-recurring and recurring tumors were identified. Cross-validation and prediction was performed as previously described, except that genes are selected based on the value of the Wilcoxon statistic for difference between the two groups.

Prediction Performance

The prediction performance was tested using from 1-200 genes in the cross-validation loops. FIG. 6 shows that the lowest error rate (8 errors) is obtained in e.g. the cross-validation model using from 39 genes. This cross-validation model was selected as the final predictor, based on these results. The prediction results from the 39 gene cross-validation loops are listed in Table 17. The predictor misclassified four of the samples in each group, and in one of the predictions the difference in the distances between the two group means is below the 5% difference limit, as described above. The probability of misclassifying 8 or less arrays by a random classification is 0.0053.

TABLE 17

Recurrence prediction results of 39 gene cross-validation loops.

| Group | Patient | Tumor (date) | Prediction | Error | Prediction strength |
|---|---|---|---|---|---|
| A | 968-1 | Ta gr2 | 0 | | 0.19 |
| A | 928-1 | Ta gr2 | 0 | | 0.49 |
| A | 934-1 | Ta gr2 (220798) | 0 | | 1.73 |
| A | 709-1 | Ta gr2 (210798) | 0 | | 0.45 |
| A | 930-1 | Ta gr2 (300698) | 0 | | 0.82 |
| A | 524-1 | Ta gr2 (201095) | 0 | | 0.14 |
| A | 455-1 | Ta gr2 (060695) | 1 | * | 0.68 |
| A | 370-1 | Ta gr2 (100195) | 0 | | 0.32 |
| A | 810-1 | Ta gr2 (031097) | 0 | | 0.45 |
| A | 1146-1 | Ta gr2 (231199) | 0 | | 0.98 |
| A | 1161-1 | Ta gr2 (101299) | 0 | | 0.03 |
| A | 1006-1 | Ta gr2 (231198) | 1 | * | 1.57 |
| A | 942-1 | Ta gr2 | 0 | | 0.31 |
| A | 1060-1 | Ta gr2 | 1 | * | 0.81 |
| A | 1255-1 | Ta gr2 | 1 | * | 0.71 |
| B | 441-1 | Ta gr2 | 1 | | 1.03 |
| B | 780-1 | Ta gr2 | 1 | | 0.37 |
| B | 815-2 | Ta gr2 | 1 | | 0.35 |
| B | 829-1 | Ta gr2 | 1 | | 0.75 |
| B | 861-1 | Ta gr2 | 0 | * | 2.55 |
| B | 925-1 | Ta gr2 | 1 | | 0.78 |
| B | 1008-1 | Ta gr2 | 0 | * | 0.12 |
| B | 1086-1 | Ta gr2 | 0 | * | 0.51 |

TABLE 17-continued

Recurrence prediction results of 39 gene cross-validation loops.

| Group | Patient | Tumor (date) | Prediction | Error | Prediction strength |
|---|---|---|---|---|---|
| B | 1105-1 | Ta gr2 | 1 | | 0.37 |
| B | 1145-1 | Ta gr2 | 1 | | 0.44 |
| B | 1327-1 | Ta gr2 | 1 | | 1.96 |
| B | 1352-1 | Ta gr2 | 0 | * | 0.97 |
| B | 1379-1 | Ta gr2 | 1 | | 0.67 |
| B | 533-1 | Ta gr2 | 1 | | 0.31 |
| B | 679-1 | Ta gr2 | 1 | | 0.82 |
| B | 692-1 | Ta gr2 | 1 | | 0.45 |

Group A: Primary tumors from patients with no recurrence of the disease for 2 years.
Group B: Primary tumors from patients with recurrence of the disease within 8 months.
Prediction, 0 = no recurrence, 1 = recurrence.

The optimal number of genes in cross-validation loops was found to be 39 (75% of the samples were correctly classified, $p<0.006$) and from this, the 26 genes that were used in at least 75% of the cross-validation loops were selected to constitute the final recurrence predictor.

Consequently, this set of genes is to be used for predicting recurrence in independent samples. The strength of the predictive genes was tested by permutation analysis, see Table 18.

The genes used in at least 29 of the 31 cross-validation loops were selected to constitute the final recurrence prediction model. The expression pattern of those 26 genes is shown in FIG. 12 of application Ser. No. 12/180,321.

TABLE 18

The 26 genes that were found optimal for recurrence prediction.

| Feature | Unigene build 168 | Description | Number* | Test (W-N)** |
|---|---|---|---|---|
| AF006041_at | Hs.336916 | NM_001350; death-associated protein 6 | 31 | 0.054 (161-7) |
| D21337_at | Hs.408 | NM_001847; type IV alpha 6 collagen isoform A precursor NM_033641; type IV alpha 6 collagen isoform B precursor | 31 | 0.058 (160-6) |
| D49387_at | Hs.294584 | NM_012212; NADP-dependent leukotriene B4 12-hydroxydehydrogenase | 31 | 0.118 (313-8) |
| D64154_at | Hs.90107 | NM_007002; adhesion regulating molecule 1 precursor NM_175573; adhesion regulating molecule 1 precursor | 31 | 0.078 (165-9) |
| D83780_at | Hs.437991 | NM_014846; KIAA0196 gene product | 31 | 0.094 (159-4) |
| D87258_at | Hs.75111 | NM_002775; protease, serine, 11 | 30 | 0.112 (168-11) |
| D87437_at | Hs.43660 | NM_014837; chromosome 1 open reading frame 16 | 31 | 0.058 (160-6) |
| HG1879-HT1919_at | | | 31 | 0.122 (314-7) |
| HG3076-HT3238_s_at | | | 31 | 0.080 (309-17) |
| HG511-HT511_at | | | 31 | 0.348 (319-2) |
| L34155_at | Hs.83450 | NM_000227; laminin alpha 3 subunit precursor | 31 | 0.122 (314-7) |
| L38928_at | Hs.118131 | NM_006441; 5,10-methenyltetrahydrofolate synthetase (5-formyltetrahydrofolate cyclo-ligase) | 29 | 0.348 (319-2) |
| L49169_at | Hs.75678 | NM_006732; FBJ murine osteosarcoma viral oncogene homolog B | 31 | 0.108 (155-2) |
| M16938_s_at | Hs.820 | NM_004503; homeo box C6 isoform 1 NM_153693; homeo box C6 isoform 2 | 29 | 0.09 (170-16) |
| M63175_at | Hs.295137 | NM_001144; autocrine motility factor receptor isoform a NM_138958; autocrine motility factor receptor isoform b | 29 | 0.098 (308-18) |
| M64572_at | Hs.405666 | NM_002829; protein tyrosine phosphatase, non-receptor type 3 | 31 | 0.064 (305-31) |
| M98528_at | Hs.79404 | NM_014392; DNA segment on chromosome 4 (unique) 234 expressed sequence | 31 | 0.122 (314-7) |
| U21858_at | Hs.60679 | NM_003187; TBP-associated factor 9 NM_016283; adrenal gland protein AD-004 | 31 | 0.122 (314-7) |
| U45973_at | Hs.178347 | NM_016532; skeletal muscle and kidney enriched inositol phosphatase isoform 1 NM_130766; skeletal muscle and kidney enriched inositol phosphatase isoform 2 | 31 | 0.094 (310-14) |

TABLE 18-continued

The 26 genes that were found optimal for recurrence prediction.

| Feature | Unigene build 168 | Description | Number* | Test (W-N)** |
|---|---|---|---|---|
| U58516_at | Hs.3745 | NM_005928; milk fat globule-EGF factor 8 protein | 29 | 0.100 (175-28) |
| U62015_at | Hs.8867 | NM_001554; cysteine-rich, angiogenic inducer, 61 | 31 | 0.106 (169-13) |
| U66702_at | Hs.74624 | NM_002847; protein tyrosine phosphatase, receptor type, N polypeptide 2 isoform 1 precursor NM_130842; protein tyrosine phosphatase, receptor type, N polypeptide 2 isoform 2 precursor NM_130843; protein tyrosine phosphatase, receptor type, N polypeptide 2 isoform 3 precursor | 31 | 0.146 (149-1) |
| U70439_s_at | Hs.84264 | NM_006401; acidic (leudne-rich) nuclear phosphoprotein 32 family, member B | 30 | 0.08 (309-17) |
| U94855_at | Hs.381255 | NM_003754; eukaryotic translation initiation factor 3, subunit 5 epsilon, 47 kDa | 30 | 0.092 (311-12) |
| X63469_at | Hs.77100 | NM_002095; general transcription factor IIE, polypeptide 2, beta 34 kDa | 31 | 0.092 (311-12) |
| Z23064_at | Hs.380118 | NM_002139; RNA binding motif protein, X chromosome | 30 | 0.066 (307-24) |

*Number: Number of times the gene has been used in a cross-validation loop.
**Test: The numbers in parenthesis are the value W of the Wilcoxon test statistic for no difference between the two groups together with the number N of genes for which the Wilcoxon test statistic is bigger than or equal to the value W. The test value is obtained from 500 permutations of the arrays. In each permutation new pseudogroups were formed where both of the pseudogroups have the same proportion of arrays from the two original groups. For each permutation the number of genes for which the Wilcoxon test statistic based on the pseudogroups is bigger than or equal to W was counted, and the test value is the proportion of the permutations for which this number is bigger than or equal to N. Thus the test value measures the significance of the observed value W. Consequently, for most of the selected genes, one only finds as least as strongly predictive genes in about 10% of the formed pseudogroups.

Data are presented here on expression patterns that classify the benign and muscle-invasive bladder carcinomas. Furthermore, one can identify subgroups of bladder cancer such as Ta tumors with surrounding CIS, Ta tumors with a high probability of progression as well as recurrence, and T2 tumors with squamous metaplasia. As a novel finding, the matrix remodelling gene cluster was specifically expressed in the tumours having the worst prognosis, namely the T2 tumours and tumours surrounded by CIS. For some of these genes new small molecule inhibitors already exist (Kerr et al. 2002), and thus they form drug targets. At present it is not possible to clinically identify patients, who will experience recurrence and non-recurrence, but it would be a great benefit to both the patients and the health system, as it would reduce the number of unnecessary control examinations in bladder tumor patients. To determine the optimal gene-set for separating non-recurrent and recurrent tumors, a cross-validation scheme using from 1-200 genes was again applied. It was determined that the optimal number of genes in cross-validation loops was 39 (75% of the samples were correctly classified, p<0.01, FIG. 7) and from this the 26 genes (FIG. 12 in Ser. No. 12/180,321) were selected that were used in at least 75% of the cross-validation loops to constitute the final recurrence predictor. Consequently, this set of genes is to be used for predicting recurrence in independent samples. The strength of the predictive genes was tested by performing 500 permutations of the arrays. This revealed that for most of the predictive genes only in a small number of the new pseudo-groups would one obtain equally as good predictors as in the real groups.

Biological Material 66 bladder tumor biopsies were sampled from patients following removal of the necessary amount of tissue for routine pathology examination. The tumors were frozen immediately after surgery and stored at −80° C. in a guanidinium thiocyanate solution. All tumors were graded according to Bergkvist et al. 1965 and re-evaluated by a single pathologist. As normal urothelial reference samples, a pool of biopsies (from 37 patients) as well as three single bladder biopsies from patients with prostatic hyperplasia or urinary incontinence were used. Informed consent was obtained in all cases and protocols were approved by the local scientific ethical committee.

RNA Purification and cRNA Preparation

Total RNA was isolated from crude tumor biopsies using a Polytron homogenisator and the RNAzol B RNA isolation method (WAK-Chemie Medical GmbH). 10 μg total RNA was used as starting material for the cDNA preparation. The first and second strand cDNA synthesis was performed using the SuperScript Choice System (Life Technologies) according to the manufacturers' instructions except using an oligo-dT primer containing a T7 RNA polymerase promoter site. Labelled cRNA was prepared using the BioArray High Yield RNA Transcript Labelling Kit (Enzo). Biotin labelled CTP and UTP (Enzo) were used in the reaction together with unlabeled NTP's. Following the IVT reaction, the unincorporated nucleotides were removed using RNeasy columns (Qiagen).

Array Hybridisation and Scanning

15 μg of cRNA was fragmented at 94° C. for 35 min in a fragmentation buffer containing 40 mM Tris-acetate pH 8.1, 100 mM KOAc, 30 mM MgOAc. Prior to hybridisation, the fragmented cRNA in a 6×SSPE-T hybridisation buffer (1 M NaCl, 10 mM Tris pH 7.6, 0.005% Triton), was heated to 95° C. for 5 min and subsequently to 45° C. for 5 min before loading onto the Affymetrix probe array cartridge (HuGeneFL). The probe array was then incubated for 16 h at 45° C. at constant rotation (60 rpm). The washing and staining procedure was performed in the Affymetrix Fluidics Station. The probe array was exposed to 10 washes in 6×SSPE-T at 25° C. followed by 4 washes in 0.5×SSPE-T at 50° C. The biotinylated cRNA was stained with a streptavidin-phycoerythrin conjugate, final concentration 2 μg/μl (Molecular Probes, Eugene, Oreg.) in 6×SSPE-T for 30 min at 25° C., followed by 10 washes in 6×SSPE-T at 25° C. The probe arrays were scanned at 560 nm using a confocal laser-scanning microscope (Hewlett Packard GeneArray Scanner G2500A). The readings from the quantitative scanning were analysed by the Affymetrix Gene Expression Analysis Software. An antibody amplification step followed using normal goat IgG as blocking reagent, final concentration 0.1 mg/ml (Sigma) and biotinylated anti-streptavidin antibody (goat), final concentration 3 mg/ml (Vector Laboratories). This was followed by a staining step with a streptavidin-phycoerythrin conjugate, final concentration 2 µg/µl (Molecular Probes, Eugene, Oreg.) in 6×SSPE-T for 30 min at 25° C. and 10 washes in 6×SSPE-T at 25° C. The arrays were then subjected to a second scan under similar conditions as described above.

Class Discovery Using Hierarchical Clustering

All microarray results were scaled to a global intensity of 150 units using the Affymetrix GeneChip software. Other ways of array normalisation exist (Li and Hung 2001), however, using the dCHIP approach did not change the expression profiles of the obtained classifier genes in this study (results not shown). For hierarchical cluster analysis and molecular classification procedures, expression level ratios between tumors and the normal urothelium reference pool were calculated using the comparison analysis implemented in the Affymetrix GeneChip software. In order to avoid expression ratios based on saturated gene-probes, the antibody amplified expression-data for genes with a mean Average Difference value across all samples below 1000 and the non-amplified expression-data for genes with values equal to or above 1000 in mean Average Difference value across all samples was used. Consequently, gene expression levels across all samples were either from the amplified or the non-amplified expression-data. Different filtering criteria were applied to the expression data in order to avoid including non-varying and very low expressed genes in the data analysis. Firstly, only genes that showed significant changes in expression levels compared to the normal reference pool in at least three samples were selected. Secondly, only genes with at least three "Present" calls across all samples were selected. Thirdly, genes varying less than 2 standard deviations across all samples were eliminated. The final gene-set contained 1767 genes following filtering. Two-way hierarchical agglomerative cluster analysis was performed using the Cluster software. Average linkage clustering with a modified Pearson correlation as a similarity metric was used. Genes and arrays were median centred and normalized to the magnitude of 1 prior to cluster analysis. The TreeView software was used for visualization of the cluster analysis results (Eisen et al. 1998). Multidimensional scaling was performed on median centered and normalized data using an implementation in the SPSS statistical software package.

Tumor Stage Classifier

The classifier was based on the log-transformed expression level ratios. For these transformed values, a normal distribution with the mean dependent on the gene and the group (Ta, T1, and T2, respectively) was used, and the variance depended only on the gene. For each gene, the variation within the groups (W) and the three variations between two groups (B(Ta/T1), B(Ta/T2), B(T1/T2)) was calculated, and the three B/W ratios were used to select genes. Those selected genes had a high value of B(Ta/T1)/W, a high value of B(Ta/T2)/W, or a high value of B(T1/T2)/W. To classify a sample, the sum over the genes of the squared distance from the sample value to the group mean, standardized by the variance, was calculated. Thus, a distance to each of the three groups and the sample was classified as belonging to the group in which the distance was smallest. When calculating these distances, the group means and the variances were estimated from all the samples in the training set excluding the sample being classified.

Recurrence Prediction Using a Supervised Learning Method

Average Difference values were generated using the Affymetrix GeneChip software and all values below 20 were set to 20 to avoid very low and negative numbers. Only genes were included that had a "Present" call in at least 7 samples and genes that showed intensity variation (Max−Min>100, Max/Min>2). The values were log were transformed and rescaled a supervised learning method was used essentially as described (Shipp et al. 2002). Genes were selected using t-test statistics and cross-validation and sample classification, performed as described above.

Immunohistochemistry

Tumor tissue microarrays were prepared essentially as described (Kononen et al. 1998), with four representative 0.6 mm paraffin cores from each study case. Immunohistochemical staining was performed using standard highly sensitive techniques after appropriate heat-induced antigen retrieval. Primary polyclonal goat antibodies against Smad 6 (S-20) and cyclin G2 (N-19) were obtained from Santa Cruz Biotechnology. Antibodies to p53 (monoclonal DO-7) and Her-2 (polyclonal anti-c-erbB-2) were from Dako A/S. Ki-67 monoclonal antibody (MIBI) was from Novocastra Laboratories Ltd. Staining intensity was scored at four levels, Negative, Weak, Moderate and Strong by an experienced pathologist who considered both color intensity and number of stained cells, and who was unaware of array results.

Example 3

A Molecular Classifier Detects Carcinoma In Situ Expression Signatures in Tumors and Normal Urothelium of the Bladder Clinical Samples Bladder tumor samples were obtained directly from surgery following removal of tissue for routine pathological examination. The samples were immediately submerged in a guadinium thiocyanate solution for RNA preservation and stored at −80° C. Informed consent was obtained in all cases, and the protocols were approved by the scientific ethical committee of Aarhus County. Samples in the No-CIS group were selected based on the following criteria: a) Ta tumors with no CIS in selected site biopsies in all visits; b) no previous muscle invasive tumour. Samples in the CIS group were selected based on the criteria: a) Ta or T1 tumours with CIS in selected site biopsies in any visit (preferably Ta tumors with CIS in the sampling visit); b) no previous muscle invasive tumors. Normal biopsies were obtained from individuals with prostatic hyperplasia or urinary incontinence. CIS and "normal" biopsies were obtained from cystectomy specimens directly following removal of the bladder. A grid was placed in the bladder for orientation and biopsies were taken from 8 positions covering the bladder surface. At each position, three biopsies were taken: two for pathologic examination and one in between these for RNA extraction for microarray expression profiling. The samples for RNA extraction were immediately transferred to the guanidinium thiocyanate solution and stored at −80° C. until used. Samples used for RNA extraction were assumed to have CIS if CIS was detected in both adjacent biopsies. The "normal" samples were assumed to be normal if both adjacent biopsies were normal.

cRNA Preparation, Array Hybridisation and Scanning

Purification of total RNA, preparation of cRNA from cDNA and hybridization and scanning were performed as previously described (Dyrskjot et al. 2003). The labelled samples were hybridized to Affymetrix U133A GeneChips.

Expression Data Analysis

Following scanning, all data were normalized using the RMA normalization approach in the Bioconductor Affy package to R. Variation filters were applied to the data to eliminate non-varying and presumably non-expressed genes. For gene-set 1, this was done by only including genes with a minimum expression above 200 in at least 5 samples and genes with max/min expression intensities above or equal to 3. The filtering for gene-set 2 including only genes with a minimum expression of 200 in at least 3 samples and genes with maximum expression intensities above or equal to 3. Average linkage hierarchical cluster analysis was carried out using the Cluster software with a modified Pearson correlation as a similarity metric (Eisen et al. 1998). TreeView software was used for visualization of the cluster analysis results (Eisen et al. 1998). Genes were log-transformed, median centered and normalized to the magnitude of 1 before clustering.

GeneCluster 2.0 (http://www-genome.wi.mitedu/cancer/software/genecluster2/gc2.html) was used for the supervised selection of markers and for permutation testing. The algorithms used in the software are based on (Golub et al. 1999, Tamayo et al. 1999). Classifiers for CIS detection were built using the same methods as described previously (Dyrskjot et al. 2003).

Gene Expression Profiling

High-density oligonucleotide microarrays were used for gene expression profiling of approximately 22,000 genes in 28 superficial bladder tumor biopsies (13 tumors with surrounding CIS and 15 without surrounding CIS) and in 13 invasive carcinomas. See table 19 for patient disease course descriptions. Furthermore, expression profiles were obtained from 9 normal biopsies and from 10 biopsies from cystectomy specimens (5 histologically normal biopsies and 5 biopsies with CIS).

TABLE 19

Clinical data on patient disease courses and results of molecular CIS classification

| Sample group[a] | Patient[b] | Previous tumors | Tumor analysed | Subsequent tumors | CIS[c] | CIS classifier[d] |
|---|---|---|---|---|---|---|
| 1 | 1060-1 | | Ta gr2 | 2 Ta | No | No CIS |
| 1 | 1146-1 | | Ta gr2 | | No | No CIS |
| 1 | 1216-1 | | Ta gr2 | | No | No CIS |
| 1 | 1303-1 | | Ta gr2 | | No | No CIS |
| 1 | 524-1 | | Ta gr2 | | No | No CIS |
| 1 | 692-1 | | Ta gr2 | 2 Ta | No | No CIS |
| 1 | 1264-1 | | Ta gr3 | 20 Ta | No | No CIS |
| 1 | 1350-1 | | Ta gr3 | 1 Ta | No | No CIS |
| 1 | 1354-1 | | Ta gr3 | 11 T1 | No | No CIS |
| 1 | 775-1 | | Ta gr3 | 1 Ta | No | No CIS |
| 1 | 1066-1 | | Ta gr3 | 1 Ta | No | No CIS |
| 1 | 1276-1 | | Ta gr3 | 2 T1 | No | No CIS |
| 1 | 1070-1 | | Ta gr3 | 1 Ta | No | No CIS |
| 1 | 989-1 | | Ta gr3 | | No | No CIS |
| 1 | 1482-1 | | Ta gr3 | 20 Ta | No | CIS |
| 2 | 1345-2 | 1 T1 | Ta gr3 | | Sampling visit | CIS |
| 2 | 1062-2 | | Ta gr3 | 1 T1 | Sampling visit | CIS |
| 2 | 956-2 | | Ta gr3 | 1 Ta | Sampling visit | CIS |
| 2 | 320-7 | 1 Ta, 2 T1 | Ta gr3 | 2 Ta | Sampling visit | CIS |
| 2 | 1330-1 | | Ta gr3 | | Sampling visit | CIS |
| 2 | 602-8 | 5 Ta | Ta gr3 | 3 Ta | Sampling visit | CIS |
| 2 | 763-1 | | Ta gr2 | 14 Ta | Sampling visit | CIS |
| 2 | 1024-1 | | T1 gr3 | 2 Ta, 1 T1 | Sampling visit | CIS |
| 2 | 1182-1 | | Ta gr3 | 7 Ta | Subsequent visit | CIS |
| 2 | 1093-1 | | Ta gr3 | 4 Ta, 1 T1 | Subsequent visit | CIS |
| 2 | 979-1 | | Ta gr3 | | Sampling visit | CIS |
| 2 | 1337-1 | | T1 gr3 | | Sampling visit | CIS |
| 2 | 1625-1 | | Ta gr2 | | Sampling visit | CIS |
| 3 | 1015-1 | | T3b gr4 | | No | — |
| 3 | 1337-1 | | T4a gr3 | | Sampling visit | — |
| 3 | 1041-1 | | T4b gr3 | | No | — |
| 3 | 1044-1 | | T4b gr3 | | ND | — |
| 3 | 1055-1 | 1 Ta gr2 | T3a gr3 | | No | — |
| 3 | 1109-1 | | T2 gr3 | 1 T2-4 | No | — |
| 3 | 1124-1 | | T4a gr3 | 2 T2-4 | No | — |
| 3 | 1154-1 | | T3a gr3 | 1 Ta, 1 T2-4 | No | — |
| 3 | 1167-1 | 1 T2-4 | T3b gr4 | 2 T2-4 | ND | — |
| 3 | 1178-1 | | T4b gr3 | | ND | — |
| 3 | 1215-1 | | T4b gr3 | | ND | — |
| 3 | 1271-1 | | T3b gr4 | | No | — |
| 3 | 1321-1 | 1 T1 | T3b gr? | | ND | — |

[a]The tumor groups involved were TCC without CIS (1), TCC with CIS (2) and invasive TCC (3).
[b]The numbers indicate the patient number followed by the clinic visit number.
[c]CIS in selected site biopsies in previous, present or subsequent visits to the clinic.
ND: not determined.
[d]Molecular classification of the samples using 25 genes in cross-validation loops.

Hierarchical Cluster Analysis

Following appropriate normalization and expression intensity calculations, genes that showed high variation across the 41 TCC samples were selected for further analysis. The filtering produced a gene-set consisting of 5,491 genes (gene-set 1) and two-way hierarchical cluster analysis was performed based on this gene-set. The sample clustering showed a separation of the three groups of samples with only few exceptions (FIG. 14a in Ser. No. 12/180,321). Superficial TCC with surrounding CIS clustered in the one main branch of the dendrogram, while the superficial TCC without CIS and the invasive TCC clustered in two separate sub-branches in the other main branch of the dendrogram. The only exceptions were that the invasive TCC samples 1044-1 and 1124-1 clustered in the CIS group, and two TCC with CIS clustered in the invasive group (samples 1330-1 and 956-2). The only TCC without CIS that clustered in the CIS group was sample 1482-1. The distinct clustering of the tumour groups indicated a large difference in gene expression patterns.

Hierarchical clustering of the genes (FIG. 14c in Ser. No. 12/180,321) identified large clusters of genes characteristic for each tumor phenotype. Cluster 1 showed a cluster of genes downregulated in cystectomy biopsies, TCC with adjacent CIS and in some invasive carcinomas (FIG. 14c in Ser. No. 12/180,321). There is no obvious functional relationship between the genes in this cluster. Cluster 2 showed a tight cluster of genes related to immunology and cluster 3 contained mostly genes expressed in muscle and connective tissue. Expression of genes in this cluster was observed in the normal and cystectomy samples, and in a fraction of the TCC with CIS and in the invasive tumours. Cluster 4 contained genes up-regulated in the cystectomy biopsies, TCC with adjacent CIS and in invasive carcinomas (FIG. 14c in Ser. No. 12/180,321). This cluster includes genes involved in cell cycle regulation, and in cell proliferation and apoptosis. However, for most of the genes in this cluster there is no apparent functional relationship. Comparisons of chromosomal location of the genes in the clusters revealed no correlation between the observed gene clusters and chromosomal position of the identified genes.

A positive correlation could have indicated chromosomal loss or gain or chromosomal inactivation by e.g. methylation of common promoter regions.

To analyze the impact of surrounding CIS lesions further, the 28 superficial tumours only were used. A new gene set was created consisting of 5,252 varying genes (gene-set 2). Hierarchical cluster analysis of the tumor samples (FIG. 13b in Ser. No. 12/180,321) based on the new gene-set separated the samples according to the presence of CIS in the surrounding urothelium, with only 1 exception (P<0.000001, $\chi^2$-test). Sample 1482-1 clustered in the TCC with CIS group; however, no CIS has been detected in selected site biopsies during routine examinations of this patient. Tumour samples 1182-1 and 1093-1 did not have CIS in selected site biopsies in the same visit as the profiled tumor, but showed this in later visits. However, the profile of these two superficial tumor samples already showed the adjacent CIS profile.

Marker Selection

Figure 9:
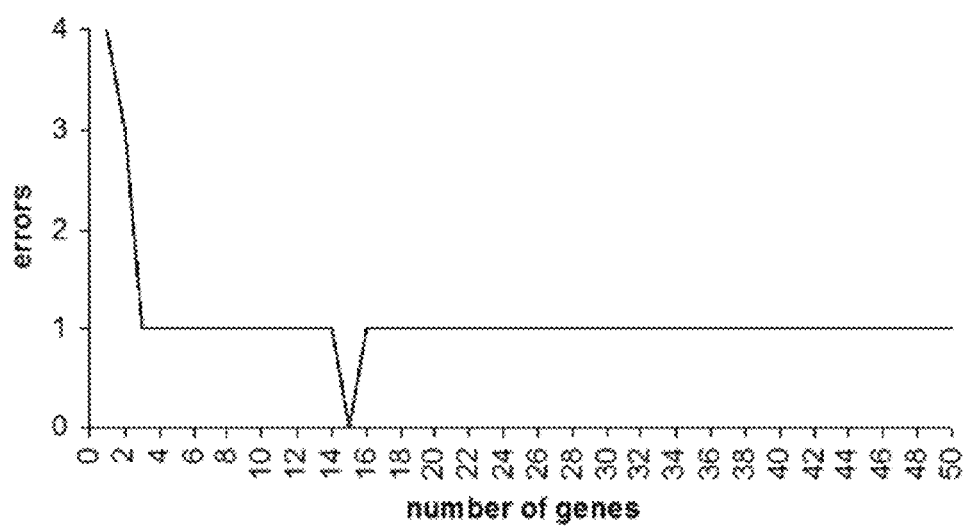
FIG. 9. Cross validation performance using half of the samples.

To delineate the tumors with surrounding CIS from the tumors without CIS, t-test statistics were used to select the 50 most up-regulated genes in each group (FIG. 9). Permutation of the sample labels 500 times revealed that the 50 genes up-regulated in the CIS-group are highly significantly differentially expressed and unlikely to be found by chance, as all markers were significant at a 5% confidence level. Consequently, in 500 random datasets, it was only possible to select equally genes in less than 5% of the datasets. The 50 genes up-regulated in the no-CIS group showed a poorer performance in the permutation tests, as these were not significant at a 5% confidence level. See Table 20 for details. The relative expression of these 100 genes in 9 normal biopsies and 10 biopsies from cystectomies with CIS is shown in FIG. 15b. The no-CIS profile was found in all of the normal samples. However, all histologically normal samples adjacent to the CIS lesions, as well as the CIS biopsies, showed the CIS profile.

TABLE 20

The best 100 markers

| Feature (U133 array) | Class | T-test | Perm 1% | Perm 5% | Perm 10% | UniGene Build 162 | RefSeq; description |
|---|---|---|---|---|---|---|---|
| 221204_s_at | no_CIS | 3.74 | 5.12 | 4.61 | 4.33 | Hs.326444 | NM_018058; cartilage acidic protein 1 |
| 205927_s_at | no_CIS | 3.67 | 4.53 | 3.98 | 3.73 | Hs.1355 | NM_001910; cathepsin E isoform a preproprotein NM_148964; cathepsin E isoform b preproprotein |
| 210143_at | no_CIS | 3.35 | 4.03 | 3.73 | 3.45 | Hs.188401 | NM_007193; annexin A10 |
| 204540_at | no_CIS | 3.15 | 3.87 | 3.51 | 3.32 | Hs.433839 | NM_001958; eukaryotic translation elongation factor 1 alpha 2 |
| 214599_at | no_CIS | 3.02 | 3.75 | 3.37 | 3.14 | Hs.157091 | NM_005547; involucrin |
| 203649_s_at | no_CIS | 2.84 | 3.63 | 3.20 | 3.00 | Hs.76422 | NM_000300; phospholipase A2, group IIA (platelets, synovial fluid) |
| 203980_at | no_CIS | 2.74 | 3.47 | 3.12 | 2.89 | Hs.391561 | NM_001442; fatty acid binding protein 4, adipocyte |
| 209270_at | no_CIS | 2.39 | 3.38 | 3.10 | 2.85 | Hs.436983 | NM_000228; laminin subunit beta 3 precursor |
| 206658_at | no_CIS | 2.35 | 3.37 | 3.05 | 2.78 | Hs.284211 | NM_030570; uroplakin 3B isoform a NM_182683; uroplakin 3B isoform c NM_182684; uroplakin 3B isoform b |

TABLE 20-continued

The best 100 markers

| Feature (U133 array) | Class | T-test | Perm 1% | Perm 5% | Perm 10% | UniGene Build 162 | RefSeq; description |
|---|---|---|---|---|---|---|---|
| 220779_at | no_CIS | 2.35 | 3.33 | 2.97 | 2.73 | Hs.149195 | NM_016233; peptidylarginine deiminase type III |
| 216971_s_at | no_CIS | 2.28 | 3.29 | 2.91 | 2.71 | Hs.79706 | NM_000445; plectin 1, intermediate filament binding protein 500 kDa |
| 206191_at | no_CIS | 2.25 | 3.24 | 2.86 | 2.68 | Hs.47042 | NM_001248; ectonucleoside triphosphate diphosphohydrolase 3 |
| 218484_at | no_CIS | 2.18 | 3.20 | 2.81 | 2.62 | Hs.221447 | NM_020142; NADH:ubiquinone oxidoreductase MLRQ subunit homolog |
| 221854_at | no_CIS | 2.1 | 3.19 | 2.80 | 2.60 | Hs.313068 | NM_000299; plakophilin 1 |
| 203792_x_at | no_CIS | 2.02 | 3.16 | 2.74 | 2.55 | Hs.371617 | NM_007144; ring finger protein 110 |
| 207862_at | no_CIS | 2.01 | 3.16 | 2.72 | 2.52 | Hs.379613 | NM_006760; uroplakin 2 |
| 218960_at | no_CIS | 1.93 | 3.14 | 2.65 | 2.47 | Hs.414005 | NM_019894; transmembrane protease, serine 4 isoform 1 NM_183247; transmembrane protease, serine 4 isoform 2 |
| 203009_at | no_CIS | 1.93 | 3.12 | 2.62 | 2.45 | Hs.155048 | NM_005581; Lutheran blood group (Auberger b antigen included) |
| 204508_s_at | no_CIS | 1.88 | 3.10 | 2.60 | 2.42 | Hs.279916 | NM_017689; hypothetical protein FLJ20151 |
| 211692_s_at | no_CIS | 1.87 | 3.06 | 2.58 | 2.39 | Hs.87246 | NM_014417; BCL2 binding component 3 |
| 206465_at | no_CIS | 1.86 | 3.04 | 2.54 | 2.38 | Hs.277543 | NM_015162; lipidosin |
| 206122_at | no_CIS | 1.85 | 2.92 | 2.52 | 2.36 | Hs.95582 | NM_006942; SRY-box 15 |
| 206393_at | no_CIS | 1.83 | 2.89 | 2.49 | 2.33 | Hs.83760 | NM_003282; troponin I, skeletal, fast |
| 214639_s_at | no_CIS | 1.79 | 2.87 | 2.49 | 2.30 | Hs.67397 | NM_005522; homeobox A1 protein isoform a NM_153620; homeobox A1 protein isoform b |
| 214630_at | no_CIS | 1.79 | 2.84 | 2.44 | 2.28 | Hs.184927 | NM_000497; cytochrome P450, subfamily XIB (steroid 11-beta-hydroxylase), polypeptide 1 precursor |
| 204465_s_at | no_CIS | 1.77 | 2.81 | 2.42 | 2.27 | Hs.76888 | NM_004692; NM_032727; internexin neuronal intermediate filament protein, alpha |
| 204990_s_at | no_CIS | 1.76 | 2.79 | 2.41 | 2.24 | Hs.85266 | NM_000213; integrin, beta 4 |
| 205453_at | no_CIS | 1.75 | 2.77 | 2.39 | 2.22 | Hs.290432 | NM_002145; homeo box B2 |
| 215812_s_at | no_CIS | 1.74 | 2.77 | 2.37 | 2.20 | Hs.499113 | NM_018058; cartilage acidic protein 1 |
| 217040_x_at | no_CIS | 1.74 | 2.75 | 2.36 | 2.18 | Hs.95582 | NM_001910; cathepsin E isoform a preproprotein NM_148964; cathepsin E isoform b preproprotein |
| 203759_at | no_CIS | 1.73 | 2.75 | 2.34 | 2.17 | Hs.75268 | NM_007193; annexin A10 |
| 211002_s_at | no_CIS | 1.73 | 2.74 | 2.33 | 2.17 | Hs.82237 | NM_001958; eukaryotic translation elongation factor 1 alpha 2 |
| 216641_s_at | no_CIS | 1.73 | 2.73 | 2.31 | 2.15 | Hs.18141 | NM_005547; involucrin |
| 221660_at | no_CIS | 1.71 | 2.67 | 2.30 | 2.13 | Hs.247831 | NM_000300; phospholipase A2, group IIA (platelets, synovial fluid) |
| 220026_at | no_CIS | 1.71 | 2.66 | 2.28 | 2.13 | Hs.227059 | NM_001442; fatty acid binding protein 4, adipocyte |
| 209591_s_at | no_CIS | 1.69 | 2.63 | 2.28 | 2.11 | Hs.170195 | NM_000228; laminin subunit beta 3 precursor |
| 219922_s_at | no_CIS | 1.68 | 2.61 | 2.26 | 2.08 | Hs.289019 | NM_030570; uroplakin 3B isoform a NM_182683; uroplakin 3B isoform c NM_182684; uroplakin 3B isoform b |
| 201641_at | no_CIS | 1.67 | 2.61 | 2.26 | 2.07 | Hs.118110 | NM_016233; peptidylarginine deiminase type III |

TABLE 20-continued

The best 100 markers

| Feature (U133 array) | Class | T-test | Perm 1% | Perm 5% | Perm 10% | UniGene Build 162 | RefSeq; description |
|---|---|---|---|---|---|---|---|
| 204952_at | no_CIS | 1.66 | 2.59 | 2.24 | 2.07 | Hs.377028 | NM_000445; plectin 1, intermediate filament binding protein 500 kDa |
| 204487_s_at | no_CIS | 1.65 | 2.59 | 2.23 | 2.06 | Hs.367809 | NM_001248; ectonucleoside triphosphate diphosphohydrolase 3 |
| 210761_s_at | no_CIS | 1.64 | 2.59 | 2.23 | 2.05 | Hs.86859 | NM_020142; NADH:ubiquinone oxidoreductase MLRQ subunit homolog |
| 217626_at | no_CIS | 1.63 | 2.58 | 2.21 | 2.04 | Hs.201967 | NM_000299; plakophilin 1 |
| 204380_s_at | no_CIS | 1.62 | 2.58 | 2.19 | 2.03 | Hs.1420 | NM_007144; ring finger protein 110 |
| 205455_at | no_CIS | 1.61 | 2.58 | 2.17 | 2.02 | Hs.2942 | NM_006760; uroplakin 2 |
| 205073_at | no_CIS | 1.61 | 2.58 | 2.17 | 2.01 | Hs.152096 | NM_019894; transmembrane protease, serine 4 isoform 1 NM_183247; transmembrane protease, serine 4 isoform 2 |
| 203287_at | no_CIS | 1.61 | 2.58 | 2.16 | 2.00 | Hs.18141 | NM_005581; Lutheran blood group (Auberger b antigen included) |
| 210735_s_at | no_CIS | 1.58 | 2.55 | 2.15 | 1.99 | Hs.5338 | NM_017689; hypothetical protein FLJ20151 |
| 203842_s_at | no_CIS | 1.57 | 2.54 | 2.15 | 1.97 | Hs.172740 | NM_014417; BCL2 binding component 3 |
| 206561_s_at | no_CIS | 1.57 | 2.53 | 2.14 | 1.96 | Hs.116724 | NM_015162; lipidosin |
| 214752_x_at | no_CIS | 1.56 | 2.52 | 2.13 | 1.95 | Hs.195464 | NM_006942; SRY-box 15 |
| 217028_at | CIS | 4.87 | 5.17 | 4.67 | 4.40 | Hs.421986 | NM_003282; troponin I, skeletal, fast |
| 213975_s_at | CIS | 4.65 | 4.43 | 4.01 | 3.76 | Hs.234734 | NM_005522; homeobox A1 protein isoform a NM_153620; homeobox A1 protein isoform b |
| 201859_at | CIS | 4.59 | 4.15 | 3.70 | 3.45 | Hs.1908 | NM_000497; cytochrome P450, subfamily XIB (steroid 11-beta-hydroxylase), polypeptide 1 precursor |
| 219410_at | CIS | 4.49 | 3.98 | 3.49 | 3.29 | Hs.104800 | NM_004692; NM_032727; internexin neuronal intermediate filament protein, alpha |
| 207173_x_at | CIS | 4.37 | 3.88 | 3.33 | 3.11 | Hs.443435 | NM_000213; integrin, beta 4 |
| 214651_s_at | CIS | 4.14 | 3.83 | 3.22 | 2.99 | Hs.127428 | NM_002145; homeo box B2 |
| 201858_s_at | CIS | 4.06 | 3.78 | 3.09 | 2.91 | Hs.1908 | NM_018058; cartilage acidic protein 1 |
| 211430_s_at | CIS | 4.03 | 3.63 | 3.05 | 2.83 | Hs.413826 | NM_001910; cathepsin E isoform a preproprotein NM_148964; cathepsin E isoform b preproprotein |
| 213891_s_at | CIS | 3.86 | 3.63 | 3.02 | 2.77 | Hs.359289 | NM_007193; annexin A10 |
| 221872_at | CIS | 3.82 | 3.52 | 2.89 | 2.73 | Hs.82547 | NM_001958; eukaryotic translation elongation factor 1 alpha 2 |
| 212386_at | CIS | 3.77 | 3.50 | 2.87 | 2.69 | Hs.359289 | NM_005547; involucrin |
| 211161_s_at | CIS | 3.76 | 3.42 | 2.84 | 2.65 | | NM_000300; phospholipase A2, group IIA (platelets, synovial fluid) |
| 214669_x_at | CIS | 3.55 | 3.36 | 2.80 | 2.62 | Hs.377975 | NM_001442; fatty acid binding protein 4, adipocyte |
| 217388_s_at | CIS | 3.44 | 3.31 | 2.79 | 2.58 | Hs.444471 | NM_000228; laminin subunit beta 3 precursor |
| 203477_at | CIS | 3.36 | 3.28 | 2.75 | 2.56 | Hs.409034 | NM_030570; uroplakin 3B isoform a NM_182683; uroplakin 3B isoform c NM_182684; uroplakin 3B isoform b |
| 204688_at | CIS | 3.35 | 3.26 | 2.74 | 2.52 | Hs.409798 | NM_016233; peptidylarginine deiminase type III |
| 218718_at | CIS | 3.35 | 3.22 | 2.70 | 2.48 | Hs.43080 | NM_000445; plectin 1, intermediate filament binding protein 500 kDa |

TABLE 20-continued

The best 100 markers

| Feature (U133 array) | Class | T-test | Perm 1% | Perm 5% | Perm 10% | UniGene Build 162 | RefSeq; description |
|---|---|---|---|---|---|---|---|
| 215176_x_at | CIS | 3.32 | 3.14 | 2.67 | 2.45 | Hs.503443 | NM_001248; ectonucleoside triphosphate diphosphohydrolase 3 |
| 201842_s_at | CIS | 3.31 | 3.11 | 2.65 | 2.44 | Hs.76224 | NM_020142; NADH:ubiquinone oxidoreductase MLRQ subunit homolog |
| 212667_at | CIS | 3.3 | 3.11 | 2.63 | 2.42 | Hs.111779 | NM_000299; plakophilin 1 |
| 209340_at | CIS | 3.27 | 3.10 | 2.61 | 2.39 | Hs.21293 | NM_007144; ring finger protein 110 |
| 215379_x_at | CIS | 3.26 | 3.10 | 2.59 | 2.39 | Hs.449601 | NM_006760; uroplakin 2 |
| 200762_at | CIS | 3.25 | 3.05 | 2.56 | 2.34 | Hs.173381 | NM_019894; transmembrane protease, serine 4 isoform 1 NM_183247; transmembrane protease, serine 4 isoform 2 |
| 211896_s_at | CIS | 3.21 | 3.05 | 2.53 | 2.32 | Hs.156316 | NM_005581; Lutheran blood group (Auberger b antigen included) |
| 204141_at | CIS | 3.19 | 3.05 | 2.53 | 2.28 | Hs.300701 | NM_017689; hypothetical protein FLJ20151 |
| 201744_s_at | CIS | 3.18 | 3.03 | 2.50 | 2.27 | Hs.406475 | NM_014417; BCL2 binding component 3 |
| 209138_x_at | CIS | 3.17 | 3.03 | 2.47 | 2.24 | Hs.505407 | NM_015162; lipidosin |
| 214677_x_at | CIS | 3.14 | 3.02 | 2.47 | 2.23 | Hs.449601 | NM_006942; SRY-box 15 |
| 212077_at | CIS | 3.11 | 2.99 | 2.46 | 2.21 | Hs.443811 | NM_003282; troponin I, skeletal, fast |
| 206392_s_at | CIS | 3.11 | 2.98 | 2.43 | 2.20 | Hs.82547 | NM_005522; homeobox A1 protein isoform a NM_153620; homeobox A1 protein isoform b |
| 212998_x_at | CIS | 3.09 | 2.94 | 2.40 | 2.19 | Hs.375115 | NM_000497; cytochrome P450, subfamily XIB (steroid 11-beta-hydroxylase), polypeptide 1 precursor |
| 201616_s_at | CIS | 3.08 | 2.93 | 2.38 | 2.18 | Hs.443811 | NM_004692; NM_032727; internexin neuronal intermediate filament protein, alpha |
| 205382_s_at | CIS | 3.07 | 2.88 | 2.37 | 2.15 | Hs.155597 | NM_000213; integrin, beta 4 |
| 212671_s_at | CIS | 3.07 | 2.85 | 2.35 | 2.14 | Hs.387679 | NM_002145; homeo box B2 |
| 215121_x_at | CIS | 3.06 | 2.84 | 2.34 | 2.13 | Hs.356861 | NM_018058; cartilage acidic protein 1 |
| 200600_at | CIS | 3.05 | 2.83 | 2.33 | 2.11 | Hs.170328 | NM_001910; cathepsin E isoform a preproprotein NM_148964; cathepsin E isoform b preproprotein |
| 202746_at | CIS | 3.03 | 2.80 | 2.32 | 2.10 | Hs.17109 | NM_007193; annexin A10 |
| 202917_s_at | CIS | 3 | 2.79 | 2.31 | 2.08 | Hs.416073 | NM_001958; eukaryotic translation elongation factor 1 alpha 2 |
| 201560_at | CIS | 3 | 2.79 | 2.30 | 2.08 | Hs.25035 | NM_005547; involucrin |
| 218918_at | CIS | 2.99 | 2.77 | 2.29 | 2.06 | Hs.8910 | NM_000300; phospholipase A2, group IIA (platelets, synovial fluid) |
| 218656_s_at | CIS | 2.99 | 2.76 | 2.27 | 2.06 | Hs.93765 | NM_001442; fatty acid binding protein 4, adipocyte |
| 201088_at | CIS | 2.99 | 2.76 | 2.26 | 2.04 | Hs.159557 | NM_000228; laminin subunit beta 3 precursor |
| 201291_s_at | CIS | 2.97 | 2.75 | 2.25 | 2.04 | Hs.156346 | NM_030570; uroplakin 3B isoform a NM_182683; uroplakin 3B isoform c NM_182684; uroplakin 3B isoform b |
| 215076_s_at | CIS | 2.95 | 2.72 | 2.24 | 2.03 | Hs.443625 | NM_016233; peptidylarginine deiminase type III |
| 212195_at | CIS | 2.94 | 2.71 | 2.22 | 2.02 | Hs.71968 | NM_000445; plectin 1, intermediate filament binding protein 500 kDa |

TABLE 20-continued

The best 100 markers

| Feature (U133 array) | Class | T-test | Perm 1% | Perm 5% | Perm 10% | UniGene Build 162 | RefSeq; description |
|---|---|---|---|---|---|---|---|
| 209732_at | CIS | 2.94 | 2.68 | 2.22 | 2.00 | Hs.85201 | NM_001248; ectonucleoside triphosphate diphosphohydrolase 3 |
| 212192_at | CIS | 2.94 | 2.67 | 2.22 | 1.99 | Hs.109438 | NM_020142; NADH:ubiquinone oxidoreductase MLRQ subunit homolog |
| 221671_x_at | CIS | 2.92 | 2.67 | 2.20 | 1.98 | Hs.377975 | NM_000299; plakophilin 1 |
| 211671_s_at | CIS | 2.91 | 2.66 | 2.20 | 1.98 | Hs.126608 | NM_007144; ring finger protein 110 |
| 214352_s_at | CIS | 2.88 | 2.66 | 2.19 | 1.97 | Hs.412107 | NM_006760; uroplakin 2 |

Feature: Probe-set on U133A GeneChip
Class: The group in which the marker is up-regulated
T-test: The t-test value
Perm 1%: The 1% permutation level
Perm 5%: The 5% permutation level
Perm 10%: The 10% permutation level Construction of a Molecular CIS Classifier A classifier able to diagnose CIS from gene expressions in TCC or in bladder biopsies may increase the detection rate of CIS. The first approach was to be able to classify superficial TCC with or without CIS in the surrounding mucosa. This could have the effect that the number of random biopsies to be taken could be reduced.

A CIS-classifier was built as previously described (Dyrskjot et al. 2003) using cross-validation for determining the optimal number of genes for classifying CIS with fewest errors. The best classifier performance (1 error) was obtained in cross-validation loops using 25 genes (see FIG. 16 in Ser. No. 12/180,321); 16 of these were included in 70% of the cross-validation loops and these were selected to represent the final classifier for OS diagnosis (FIG. 9 and table 21). Permutation analysis showed that 13 of these were significant at a 1% confidence level—the remaining three genes were above a 10% confidence level.

TABLE 21

The 16 gene molecular classifier of CIS

| Feature (U133a array) | Class | t-test | Perm 1% | Perm 5% | Perm 10% | UniGene Build 162 | RefSeq; description |
|---|---|---|---|---|---|---|---|
| 213633_at | no_CIS | 1.51 | 2.46 | 2.04 | 1.85 | Hs.97858 | NM_018957; SH3-domain binding protein 1 |
| 212784_at | no_CIS | 1.36 | 2.27 | 1.86 | 1.70 | Hs.388236 | NM_015125; capicua homolog |
| 209241_x_at | no_CIS | 1.13 | 1.78 | 1.48 | 1.33 | Hs.112028 | NM_015716; misshapen/NIK-related kinase isoform 1 NM_153827; misshapen/NIK-related kinase isoform 3 NM_170663; misshapen/NIK-related kinase isoform 2 |
| 217941_s_at | CIS | 2.3 | 1.96 | 1.66 | 1.47 | Hs.8117 | NM_018695; erbb2 interacting protein |
| 201877_s_at | CIS | 2.27 | 1.90 | 1.62 | 1.45 | Hs.249955 | NM_002719; gamma isoform of regulatory subunit B56, protein phosphatase 2A isoform a NM_178586; gamma isoform of regulatory subunit B56, protein phosphatase 2A isoform b NM_178587; gamma isoform of regulatory subunit B56, protein phosphatase 2A isoform c NM_178588; gamma isoform of regulatory subunit B56, protein phosphatase 2A isoform d |
| 209630_s_at | CIS | 1.97 | 1.54 | 1.31 | 1.15 | Hs.444354 | NM_012164; F-box and WD-40 domain protein 2 |

TABLE 21-continued

The 16 gene molecular classifier of CIS

| Feature (U133a array) | Class | t-test | Perm 1% | Perm 5% | Perm 10% | UniGene Build 162 | RefSeq; description |
|---|---|---|---|---|---|---|---|
| 202777_at | CIS | 1.93 | 1.51 | 1.29 | 1.12 | Hs.104315 | NM_007373; soc-2 suppressor of clear homolog |
| 200958_s_at | CIS | 1.92 | 1.49 | 1.28 | 1.11 | Hs.164067 | NM_005625; syndecan binding protein (syntenin) |
| 209579_s_at | CIS | 1.79 | 1.36 | 1.16 | 1.01 | Hs.35947 | NM_003925; methyl-CpG binding domain protein 4 |
| 209004_s_at | CIS | 1.63 | 1.21 | 1.00 | 0.89 | Hs.5548 | NM_012161; F-box and leucine-rich repeat protein 5 isoform 1 NM_033535; F-box and leucine-rich repeat protein 5 isoform 2 |
| 218150_at | CIS | 1.6 | 1.18 | 0.98 | 0.86 | Hs.342849 | NM_012097; ADP-ribosylation factor-like 5 isoform 1 NM_177985; ADP-ribosylation factor-like 5 isoform 2 |
| 202076_at | CIS | 1.53 | 1.12 | 0.92 | 0.82 | Hs.289107 | NM_001166; baculoviral IAP repeat-containing protein 2 |
| 204640_s_at | CIS | 1.45 | 1.03 | 0.83 | 0.75 | Hs.129951 | NM_003563; speckle-type POZ protein |
| 201887_at | CIS | 1.32 | 0.92 | 0.74 | 0.66 | Hs.285115 | NM_001560; interleukin 13 receptor, alpha 1 precursor |
| 212802_s_at | CIS | 1.31 | 0.91 | 0.72 | 0.65 | Hs.287266 | GTPase activating protein and VPS9 domains 1; GAPVD1 |
| 212899_at | CIS | 1.29 | 0.89 | 0.71 | 0.64 | Hs.129836 | NM_015076; cyclin-dependent kinase (CDC2-like) 11 |

Feature: Probe-set on U133A GeneChip
Class: The group in which the marker is up-regulated
T-test: The t-test value
Perm 1%: The 1% permutation level
Perm 5%: The 5% permutation level
Perm 10%: The 10% permutation level Exploration of Strength of CIS Classifier To further explore the strength of classifying CIS a classifier was built by randomly selecting half of the samples for training and the other half was used for testing. Cross validation was used again in the training of this classifier for optimization of the gene-set for classifying independent samples. Cross-validation with 15 genes showed a good performance (see FIG. 18) and 7 of these genes were included in 70% of the class-validation loops. These 7 genes classified the samples in the test set with one error only—sample 1482-1 ($\chi^2$-test, P<0.002). Only two of the genes were also included in the 16-gene classifier, which is understandable considering the number of tests performed and the limitations in sample size. This classification performance is notable considering the small number of samples used for training the classifier.

Grouping of Normal and Cystectomies with CIS

Hierarchical cluster analysis was used to group the 9 normal and 10 biopsies from cystectomies with CIS based on the normalized expression profiles of the 16 classifier genes. This clustering separated the samples from cystectomies with CIS lesions from the normal samples with only few exceptions, as 8 of the 10 biopsies from cystectomies were found in the one main branch of the dendrogram and 8 of the 9 normal biopsies were found on the other main branch ($\chi^2$-test, P<0.002).

The specific methods and compositions described herein are representative of preferred embodiments and are exemplary and not intended as limitations on the scope of the invention.

Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, any of the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

Pisani, P., Parkin, D. M., Bray, F. & Ferlay, J. Estimates of the worldwide mortality from 25 cancers in 1990. *Int J Cancer* 83, 18-29 (1999).

Wolf, H. et al. Bladder tumors. Treated natural history. *Prog Clin Biol Res* 221, 223-55 (1986).

Althausen, A. F., Prout, G. R., Jr., and Daly, J. J. Non-invasive papillary carcinoma of the bladder associated with carcinoma in situ. J Urol, 116: 575-580, 1976.

Spruck, C. H., 3rd, Ohneseit, P. F., Gonzalez-Zulueta, M., Esrig, D., Miyao, N., Tsai, Y. C., Lerner, S. P., Schmutte, C., Yang, A. S., Cote, R., and et al. Two molecular pathways to transitional cell carcinoma of the bladder. Cancer Res, 54: 784-788, 1994.

Rosin, M. P., Cairns, P., Epstein, J. I., Schoenberg, M. P., and Sidransky, D. Partial allelotype of carcinoma in situ of the human bladder. Cancer Res, 55: 5213-5216, 1995.

Anderstrom, C., Johansson, S., and Nilsson, S. The significance of lamina propria invasion on the prognosis of patients with bladder tumors. J Urol, 124: 23-26, 1980.

Cummings, K. B. Carcinoma of the bladder: predictors. Cancer, 45: 1849-1855, 1980.

Cheng, L., Cheville, J. C., Neumann, R. M., Leibovich, B. C., Egan, K. S., Spotts, B. E., and Bostwick, D. G. Survival of patients with carcinoma in situ of the urinary bladder. Cancer, 85: 2469-2474, 1999.

Kriegmair, M., Baumgartner, R., Lumper, W., Waidelich, R., and Hofstetter, A. Early clinical experience with 5-aminolevulinic acid for the photodynamic therapy of superficial bladder cancer. Br J Urol, 77: 667-671, 1996.

van't Veer, L. J. et al. Gene expression profiling predicts clinical outcome of breast cancer. Nature 415, 530-6 (2002).

Ambrosini, G., Adida, C. & Altieri, D. C. A novel anti-apoptosis gene, survivin, expressed in cancer and lymphoma. *Nat Med* 3, 917-21 (1997).

Sidransky, D. et al. Clonal origin bladder cancer. *N Engl J Med* 326, 737-40 (1992).

Primdahl, H. et al. Allelic imbalances in human bladder cancer: genome-wide detection with high-density single-nucleotide polymorphism arrays. *J Natl Cancer Inst* 94, 216-23 (2002).

Eaves, I. A. et al. Combining mouse congenic strains and microarray gene expression analyses to study a complex trait: the NOD model of type 1 diabetes. *Genome Res* 12, 232-43 (2002).

Ghandour, G. & Glynne, R. Method and apparatus for analysis of data from biomolecular arrays. International patent No. WO0079465 (2000).

Turkey, J. *Exploratory Data Analysis*, (Addison-Wesley, Reading, Mass., 1977).

Kruhoffer, M., Magnusson, N. E., Aaboe, M., Dyrskjot, L. & Orntoft, T. F. Microarrays for gene expression profiling: Fabrication of Oligonucleotide microarrays, Isolation of RNA, Fluorescent labelling of cRNA, Hybridisation, and Scanning. in *Cell Biology—A laboratory handbook* (ed. Celis, J. E.) (To appear in the 4th edition of this book).

Jain, A. N. et al. Fully automatic quantification of microarray image data. *Genome Res* 12, 32.5-32 (2002).

Eisen, M. B., Spellman, P. T., Brown, P. O. & Botstein, D. Cluster analysis and display of genome-wide expression patterns. *Proc Natl Acad Sci USA* 95, 14863-8 (1998).

Seymour, L. Novel anti-cancer agents in development: exciting prospects and new challenges. *Cancer Treat. Rev.* 25, 301-312 (1999).

Fox, S. B., Gasparini, G., & Harris, A. L. Angiogenesis: pathological, prognostic, and growth-factor pathways and their link to trial design and anticancer drugs. *Lancet Oncol.* 2, 278-289 (2001).

Shipp, M. A. et al. Diffuse large B-cell lymphoma outcome prediction by gene-expression profiling and supervised machine learning. *Nat. Med.* 8, 68-74 (2002).

Kerr, J. S., Slee, A. M., & Mousa, S. A. Small molecule alpha(v) integrin antagonists: novel anticancer agents. *Expert. Opin. Investig. Drugs* 9, 1271-1279 (2000).

Bergkvist, A., Ljungqvist, A., & Moberger, G. Classification of bladder tumours based on the cellular pattern. Preliminary report of a clinical-pathological study of 300 cases with a minimum follow-up of eight years. *Acta Chir. Scand.* 130, 371-378 (1965).

Li, C. & Hung, W. W. Model-based analysis of oligonucleotide arrays: model validation, design issues and standard error application. *Genome Biol.* 2, RESEARCH0032 (2001).

Kononen, J. et al. Tissue microarrays for high-throughput molecular profiling of tumor specimens. *Nat. Med.* 4, 844-847 (1998).

What is claimed is:

1. A method for treating stage Ta or T1 bladder cancer, comprising:
   a. determining the likelihood of progression of an individual's bladder cancer, by, determining in a bladder tumor sample biopsied from the individual:
   the level of gene expression from the markers MBNL2 and FABP4 wherein if the expression level determined for both MBNL2 and FABP4 is increased as compared to their expression levels in a control or different bladder cancer sample, it indicates a decreased risk of progression relative to said control or different bladder cancer sample; and wherein if the expression level for both MBNL2 and FABP4 is decreased as compared to their expression levels in a control or different bladder cancer sample, it indicates an increased risk of progression relative to said control or different bladder cancer sample; and
   b. administering a chemotherapeutic agent to the individual if the expression levels determined for both MBNL2 and FABP4 are decreased as compared to their expression levels in a control or different bladder cancer sample.

2. The method of claim 1 wherein the method further includes determining, in the bladder tumor sample, the level of gene expression from the marker UBE2C wherein if the expression level determined for FABP4 is increased and the expression level for UBE2C is decreased, as compared to their respective relative expression levels in a control or different bladder cancer sample, it indicates a decreased risk of progression relative to said control or different bladder cancer sample, and if the expression level for UBE2C is increased and the expression level for FABP4 is decreased, as compared to their respective relative expression levels in said control or different bladder cancer sample, it indicates an increased risk of progression relative to said control or different bladder cancer sample.

3. The method of claim 1 wherein the method further includes determining, in the bladder tumor sample, the level of gene expression from the marker BIRC5 wherein if the expression level determined for FABP4 is increased and the expression level for BIRC5 is decreased, as compared to their respective relative expression levels in a control or different bladder cancer sample, it indicates a decreased risk of progression relative to said control or different bladder cancer sample, and if the expression level for BIRC5 is increased and the expression level for FABP4 is decreased, as compared to their respective relative expression levels in said control or different bladder cancer sample, it indicates an increased risk of progression relative to said control or different bladder cancer sample.

4. The method of claim 1 wherein the method further includes determining, in the bladder tumor sample, the level of gene expression from the markers MBNL2 and BIRC5, wherein if the expression level determined for either or both FABP4 and MBNL2 is increased and the expression level for BIRC5 is decreased, as compared to their respective relative expression levels in a control or different bladder cancer sample, it indicates a decreased risk of progression relative to said control or different bladder cancer sample, and if the expression level for BIRC5 is increased and the expression level for either or both FABP4 and MBNL2 is decreased, as compared to their respective relative expression levels in said control or different bladder cancer sample, it indicates an increased risk of progression relative to said control or different bladder cancer sample.

5. The method of claim 1 wherein the method further includes determining, in the bladder tumor sample, the level of gene expression from the markers MBNL2 and UBE2C, wherein if the expression level for either or both FABP4 and MBNL2 is increased and the expression level for UBE2C is decreased, as compared to their respective relative expression levels in a control or different bladder cancer sample, it indicates a decreased risk of progression relative to said control or different bladder cancer sample, and if the expression level for UBE2C is increased and the expression level for either or both FABP4 and MBNL2 is decreased, as compared to their respective relative expression levels in said control or different bladder cancer sample, it indicates an increased risk of progression relative to said control or different bladder cancer sample.

6. The method of claim 1 wherein the method further includes determining, in the bladder tumor sample, the level of gene expression from the markers UBE2C and BIRC5, wherein if the expression level for FABP4 is increased and the expression level for either or both UBE2C and BIRC5 is decreased, as compared to their respective relative expression levels in a control or different bladder cancer sample, it indicates a decreased risk of progression relative to said control or different bladder cancer sample, and if the expression level for either or both UBE2C and BIRC5 is increased and the expression level for FABP4 is decreased, as compared to their respective relative expression levels in said control or different bladder cancer sample, it indicates an increased risk of progression relative to said control or different bladder cancer sample.

7. A method of claim 1 for determining the likelihood of progression of an individual's bladder cancer, comprising: determining, in a bladder tumor sample from the individual, expression levels for a signature comprising the markers FABP4, MBNL2, UBE2C and BIRC5, wherein if the expression levels for either FABP4 or both FABP4 and MBNL2 are higher than the expression levels for either or both UBE2C and BIRC5 as compared to their respective relative expression levels in a control or different bladder cancer sample, this indicates a decreased risk of progression.

8. A method of claim 1 for determining the likelihood of progression of an individual's bladder cancer, comprising: determining, in a bladder tumor sample from the individual, expression levels for a signature comprising the markers FABP4, MBNL2, UBE2C and BIRC5, wherein if the expression levels for either FABP4 or both FABP4 and MBNL2 are lower than the expression levels for either or both UBE2C and BIRC5 as compared to their respective relative expression levels in a control or different bladder cancer sample, this indicates an increased risk of progression.

9. A method of claim 7 wherein said signature further includes one or more of the markers COL18A1, COL4A1, ACTA2, MSN, KPNA2, and CDC25B; and wherein the expression levels are determined for all markers in the signature, whereby if the expression levels for COL18A1, COL4A1, ACTA2, MSN, KPNA2, CDC25B, BIRC5 and/or UBE2C are decreased relative to the expression levels for either or both FABP4 and MBNL2, as compared to their respective relative expression levels in a control or different bladder cancer sample, it indicates a decreased risk of progression relative to said control or different bladder cancer sample.

10. A method of claim 8 wherein said signature further includes one or more of the markers COL18A1, COL4A1, ACTA2, MSN, KPNA2, and CDC25B; and wherein the expression levels are determined for all markers in the signature, whereby if the expression levels for COL18A1, COL4A1, ACTA2, MSN, KPNA2, CDC25B, BIRC5 and/or UBE2C are increased relative to the expression levels for either or both FABP4 and MBNL2, as compared to their respective relative expression levels in a control or different bladder cancer sample, it indicates an increased risk of progression relative to said control or different bladder cancer sample.

11. A method of claim 5 wherein said determining of the level of gene expression in said bladder tumor sample from said individual further includes determining the expression levels of COL18A1, COL4A1, ACTA2, MSN, KPNA2, and CDC25B; wherein if the expression level for either or both FABP4 and MBNL2 is increased and the expression levels for UBE2C, COL18A1, COL4A1, ACTA2, MSN, KPNA2, and/or CDC25B are decreased, as compared to their respective relative expression levels in a control or different bladder cancer sample, it indicates a decreased risk of progression relative to said control or different bladder cancer sample, and if the expression levels for UBE2C, COL18A1, COL4A1, ACTA2, MSN, KPNA2, and/or CDC25B are increased and the expression level for either or both FABP4 and MBNL2 is decreased, as compared to their respective relative expression levels in said control or different bladder cancer sample, it indicates an increased risk of progression relative to said control or different bladder cancer sample.

12. A method for treating stage Ta or T1 bladder cancer, comprising:
  a. determining the likelihood of progression of an individual's bladder cancer, by, determining in a bladder tumor sample biopsied from the individual:
    the level of gene expression from the markers MBNL2 and FABP4 and if the expression level determined for both MBNL2 and FABP4 is increased as compared to their expression levels in a control or different bladder cancer sample, it indicates a decreased risk of progression relative to said control or different bladder cancer sample; and if the expression level for both MBNL2 and FABP4 is decreased as compared to their expression levels in a control or different bladder cancer sample, it indicates an increased risk of progression relative to said control or different bladder cancer sample; and
  b. performing cystectomy on the individual if the expression levels determined for both MBNL2 and FABP4 are decreased as compared to their expression levels in a control or different bladder cancer sample.

* * * * *

SEQUENCE LISTING

<160> NUMBER OF SEQ ID NOS: 10

<210> SEQ ID NO 1
<211> LENGTH: 823
<212> TYPE: DNA
<213> ORGANISM: Homo sapiens
<220> FEATURE:
<223> OTHER INFORMATION: Homo sapiens ubiquitin-conjugating enzyme E2C
      (UBE2C), transcript variant 1, mRNA

```
<400> SEQUENCE: 1
aaacgcgggc gggcgggccc gcagtcctgc agttgcagtc gtgttctccg agttcctgtc    60
tctctgccaa cgccgcccgg atggcttccc aaaaccgcga cccagccgcc actagcgtcg   120
ccgccgcccg taaaggagct gagccgagcg ggggcgccgc ccggggtccg gtgggcaaaa   180
ggctacagca ggagctgatg accctcatga tgtctggcga taaagggatt tctgccttcc   240
ctgaatcaga caacctttc aaatgggtag gaccatcca tggagcagct ggaacagtat    300
atgaagacct gaggtataag ctctcgctag agttccccag tggctaccct acaatgcgc    360 ccacagtgaa gttcctcacg ccctgctatc accccaacgt ggacacccag ggtaacatat   420
gcctggacat cctgaaggaa aagtggtctg ccctgtatga tgtcaggacc attctgctct   480
ccatccagag ccttctagga gaacccaaca ttgatagtcc cttgaacaca catgctgccg   540
agctctggaa aaaccccaca gcttttaaga agtacctgca agaaacctac tcaaagcagg   600
tcaccagcca ggagccctga cccaggctgc ccagcctgtc cttgtgtcgt cttttttaatt  660 tttccttaga tggtctgtcc ttttttgtgat ttctgtatag gactctttat cttgagctgt   720 ggtattttg ttttgttttt gtcttttaaa ttaagcctcg gttgagccct tgtatattaa    780
ataaatgcat ttttgtcctt ttttagacaa aaaaaaaaaa aaa                     823

<210> SEQ ID NO 2
<211> LENGTH: 4665
<212> TYPE: DNA
<213> ORGANISM: Homo sapiens
<220> FEATURE:
<223> OTHER INFORMATION: Homo sapiens muscleblind-like 2 (Drosophila)
      (MBNL2), transcript variant 1, mRNA

<400> SEQUENCE: 2
tgaaggtaaa attttccaga tacggcagac ggctttcaga gtacaataaa cagggaatga    60
gaactattta catggaagtt tcttttctcat gatgcggtgg agaagcctcg gccacttggt   120
tctgccagat gttcctgggg ttactgtaaa tgggaaggac aggcagagct aaacaaggtt   180
tatcatttaa aagtgcctgt gtgaagtcac ttttgctgga aaactgcagc ttgggagctt   240
tctttgtatt cacatcccac tcttctgtca agtacacttt accctgacct tatgagtgga   300
tgaagatacc tcagttgtct gactttgcca attgcttaat ttcagaattt aaaaagggga   360
aagaaaaaca tcctgctaaa atatgaacat ctgagtgtct tattttccaa catcgtcaat   420
agctgtgagc gtcagcatta atattctcc caaggagtgc catgatattg aagtcacttt    480
attaataaca gctgtatctg caaacagtc aagagactcg gacgttgaaa gccagagatg    540
acactgagca tgctttattt gcggcctacc atctttaagt gggacatatt gattgatgag   600
tgattgcctg tccatacact ctctcatcat cctgttcctt ggattggact tcactaagca   660
atttatcact caccttcaga cttacatgtg ggagttttca acagtagt tttgaatca    720 ttagaacttg gattgatttc atcatttaac agaaacaaac agcccaaatt actttatcac   780
catggctttg aacgttgccc cagtcagaga tacaaaatgg ctgacattag aagtctgcag   840
acagtttcaa agaggaacat gctcacgctc tgatgaagaa tgcaaatttg ctcatccccc   900
caaaagttgt caggttgaaa atggaagagt aattgcctgc tttgattccc taagggccg    960 ttgttcgaga gagaactgca agtatcttca ccctccgaca cacttaaaaa ctcaactaga  1020
aattaatgga aggaacaatt tgattcagca aaaaactgca gcagcaatgc ttgcccagca  1080
gatgcaattt atgtttccag gaacaccact tcatccagtg cccactttcc ctgtaggtcc  1140
```

```
cgcgataggg acaaatacgg ctattagctt tgctccttac ctagcacctg taacccctgg     1200
agttgggttg gtcccaacgg aaattctgcc caccacgcct gttattgttc ccggaagtcc     1260
accggtcact gtcccgggct caactgcaac tcagaaactt ctcaggactg acaaactgga     1320
ggtatgcagg gagttccagc gaggaaactg tgcccgggga gagaccgact gccgctttgc     1380
acaccccgca gacagcacca tgatcgacac aagtgacaac accgtaaccg tttgtatgga     1440
ttacataaag gggcgttgca tgagggagaa atgcaaatat tttcaccctc ctgcacactt     1500
gcaggccaaa atcaaagctg cgcagcacca agccaaccaa gctgcggtgg ccgcccaggc     1560
agccgcggcc gcggcacag tcatggcctt tcccctggt gctcttcatc ctttaccaaa      1620
gagacaagca cttgaaaaaa gcaatggtac cagcgcggtc tttaaccca gcgtcttgca     1680 ctaccagcag gctctcacca gcgcacagtt gcagcaacac gccgcgttca ttccaacagg    1740
gtcagttttg tgcatgacac ccgctaccag tattgtaccc atgatgcaca gcgctacgtc    1800
cgccactgtc tctgcagcaa caactcctgc aacaagtgtc cccttcgcag caacagccac    1860
agccaatcag ataattctga ataatcagc agaaacggaa tggaatgcca agaatctgca    1920
ttgagaataa ctaaacattg ttactgtaca tactatcctg tttcctcctc aatagaattg    1980
ccacaaactg catgctaaat aaagatgtag ttcttctgga cagaccacaa ctctaagaag    2040
ctagtgctgc tatctcatat atgagtatta aatatggtat gcttagtata ttccaaccta    2100
agatagttaa ctacctgaga ccagctgtga tgtttaaaga cataaaggat aaagtttact    2160
tttaaagggt ttctaaacat agtttctgtc ctaggaatat tgtcttatct ccataactat    2220
agctgatgca gaaagtccag ccagtttact catttcgatt cagaatattt caaatttagc    2280
aataaacaat tagcattagt taaaaaagaa acatattcca agggcaggtt cgattctagc    2340
tctaattact gtcatgtcat ttacccactg gatcaaaggg tatgtttcac ttcttgacaa    2400
tataaatgct gcagcaaaga tgagaggtga agtaaaaccg atacctgtcc tgcaggtcta    2460
aaatttgaat ggaaattcaa gcacaagtac tggggacaca tcaaagtgtg gtgtttggtt    2520
tgcctggaga tgccacgttg aatcatgtga ttctagatta acattaaata gattgaaaaa    2580
gaaactttgc acggtatgag cttcataccc caccaaacaa agtcttgaag gtattatttt    2640
acaagtatat ttttaaagtt gttttataag agagactttg tagaagtgcc tagattttgc    2700
cagacttcat ccagcttgac aagattgaga ggcccatgcc aacagtctaa tctaagagat    2760
tagtctttca aactcaccat ccagttgcct gttacagaat aactcttctt aactaaaaac    2820
ctagtcaaac aaggaagctg taggtgagga gatctgtata atattctaat ttaagtaagt    2880
ttgagtttag tcactgcaaa tttgactgtg actttaatct aaattactat gtaaacaaaa    2940
agtagatagt ttcacttttt aaaaaatcca ttactgtttt gcatttcaaa agttggatta    3000
aagggttgta actgactaca gcatggaaaa aaatagttct tttaattctt tcaccttaaa    3060
gcatatttta tgtctcaaaa gtataaaaaa ctttaataca agtacataca tattatatat    3120
acacatacat atatatacta tatatggatg aaacatattt taatgttgtt actttttta    3180 aatacttggt tgatcttcaa ggtaatagcg atacaattaa attttgttca gaaagtttgt    3240
tttaagtttt attttaagca ctatcgtacc aaatatttca tatttcacat tttatatgtt    3300
gcacatagcc tatacagtac ctacatagtt tttaaattat tgtttaaaaa acaaaacagc    3360
tgttataaat gaatattatg tgtaattgtt tcaaacatcc attttctttg tgaacatatt    3420
agtgattgaa gtatttgac ttttgagatt gaatgtaaaa tattttaaat ttgggatcat     3480
cgcctgttct gaaaactaga tgcaccaacc gtatcattat ttgtttgagg aaaaaaagaa    3540
```

```
atctgcattt taattcatgt tggtcaaagt cgaattacta tctatttatc ttatatcgta    3600
gatctgataa ccctatctaa aagaaagtca cacgctaaat gtattcttac atagtgcttg    3660
tatcgttgca tttgttttaa tttgtggaaa agtattgtat ctaacttgta ttactttggt    3720
agtttcatct ttatgtatta ttgatatttg taattttctc aactataaca atgtagttac    3780
gctacaactt gcctaaaaca ttcaaacttg ttttcttttt tctgtttttt tctttgttaa    3840
ttcatttaaa ctcattgaaa acatagtata cattactaaa aggtaaatta tgggaatcac    3900
tgaaatattt ttgtagatta attgttgtaa cattgtcttt cttttttttc ttttgtttca    3960
tgattttgat ttttaaaatt attagcacac aactattttc agcccttaa taatggagca     4020 tcaaaaacat cacctgtaac cccaagcaaa tatagaagac tgtatttttt actatgatat    4080
ccattttcca gaattgtgat tacaatatgc aaagagtcat aaatatgcca tttacaataa    4140
ggaggaggca aggcaaatgc atagatgtac aaatatatgt acaacagatt ttgctttta    4200 tttatttata atgtaatttt atagaataat tctgggatt gagaggatct aaaactattt    4260
ttctgtataa atattatttg ccaaaagttt gtttatattc agaagtctga ctatgatgaa    4320
taaatcttaa atgctttgtt taattaaaaa acaaaaatca ccaatatcca agacatgaag    4380
atatcagttc aacaaatact gtagttaaga gactaactct ccacttgtat gggaactaca    4440
tttcactctt ggttttcagg atataacagc acttcaccga aatattcttt cagccatacc    4500
actggtaaca tttctactaa atctttctgt aacacttaaa gaattccctc attcattacc    4560
ttacagtgta aacaggagtc taatttgtat caatactatg ttttggttgt aatattcagt    4620
tcactcaccc aatgtacaac caatgaaata aagaagcat ttaaa                     4665
```

<210> SEQ ID NO 3
<211> LENGTH: 619
<212> TYPE: DNA
<213> ORGANISM: Homo sapiens
<220> FEATURE:
<223> OTHER INFORMATION: Homo sapiens fatty acid binding protein 4,
      adipocyte (FABP4), mRNA

<400> SEQUENCE: 3

```
tgcagcttcc ttctcacctt gaagaataat cctagaaaac tcacaaaatg tgtgatgctt     60
ttgtaggtac ctggaaactt gtctccagtg aaaactttga tgattatatg aaagaagtag    120
gagtgggctt tgccaccagg aaagtggctg gcatggccaa acctaacatg atcatcagtg    180
tgaatgggga tgtgatcacc attaaatctg aaagtacctt taaaaatact gagatttcct    240
tcatactggg ccaggaattt gacgaagtca ctgcagatga caggaaagtc aagagcacca    300
taaccttaga tgggggtgtc ctggtacatg tgcagaaatg ggatggaaaa tcaaccacca    360
taaagagaaa acgagaggat gataaactgg tggtggaatg cgtcatgaaa ggcgtcactt    420
ccacgagagt ttatgagaga gcataagcca agggacgttg acctggactg aagttcgcat    480
tgaactctac aacattctgt gggatatatt gttcaaaaag atattgttgt tttccctgat    540
ttagcaagca agtaattttc tcccaagctg attttattca atatggttac gttggttaaa    600 taacttttttt tagatttag                                                619
```

<210> SEQ ID NO 4
<211> LENGTH: 1619
<212> TYPE: DNA
<213> ORGANISM: Homo sapiens
<220> FEATURE:
<223> OTHER INFORMATION: Homo sapiens baculoviral IAP repeat-containing
      5 (survivin) (BIRC5), mRNA

<400> SEQUENCE: 4

```
ccgccagatt tgaatcgcgg gacccgttgg cagaggtggc ggcggcggca tgggtgcccc      60
gacgttgccc cctgcctggc agcccttcct caaggaccac cgcatctcta cattcaagaa     120
ctggcccttc ttggagggct cgcctgcac cccggagcgg atggccgagg ctggcttcat      180
ccactgcccc actgagaacg agccagactt ggcccagtgt ttcttctgct tcaaggagct     240
ggaaggctgg gagccagatg acgacccat agaggaacat aaaaagcatt cgtccggttg      300
cgctttcctt tctgtcaaga agcagtttga agaattaacc cttggtgaat ttttgaaact     360
ggacagagaa agagccaaga acaaaattgc aaaggaaacc aacaataaga gaaagaatt      420
tgaggaaact gcgaagaaag tgcgccgtgc catcgagcag ctggctgcca tggattgagg     480
cctctggccg gagctgcctg gtcccagagt ggctgcacca cttccagggt ttattccctg     540
gtgccaccag ccttcctgtg ggccccttag caatgtctta ggaaaggaga tcaacatttt     600
caaattagat gtttcaactg tgctcctgtt ttgtcttgaa agtggcacca gaggtgcttc     660
tgcctgtgca gcgggtgctg ctggtaacag tggctgcttc tctctctctc tctctttttt     720
gggggctcat ttttgctgtt ttgattcccg ggcttaccag gtgagaagtg agggaggaag     780
aaggcagtgt cccttttgct agagctgaca gctttgttcg cgtgggcaga gccttccaca     840
gtgaatgtgt ctggacctca tgttgttgag gctgtcacag tcctgagtgt ggacttggca     900
ggtgcctgtt gaatctgagc tgcaggttcc ttatctgtca cacctgtgcc tcctcagagg     960
acagttttt  tgttgttgtg ttttttgtt  ttttttttt  ggtagatgca tgacttgtgt    1020
gtgatgagag aatggagaca gagtccctgg ctcctctact gtttaacaac atggctttct    1080
tattttgttt gaattgttaa ttcacagaat agcacaaact acaattaaaa ctaagcacaa    1140
agccattcta agtcattggg gaaacggggt gaacttcagg tggatgagga gacagaatag    1200
agtgatagga agcgtctggc agatactcct tttgccactg ctgtgtgatt agacaggccc    1260
agtgagccgc ggggcacatg ctggccgctc ctccctcaga aaaaggcagt ggcctaaatc    1320
ctttttaaat gacttggctc gatgctgtgg gggactggct gggctgctgc aggccgtgtg    1380
tctgtcagcc caaccttcac atctgtcacg ttctccacac gggggagaga cgcagtccgc    1440
ccaggtcccc gctttctttg gaggcagcag ctcccgcagg gctgaagtct ggcgtaagat    1500
gatggatttg attcgccctc ctccctgtca tagagctgca gggtggattg ttacagcttc    1560
gctggaaacc tctggaggtc atctcggctg ttcctgagaa ataaaaagcc tgtcatttc     1619
```

<210> SEQ ID NO 5
<211> LENGTH: 5910
<212> TYPE: DNA
<213> ORGANISM: Homo sapiens
<220> FEATURE:
<223> OTHER INFORMATION: Homo sapiens collagen, type XVIII, alpha 1
      (COL18A1), transcript variant 1, mRNA

<400> SEQUENCE: 5

```
agctccagcc gcactgcccc gatggctccc taccctgtg gctgccacat cctgctgctg        60
ctcttctgct gcctggcggc tgcccgggcc aacctgctga acctgaactg gctttggttc     120
aataatgagg acaccagcca cgcagctacc acgatccctg agcccagggg gcccctgcct     180
gtgcagccca cagcagatac caccacacac gtgacccccg gaatggttc cacagagcca     240
gcgacagccc ctggcagccc tgagccaccc tcagagctgc tggaagatgg ccaggacacc     300
cccacttctg ccgagagccc ggacgcgcca gaggagaaca ttgccggtgt cggagccgag     360
```

| | |
|---|---|
| atcctgaacg tggccaaagg catccggagc ttcgtccagc tgtggaatga cactgtcccc | 420 |
| actgagagct tggccagggc ggaaaccctg gtcctggaga ctcctgtggg cccccttgcc | 480 |
| ctcgctgggc cttccagcac ccccccaggag aatgggacca ctctctggcc cagccgtggc | 540 |
| attcctagct ctccgggcgc ccacacaacc gaggctggca ccttgcctgc acccacccca | 600 |
| tcgcctccgt ccctgggcag gccctgggca ccactcacgg ggccctcagt gccaccacca | 660 |
| tcttcagagc gcatcagcga ggaggtgggg ctgctgcagc tccttgggga ccccccgccc | 720 |
| cagcaggtca cccagacgga tgaccccgac gtcgggctgg cctacgtctt tgggccagat | 780 |
| gccaacagtg gccaagtggc ccggtaccac ttccccagcc tcttcttccg tgacttctca | 840 |
| ctgctgttcc acatccggcc agccacagag ggcccagggg tgctgttcgc catcacggac | 900 |
| tcggcgcagg ccatggtctt gctgggcgtg aagctctctg gggtgcagga cgggcaccag | 960 |
| gacatctccc tgctctacac agaacctggt gcaggccaga cccacacagc cgccagcttc | 1020 |
| cggctccccg ccttcgtcgg ccagtggaca cacttagccc tcagtgtggc aggtggcttt | 1080 |
| gtggccctct acgtggactg tgaggagttc cagagaatgc cgcttgctcg gtcctcacgg | 1140 |
| ggcctggagc tggagcctgg cgccgggctc ttcgtggctc aggcgggggg agcggaccct | 1200 |
| gacaagttcc aggggtgat cgctgagctg aaggtgcgca gggaccccca ggtgagcccc | 1260 |
| atgcactgcc tggacgagga aggcgatgac tcagatgggg cattcggaga ctctggcagc | 1320 |
| gggctcgggg acgcccggga gcttctcagg gaggagacgg cgcggccct aaaacccagg | 1380 |
| ctccccgcgc cacccccgt caccacgcca cccttggctg gaggcagcag cacggaagat | 1440 |
| tccagaagtg aagaagtcga ggagcagacc acggtggctt cgttaggagc tcagacactt | 1500 |
| cctggctcag attctgtctc cacgtgggac gggagtgtcc ggaccctgg gggccgcgtg | 1560 |
| aaagagggcg gcctgaaggg gcagaaaggg gagccaggtg ttccgggccc acctggccgg | 1620 |
| gcaggccccc caggatcccc atgcctacct ggtcccccgg gtctcccgtg cccagtgagt | 1680 |
| cccctgggtc ctgcaggccc agcgttgcaa actgtccccg gaccacaagg accccaggg | 1740 |
| cctccgggga gggacggcac cctggaagg acggcgagc cgggcgaccc cggtgaagac | 1800 |
| ggaaagccgg gcgacaccgg gccacaaggc ttccctggga ctccagggga tgtaggtccc | 1860 |
| aagggagaca agggagaccc tggggttgga gagagagggc cccaggacc caagggcct | 1920 |
| ccagggcccc caggaccctc cttcagacac gacaagctga ccttcattga catgagggga | 1980 |
| tctggctttg ggggcgatct ggaggccctg cggggtcctc gaggcttccc tggacctccc | 2040 |
| ggacccccg tgtcccagg cctgccggc gagccaggcc gctttgggt gaacagctcc | 2100 |
| gacgtcccag gacccgccgg ccttcctggt gtgcctgggc gcgagggtcc ccccgggttt | 2160 |
| cctggcctcc cggacccccc aggccctccg gaagagagg ggcccccagg aaggactggg | 2220 |
| cagaaaggca gcctgggtga agcaggcgcc ccaggacata aggggagcaa gggagccccc | 2280 |
| ggtcctgctg gtgctcgtgg ggagagcggc ctgcaggag cccccggacc tgctggacca | 2340 |
| ccaggccccc ctgggcccccc tgggcccccca ggaccaggac tccccgctgg atttgatgac | 2400 |
| atggaaggct ccgggggggcc cttctggtca acagcccgaa gcgctgatgg gccacaggga | 2460 |
| cctcccggcc tgccgggact taaggggggat cctggcgtgc ctgggctgcc ggggggcgaag | 2520 |
| ggagaagttg gagcagatgg aatccccggg ttccccggcc tccctggcag agagggcatt | 2580 |
| gctgggcccc aggggccaaa gggagacaga ggcagccggg gagaaaaggg agatccaggg | 2640 |
| aaggacggag tcgggcagcc gggcctccct ggccccccccg gaccccgggg acctgtggtc | 2700 |
| tacgtgtcgg agcaggacgg atccgtcctg agcgtgccgg gacctgaggg ccggccgggt | 2760 |

```
ttcgcaggct ttcccggacc tgcaggaccc aagggcaacc tgggctctaa gggcgaacga    2820
ggctccccgg gacccaaggg tgagaagggt gaaccgggca gcatcttcag ccccgacggc    2880
ggtgccctgg gccctgccca gaaggagcc aagggagagc cgggcttccg aggaccccg     2940
ggtccatacg gacggccggg gtacaaggga gagattggct ttcctggacg gccgggtcgc    3000
cccgggatga acggattgaa aggagagaaa ggggagccgg gagatgccag ccttggattt    3060
ggcatgaggg gaatgcccgg ccccccagga cctccagggc ccccaggccc tcagggact     3120
cctgtttacg acagcaatgt gtttgctgag tccagccgcc ccgggcctcc aggattgcca    3180
gggaatcagg gccctccagg acccaagggc gccaaaggag aagtgggccc ccccggacca    3240
ccagggcagt ttccgtttga cttcttcag ttggaggctg aaatgaaggg ggagaaggga    3300
gaccgaggtg atgcaggaca gaaaggcgaa aggggggagc ccgggggcgg cggtttcttc    3360
ggctccagcc tgcccggccc ccccggcccc ccaggcccac gtggctaccc tgggattcca    3420
ggtcccaagg gagagagcat ccggggccag cccggcccac ctggacctca ggacccccc    3480
ggcatcggct acgaggggcg ccaggccct cccggcccc caggccccc agggccccct     3540
tcatttcctg gccctcacag gcagactatc agcgttcccg gccctccggg cccccctggg    3600
cccccctggg cccctggaac catgggcgcc tcctcagggg tgaggctctg ggctacacgc    3660
caggccatgc tgggccaggt gcacgaggtt cccgagggct ggctcatctt cgtggccgag    3720
caggaggagc tctacgtccg cgtgcagaac gggttccgga aggtccagct ggaggcccgg    3780
acaccactcc cacgagggac ggacaatgaa gtggccgcct gcagcccccc cgtggtgcag    3840
ctgcacgaca gcaaccccta cccgcggcgg gagcaccccc accccaccgc gcggccctgg    3900
cgggcagatg acatcctggc cagcccccct cgcctgcccg agcccagcc ctaccccgga    3960
gccccgcacc acagctccta cgtgcacctg cggccggcgc gacccacaag cccaccgcc    4020
cacagccacc gcgacttcca gccggtgctc cacctggttg cgctcaacag ccccctgtca    4080
ggcggcatgc gggcatccg cggggccgac ttcagtgct ccagcaggc gcgggccgtg     4140
gggctggcgg gcaccttccg cgccttcctg tcctcgcgcc tgcaggacct gtacagcatc    4200
gtgcgccgtg ccgaccgcgc agccgtgccc atcgtcaacc tcaaggacga gctgctgttt    4260
cccagctggg aggctctgtt ctcaggctct gagggtccgc tgaagcccgg ggcacgcatc    4320
ttctcctttg acggcaagga cgtcctgagg cacccccact ggcccagaa gagcgtgtgg    4380
catggctcgg accccaacgg gcgcaggctg accgagagct actgtgagac gtggcggacg    4440
gaggctccct cggccacggg ccaggcctcc tcgctgctgg ggcaggct cctggggcag    4500
agtgccgcga gctgccatca cgcctacatc gtgctctgca ttgagaacag cttcatgact    4560
gcctccaagt agccaccgcc tggatgcgga tggccggaga ggaccggcgg ctcggaggaa    4620
gccccaccg tgggcaggga gcggccggcc agcccctggc cccaggacct ggctgccata    4680
ctttcctgta tagttcacgt ttcatgtaat cctcaagaaa taaaggaag ccaagagtg     4740
tatttttta aaagtttaaa acagaagcct gatgctgaca ttcacctgcc ccaactctcc    4800
cctgacctgt gagcccagct gggtcaggca gggtgcagta tcatgccctg tgcaacctct    4860
tggcctgatc agaccacggc tcgatttctc caggatttcc tgctttggga agccgtgctc    4920
gccccagcag gtgctgactt catctcccac ctagcagcac cgttctgtgc acaaaaccca    4980
gacctgttag cagacaggcc ccgtgaggca atgggagctg aggccacact cagcacaagg    5040
ccatctgggc tcctccaggg tgtgtgctcg ccctgcggta gatgggaggg aggctcaggt    5100
ccctggggct agggggagcc ccttctgctc agctctgggc cattctccac agcaacccca    5160
```

| | |
|---|---|
| ggctgaagca ggttcccaag ctcagaggcg cactgtgacc cccagctccg gcctgtcctc | 5220 |
| caacaccaag cacagcagcc tggggctggc ctcccaaatg agccatgaga tgatacatcc | 5280 |
| aaagcagaca gctccaccct ggccgagtcc aagctgggag attcaaggga cccatgagtt | 5340 |
| ggggtctggc agcctcccat ccagggcccc catctcatgc ccctggctgg acgtggctc | 5400 |
| agccagcact tgtccagctg agcgccagga tggaacacgg ccacatcaaa gaggctgagg | 5460 |
| ctggcacagg acatgcggta gccagcacac agggcagtga gggagggctg tcatctgtgc | 5520 |
| actgcccatg gacaggctgg ctccagatgc agggcagtca ttggctgtct cctaggaaac | 5580 |
| ccatatcctt accctccttg ggactgaagg ggaaccccgg ggtgcccaca ggccgccctg | 5640 |
| cgggtgaaca aagcagccac gaggtgcaac aaggtcctct gtcagtcaca gccacccctg | 5700 |
| agatccggca acatcaaccc gagtcattcg ttctgtggag ggacaagtgg actcagggca | 5760 |
| gcgccaggct gaccacagca cagccaacac gcacctgcct caggactgcg acgaaaccgg | 5820 |
| tggggctggt tctgtaattg tgtgtgatgt gaagccaatt cagacaggca aataaaagtg | 5880 |
| accttttaca ctgaaaaaaa aaaaaaaaaa | 5910 |

<210> SEQ ID NO 6
<211> LENGTH: 6447
<212> TYPE: DNA
<213> ORGANISM: Homo sapiens
<220> FEATURE:
<223> OTHER INFORMATION: Homo sapiens collagen, type IV, alpha 1
    (COL4A1), mRNA

<400> SEQUENCE: 6

| | |
|---|---|
| aggtctccgc ttggagccgc cgcacccggg acggtgcgta tcgctggaag tccggccttc | 60 |
| cgagagctag ctgtccgccg cggccccgc acgccgggca gccgtccctc gcgcctcggg | 120 |
| cgcgccacca tggggccccg gctcagcgtc tggctgctgc tgctgccgc cgcccttctg | 180 |
| ctccacgagg agcacagccg ggccgctgcg aaggggtggc tgtgctggctc tggctgtggc | 240 |
| aaatgtgact gccatggagt gaagggacaa aagggtgaaa gaggcctccc ggggttacaa | 300 |
| ggtgtcattg ggtttcctgg aatgcaagga cctgaggggc cacaggacc accaggacaa | 360 |
| aagggtgata ctggagaacc aggactacct ggaacaaaag ggacaagagg acctccggga | 420 |
| gcatctggct accctggaaa cccaggactt cccggaattc ctggccaaga cggcccgcca | 480 |
| ggcccccag gtattccagg atgcaatggc acaaaggggg agagagggcc gctcgggcct | 540 |
| cctggcttgc ctggtttcgc aggaaatccc ggaccaccag gcttaccagg atgaagggt | 600 |
| gatccaggtg agatacttgg ccatgtgccc gggatgctgt tgaaaggtga agaggatttt | 660 |
| cccgaatcc cagggactcc aggcccacca ggactgccag gcttcaagg tcctgttggg | 720 |
| cctccaggat ttaccggacc accaggtccc caggccctc ccggccctcc aggtgaaaag | 780 |
| ggacaaatgg gcttaagttt tcaaggacca aaggtgaca gggtgacca aggggtcagt | 840 |
| gggcctccag gagtaccagg acaagctcaa gttcaagaaa aaggagactt cgccaccaag | 900 |
| ggagaaaagg gccaaaaagg tgaacctgga tttcagggga tgccagggt cggagagaaa | 960 |
| ggtgaacccg gaaaccagg acccagaggc aaacccggaa agatggtgaa caagggaa | 1020 |
| aaagggagtc ccggtttccc tggtgaaccc gggtacccag gactcatagg ccgccagggc | 1080 |
| ccgcaggag aaaagggtga agcaggtcct cctggcccac ctggaattgt tataggcaca | 1140 |
| ggaccttgg gagaaaaagg agagagggc taccctgaa ctccgggcc aagaggagag | 1200 |
| ccaggcccaa aaggtttccc aggactacca ggccaacccg gacctccagg cctccctgta | 1260 |

```
cctgggcagg ctggtgcccc tggcttccct ggtgaaagag gagaaaaagg tgaccgagga    1320
tttcctggta catctctgcc aggaccaagt ggaagagatg ggctcccggg tcctcctggt    1380
tcccccgggc cccctgggca gcctggctac acaaatggaa ttgtggaatg tcagcccgga    1440
cctccaggtg accagggtcc tcctggaatt ccagggcagc caggatttat aggcgaaatt    1500
ggagagaaag gtcaaaaagg agagagttgc ctcatctgtg atatagacgg atatcggggg    1560
cctcccgggc cacagggacc cccgggagaa ataggtttcc cagggcagcc aggggccaag    1620
ggcgacagag gtttgcctgg cagagatggt gttgcaggag tgccaggccc tcaaggtaca    1680
ccagggctga taggccagcc aggagccaag ggggagcctg gtgagtttta tttcgacttg    1740
cggctcaaag gtgacaaagg agacccaggc tttccaggac agcccggcat gccagggaga    1800
gcgggttctc ctggaagaga tggccatccg ggtcttcctg gccccaaggg ctcgccgggt    1860
tctgtaggat tgaaaggaga gcgtggcccc cctggaggag ttggattccc aggcagtcgt    1920
ggtgacaccg gccccctgg gcctccagga tatggtcctg ctggtcccat tggtgacaaa    1980
ggacaagcag gctttcctgg aggccctgga tccccaggcc tgccaggtcc aaagggtgaa    2040
ccaggaaaaa ttgttccttt accaggcccc cctggagcag aaggactgcc ggggtcccca    2100
ggcttcccag gtccccaagg agaccgaggc tttcccggaa ccccaggaag gccaggcctg    2160
ccaggagaga agggcgctgt gggccagcca ggcattggat tccagggcc ccggccc       2220 aaaggtgttg acggcttacc tggagacatg gggccaccgg ggactccagg tcgcccggga    2280
tttaatggct tacctgggaa cccaggtgtg cagggccaga agggagagcc tggagttggt    2340
ctaccgggac tcaaaggttt gccaggtctt cccggcattc ctggcacacc cggggagaag    2400
gggagcattg gggtaccagg cgttcctgga gaacatggag cgatcggacc ccctgggctt    2460
caggggatca gaggtgaacc gggacctcct ggattgccag gctccgtggg gtctccagga    2520
gttccaggaa taggccccc tggagctagg ggtcccctg gaggacaggg accaccgggg    2580
ttgtcaggcc ctcctggaat aaaaggagag aagggtttcc ccggattccc tggactggac    2640
atgccgggcc ctaaaggaga taaaggggct caaggactcc ctggcataac gggacagtcg    2700
gggctccctg gccttcctgg acagcagggg ctcctggga ttcctgggtt tccaggttcc    2760
aagggagaaa tgggcgtcat ggggacccc gggcagccgg gctcaccagg accagtgggt    2820
gctcctggat taccgggtga aaaggggac catggctttc cggctcctc aggacccagg    2880 ggagaccctg gcttgaaagg tgataagggg gatgtcggtc tccctggcaa gcctggctcc    2940
atggataagg tggacatggg cagcatgaag ggccagaaag gagaccaagg agagaaagga    3000
caaattggac caattggtga agggatcc cgaggagacc ctgggacccc aggagtgcct    3060
ggaaaggacg ggcaggcagg acagcctggg cagccaggac ctaaaggtga tccaggtata    3120
agtggaaccc caggtgctcc aggacttccg ggaccaaaag gatctgttgg tggaatggc    3180 ttgccaggaa cacctggaga gaaggtgtg cctggcatcc ctggcccaca aggttcacct    3240
ggcttacctg gagacaaagg tgcaaaagga gagaagggc aggcaggccc acctggcata    3300
ggcatcccag gactgcgtgg tgaaagggga gatcaaggga tagcgggttt cccaggaagc    3360
cctggagaga agggagaaaa aggaagcatt gggatcccag gaatgccagg gtccccaggc    3420 cttaaaggt ctcccgggag tgttggctat ccaggaagtc ctgggctacc tggagaaaaa    3480
ggtgacaaag gcctcccagg attggatggc atccctggtg tcaaaggaga agcaggtctt    3540
cctgggactc ctgccccac aggcccagct ggccagaaag gggagccagg cagtgatgga    3600
atcccggggt cagcaggaga gaagggtgaa ccaggtctac caggaagagg attcccaggg    3660
```

```
tttccagggg ccaaaggaga caaaggttca aagggtgagg tgggtttccc aggattagcc    3720
gggagcccag gaattcctgg atccaaagga gagcaaggat tcatgggtcc tccggggccc    3780
cagggacagc cggggttacc gggatcccca ggccatgcca cggaggggcc caaaggagac    3840
cgcggacctc agggccagcc tggcctgcca ggacttccgg gacccatggg gcctccaggg    3900
cttcctggga ttgatggagt taaaggtgac aaaggaaatc caggctggcc aggagcaccc    3960
ggtgtcccag ggcccaaggg agaccctgga ttcagggca tgcctggtat tggtggctct     4020
ccaggaatca caggctctaa gggtgatatg gggcctccag gagttccagg atttcaaggt    4080
ccaaaaggtc ttcctggcct ccagggaatt aaaggtgatc aaggcgatca aggcgtcccg    4140
ggagctaaag gtctcccggg tcctcctggc cccccaggtc cttacgacat catcaaaggg    4200
gagcccgggc tccctggtcc tgagggcccc cagggctga aagggcttca gggactgcca     4260
ggcccgaaag gccagcaagg tgttacagga ttggtgggta tacctggacc tccaggtatt    4320
cctgggtttg acggtgcccc tggccagaaa ggagagatgg gacctgccgg gcctactggt    4380
ccaagaggat ttccaggtcc accaggcccc gatgggttgc aggatccat ggggcccca     4440
ggcaccccat ctgttgatca cggcttcctt gtgaccaggc atagtcaaac aatagatgac    4500
ccacagtgtc cttctgggac caaaattctt taccacgggt actctttgct ctacgtgcaa    4560
ggcaatgaac gggcccatgg acaggacttg gcacggccg gcagctgcct gcgcaagttc    4620
agcacaatgc ccttcctgtt ctgcaatatt acaacgtgt gcaactttgc atcacgaaat    4680
gactactcgt actggctgtc cacccctgag cccatgccca tgtcaatggc acccatcacg    4740
ggggaaaaca taagaccatt tattagtagg tgtgctgtgt gtgaggcgcc tgccatggtg    4800
atggccgtgc acagccagac cattcagatc ccaccgtgcc ccagcgggtg gtcctcgctg    4860
tggatcggct actcttttgt gatgcacacc agcgctggtg cagaaggctc tggccaagcc    4920
ctggcgtccc ccggctcctg cctggaggag tttagaagtg cgccattcat cgagtgtcac    4980
ggccgtggga cctgcaatta ctacgcaaac gcttacagct tttggctcgc caccatagag    5040
aggagcgaga tgttcaagaa gcctacgccg tccaccttga aggcagggga gctgcgcacg    5100
cacgtcagcc gctgccaagt ctgtatgaga agaacataag aagcctgact cagctaatgt    5160
cacaacatgg tgctacttct tcttcttttt gttaacagca acgaacccta gaaatatatc    5220
ctgtgtacct cactgtccaa tatgaaaacc gtaaagtgcc ttataggaat ttgcgtaact    5280
aacacaccct gcttcattga cctctacttg ctgaaggaga aaagacagc gataagcttc     5340
aatagtggca taccaaatgg cacttttgat gaaataaaat atcaatattt tctgcaatcc    5400
aatgcactga tgtgtgaagt gagaactcca tcagaaaacc aaagggtgct aggaggtgtg    5460
ggtgccttcc atactgtttg cccatttca ttcttgtatt ataattaatt ttctacccccc    5520
agagataaat gtttgtttat atcactgtct agctgtttca aaatttaggt cccttggtct    5580
gtacaaataa tagcaatgta aaatggtttt tttgaacctc caaatggaat tacagactca    5640
gtagccatat cttccaaccc cccagtataa atttctgtct ttctgctatg tgtggtactt    5700
tgcagctgct tttgcagaaa tcacaatttt cctgtggaat aaagatggtc caaaaatagt    5760
caaaaattaa atatatatat atattagtaa tttatataga tgtcagcaat taggcagatc    5820
aaggtttagt ttaacttcca ctgttaaaat aaagcttaca tagttttctt ccttttgaaag   5880
actgtgctgt cctttaacat aggttttttaa agactaggat attgaatgtg aaacatccgt   5940
tttcattgtt cacttctaaa ccaaaaatta tgtgttgcca aaaccaaacc caggttcatg    6000
aatatggtgt ctattatagt gaaacatgta ctttgagctt attgttttta ttctgtatta    6060
```

```
aatatttca gggttttaaa cactaatcac aaactgaatg acttgacttc aaaagcaaca    6120
accttaaagg ccgtcatttc attagtattc ctcattctgc atcctggctt gaaaaacagc    6180
tctgttgaat cacagtatca gtattttcac acgtaagcac attcgggcca tttccgtggt    6240
ttctcatgag ctgtgttcac agacctcagc agggcatcgc atggaccgca ggagggcaga    6300
ttcggaccac taggcctgaa atgacatttc actaaaagtc tccaaaacat ttctaagact    6360
actaaggcct tttatgtaat ttcttaaat gtgtatttct taagaattca aatttgtaat     6420
aaaactattt gtataaaaat taagctt                                       6447
```

<210> SEQ ID NO 7
<211> LENGTH: 1798
<212> TYPE: DNA
<213> ORGANISM: Homo sapiens
<220> FEATURE:
<223> OTHER INFORMATION: Homo sapiens actin, alpha 2, smooth muscle, aorta (ACTA2), transcript variant 1, mRNA

<400> SEQUENCE: 7

```
ctctccccgc cccgcgggg cggcgcgcac tcacccaccc gcgccggagc ggacctttgg      60
cttggcttgt cagggcttgt ccaggagttc cgctcctctc tccaaccggg gtcccctcc     120 agcgaccta aagcttccca gacttccgct tcaattcctg tccgcacccc acgcccacct    180
caacgtggag cgcagtggtc tccgaggagc gccggagctg ccccgcctgc ccagcggggt    240
cagcacttcg catcaaggcc caagaaaagc aagtcctcca gcgttctgag cacccgggcc    300
tgagggaagg tcctaacagc ccccgggagc cagtctccaa cgcctcccgc agcagcccgc    360
cgctcccagg tgcccgcgtg cgccgctgcc gccgcaatcc cgcacgcgtc ccgcgcccgc    420
cccactttgc ctatccccgg gactaagacg ggaatcctgt gaagcagctc cagctatgtg    480
tgaagaagag gacagcactg ccttggtgtg tgacaatggc tctgggctct gtaaggccgg    540
ctttgctggg gacgatgctc ccagggctgt tttcccatcc attgtgggac gtcccagaca    600 tcaggggggtg atggtgggaa tgggacaaaa agacagctac gtgggtgacg aagcacagag    660
caaaagagga atcctgaccc tgaagtaccc gatagaacat ggcatcatca ccaactggga    720
cgacatggaa aagatctggc accactcttt ctacaatgag cttcgtgttg cccctgaaga    780
gcatcccacc ctgctcacgg aggcaccct gaaccccaag gccaaccggg agaaaatgac    840
tcaaattatg tttgagactt tcaatgtccc agccatgtat gtggctatcc aggcggtgct    900
gtctctctat gcctctggac gcacaactgg catcgtgctg actctggag atggtgtcac    960 ccacaatgtc cccatctatg agggctatgc cttgccccat gccatcatgc gtctggatct   1020
ggctggccga gatctcactg actacctcat gaagatcctg actgagcgtg gctattcctt   1080
cgttactact gctgagcgtg agattgtccg ggacatcaag gagaaactgt gttatgtagc   1140
tctggacttt gaaaatgaga tggcactgc cgcatcctca tcctcccttg agaagagtta   1200
cgagttgcct gatgggcaag tgatcaccat cggaaatgaa cgtttccgct gcccagagac   1260
cctgttccag ccatccttca tcgggatgga gtctgctggc atccatgaaa ccacctacaa   1320
cagcatcatg aagtgtgata ttgacatcag gaaggacctc tatgctaaca atgtcctatc   1380 aggggggcacc actatgtacc ctggcattgc cgaccgaatg cagaaggaga tcacggccct   1440
agcacccagc accatgaaga tcaagatcat tgcccctccg gagcgcaaat actctgtctg   1500
gatcggtggc tccatcctgg cctctctgtc caccttccag cagatgtgga tcagcaaaca   1560
ggaatacgat gaagccgggc cttccattgt ccaccgcaaa tgcttctaaa acacttttcct   1620
```

| | |
|---|---|
| gctcctctct gtctctagca cacaactgtg aatgtcctgt ggaattatgc cttcagttct | 1680 |
| tttccaaatc attcctagcc aaagctctga ctcgttacct atgtgttttt taataaatct | 1740 |
| gaaataggct actggtaaaa aaaaaaaaaa aaaaaaaaaa aaaaaaaaaa aaaaaaaa | 1798 |

<210> SEQ ID NO 8
<211> LENGTH: 3879
<212> TYPE: DNA
<213> ORGANISM: Homo sapiens
<220> FEATURE:
<223> OTHER INFORMATION: Homo sapiens moesin (MSN), mRNA

<400> SEQUENCE: 8

| | |
|---|---|
| ggcacgaggc cagccgaatc caagccgtgt gtactgcgtg ctcagcactg cccgacagtc | 60 |
| ctagctaaac ttcgccaact ccgctgcctt tgccgccacc atgccaaaaa cgatcagtgt | 120 |
| gcgtgtgacc accatggatg cagagctgga gtttgccatc cagcccaaca ccaccgggaa | 180 |
| gcagctattt gaccaggtgg tgaaaactat tggcttgagg aagtttggt tctttggtct | 240 |
| gcagtaccag gacactaaag gtttctccac ctggctgaaa ctcaataaga aggtgactgc | 300 |
| ccaggatgtg cggaaggaaa gcccctgct ctttaagttc cgtgccaagt tctaccctga | 360 |
| ggatgtgtcc gaggaattga ttcaggacat cactcagcgc ctgttctttc tgcaagtgaa | 420 |
| agagggcatt ctcaatgatg atatttactg cccgcctgag accgctgtgc tgctggcctc | 480 |
| gtatgctgtc cagtctaagt atggcgactt caataaggaa gtgcataagt ctggctacct | 540 |
| ggccggagac aagttgctcc cgcagagagt cctggaacag cacaaactca caaggacca | 600 |
| gtgggaggag cggatccagg tgtggcatga ggaacaccgt ggcatgctca gggaggatgc | 660 |
| tgtcctggaa tatctgaaga ttgctcaaga tctggagatg tatggtgtga actacttcag | 720 |
| catcaagaac aagaaaggct cagagctgtg gctgggggtg gatgccctgg gtctcaacat | 780 |
| ctatgagcag aatgacagac taactcccaa gataggcttc cctggagtg aaatcaggaa | 840 |
| catctctttc aatgataaga aatttgtcat caagcccatt gacaaaaaag ccccggactt | 900 |
| cgtcttctat gctccccggc tgcggattaa caagcggatc ttggccttgt gcatggggaa | 960 |
| ccatgaacta tacatgcgcc gtcgcaagcc tgataccatt gaggtgcagc agatgaaggc | 1020 |
| acaggcccgg gaggagaagc accagaagca gatggagcgt gctatgctgg aaaatgagaa | 1080 |
| gaagaagcgt gaaatggcag agaaggagaa agagaagatt gaacgggaga aggaggagct | 1140 |
| gatggagagg ctgaagcaga tcgaggaaca gactaagaag gctcagcaag aactggaaga | 1200 |
| acagacccgc aggcctctgg aacttgagca ggaacggaag cgtgcccaga gcgaggctga | 1260 |
| aaagctggcc aaggagcgtc aagaagctga agaggccaag gaggccttgc tgcaggcctc | 1320 |
| ccgggaccag aaaaagactc aggaacagct ggccttggaa atggcagagc tgacagctcg | 1380 |
| aatctcccag ctggagatgg cccgacagaa gaaggagagt gaggctgtgg agtggcagca | 1440 |
| gaaggcccag atggtacagg aagacttgga gaagacccgt gctgagctga agactgccat | 1500 |
| gagtacacct catgtggcag agcctgctga gaatgagcag gatgagcagg atgagaatgg | 1560 |
| ggcagaggct agtgctgacc tacgggctga tgctatggcc aaggaccgca gtgaggagga | 1620 |
| acgtaccact gaggcagaga agaatgagcg tgtgcagaag cacctgaagg ccctcacttc | 1680 |
| ggagctggcc aatgccagag atgagtccaa gaagactgcc aatgacatga tccatgctga | 1740 |
| gaacatgcga ctgggccgag acaaatacaa gacccctgcg cagatccggc agggcaacac | 1800 |
| caagcagcgc attgacgaat ttgagtctat gtaatgggca cccagcctct agggaccct | 1860 |
| ccctcccttt tccttgtccc cacactccta cacctaactc acctaactca tactgtgctg | 1920 |

```
gagccactaa ctagagcagc cctggagtca tgccaagcat ttaatgtagc catgggacca    1980
aacctagccc cttagccccc acccacttcc ctgggcaaat gaatggctca ctatggtgcc    2040
aatggaacct cctttctctt ctctgttcca ttgaatctgt atggctagaa tatcctactt    2100
ctccagccta gaggtacttt ccacttgatt ttgcaaatgc ccttacactt actgttgtcc    2160
tatgggagtc aagtgtggag taggttggaa gctagctccc ctcctctccc ctccactgtc    2220
ttcttcaggt cctgagatta cacggtggag tgtatgcggt ctaggaatga gacaggacct    2280
agatatcttc tccagggatg tcaactgacc taaaatttgc cctcccatcc cgtttagagt    2340
tatttaggct ttgtaacgat tgggggaata aaaagatgtt cagtcatttt tgtttctacc    2400
tcccagatcg gatctgttgc aaactcagcc tcaataagcc ttgtcgttga ctttagggac    2460
tcaatttctc cccagggtgg atggggyaaa tggtgccttc aagaccttca ccaaacatac    2520
tagaagggca ttggccattc tattgtggca aggctgagta aagatcctac ccccaattcc    2580
ttgtaggagt ataggccggt ctaaagtgag ctctatgggc agatctaccc cttacttatt    2640
attccagatc tgcagtcact tcgtgggatc tgcccctccc tgcttcaata cccaaatcct    2700
ctccagctat aacagtaggg atgagtaccc aaaagctcag ccagccccat caggactctt    2760
gtgaaaagag aggatatgtt cacacctagc gtcagtattt ccctgctag  ggttttagg    2820 tctcttcccc tctcagagct acttgggcca tagctcctgc tccacagcca tcccagcctt    2880
ggcatctaga gcttgatgcc agtaggctca actagggagt gagtgcaaaa agctgagtat    2940
ggtgagagaa gcctgtgccc tgatccaagt ttactcaacc ctctcaggtg accaaaatcc    3000
ccttctcatc actcccctca agaggtgac  tgggccctgc ctctgtttga caaacctcta    3060
acccaggtct tgacaccagc tgttctgtcc cttggagctg taaaccagag agctgctggg    3120
ggattctggc ctagtccctt ccacaccccc accccttgct ctcaacccag gagcatccac    3180
ctccttctct gtctcatgtg tgctcttctt cttt ctacag tattatgtac tctactgata    3240
tctaaatatt gatttctgcc ttccttgcta atgcaccatt agaagatatt agtcttgggg    3300
caggatgatt ttggcctcat tactttacca ccccacacc  tggaaagcat atactatatt    3360
acaaaatgac attttgccaa aattattaat ataagaagct ttcagtatta gtgatgtcat    3420
ctgtcactat aggtcataca atccattctt aaagtacttg ttatttgttt ttattattac    3480
tgtttgtctt ctccccaggg ttcagtccct caaggggcca tcctgtccca ccatgcagtg    3540 cccccctagct tagagcctcc ctcaattccc cctggccacc acccccccact ctgtgcctga   3600 ccttgaggag tcttgtgtgc attgctgtga attagctcac ttggtgatat gtcctatatt    3660
ggctaaattg aaacctggaa ttgtggggca atctattaat agctgcctta aagtcagtaa    3720 cttacccctta gggaggctgg gggaaaaggt tagattttgt attcagggt  ttttgtgta    3780 cttttttgggt ttttaaaaaa ttgttttttgg aggggtttat gctcaatcca tgttctattt    3840
cagtgccaat aaaatttagg tgacttcaaa aaaaaaaa                            3879
```

<210> SEQ ID NO 9
<211> LENGTH: 1976
<212> TYPE: DNA
<213> ORGANISM: Homo sapiens
<220> FEATURE:
<223> OTHER INFORMATION: Homo sapiens karyopherin alpha 2 (RAG cohort 1, importin alpha 1) (KPNA2), mRNA

<400> SEQUENCE: 9

```
gccacacggt ctttgagctg agtcgaggtg gacccttttga acgcagtcgc cctacagccg      60
ctgattcccc ccgcatcgcc tcccgtggaa gcccaggccc gcttcgcagc tttctccctt     120
tgtctcataa ccatgtccac caacgagaat gctaatacac cagctgcccg tcttcacaga     180
ttcaagaaca agggaaaaga cagtacagaa atgaggcgtc gcagaataga ggtcaatgtg     240
gagctgagga aagctaagaa ggatgaccag atgctgaaga ggagaaatgt aagctcattt     300
cctgatgatg ctacttctcc gctgcaggaa aaccgcaaca accagggcac tgtaaattgg     360
tctgttgatg acattgtcaa aggcataaat agcagcaatg tggaaaatca gctccaagct     420
actcaagctg ccaggaaact actttccaga gaaaaacagc cccccataga caacataatc     480
cgggctggtt tgattccgaa atttgtgtcc ttcttgggca gaactgattg tagtcccatt     540
cagtttgaat ctgcttgggc actcactaac attgcttctg ggacatcaga acaaaccaag     600
gctgtggtag atggaggtgc catcccagca ttcatttctc tgttggcatc tccccatgct     660
cacatcagtg aacaagctgt ctgggctcta ggaaacattg caggtgatgg ctcagtgttc     720
cgagacttgg ttattaagta cggtgcagtt gacccactgt tggctctcct tgcagttcct     780
gatatgtcat ctttagcatg tggctactta cgtaatctta cctggacact ttctaatctt     840
tgccgcaaca agaatcctgc accccgata gatgctgttg agcagattct tcctaccttta     900
gttcggctcc tgcatcatga tgatccagaa gtgttagcag atacctgctg ggctatttcc     960
taccttactg atggtccaaa tgaacgaatt ggcatggtgg tgaaaacagg agttgtgccc    1020
caacttgtga agcttctagg agcttctgaa ttgccaattg tgactcctgc cctaagagcc    1080
atagggaata ttgtcactgg tacagatgaa cagactcagg ttgtgattga tgcaggagca    1140
ctcgccgtct ttcccagcct gctcaccaac cccaaaacta acattcagaa ggaagctacg    1200
tggacaatgt caaacatcac agccggccgc caggaccaga tacagcaagt tgtgaatcat    1260
ggattagtcc cattccttgt cagtgttctc tctaaggcag atttttaagac acaaaaggaa    1320
gctgtgtggg ccgtgaccaa ctataccagt ggtggaacag ttgaacagat tgtgtacctt    1380
gttcactgtg gcataataga accgttgatg aacctcttaa ctgcaaaaga taccaagatt    1440
attctggtta tcctggatgc catttcaaat atctttcagg ctgctgagaa actaggtgaa    1500
actgagaaac ttagtataat gattgaagaa tgtggaggct tagacaaaat tgaagctcta    1560
caaaaccatg aaaatgagtc tgtgtataag gcttcgttaa gcttaattga gaagtatttc    1620
tctgtagagg aagaggaaga tcaaaacgtt gtaccagaaa ctacctctga aggctacact    1680
ttccaagttc aggatggggc tcctgggacc tttaactttt agatcatgta gctgagacat    1740
aaatttgttg tgtactacgt ttggtatttt gtcttattgt ttctctacta agaactcttt    1800
cttaaatgtg gtttgttact gtagcacttt ttacactgaa actatacttg aacagttcca    1860
actgtacata catactgtat gaagcttgtc ctctgactag gtttctaatt tctatgtgga    1920
atttcctatc ttgcagcatc ctgtaaataa acattcaagt ccacccttaa aaaaaa       1976
```

<210> SEQ ID NO 10
<211> LENGTH: 3701
<212> TYPE: DNA
<213> ORGANISM: Homo sapiens
<220> FEATURE:
<223> OTHER INFORMATION: Homo sapiens cell division cycle 25 homolog B
    (S. pombe) (CDC25B), transcript variant 1, mRNA

```
<400> SEQUENCE: 10
gcagccagtc gcggaggcgg ggaggctgcg cggtcagagg cgcctggagc gagcgaatcc      60
tggcccaccg cctgcccaac cgcgtgacct tgattgagtt aatgaacttc acgcctcagc     120
gtccaggtct gtaaaatggg gtgtctaacg cagaccgtac agcccagctg ggtttagcaa     180
acttccggga gccagttgga gcctctcccc atccctagcg gtgatcccag gtgacgacat     240
gccgcggggg gtcctgcgga ggccacccta gggcgttgct gctgcctttg ggagtgtgga     300
gctccaaacc atgtcgcgag aggcggattt tgggaggccg ggatcctcgc gccaggggga     360
tgtgcgaggg tgtgggataa atcttaattc ctccggccca cccaaagcct ggaaatccag     420
cctccgcgcc tcttgccctg cgggccccgc cctcagtccc gccctcatct aacccgctac     480
cccattggtg gcgtccggcg gcgcggctgc tgttattttt cgaatatata aggaggtgga     540
agtggcagct gcaactagag gcttccctgg ctggtgcctg agcccggcgt ccctcgcccc     600
ccgccctccc cgcatccctc tcctcccctcg cgcctggccc tgtggctctt cctccctccc     660
tccttccccc cccccccacc cctcgcccgc tgcctccctc ggcccagcca gctgtgccgg     720
cgtttgttgg ctgccctgcg cccggccctc cagccagcct tctgccggcc ccgccgcgat     780
ggaggtgccc cagccggagc ccgcgccagg ctcggctctc agtccagcag gcgtgtgcgg     840
tggcgcccag cgtccgggcc acctcccggg cctcctgctg ggatctcatg gcctcctggg     900
gtccccggtg cgggcggccg cttcctcgcc ggtcaccacc ctcacccaga ccatgcacga     960
cctcgccggg ctcggcagcg aaaccccaaa gagtcaggta gggaccctgc tcttccgcag    1020
ccgcagccgc ctgacgcacc tatccctgtc tcgacgggca tccgaatcct ccctgtcgtc    1080
tgaatcctcc gaatcttctg atgcaggtct ctgcatggat tcccccagcc ctatggaccc    1140
ccacatggcg gagcagacgt ttgaacaggc catccaggca gccagccgga tcattcgaaa    1200
cgagcagttt gccatcagac gcttccagtc tatgccggtg aggctgctgg ccacagccc    1260
cgtgcttcgg aacatcacca actcccaggc gcccgacggc cggaggaaga gcgaggcggg    1320
cagtggagct gccagcagct ctggggaaga caaggagaat gatggatttg tcttcaagat    1380
gccatggaag cccacacatc ccagctccac ccatgctctg gcagagtggg ccagccgcag    1440
ggaagccttt gcccagagac ccagctcggc ccccgacctg atgtgtctca gtcctgaccg    1500
gaagatggaa gtggaggagc tcagcccccct ggccctaggt cgcttctctc tgaccccctgc   1560
agaggggat actgaggaag atgatggatt tgtggacatc ctagagagtg acttaaagga    1620
tgatgatgca gttccccag gcatggagag tctcattagt gccccactgg tcaagacctt    1680
ggaaaaggaa gaggaaaagg acctcgtcat gtacagcaag tgccagcggc tcttccgctc    1740
tccgtccatg ccctgcagcg tgatccggcc catcctcaag aggctggagc ggccccagga    1800
cagggacacg cccgtgcaga ataagcggag gcggagcgtg acccctcctg aggagcagca    1860
ggaggctgag gaacctaaag cccgcgtcct ccgctcaaaa tcactgtgtc acgatgagat    1920
cgagaacctc ctggacagtg accaccgaga gctgattgga gattactcta aggccttcct    1980
cctacagaca gtagacggaa agcaccaaga cctcaagtac atctcaccag aaacgatggt    2040
ggccctattg acgggcaagt tcagcaacat cgtggataag tttgtgattg tagactgcag    2100
ataccccctat gaatatgaag gcgggcacat caagactgcg gtgaacttgc ccctggaacg    2160
cgacgccgag agcttcctac tgaagagccc catcgcgccc tgtagcctgg acaagagagt    2220
catcctcatt ttccactgtg aattctcatc tgagcgtggg ccccgcatgt gccgtttcat    2280
cagggaacga gaccgtgctg tcaacgacta ccccagcctc tactaccctg agatgtatat    2340
```

```
cctgaaaggc ggctacaagg agttcttccc tcagcacccg aacttctgtg aaccccagga      2400
ctaccggccc atgaaccacg aggccttcaa ggatgagcta aagaccttcc gcctcaagac      2460
tcgcagctgg gctggggagc ggagccggcg ggagctctgt agccggctgc aggaccagtg      2520
aggggcctgc gccagtcctg ctacctccct tgcctttcga ggcctgaagc cagctgccct      2580
atgggcctgc cgggctgagg gcctgctgga ggcctcaggt gctgtccatg ggaaagatgg      2640
tgtgggtgtc ctgcctgtct gccccagccc agattcccct gtgtcatccc atcattttcc      2700
atatcctggt gcccccacc cctggaagag cccagtctgt tgagttagtt aagttgggtt       2760
aataccagct taaaggcagt attttgtgtc ctccaggagc ttcttgtttc cttgttaggg      2820
ttaacccttc atcttcctgt gtcctgaaac gctcctttgt gtgtgtgtca gctgaggctg      2880
ggggagagcc gtggtccctg aggatgggtc agagctaaac tccttcctgg cctgagagtc      2940
agctctctgc cctgtgtact tcccgggcca gggctgcccc taatctctgt aggaaccgtg      3000
gtatgtctgc catgttgccc ctttctcttt tcccctttcc tgtcccacca tacgagcacc      3060
tccagcctga acagaagctc ttactctttc ctatttcagt gttacctgtg tgcttggtct      3120
gtttgacttt acgcccatct caggacactt ccgtagactg tttaggttcc cctgtcaaat      3180
atcagttacc cactcggtcc cagttttgtt gccccagaaa gggatgttat tatccttggg      3240
ggctcccagg gcaagggtta aggcctgaat catgagcctg ctggaagccc agccctact      3300 gctgtgaacc ctggggcctg actgctcaga acttgctgct gtcttgttgc ggatggatgg      3360
aaggttggat ggatgggtgg atggccgtgg atggccgtgg atgcgcagtg ccttgcatac      3420
ccaaaccagg tgggagcgtt ttgttgagca tgacagcctg cagcaggaat atatgtgtgc      3480
ctatttgtgt ggacaaaaat atttacactt agggtttgga gctattcaag aggaaatgtc      3540
acagaagcag ctaaaccaag gactgagcac cctctggatt ctgaatctca agatgggggc      3600
agggctgtgc ttgaaggccc tgctgagtca tctgttaggg ccttggttca ataaagcact      3660
gagcaagttg agaaaaaaaa aaaaaaaaaa aaaaaaaaa a                           3701
```